United States Patent
Brown et al.

(10) Patent No.: US 10,435,692 B2
(45) Date of Patent: *Oct. 8, 2019

(54) METHODS AND COMPOSITIONS FOR THE SPECIFIC INHIBITION OF GLYCOLATE OXIDASE (HAO1) BY DOUBLE-STRANDED RNA

(71) Applicant: Dicerna Pharmaceuticals, Inc., Cambridge, MA (US)

(72) Inventors: Bob D. Brown, Littleton, MA (US); Henryk T. Dudek, Wellesley, MA (US)

(73) Assignee: Dicerna Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/793,441

(22) Filed: Oct. 25, 2017

(65) Prior Publication Data

US 2018/0291379 A1 Oct. 11, 2018

Related U.S. Application Data

(60) Continuation of application No. 15/616,254, filed on Jun. 7, 2017, now Pat. No. 9,828,606, which is a division of application No. 14/583,200, filed on Dec. 26, 2014, now Pat. No. 9,701,966.

(60) Provisional application No. 61/937,838, filed on Feb. 10, 2014, provisional application No. 61/921,181, filed on Dec. 27, 2013.

(51) Int. Cl.
C12N 15/113 (2010.01)
C12N 9/04 (2006.01)

(52) U.S. Cl.
CPC ........ *C12N 15/1137* (2013.01); *C12N 9/0006* (2013.01); *C12Y 101/03015* (2013.01); *C12N 2310/11* (2013.01); *C12N 2310/14* (2013.01)

(58) Field of Classification Search
CPC .......... C12N 2310/14; C12N 2310/321; C12N 2310/322; C12N 2310/352; C12N 15/113
USPC .......... 435/6.1, 6.11, 91.1, 91.31, 375, 455; 514/44; 536/23.1, 24.5
See application file for complete search history.

(56) References Cited

U.S. PATENT DOCUMENTS

| | | |
|---|---|---|
| 8,084,599 B2 | 12/2011 | Rossi et al. |
| 8,349,809 B2 | 1/2013 | Brown |
| 8,513,207 B2 | 8/2013 | Brown |
| 9,701,966 B2 * | 7/2017 | Brown ................ C12N 9/0006 |
| 9,828,606 B2 | 11/2017 | Brown et al. |
| 2005/0255487 A1 | 11/2005 | Khvorova et al. |
| 2005/0277610 A1 | 12/2005 | Rossi et al. |
| 2007/0265220 A1 | 11/2007 | Rossi et al. |
| 2010/0144851 A1 | 6/2010 | McSwiggen et al. |
| 2010/0298161 A1 | 11/2010 | Hu et al. |
| 2011/0178283 A1 | 7/2011 | Rigoutsos et al. |
| 2012/0052487 A9 | 3/2012 | Khvorova et al. |
| 2015/0111841 A1* | 4/2015 | Bettencourt ......... A61K 31/713 514/25 |
| 2018/0201934 A1* | 7/2018 | Khvorova .......... C12N 15/8218 |

FOREIGN PATENT DOCUMENTS

| | | |
|---|---|---|
| JP | 2012-512651 | 6/2012 |
| JP | 2013-514089 | 4/2013 |
| WO | WO 2005/116204 A1 | 12/2005 |
| WO | WO 2006/006948 A2 | 1/2006 |
| WO | WO 2010/080129 A2 | 7/2010 |
| WO | WO 2011/075188 A1 | 6/2011 |
| WO | WO 2016/057893 A1 | 4/2016 |

OTHER PUBLICATIONS

Cochat et al., N. E. J. M., vol. 369, No. 7, pp. 649-658 (Aug. 2013) (Year: 2013).*
Recalcati et al., Hepatology, vol. 38, No. 5, pp. 1159-1166 (2003) (Year: 2003).*
Salido et al., Biochim. Biophys. Acta, vol. 1822, pp. 1453-1464 (2012) (Year: 2012).*
Brzica et al., Oxalate: From the Environment to Kidney Stones. Arh Hig Rada Toksikol. 2013;64:609-630.
Cochat et al., Epidemiology of primary hyperoxaluria type 1. Societe de Nephrologie and the Societe de Nephrologie Pediatrique. Nephrol Dial Transplant. 1995;10 Suppl 8:3-7.
Cochat et al., Primary hyperoxaluria Type 1: indications for screening and guidance for diagnosis and; treatment. Nephrol Dial Transplant. May 2012;27(5):1729-36.
GenBank Accession No. NM_017545.2 4 pages. Mar. 15, 2015.
Harambat et al., Characteristics and outcomes of children with primary oxalosis requiring renal replacement therapy. Clin J Am Soc Nephrol. Mar. 2012;7(3):458-65.
Holmes, Pharmacological approaches in the treatment of primary hyperoxaluria. J Nephrol. Mar.-Apr. 1998;11 Suppl 1:32-5.
Kamoun et al., End-stage renal disease of the Tunisian child: epidemiology, etiologies, and outcome. Pediatr Nephrol. Aug. 1996;10(4):479-82.
Recalcati et al., Oxidative stress-mediated down-regulation of rat hydroxyacid oxidase 1, a liver-specific peroxisomal enzyme. Hepatology. Nov. 2003;38(5):1159-66.
Van Woerden et al., Primary hyperoxaluria type 1 in The Netherlands: prevalence and outcome. Nephrol Dial Transplant. Feb. 2003;18(2):273-9.
Wood et al., RNA interference in the treatment of renal stone disease: Current status and future potentials. Int J Surg. Dec. 2016;36(Pt D):713-716. doi: 10.1016/j.ijsu.2016.11.027. Epub Nov. 12, 2016.

* cited by examiner

*Primary Examiner* — Jane J Zara
(74) *Attorney, Agent, or Firm* — Polsinelli, P.C.; Byron V. Olsen

(57) ABSTRACT

This invention relates to compounds, compositions, and methods useful for reducing Glycolate Oxidase (HAO1) target RNA and protein levels via use of dsRNAs, e.g., Dicer substrate siRNA (DsiRNA) agents.

20 Claims, 77 Drawing Sheets

Specification includes a Sequence Listing.

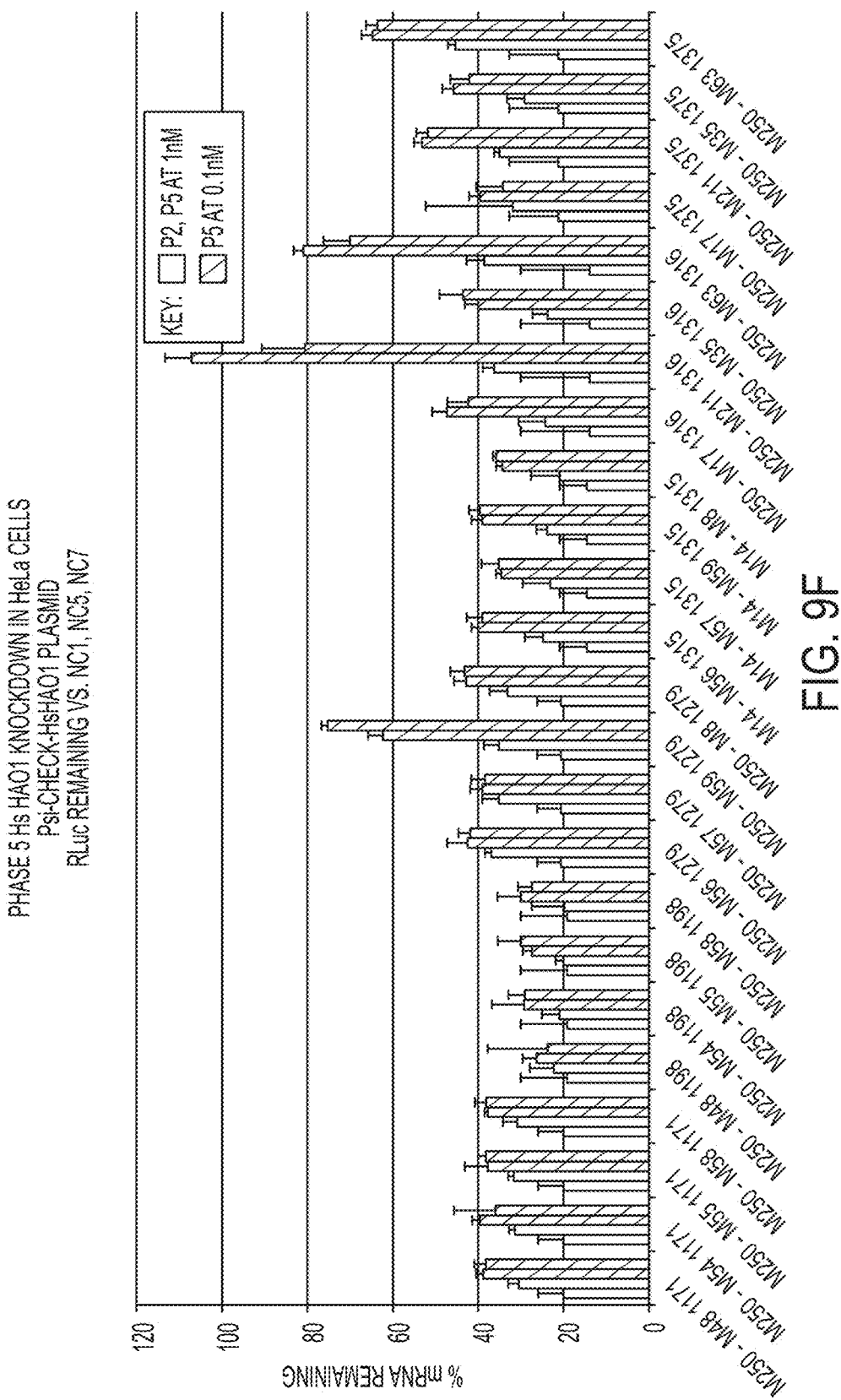

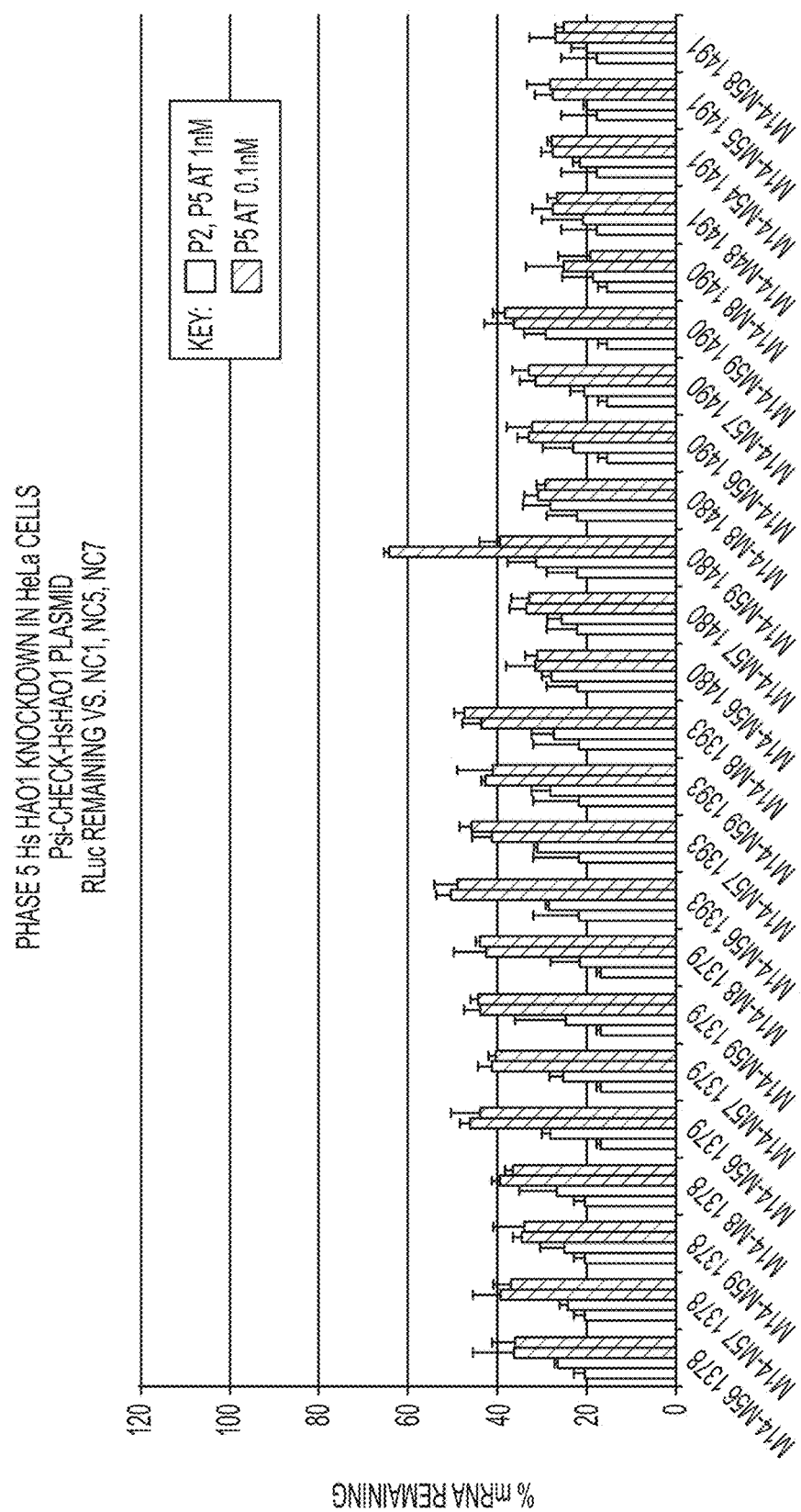

FIG. 10J

MODIFICATION PATTERNS, PHASE 6 SCREEN (CONT.)
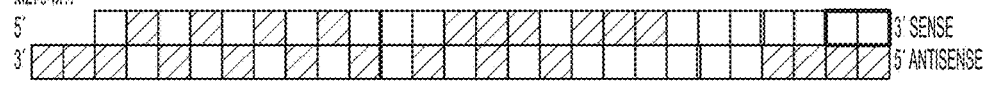
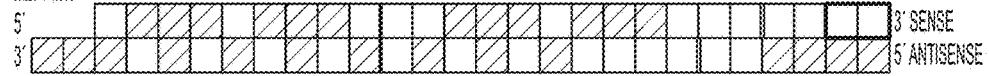
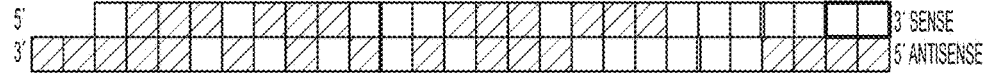
FIG. 10K

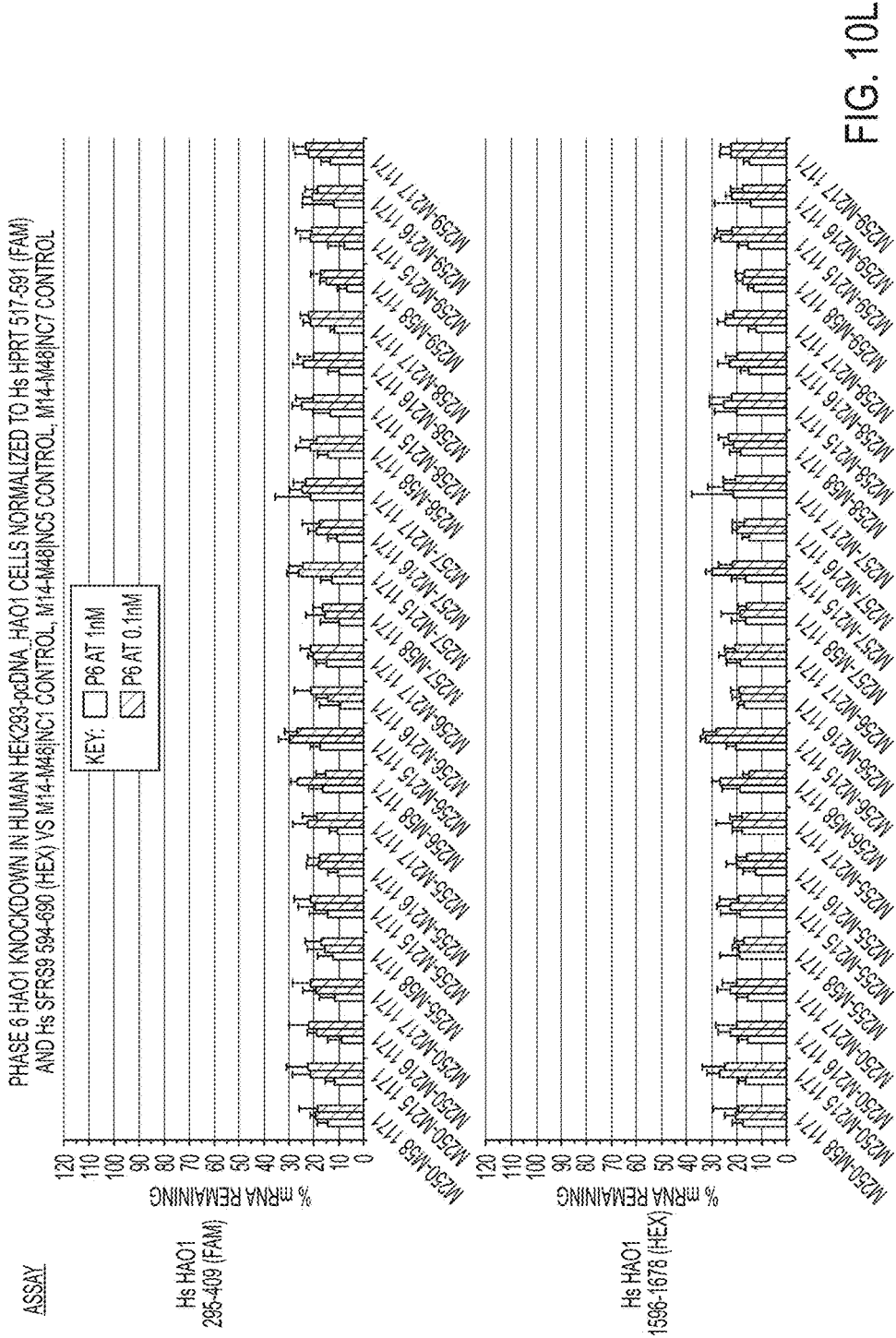

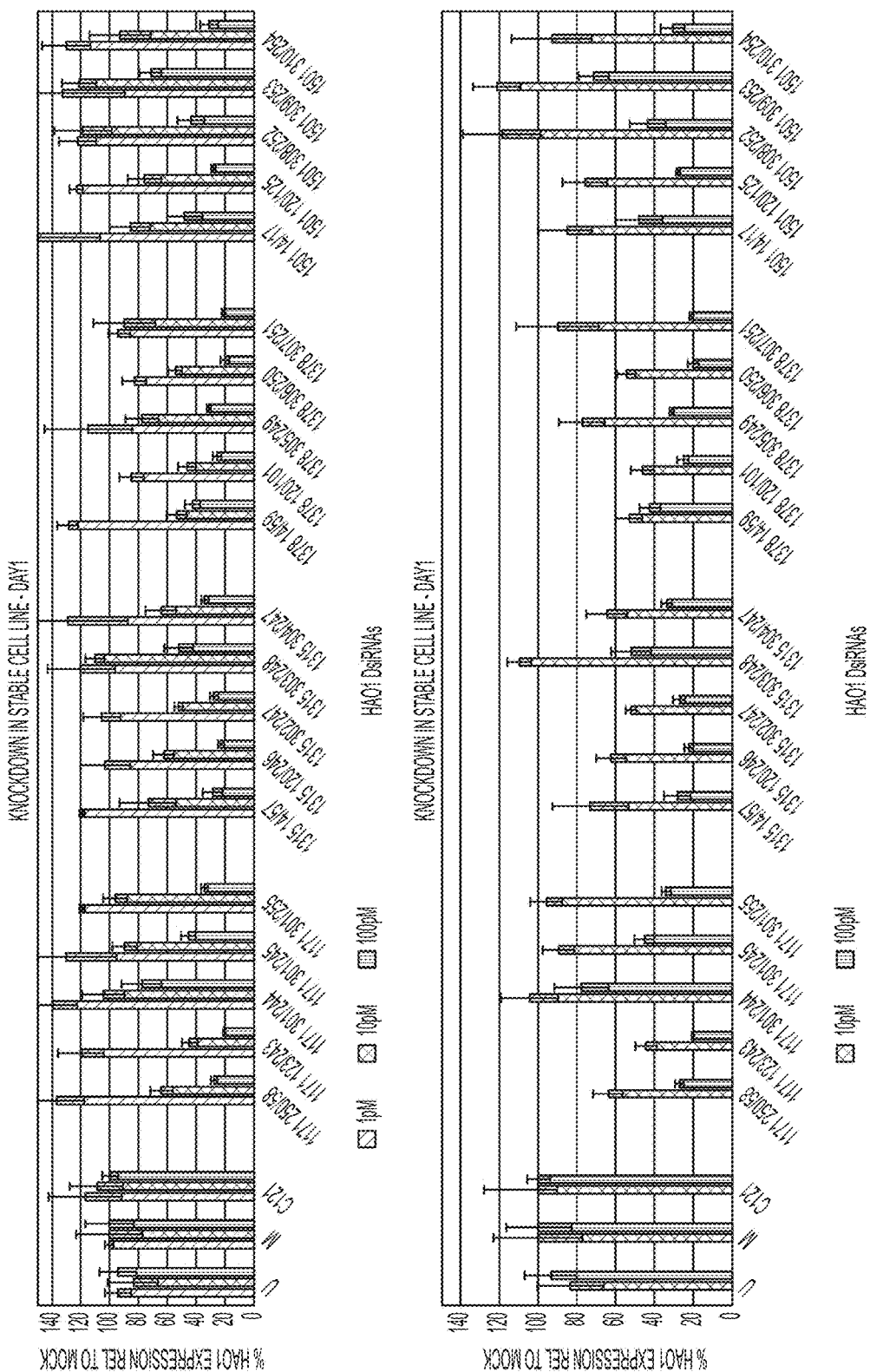

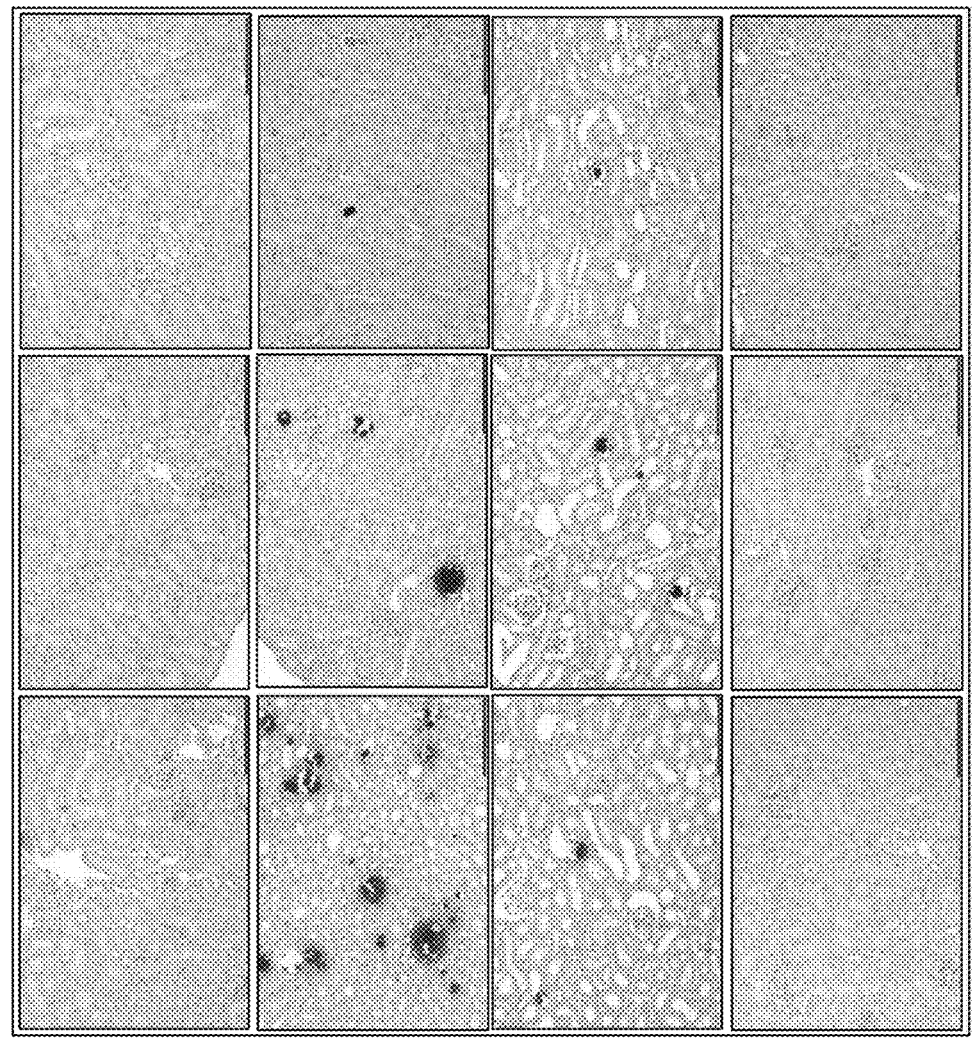
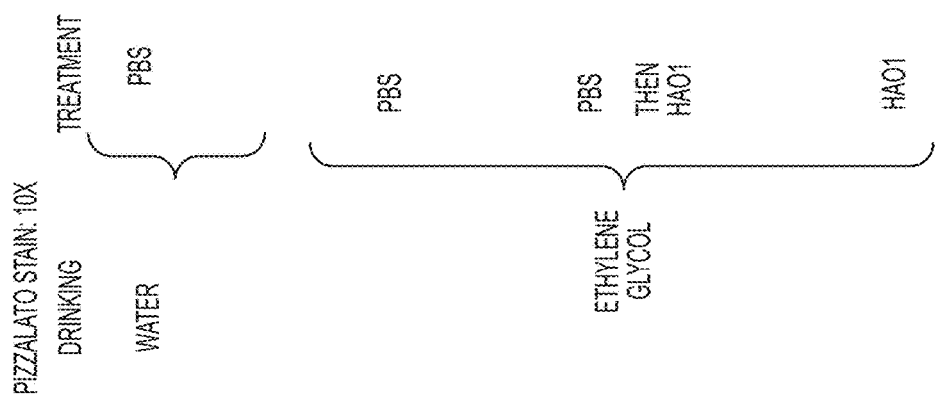
FIG. 13G

METHODS AND COMPOSITIONS FOR THE SPECIFIC INHIBITION OF GLYCOLATE OXIDASE (HAO1) BY DOUBLE-STRANDED RNA

RELATED APPLICATIONS

This application is a continuation of U.S. patent application Ser. No. 15/616,254, entitled "Methods and Compositions for the Specific Inhibition of Glycolate Oxidase (HAO1) by Double-Stranded RNA," filed Jun. 7, 2017 (now U.S. Pat. No. 9,828,606), which is a divisional of U.S. patent application Ser. No. 14/583,200, entitled "Methods and Compositions for the Specific Inhibition of Glycolate Oxidase (HAO1) by Double-Stranded RNA," filed Dec. 26, 2014 (now U.S. Pat. No. 9,701,966), which claims priority under 35 U.S.C. § 119(e) to U.S. provisional patent application No. 61/921,181, entitled "Methods and Compositions for the Specific Inhibition of Glycolate Oxidase (HAO1) by Double-Stranded RNA," filed Dec. 27, 2013, and to U.S. provisional application No. 61/937,838, entitled "Methods and Compositions for the Specific Inhibition of Glycolate Oxidase (HAO1) by Double-Stranded RNA," filed Feb. 10, 2014. The entire contents of the aforementioned patent applications are incorporated herein by this reference.

FIELD OF THE INVENTION

The present invention relates to compounds, compositions, and methods for the study, diagnosis, and treatment of traits, diseases and conditions that respond to the modulation of Glycolate Oxidase (HAO1) gene expression and/or activity.

SEQUENCE SUBMISSION

The present application is being filed along with a Sequence Listing in electronic format. The Sequence Listing is entitled "D080070006US04-SEQ-DWY", was created on Oct. 11, 2017 and is 2.87 MB in size. The information in the electronic format of the Sequence Listing is part of the present application and is incorporated herein by reference in its entirety.

BACKGROUND OF THE INVENTION

Primary hyperoxaluria Type 1 ("PH1") is a rare autosomal recessive inborn error of glyoxylate metabolism, caused by a deficiency of the liver-specific enzyme alanine:glyoxylate aminotransferase. The disorder results in overproduction and excessive urinary excretion of oxalate, causing recurrent urolithiasis and nephrocalcinosis. As glomerular filtration rate declines due to progressive renal involvement, oxalate accumulates leading to systemic oxalosis. The diagnosis is based on clinical and sonographic findings, urine oxalate assessment, enzymology and/or DNA analysis. While early conservative treatment has aimed to maintain renal function, in chronic kidney disease Stages 4 and 5, the best outcomes to date have been achieved with combined liver-kidney transplantation (Cochat et al. *Nephrol Dial Transplant* 27: 1729-36).

PH1 is the most common form of primary hyperoxaluria and has an estimated prevalence of 1 to 3 cases per 1 million population and an incidence rate of approximately 1 case per 120.000 live births per year in Europe (Cochat el al. *Nephrol Dial Transplant* 10 (Suppl 8): 3-7; van Woerden et al. Nephrol Dial Transplant 18: 273-9). It accounts for 1 to 2% of cases of pediatric end-stage renal disease (ESRD), according to registries from Europe, the United States, and Japan (Harambat et al. *Clin J Am Soc Nephrol* 7: 458-65), but it appears to be more prevalent in countries in which consanguineous marriages are common (with a prevalence of 10% or higher in some North African and Middle Eastern nations; Kamoun and Lakhoua Pediatr Nephrol 10: 479-82; see Cochat and Rumsby *N Engl J Med* 369(7):649-58).

Glycolate oxidase (the product of the HAO1, for "hydroxyacid oxidase 1", gene) is the enzyme responsible for converting glycolate to glyoxylate in the mitochondrial/peroxisomal glycine metabolism pathway in the liver and pancreas. While glycolate is a harmless intermediate of the glycine metabolism pathway, accumulation of glyoxylate (via, e.g., AGT1 mutation) drives oxalate accumulation, which ultimately results in the PH1 disease.

Double-stranded RNA (dsRNA) agents possessing strand lengths of 25 to 35 nucleotides have been described as effective inhibitors of target gene expression in mammalian cells (Rossi et al., U.S. Pat. No. 8,084,599 and U.S. Patent Application No. 2005/0277610), dsRNA agents of such length are believed to be processed by the Dicer enzyme of the RNA interference (RNAi) pathway, leading such agents to be termed "Dicer substrate siRNA" ("DsiRNA") agents. Additional modified structures of DsiRNA agents were previously described (Rossi et al., U.S. Patent Application No. 2007/0265220). Effective extended forms of Dicer substrates have also recently been described (Brown, U.S. Pat. Nos. 8,349,809 and 8,513,207).

BRIEF SUMMARY OF THE INVENTION

The present invention is based, at least in part, upon the identification of HAO1 as an attractive target for dsRNA-based knockdown therapies. In particular, provided herein are nucleic acid agents that target and reduce expression of HAO1. Such compositions contain nucleic acids such as double stranded RNA ("dsRNA"), and methods for preparing them. The nucleic acids of the invention are capable of reducing the expression of a target Glycolate Oxidase gene in a cell, either in vitro or in a mammalian subject.

In one aspect, the invention provides a nucleic acid possessing an oligonucleotide strand of 15-80 nucleotides in length, where the oligonucleotide strand is sufficiently complementary to a target HAO1 mRNA sequence of SEQ ID NOs: 1921-2304 along at least 15 nucleotides of the oligonucleotide strand length to reduce HAO1 target mRNA expression when the nucleic acid is introduced into a mammalian cell.

Another aspect of the invention provides a nucleic acid possessing an oligonucleotide strand of 19-80 nucleotides in length, where the oligonucleotide strand is sufficiently complementary to a target HAO1 mRNA sequence of SEQ ID NOs: 1921-2304 along at least 19 nucleotides of the oligonucleotide strand length to reduce HAO1 target mRNA expression when the nucleic acid is introduced into a mammalian cell.

In one embodiment, the oligonucleotide strand is 19-35 nucleotides in length.

An additional aspect of the invention provides a double stranded nucleic acid (dsNA) possessing first and second nucleic acid strands including RNA, where the first strand is 15-66 nucleotides in length and the second strand of the dsNA is 19-66 nucleotides in length, where the second oligonucleotide strand is sufficiently complementary to a target HAO1 mRNA sequence of SEQ ID NOs: 1921-2304 along at least 15 nucleotides of the second oligonucleotide strand length to reduce HAO1 target mRNA expression when the double stranded nucleic acid is introduced into a mammalian cell.

Another aspect of the invention provides a double stranded nucleic acid (dsNA) possessing first and second nucleic acid strands, where the first strand is 15-66 nucleotides in length and the second strand of the dsNA is 19-66 nucleotides in length, where the second oligonucleotide strand is sufficiently complementary to a target HAO1 mRNA sequence of SEQ ID NOs: 1921-2304 along at least 19 nucleotides of the second oligonucleotide strand length to reduce HAO1 target mRNA expression when the double stranded nucleic acid is introduced into a mammalian cell.

A further aspect of the invention provides a double stranded nucleic acid (dsNA) possessing first and second nucleic acid strands, where the first strand is 15-66 nucleotides in length and the second strand of the dsNA is 19-66 nucleotides in length, where the second oligonucleotide strand is sufficiently complementary to a target HAO1 mRNA sequence of SEQ ID NOs: 1921-2304 along at least 19 nucleotides of the second oligonucleotide strand length to reduce HAO1 target mRNA expression, and where, starting from the 5' end of the HAO1 mRNA sequence of SEQ ID NOs: 1921-2304 (position 1), mammalian Ago2 cleaves the mRNA at a site between positions 9 and 10 of the sequence, when the double stranded nucleic acid is introduced into a mammalian cell.

Another aspect of the invention provides a dsNA molecule, consisting of: (a) a sense region and an antisense region, where the sense region and the antisense region together form a duplex region consisting of 25-66 base pairs and the antisense region includes a sequence that is the complement of a sequence of SEQ ID NOs: 1921-2304; and (b) from zero to two 3' overhang regions, where each overhang region is six or fewer nucleotides in length, and where, starting from the 5' end of the HAO1 mRNA sequence of SEQ ID NOs: 1921-2304 (position 1), mammalian Ago2 cleaves the mRNA at a site between positions 9 and 10 of the sequence, when the double stranded nucleic acid is introduced into a mammalian cell.

An additional aspect of the invention provides a double stranded nucleic acid (dsNA) possessing first and second nucleic acid strands and a duplex region of at least 25 base pairs, where the first strand is 25-65 nucleotides in length and the second strand of the dsNA is 26-66 nucleotides in length and includes 1-5 single-stranded nucleotides at its 3' terminus, where the second oligonucleotide strand is sufficiently complementary to a target HAO1 mRNA sequence of SEQ ID NOs: 1921-2304 along at least 19 nucleotides of the second oligonucleotide strand length to reduce HAO1 target gene expression when the double stranded nucleic acid is introduced into a mammalian cell.

Another aspect of the invention provides a double stranded nucleic acid (dsNA) possessing first and second nucleic acid strands and a duplex region of at least 25 base pairs, where the first strand is 25-65 nucleotides in length and the second strand of the dsNA is 26-66 nucleotides in length and includes 1-5 single-stranded nucleotides at its 3' terminus, where the 3' terminus of the first oligonucleotide strand and the 5' terminus of the second oligonucleotide strand form a blunt end, and the second oligonucleotide strand is sufficiently complementary to a target HAO1 sequence of SEQ ID NOs: 1921-2304 along at least 19 nucleotides of the second oligonucleotide strand length to reduce HAO1 mRNA expression when the double stranded nucleic acid is introduced into a mammalian cell.

In one embodiment, the first strand is 15-35 nucleotides in length.

In another embodiment, the second strand is 19-35 nucleotides in length.

In an additional embodiment, the dsNA possesses a duplex region of at least 25 base pairs; 19-21 base pairs or 21-25 base pairs.

Optionally, the second oligonucleotide strand includes 1-5 single-stranded nucleotides at its 3' terminus.

In one embodiment, the second oligonucleotide strand includes 5-35 single-stranded nucleotides at its 3' terminus.

In another embodiment, the single-stranded nucleotides include modified nucleotides. Optionally, the single-stranded nucleotides include 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino and/or 2'-O—(N-methlycarbamate) modified nucleotides.

In certain embodiments, the single-stranded nucleotides include ribonucleotides. Optionally, the single-stranded nucleotides include deoxyribonucleotides.

In certain embodiments, the 3' end of the first strand and the 5' end of the second strand of a dsNA or hybridization complex of the invention are joined by a polynucleotide sequence that includes ribonucleotides, deoxyribonucleotides or both, optionally the polynucleotide sequence includes a tetraloop sequence.

In one embodiment, the first strand is 25-35 nucleotides in length. Optionally, the second strand is 25-35 nucleotides in length.

In one embodiment, the second oligonucleotide strand is complementary to target HAO1 cDNA sequence GenBank Accession No. NM_017545.2 along at most 27 nucleotides of the second oligonucleotide strand length.

In another embodiment, starting from the first nucleotide (position 1) at the 3' terminus of the first oligonucleotide strand, position 1, 2 and/or 3 is substituted with a modified nucleotide.

Optionally, the first strand and the 5' terminus of the second strand form a blunt end.

In one embodiment, the first strand is 25 nucleotides in length and the second strand is 27 nucleotides in length.

In another embodiment, starting from the 5' end of a HAO1 mRNA sequence of SEQ ID NOs: 1921-2304 (position 1), mammalian Ago2 cleaves the mRNA at a site between positions 9 and 10 of the sequence, thereby reducing HAO1 target mRNA expression when the double stranded nucleic acid is introduced into a mammalian cell.

In one embodiment, the second strand includes a sequence of SEQ ID NOs: 385-768. In an additional embodiment, the first strand includes a sequence of SEQ ID NOs: 1-384.

In another embodiment, the dsNA of the invention possesses a pair of first strand/second strand sequences of Table 2.

Optionally, the modified nucleotide residue of the 3' terminus of the first strand is a deoxyribonucleotide, an acyclonucleotide or a fluorescent molecule.

In one embodiment, position 1 of the 3' terminus of the first oligonucleotide strand is a deoxyribonucleotide.

In another embodiment, the nucleotides of the 1-5 or 5-35 single-stranded nucleotides of the 3' terminus of the second strand comprise a modified nucleotide.

In one embodiment, the modified nucleotide of the 1-5 or 5-35 single-stranded nucleotides of the 3' terminus of the second strand is a 2'-O-methyl ribonucleotide.

In an additional embodiment, all nucleotides of the 1-5 or 5-35 single-stranded nucleotides of the 3' terminus of the second strand are modified nucleotides.

In another embodiment, the dsNA includes a modified nucleotide. Optionally, the modified nucleotide residue is 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino or 2'-O—(N-methylcarbamate).

In one embodiment, the 1-5 or 5-35 single-stranded nucleotides of the 3' terminus of the second strand are 1-3 nucleotides in length, optionally 1-2 nucleotides in length.

In another embodiment, the 1-5 or 5-35 single-stranded nucleotides of the 3' terminus of the second strand is two nucleotides in length and includes a 2'-O-methyl modified ribonucleotide.

In one embodiment, the second oligonucleotide strand includes a modification pattern of AS-M1 to AS-M96 and AS-M1* to AS-M96*.

In another embodiment, the first oligonucleotide strand includes a modification pattern of SM1 to SM119.

In an additional embodiment, each of the first and the second strands has a length which is at least 26 and at most 30 nucleotides.

In one embodiment, the dsNA is cleaved endogenously in the cell by Dicer.

In another embodiment, the amount of the nucleic acid sufficient to reduce expression of the target gene is of 1 nanomolar or less, 200 picomolar or less, 100 picomolar or less, 50 picomolar or less, 20 picomolar or less, 10 picomolar or less, 5 picomolar or less, 2, picomolar or less and 1 picomolar or less in the environment of the cell.

In one embodiment, the dsNA possesses greater potency than a 21 mer siRNA directed to the identical at least 19 nucleotides of the target HAO1 mRNA in reducing target HAO1 mRNA expression when assayed in vitro in a mammalian cell at an effective concentration in the environment of a cell of 1 nanomolar or less.

In an additional embodiment, the nucleic acid or dsNA is sufficiently complementary to the target HAO1 mRNA sequence to reduce HAO1 target mRNA expression by an amount (expressed by %) of at least 10%, at least 50%, at least 80-90%, at least 95%, at least 98%, or at least 99% when the double stranded nucleic acid is introduced into a mammalian cell.

In one embodiment, the first and second strands are joined by a chemical linker.

In another embodiment, the 3' terminus of the first strand and the 5' terminus of the second strand are joined by a chemical linker.

In an additional embodiment, a nucleotide of the second or first strand is substituted with a modified nucleotide that directs the orientation of Dicer cleavage.

In one embodiment, the nucleic acid, dsNA or hybridization complex possesses a deoxyribonucleotide, a dideoxyribonucleotide, an acyclonucleotide, a 3'-deoxyadenosine (cordycepin), a 3'-azido-3'-deoxythymidine (AZT), a 2',3'-dideoxyinosine (ddI), a 2',3'-dideoxy-3'-thiacytidine (3TC), a 2',3'-didehydro-2',3'-dideoxythymidine (d4T), a monophosphate nucleotide of 3'-azido-3'-deoxythymidine (AZT), a 2',3'-dideoxy-3'-thiacytidine (3TC) and a monophosphate nucleotide of 2',3'-didehydro-2',3'-dideoxythymidine (d4T), a 4-thiouracil, a 5-bromouracil, a 5-iodouracil, a 5-(3-aminoallyl)-uracil, a 2'-O-alkyl ribonucleotide, a 2'-O-methyl ribonucleotide, a 2'-amino ribonucleotide, a 2'-fluoro ribonucleotide, or a locked nucleic acid modified nucleotide.

In another embodiment, the nucleic acid, dsNA or hybridization complex includes a phosphonate, a phosphorothioate or a phosphotriester phosphate backbone modification.

In one embodiment, the nucleic acid, dsNA or hybridization complex includes a morpholino nucleic acid or a peptide nucleic acid (PNA).

In an additional embodiment, the nucleic acid, dsNA or hybridization complex is attached to a dynamic polyconjugate (DPC).

In one embodiment, the nucleic acid, dsNA or hybridization complex is administered with a DPC, where the dsNA and DPC are optionally not attached.

In another embodiment, the nucleic acid, dsNA or hybridization complex is attached to a GalNAc moiety, a cholesterol and/or a cholesterol targeting ligand.

Another aspect of the invention provides a composition of the following:

a dsNA possessing first and second nucleic acid strands, where the first strand is 15-35 nucleotides in length and the second strand of the dsNA is 19-35 nucleotides in length, where the second oligonucleotide strand is sufficiently complementary to a target HAO1 mRNA sequence of SEQ ID NOs: 1921-2304 along at least 19 nucleotides of the second oligonucleotide strand length to reduce HAO1 target mRNA expression when the double stranded nucleic acid is introduced into a mammalian cell;

a dsNA possessing first and second nucleic acid strands, where the first strand is 15-35 nucleotides in length and the second strand of the dsNA is 19-35 nucleotides in length, where the second oligonucleotide strand is sufficiently complementary to a target HAO1 mRNA sequence of SEQ ID NOs: 1921-2304 along at least 19 nucleotides of the second oligonucleotide strand length to reduce HAO1 target mRNA expression, and where, starting from the 5' end of the HAO1 mRNA sequence of SEQ ID NOs: 1921-2304 (position 1), mammalian Ago2 cleaves the mRNA at a site between positions 9 and 10 of the sequence, when the double stranded nucleic acid is introduced into a mammalian cell;

a dsNA molecule, consisting of: (a) a sense region and an antisense region, where the sense region and the antisense region together form a duplex region consisting of 25-35 base pairs and the antisense region includes a sequence that is the complement of a sequence of SEQ ID NOs: 1921-2304; and (b) from zero to two 3' overhang regions, where each overhang region is six or fewer nucleotides in length, and where, starting from the 5' end of the HAO1 mRNA sequence of SEQ ID NOs: 1921-2304 (position 1), mammalian Ago2 cleaves the mRNA at a site between positions 9 and 10 of the sequence, when the double stranded nucleic acid is introduced into a mammalian cell;

a dsNA possessing first and second nucleic acid strands and a duplex region of at least 25 base pairs, where the first strand is 25-34 nucleotides in length and the second strand of the dsNA is 26-35 nucleotides in length and includes 1-5 single-stranded nucleotides at its 3' terminus, where the second oligonucleotide strand is sufficiently complementary to a target HAO1 mRNA sequence of SEQ ID NOs: 1921-2304 along at least 19 nucleotides of the second oligonucleotide strand length to reduce HAO1 target gene expression when the double stranded nucleic acid is introduced into a mammalian cell;

a dsNA possessing first and second nucleic acid strands and a duplex region of at least 25 base pairs, where the first strand is 25-34 nucleotides in length and the second strand of the dsNA is 26-35 nucleotides in length and includes 1-5 single-stranded nucleotides at its 3' terminus, where the 3' terminus of the first oligonucleotide strand and the 5' terminus of the second oligonucleotide strand form a blunt end, and the second oligonucleotide strand is sufficiently complementary to a target HAO1 sequence of SEQ ID NOs: 1921-2304 along at least 19 nucleotides of the second oligonucleotide strand length to reduce HAO1 mRNA expression when the double stranded nucleic acid is introduced into a mammalian cell;

a nucleic acid possessing an oligonucleotide strand of 19-35 nucleotides in length, where the oligonucleotide strand is sufficiently complementary to a target HAO1 mRNA sequence of SEQ ID NOs: 1921-2304 along at least 19 nucleotides of the oligonucleotide strand length to reduce HAO1 target mRNA expression when the nucleic acid is introduced into a mammalian cell;

a nucleic acid possessing an oligonucleotide strand of 15-35 nucleotides in length, where the oligonucleotide strand is hybridizable to a target HAO1 mRNA sequence of SEQ ID NOs: 1921-2304 along at least 15 nucleotides of the oligonucleotide strand length;

a dsNA possessing first and second nucleic acid strands possessing RNA, where the first strand is 15-35 nucleotides in length and the second strand of the dsNA is 19-35 nucleotides in length, where the second oligonucleotide strand is hybridizable to a target HAO1 mRNA sequence of SEQ ID NOs: 1921-2304 along at least 15 nucleotides of the second oligonucleotide strand length;

a dsNA possessing first and second nucleic acid strands possessing RNA, where the first strand is 15-35 nucleotides in length and the second strand of the dsNA is at least 35 nucleotides in length and optionally includes a sequence of at least 25 nucleotides in length of SEQ ID NOs: 385-768, where the second oligonucleotide strand is sufficiently complementary to a target HAO1 mRNA sequence of SEQ ID NOs: 1921-2304 along at least 15 nucleotides of the second oligonucleotide strand length to reduce HAO1 target mRNA expression when the double stranded nucleic acid is introduced into a mammalian cell;

a dsNA possessing a first oligonucleotide strand having a 5' terminus and a 3' terminus and a second oligonucleotide strand having a 5' terminus and a 3' terminus, where the first strand is 25 to 53 nucleotide residues in length, where starting from the first nucleotide (position 1) at the 5' terminus of the first strand, positions 1 to 23 of the first strand are ribonucleotides or modified ribonucleotides; the second strand is 27 to 53 nucleotide residues in length and includes 23 consecutive ribonucleotides or modified ribonucleotides that base pair with the ribonucleotides or ribonucleotides of positions 1 to 23 of the first strand to form a duplex; the 5' terminus of the first strand and the 3' terminus of the second strand form a structure of a blunt end, a 1-6 nucleotide 5' overhang and a 1-6 nucleotide 3' overhang; the 3' terminus of the first strand and the 5' terminus of the second strand form a structure of a blunt end, a 1-6 nucleotide 5' overhang and a 1-6 nucleotide 3' overhang; at least one of positions 24 to the 3' terminal nucleotide residue of the first strand is a deoxyribonucleotide or modified ribonucleotide that optionally base pairs with a deoxyribonucleotide of the second strand; and the second strand is sufficiently complementary to a target HAO1 mRNA sequence of SEQ ID NOs: 1921-2304 along at least 15 nucleotides of the second oligonucleotide strand length to reduce HAO1 target mRNA expression when the double stranded nucleic acid is introduced into a mammalian cell;

a dsNA possessing a first oligonucleotide strand having a 5' terminus and a 3' terminus and a second oligonucleotide strand having a 5' terminus and a 3' terminus, where the second strand is 27 to 53 nucleotide residues in length, where starting from the first nucleotide (position 1) at the 5' terminus of the second strand, positions 1 to 23 of the second strand are ribonucleotides or modified ribonucleotides; the first strand is 25 to 53 nucleotide residues in length and includes 23 consecutive ribonucleotides or modified ribonucleotides that base pair sufficiently with the ribonucleotides of positions 1 to 23 of the second strand to form a duplex; at least one of positions 24 to the 3' terminal nucleotide residue of the second strand is a deoxyribonucleotide or modified ribonucleotide, optionally that base pairs with a deoxyribonucleotide or modified ribonucleotide of the first strand; and the second strand is sufficiently complementary to a target HAO1 mRNA sequence of SEQ ID NOs: 1921-2304 along at least 15 nucleotides of the second oligonucleotide strand length to reduce HAO1 target mRNA expression when the double stranded nucleic acid is introduced into a mammalian cell;

a dsNA possessing a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the first strand (or the second strand) is 25-30 nucleotide residues in length, where starting from the 5' terminal nucleotide (position 1) positions 1 to 23 of the first strand (or the second strand) include at least 8 ribonucleotides; the second strand (or the first strand) is 36-66 nucleotide residues in length and, starting from the 3' terminal nucleotide, includes at least 8 ribonucleotides in the positions paired with positions 1-23 of the first strand to form a duplex; where at least the 3' terminal nucleotide of the second strand (or the first strand) is unpaired with the first strand (or the second strand), and up to 6 consecutive 3' terminal nucleotides are unpaired with the first strand (or the second strand), thereby forming a 3' single stranded overhang of 1-6 nucleotides; where the 5' terminus of the second strand (or the first strand) includes from 10-30 consecutive nucleotides which are unpaired with the first strand (or the second strand), thereby forming a 10-30 nucleotide single stranded 5' overhang; where at least the first strand (or the second strand) 5' terminal and 3' terminal nucleotides are base paired with nucleotides of the second strand (or first strand) when the first and second strands are aligned for maximum complementarity, thereby forming a substantially duplexed region between the first and second strands; and the second strand is sufficiently complementary to a target RNA along at least 19 ribonucleotides of the second strand length to reduce target gene expression when the double stranded nucleic acid is introduced into a mammalian cell;

a dsNA possessing a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the first strand is 25-35 nucleotide residues in length, where starting from the 5' terminal nucleotide (position 1) positions 1 to 25 of the second strand include at least 8 ribonucleotides; the second strand is 30-66 nucleotide residues in length and, starting from the 3' terminal nucleotide, includes at least 8 ribonucleotides in the positions paired with positions 1-25 of the first strand to form a duplex; where the 5' terminus of the second strand includes from 5-35 consecutive nucleotides which are unpaired with the first strand, thereby forming a 5-35 nucleotide single stranded 5' overhang: where at least the first strand 5' terminal and 3' terminal nucleotides are base paired with nucleotides of the second strand when the first and second strands are aligned for maximum complementarity, thereby forming a substantially duplexed region between the first and second strands; and the second strand is sufficiently complementary to a target HAO1 mRNA sequence of SEQ ID NOs: 1921-2304 along at least 15 nucleotides of the second oligonucleotide strand length to reduce HAO1 target mRNA expression when the double stranded nucleic acid is introduced into a mammalian cell;

a dsNA possessing a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the second strand is 19-30 nucleotide residues in length and optionally 25-30 nucleotide residues in length, where starting from the 5' terminal nucleotide (position 1) positions 1 to 17 (optionally positions 1 to 23) of the second strand include at least 8 ribonucleotides; the first strand is 24-66 nucleotide residues in length (optionally 30-66 nucleotide residues in length) and, starting from the 3' terminal nucleotide, includes at least 8 ribonucleotides in the positions paired with positions 1 to 17 (optionally positions 1 to 23) of the second strand to form a duplex; where the 3' terminus of the first strand and the 5' terminus of the second strand comprise a structure of a blunt end, a 3' overhang and a 5' overhang, optionally where the overhang is 1-6 nucleotides in length; where the 5' terminus of the first strand includes from 5-35 consecutive nucleotides which are unpaired with the second strand, thereby forming a 5-35 nucleotide single-stranded 5' overhang; where at least the second strand 5' terminal and 3' terminal nucleotides are base paired with nucleotides of the first strand when the first and second strands are aligned for maximum complementarity, thereby forming a substantially duplexed region between the first and second strands; and the second strand is sufficiently complementary to a target HAO1 mRNA sequence of SEQ ID NOs: 1921-2304 along at least 15 nucleotides of the second oligonucleotide strand length to reduce HAO1 target mRNA expression when the double stranded nucleic acid is introduced into a mammalian cell;

a dsNA possessing a first strand and a second strand, where the first strand and the second strand form a duplex region of 19-25 nucleotides in length, where the first strand includes a 3' region that extends beyond the first strand-second strand duplex region and includes a tetraloop, and the dsNA further includes a discontinuity between the 3' terminus of the first strand and the 5' terminus of the second strand, and the first or second strand is sufficiently complementary to a target HAO1 mRNA sequence of SEQ ID NOs: 1921-2304 along at least 15 nucleotides of the first or second strand length to reduce HAO1 target mRNA expression when the dsNA is introduced into a mammalian cell;

a dsNA possessing a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the first oligonucleotide strand is 25-53 nucleotides in length and the second is oligonucleotide strand is 25-53 nucleotides in length, and where the dsNA is sufficiently highly modified to substantially prevent dicer cleavage of the dsNA, optionally where the dsNA is cleaved by non-dicer nucleases to yield one or more 19-23 nucleotide strand length dsNAs capable of reducing LDH mRNA expression in a mammalian cell;

an in vivo hybridization complex within a cell of an exogenous nucleic acid sequence and a target HAO1 mRNA sequence of SEQ ID NOs: 1921-2304; and an in vitro hybridization complex within a cell of an exogenous nucleic acid sequence and a target HAO1 mRNA sequence of SEQ ID NOs: 1921-2304.

In one embodiment, a dsNA of the invention possesses a duplex region of at least 25 base pairs, where the dsNA possesses greater potency than a 21mer siRNA directed to the identical at least 19 nucleotides of the target HAO1 mRNA in reducing target HAO1 mRNA expression when assayed in vitro in a mammalian cell at an effective concentration in the environment of a cell of 1 nanomolar or less.

In another embodiment, the dsNA of the invention has a duplex region of at least 25 base pairs, where the dsNA possesses greater potency than a 21 mer siRNA directed to the identical at least 19 nucleotides of the target HAO1 mRNA in reducing target HAO1 mRNA expression when assayed in vitro in a mammalian cell at a concentration of 1 nanomolar, 200 picomolar, 100 picomolar, 50 picomolar, 20 picomolar, 10 picomolar, 5 picomolar, 2, picomolar and 1 picomolar.

In an additional embodiment, the dsNA of the invention possesses four or fewer mismatched nucleic acid residues with respect to the target HAO1 mRNA sequence along 15 or 19 consecutive nucleotides of the at least 15 or 19 nucleotides of the second oligonucleotide strand when the 15 or 19 consecutive nucleotides of the second oligonucleotide are aligned for maximum complementarity with the target HAO1 mRNA sequence.

In another embodiment, the dsNA of the invention possesses three or fewer mismatched nucleic acid residues with respect to the target HAO1 mRNA sequence along 15 or 19 consecutive nucleotides of the at least 15 or 19 nucleotides of the second oligonucleotide strand when the 15 or 19 consecutive nucleotides of the second oligonucleotide are aligned for maximum complementarity with the target HAO1 mRNA sequence.

Optionally, the dsNA of the invention possesses two or fewer mismatched nucleic acid residues with respect to the target HAO1 mRNA sequence along 15 or 19 consecutive nucleotides of the at least 15 or 19 nucleotides of the second oligonucleotide strand when the 15 or 19 consecutive nucleotides of the second oligonucleotide are aligned for maximum complementarity with the target HAO1 mRNA sequence.

In certain embodiments, the dsNA of the invention possesses one mismatched nucleic acid residue with respect to the target HAO1 mRNA sequence along 15 or 19 consecutive nucleotides of the at least 15 or 19 nucleotides of the second oligonucleotide strand when the 15 or 19 consecutive nucleotides of the second oligonucleotide are aligned for maximum complementarity with the target HAO1 mRNA sequence.

In one embodiment, 15 or 19 consecutive nucleotides of the at least 15 or 19 nucleotides of the second oligonucleotide strand are completely complementary to the target HAO1 mRNA sequence when the 15 or 19 consecutive nucleotides of the second oligonucleotide are aligned for maximum complementarity with the target HAO1 mRNA sequence.

Optionally, a nucleic acid, dsNA or hybridization complex of the invention is isolated.

Another aspect of the invention provides a method for reducing expression of a target HAO1 gene in a mammalian cell involving contacting a mammalian cell in vitro with a nucleic acid, dsNA or hybridization complex of the invention in an amount sufficient to reduce expression of a target HAO1 mRNA in the cell.

Optionally, target HAO1 mRNA expression is reduced by an amount (expressed by %) of at least 10%, at least 50% and at least 80-90%.

In one embodiment, HAO1 mRNA levels are reduced by an amount (expressed by %) of at least 90% at least 8 days after the cell is contacted with the dsNA.

In another embodiment, HAO1 mRNA levels are reduced by an amount (expressed by %) of at least 70% at least 10 days after the cell is contacted with the dsNA.

A further aspect of the invention provides a method for reducing expression of a target HAO1 mRNA in a mammal possessing administering a nucleic acid, dsNA or hybridization complex of the invention to a mammal in an amount sufficient to reduce expression of a target HAO1 mRNA in the mammal.

In one embodiment, the nucleic acid, dsNA or hybridization complex is formulated in a lipid nanoparticle (LNP).

In another embodiment, the nucleic acid, dsNA or hybridization complex is administered at a dosage of 1 microgram to 5 milligrams per kilogram of the mammal per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, and 0.1 to 2.5 micrograms per kilogram.

In certain embodiments, the nucleic acid, dsNA or hybridization complex possesses greater potency than 21 mer siRNAs directed to the identical at least 19 nucleotides of the target HAO1 mRNA in reducing target HAO1 mRNA expression when assayed in vitro in a mammalian cell at an effective concentration in the environment of a cell of 1 nanomolar or less.

In one embodiment, HAO1 mRNA levels are reduced in a tissue of the mammal by an amount (expressed by %) of at least 70% at least 3 days after the dsNA is administered to the mammal.

Optionally, the tissue is liver tissue.

In certain embodiments, the administering step involves intravenous injection, intramuscular injection, intraperitoneal injection, infusion, subcutaneous injection, transdermal, aerosol, rectal, vaginal, topical, oral or inhaled delivery.

Another aspect of the invention provides a method for treating or preventing a disease or disorder in a subject that involves administering to the subject an amount of a nucleic acid, dsNA or hybridization complex of the invention in an amount sufficient to treat or prevent the disease or disorder in the subject.

In one embodiment, the disease or disorder is primary hyperoxaluria 1 (PH1).

Optionally, the subject is human.

A further aspect of the invention provides a formulation that includes the nucleic acid, dsNA or hybridization complex of the invention, where the nucleic acid, dsNA or hybridization complex is present in an amount effective to reduce target HAO1 mRNA levels when the nucleic acid, dsNA or hybridization complex is introduced into a mammalian cell in vitro by an amount (expressed by %) of at least 10%, at least 50% and at least 80-90%.

In one embodiment, the effective amount is of 1 nanomolar or less, 200 picomolar or less, 100 picomolar or less, 50 picomolar or less, 20 picomolar or less, 10 picomolar or less, 5 picomolar or less, 2, picomolar or less and 1 picomolar or less in the environment of the cell.

In another embodiment, the nucleic acid, dsNA or hybridization complex is present in an amount effective to reduce target HAO1 mRNA levels when the nucleic acid, dsNA or hybridization complex is introduced into a cell of a mammalian subject by an amount (expressed by %) of at least 10%, at least 50% and at least 80-90%.

Optionally, the effective amount is a dosage of 1 microgram to 5 milligrams per kilogram of the subject per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, or 0.1 to 2.5 micrograms per kilogram.

In another embodiment, the nucleic acid, dsNA or hybridization complex possesses greater potency than an 21mer siRNA directed to the identical at least 19 nucleotides of the target HAO1 mRNA in reducing target HAO1 mRNA levels when assayed in vitro in a mammalian cell at an effective concentration in the environment of a cell of 1 nanomolar or less.

A further aspect of the invention provides a mammalian cell containing the nucleic acid, dsNA or hybridization complex of the invention.

Another aspect of the invention provides a pharmaceutical composition that includes the nucleic acid, dsNA or hybridization complex of the invention and a pharmaceutically acceptable carrier.

An additional aspect of the invention provides a kit including the nucleic acid, dsNA or hybridization complex of the invention and instructions for its use.

A further aspect of the invention provides a composition possessing HAO1 inhibitory activity consisting essentially of a nucleic acid, dsNA or hybridization complex of the invention.

BRIEF DESCRIPTION OF THE DRAWINGS

FIGS. 3A and 3B) or mouse cells (Hepa1-6 cell assays; FIGS. 3C to 3F). In phase 2, DsiRNAs were tested at 1 nM and 0.1 nM (in duplicate) in the environment of HeLa cells or mouse Hepa1-6 cells. Individual bars represent average human (FIGS. 3A and 3B) or mouse (FIGS. 3C to 3F) Glycolate Oxidase levels observed in triplicate, with standard errors shown. Mouse Glycolate Oxidase levels were normalized to HPRT and Rp123 levels.

FIGS. 9A to 9L present modification pattern diagrams and histograms showing efficacy data for 24 independent HAO1-targeting DsiRNA sequences across indicated passenger (sense) and guide (antisense) strand 2'-O-methyl modification patterns (noting that modification patterns are recited as passenger strand modification pattern-guide strand modification pattern) in human HeLa cells (FIGS. 9E to 9H) or HEK293-pcDNA HAO1 Cells (FIGS. 9I to 9L), tested at 0.1 nM (duplicate assays) and 1 nM, employing either a PsiCheck-HsHAO1 plasmid reporter assay, monitoring for knockdown of Renilla luciferase production (FIGS. 9E to 9H), or HEK293 cells stably transfected with HAO1 (HEK293-pcDNA HAO1 Cells; FIGS. 9I to 9L).

FIGS. 11A to 11F present modification patterns and sequences of HAO1-1171, HAO1-1315, HAO1-1378 and HAO1-1501 DsiRNAs, and associated inhibitory efficacy results (histograms and $IC_{50}$ curves), when assayed in HEK293 cells stably transfected with HAO1 (HEK293-pcDNA HAO1 Cells), at 0.1 nM, 0.01 nM and 0.001 nM HAO1-targeting DsiRNA concentrations.

FIGS. 12A to 12F present modification patterns and sequences of extensively modified HAO1-1171 and HAO1-1376 DsiRNAs as indicated (FIGS. 12A to 12D), and associated inhibitory efficacy results (histograms of FIGS. 12E and 12F), when assayed in HEK293 cells stably transfected with HAO1 (HEK293-pcDNA HAO1 Cells), at 0.1 nM, 0.01 nM and 0.001 nM concentrations of HAO1-targeting DsiRNAs.

FIGS. 13A to 13L demonstrate the in vivo efficacy—including kinetics and duration of inhibition—of extensively modified forms of LNP-formulated HAO1-targeting duplexes, both in mice (FIGS. 13A to 13K) and in non-human primates (FIG. 13L).

DETAILED DESCRIPTION OF THE INVENTION

Figure 1:
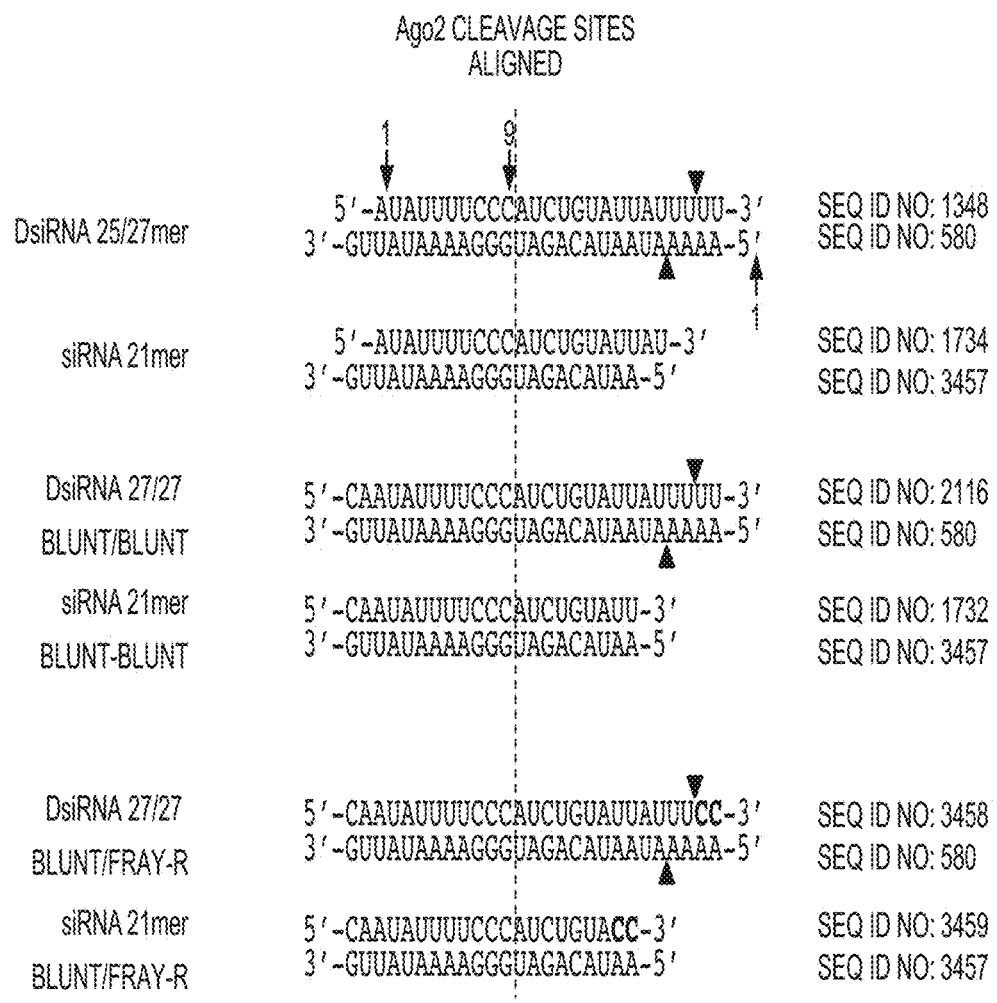
FIG. 1 shows the structures of exemplary DsiRNA agents of the invention targeting a site in the Glycolate Oxidase RNA referred to herein as the "HAO1-1171" target site. UPPER case=unmodified RNA, lower case=DNA, Bold=mismatch base pair nucleotides; arrowheads indicate projected Dicer enzyme cleavage sites; dashed line indicates sense strand (top strand) sequences corresponding to the projected Argonaute 2 (Ago2) cleavage site within the targeted Glycolate Oxidase sequence.
Figure 2A:
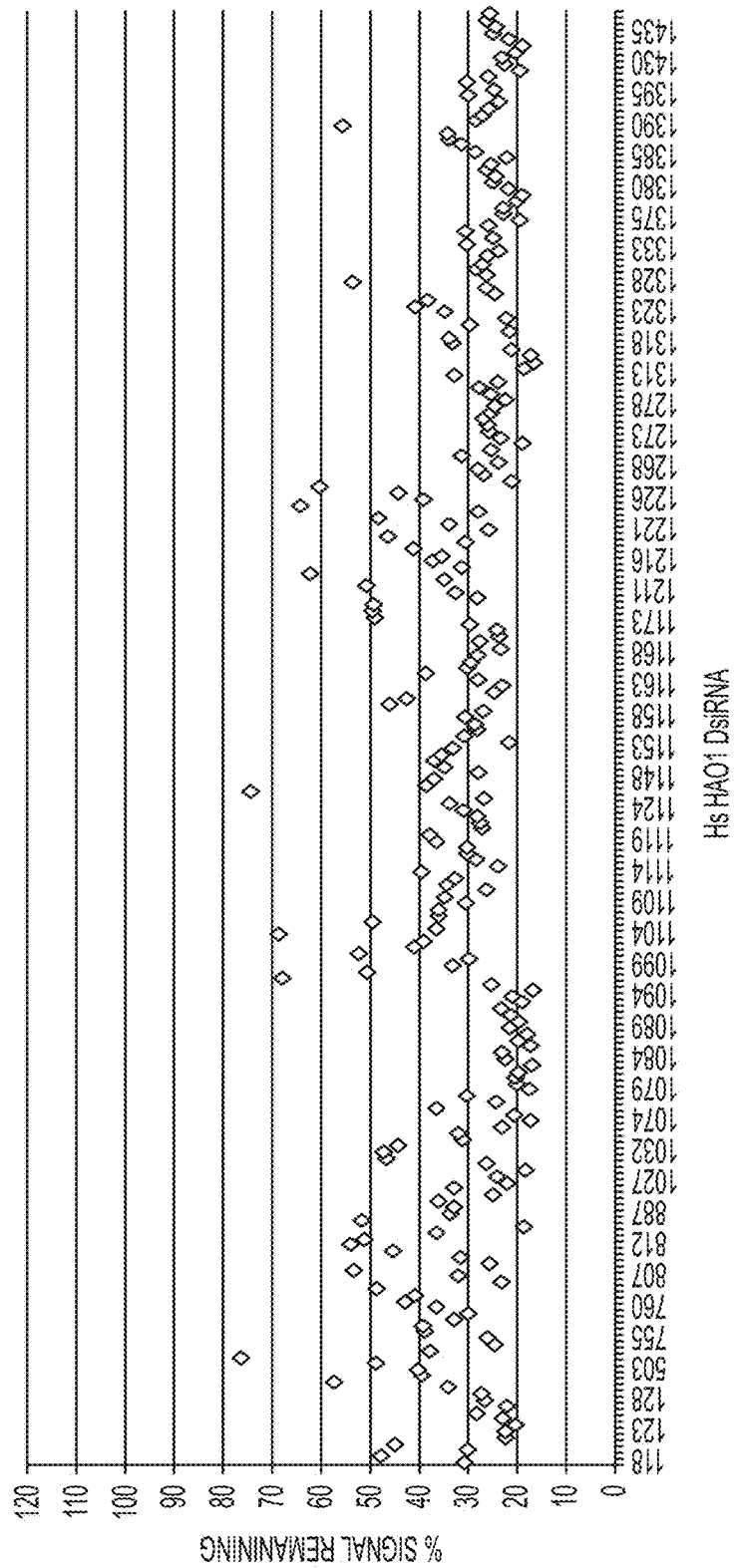
FIGS. 2A to 2F present primary screen data showing DsiRNA-mediated knockdown of human Glycolate Oxidase (FIGS. 2A and 2B show results for human-mouse common DsiRNAs, while FIGS. 2C and 2D show results for human unique DsiRNAs) and mouse Glycolate Oxidase (FIGS. 2C and 2D) in human (HeLa) and mouse (Hepa1-6) cells, respectively. Activity in human HeLa cells was assessed using a Psi-Check-HsHAO1 plasmid reporter assay, monitoring for knockdown of *Renilla* luciferase production. For each DsiRNA tested in mouse cells, two independent qPCR amplicons were assayed (amplicons "476-611" and "1775-1888").
Figure 2B:
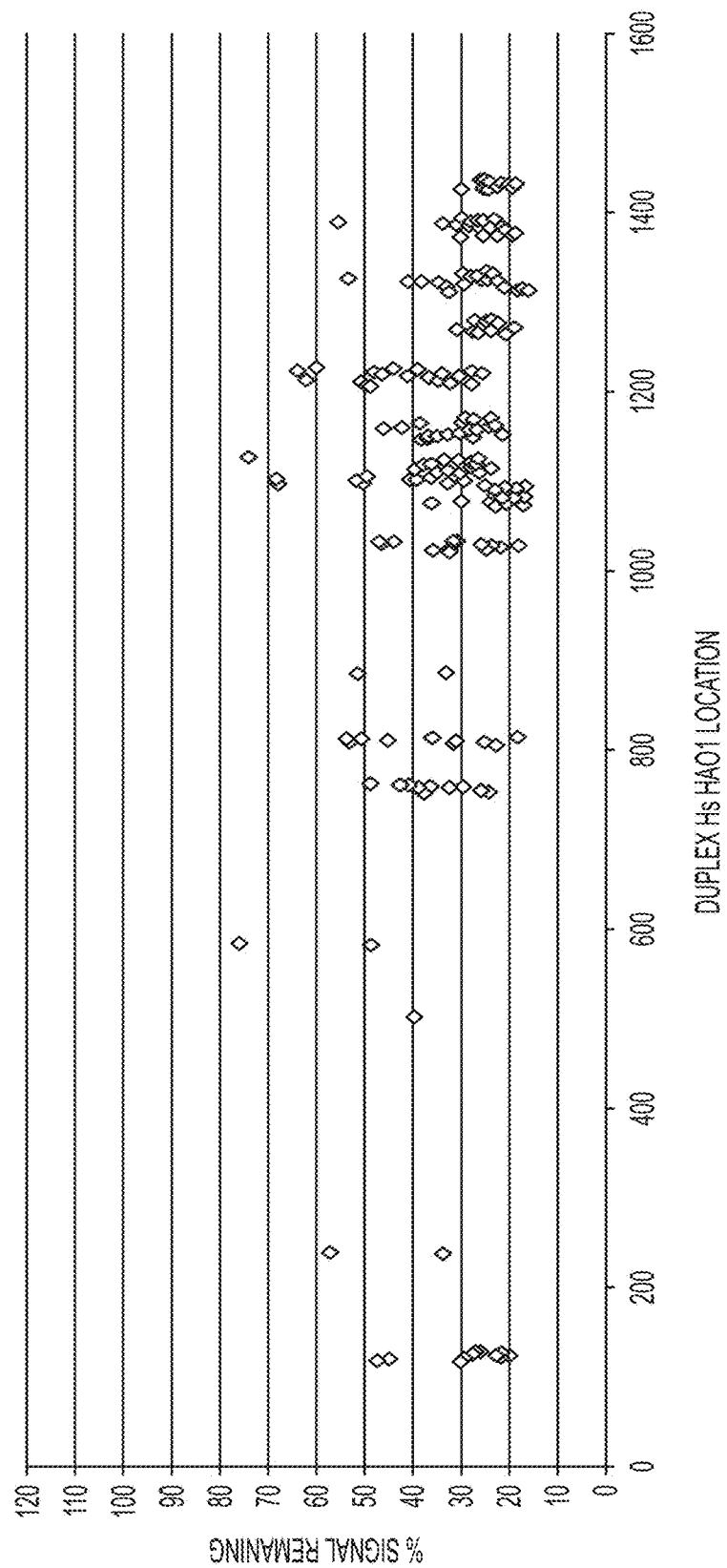
Figure 2C:
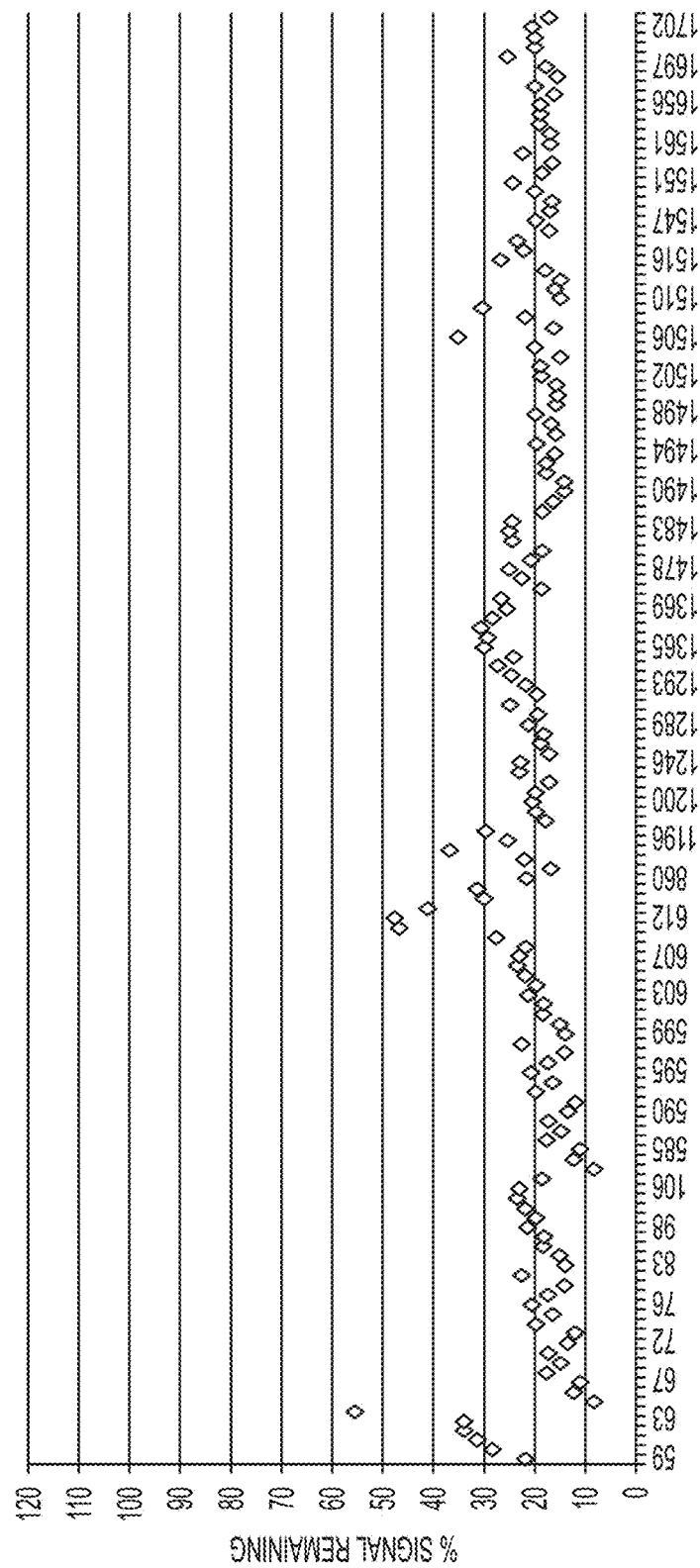
Figure 2D:
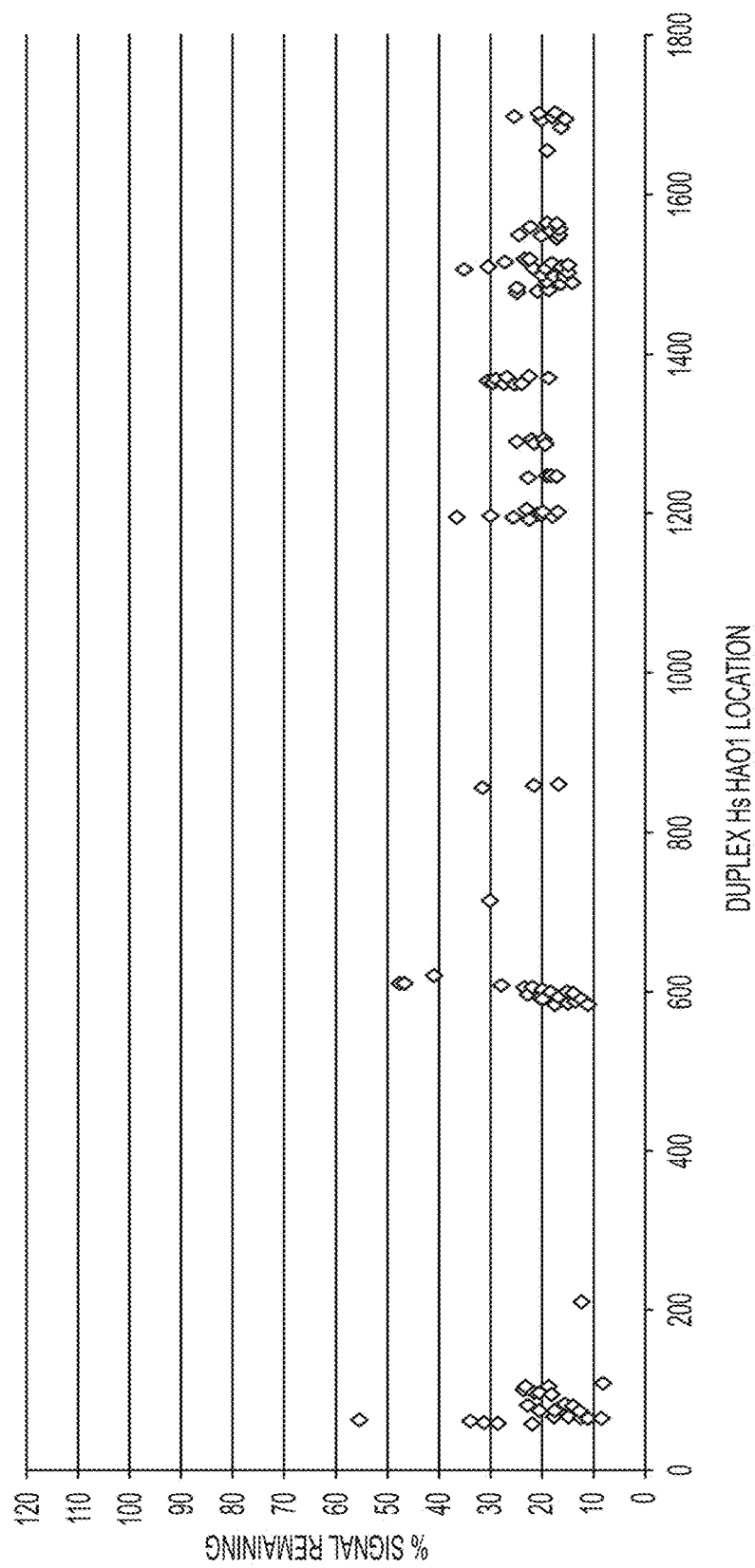
Figure 2E:
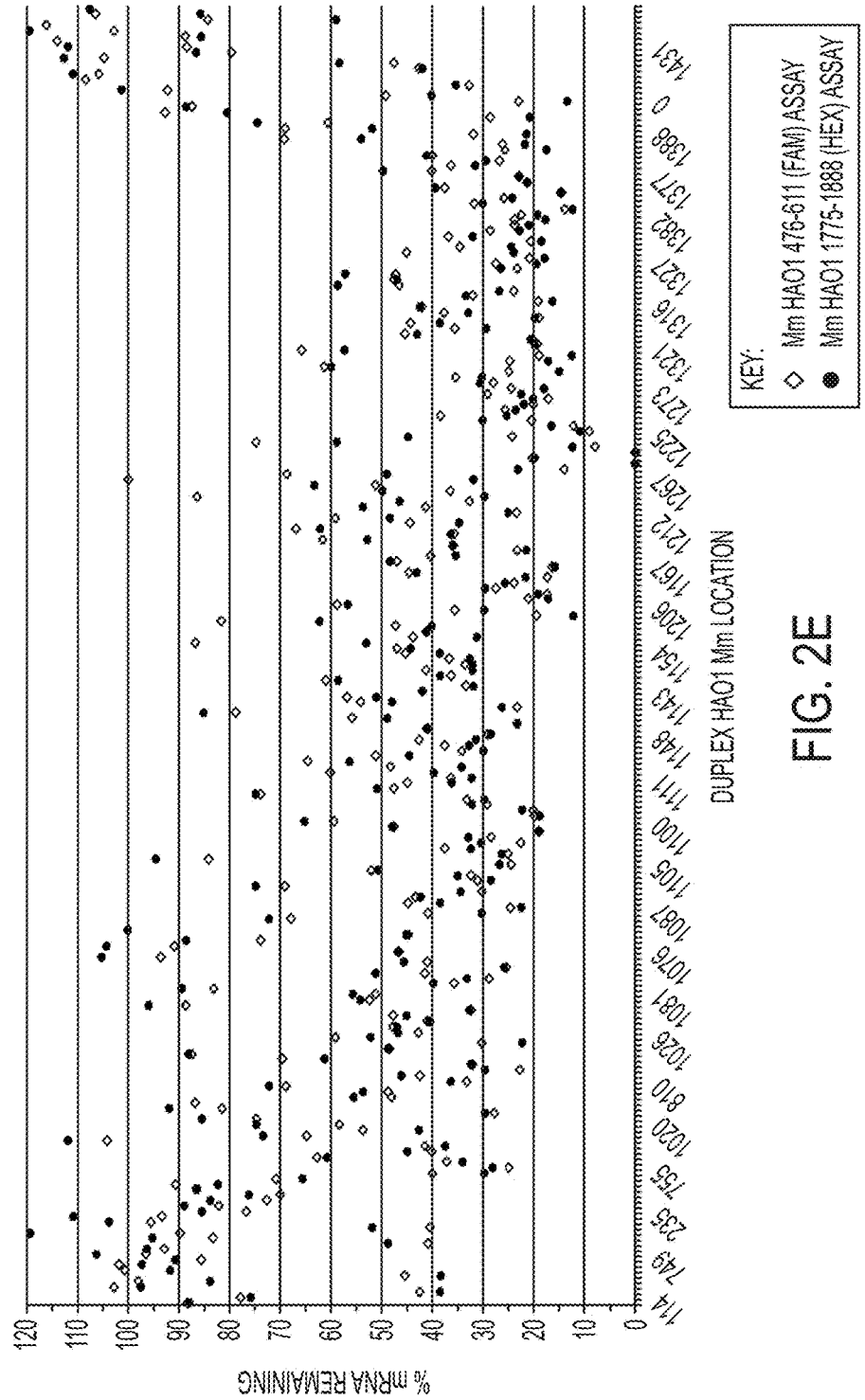
Figure 2F:
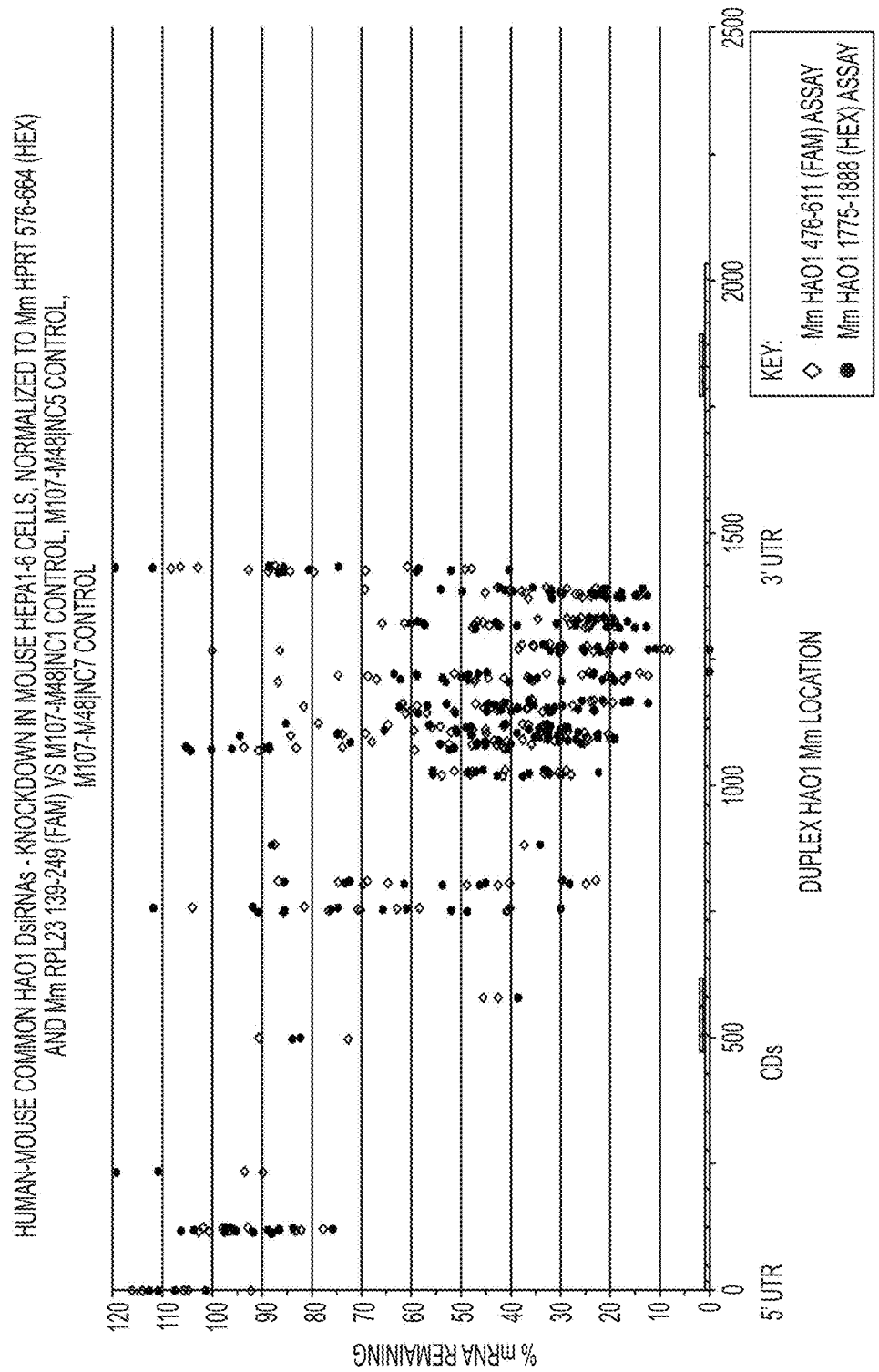

The present invention is directed to compositions that contain nucleic acids, for example double stranded RNA ("dsRNA"), and methods for preparing them, that are capable of reducing the level and/or expression of the Glycolate Oxidase (HAO1) gene in vivo or in vitro. One of the strands of the dsRNA contains a region of nucleotide sequence that has a length that ranges from 19 to 35 nucleotides that can direct the destruction and/or translational inhibition of the targeted HAO1 transcript.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988): The Glossary of Genetics, 5th Ed., R. Rieger et al. (eds.) Springer Verlag (1991); and Hale & Marham, The Harper Collins Dictionary of Biology (1991). As used herein, the following terms have the meanings ascribed to them below, unless specified otherwise.

The present invention features one or more DsiRNA molecules that can modulate (e.g., inhibit) Glycolate Oxidase expression. The DsiRNAs of the invention optionally can be used in combination with modulators of other genes and/or gene products associated with the maintenance or development of diseases or disorders associated with Glycolate Oxidase misregulation (e.g., primary hyperoxaluria 1 (PH1) or other disease or disorder of the liver, kidneys, etc.). The DsiRNA agents of the invention modulate Glycolate Oxidase (Hydroxyacid Oxidase 1, HAO1) RNAs such as those corresponding to the cDNA sequences referred to by GenBank Accession Nos. NM_017545.2 (human HAO1) and NM_010403.2 (mouse HAO1), which are referred to herein generally as "Glycolate Oxidase" or "Hydroxyacid Oxidase 1."

The below description of the various aspects and embodiments of the invention is provided with reference to exemplary Glycolate Oxidase RNAs, generally referred to herein as Glycolate Oxidase. However, such reference is meant to be exemplary only and the various aspects and embodiments of the invention are also directed to alternate Glycolate Oxidase RNAs, such as mutant Glycolate Oxidase RNAs or additional Glycolate Oxidase splice variants. Certain aspects and embodiments are also directed to other genes involved in Glycolate Oxidase pathways, including genes whose misregulation acts in association with that of Glycolate Oxidase (or is affected or affects Glycolate Oxidase regulation) to produce phenotypic effects that may be targeted for treatment (e.g., glyoxylate and/or oxalate overproduction). DAO and AGT are examples of genes that interact with Glycolate Oxidase. Such additional genes, including those of pathways that act in coordination with Glycolate Oxidase, can be targeted using dsRNA and the methods described herein for use of Glycolate Oxidase-targeting dsRNAs. Thus, the inhibition or and the effects of such inhibition, or up-regulation and the effects of such, of the other genes can be performed as described herein.

The term "Glycolate Oxidase" refers to nucleic acid sequences encoding a Glycolate Oxidase protein, peptide, or polypeptide (e.g., Glycolate Oxidase transcripts, such as the sequences of Glycolate Oxidase (HAO1) Genbank Accession Nos. NM_017545.2 and NM_010403.2). In certain embodiments, the term "Glycolate Oxidase" is also meant to include other Glycolate Oxidase encoding sequence, such as other Glycolate Oxidase isoforms, mutant Glycolate Oxidase genes, splice variants of Glycolate Oxidase genes, and Glycolate Oxidase gene polymorphisms. The term "Glycolate Oxidase" is also used to refer to the polypeptide gene product of an Glycolate Oxidase gene/transript, e.g., a Glycolate Oxidase protein, peptide, or polypeptide, such as those encoded by Glycolate Oxidase (HAO1) Genbank Accession Nos. NP_060015.1 and NP_034533.1.

As used herein, a "Glycolate Oxidase-associated disease or disorder" refers to a disease or disorder known in the art to be associated with altered Glycolate Oxidase expression, level and/or activity. Notably, a "Glycolate Oxidase-associated disease or disorder" or "HAO1-associated disease or disorder" includes diseases or disorders of the kidney, liver, skin, bone, eye and other organs including, but not limited to, primary hyperoxaluria (PH1).

In certain embodiments, dsRNA-mediated inhibition of a Glycolate Oxidase target sequence is assessed. In such embodiments, Glycolate Oxidase RNA levels can be assessed by art-recognized methods (e.g., RT-PCR, Northern blot, expression array, etc.), optionally via comparison of Glycolate Oxidase levels in the presence of an anti-Glycolate Oxidase dsRNA of the invention relative to the absence of such an anti-Glycolate Oxidase dsRNA. In certain embodiments, Glycolate Oxidase levels in the presence of an anti-Glycolate Oxidase dsRNA are compared to those observed in the presence of vehicle alone, in the presence of a dsRNA directed against an unrelated target RNA, or in the absence of any treatment.

It is also recognized that levels of Glycolate Oxidase protein can be assessed and that Glycolate Oxidase protein levels are, under different conditions, either directly or indirectly related to Glycolate Oxidase RNA levels and/or the extent to which a dsRNA inhibits Glycolate Oxidase expression, thus art-recognized methods of assessing Glycolate Oxidase protein levels (e.g., Western blot, immunoprecipitation, other antibody-based methods, etc.) can also be employed to examine the inhibitory effect of a dsRNA of the invention.

An anti-Glycolate Oxidase dsRNA of the invention is deemed to possess "Glycolate Oxidase inhibitory activity" if a statistically significant reduction in Glycolate Oxidase RNA (or when the Glycolate Oxidase protein is assessed, Glycolate Oxidase protein levels) is seen when an anti-Glycolate Oxidase dsRNA of the invention is administered to a system (e.g., cell-free in vitro system), cell, tissue or organism, as compared to a selected control. The distribution of experimental values and the number of replicate assays performed will tend to dictate the parameters of what levels of reduction in Glycolate Oxidase RNA (either as a % or in absolute terms) is deemed statistically significant (as assessed by standard methods of determining statistical significance known in the art). However, in certain embodiments, "Glycolate Oxidase inhibitory activity" is defined based upon a % or absolute level of reduction in the level of Glycolate Oxidase in a system, cell, tissue or organism. For example, in certain embodiments, a dsRNA of the invention is deemed to possess Glycolate Oxidase inhibitory activity if at least a 5% reduction or at least a 10% reduction in Glycolate Oxidase RNA is observed in the presence of a dsRNA of the invention relative to Glycolate Oxidase levels seen for a suitable control. (For example, in vivo Glycolate Oxidase levels in a tissue and/or subject can, in certain embodiments, be deemed to be inhibited by a dsRNA agent of the invention if, e.g., a 5% or 10% reduction in Glycolate Oxidase levels is observed relative to a control.) In certain other embodiments, a dsRNA of the invention is deemed to possess Glycolate Oxidase inhibitory activity if Glycolate Oxidase RNA levels are observed to be reduced by at least 15% relative to a selected control, by at least 20% relative to a selected control, by at least 25% relative to a selected control, by at least 30% relative to a selected control, by at least 35% relative to a selected control, by at least 40% relative to a selected control, by at least 45% relative to a selected control, by at least 50% relative to a selected control, by at least 55% relative to a selected control, by at least 60% relative to a selected control, by at least 65% relative to a selected control, by at least 70% relative to a selected control, by at least 75% relative to a selected control, by at least 80% relative to a selected control, by at least 85% relative to a selected control, by at least 90% relative to a selected control, by at least 95% relative to a selected control, by at least 96% relative to a selected control, by at least 97% relative to a selected control, by at least 98% relative to a selected control or by at least 99% relative to a selected control. In some embodiments, complete inhibition of Glycolate Oxidase is required for a dsRNA to be deemed to possess Glycolate Oxidase inhibitory activity. In certain models (e.g., cell culture), a dsRNA is deemed to possess Glycolate Oxidase inhibitory activity if at least a 50% reduction in Glycolate Oxidase levels is observed relative to a suitable control. In certain other embodiments, a dsRNA is deemed to possess Glycolate Oxidase inhibitory activity if at least an 80% reduction in Glycolate Oxidase levels is observed relative to a suitable control.

By way of specific example, in Example 2 below, a series of DsiRNAs targeting Glycolate Oxidase were tested for the ability to reduce Glycolate Oxidase mRNA levels in human HeLa or mouse Hepa1-6 cells in vitro, at 1 nM concentrations in the environment of such cells and in the presence of a transfection agent (Lipofectamine™ RNAiMAX, Invitrogen). Within Example 2 below, Glycolate Oxidase inhibitory activity was ascribed to those DsiRNAs that were observed to effect at least a 50% reduction of Glycolate Oxidase mRNA levels under the assayed conditions. It is contemplated that Glycolate Oxidase inhibitory activity could also be attributed to a dsRNA under either more or less stringent conditions than those employed for Example 2 below, even when the same or a similar assay and conditions are employed. For example, in certain embodiments, a tested dsRNA of the invention is deemed to possess Glycolate Oxidase inhibitory activity if at least a 10% reduction, at least a 20% reduction, at least a 30% reduction, at least a 40% reduction, at least a 50% reduction, at least a 60% reduction, at least a 70% reduction, at least a 75% reduction, at least an 80% reduction, at least an 85% reduction, at least a 90% reduction, or at least a 95% reduction in Glycolate Oxidase mRNA levels is observed in a mammalian cell line in vitro at 1 nM dsRNA concentration or lower in the environment of a cell, relative to a suitable control.

Use of other endpoints for determination of whether a double stranded RNA of the invention possesses Glycolate Oxidase inhibitory activity is also contemplated. Specifically, in one embodiment, in addition to or as an alternative to assessing Glycolate Oxidase mRNA levels, the ability of a tested dsRNA to reduce Glycolate Oxidase protein levels (e.g., at 48 hours after contacting a mammalian cell in vitro or in vivo) is assessed, and a tested dsRNA is deemed to possess Glycolate Oxidase inhibitory activity if at least a 10% reduction, at least a 20% reduction, at least a 30% reduction, at least a 40% reduction, at least a 50% reduction, at least a 60% reduction, at least a 70% reduction, at least a 75% reduction, at least an 80% reduction, at least an 85% reduction, at least a 90% reduction, or at least a 95% reduction in Glycolate Oxidase protein levels is observed in a mammalian cell contacted with the assayed double stranded RNA in vitro or in vivo, relative to a suitable control. Additional endpoints contemplated include, e.g., assessment of a phenotype associated with reduction of Glycolate Oxidase levels—e.g., reduction of phenotypes associated with elevated levels of glyoxylate-derived deposits (e.g., deposits of calcium oxalate) throughout the body.

Glycolate Oxidase inhibitory activity can also be evaluated over time (duration) and over concentration ranges (potency), with assessment of what constitutes a dsRNA possessing Glycolate Oxidase inhibitory activity adjusted in accordance with concentrations administered and duration of time following administration. Thus, in certain embodiments, a dsRNA of the invention is deemed to possess Glycolate Oxidase inhibitory activity if at least a 50% reduction in Glycolate Oxidase activity is observed/persists at a duration of time of 2 hours, 5 hours, 10 hours, 1 day, 2 days, 3 days, 4 days, 5 days, 6 days, 7 days, 8 days, 9 days, 10 days or more after administration of the dsRNA to a cell or organism. In additional embodiments, a dsRNA of the invention is deemed to be a potent Glycolate Oxidase inhibitory agent if Glycolate Oxidase inhibitory activity (e.g., in certain embodiments, at least 50% inhibition of Glycolate Oxidase) is observed at a concentration of 1 nM or less, 500 pM or less, 200 pM or less, 100 pM or less, 50 pM or less, 20 pM or less, 10 pM or less, 5 pM or less, 2 pM or less or even 1 pM or less in the environment of a cell, for example, within an in vitro assay for Glycolate Oxidase inhibitory activity as described herein. In certain embodiments, a potent Glycolate Oxidase inhibitory dsRNA of the invention is defined as one that is capable of Glycolate Oxidase inhibitory activity (e.g., in certain embodiments, at least 20% reduction of Glycolate Oxidase levels) at a formulated concentration of 10 mg/kg or less when administered to a subject in an effective delivery vehicle (e.g., an effective lipid nanoparticle formulation). Preferably, a potent Glycolate Oxidase inhibitory dsRNA of the invention is defined as one that is capable of Glycolate Oxidase inhibitory activity (e.g., in certain embodiments, at least 50% reduction of Glycolate Oxidase levels) at a formulated concentration of 5 mg/kg or less when administered to a subject in an effective delivery vehicle. More preferably, a potent Glycolate Oxidase inhibitory dsRNA of the invention is defined as one that is capable of Glycolate Oxidase inhibitory activity (e.g., in certain embodiments, at least 50% reduction of Glycolate Oxidase levels) at a formulated concentration of 5 mg/kg or less when administered to a subject in an effective delivery vehicle. Optionally, a potent Glycolate Oxidase inhibitory dsRNA of the invention is defined as one that is capable of Glycolate Oxidase inhibitory activity (e.g., in certain embodiments, at least 50% reduction of Glycolate Oxidase levels) at a formulated concentration of 2 mg/kg or less, or even 1 mg/kg or less, when administered to a subject in an effective delivery vehicle.

In certain embodiments, potency of a dsRNA of the invention is determined in reference to the number of copies of a dsRNA present in the cytoplasm of a target cell that are required to achieve a certain level of target gene knockdown. For example, in certain embodiments, a potent dsRNA is one capable of causing 50% or greater knockdown of a target mRNA when present in the cytoplasm of a target cell at a copy number of 1000 or fewer RISC-loaded antisense strands per cell. More preferably, a potent dsRNA is one capable of producing 50% or greater knockdown of a target mRNA when present in the cytoplasm of a target cell at a copy number of 500 or fewer RISC-loaded antisense strands per cell. Optionally, a potent dsRNA is one capable of producing 50% or greater knockdown of a target mRNA when present in the cytoplasm of a target cell at a copy number of 300 or fewer RISC-loaded antisense strands per cell.

In further embodiments, the potency of a DsiRNA of the invention can be defined in reference to a 19 to 23mer dsRNA directed to the same target sequence within the same target gene. For example, a DsiRNA of the invention that possesses enhanced potency relative to a corresponding 19 to 23mer dsRNA can be a DsiRNA that reduces a target gene by an additional 5% or more, an additional 10% or more, an additional 20% or more, an additional 30% or more, an additional 40% or more, or an additional 50% or more as compared to a corresponding 19 to 23mer dsRNA, when assayed in an in vitro assay as described herein at a sufficiently low concentration to allow for detection of a potency difference (e.g., transfection concentrations at or below 1 nM in the environment of a cell, at or below 100 pM in the environment of a cell, at or below 10 pM in the environment of a cell, at or below 1 nM in the environment of a cell, in an in vitro assay as described herein; notably, it is recognized that potency differences can be best detected via performance of such assays across a range of concentrations—e.g., 0.1 pM to 10 nM—for purpose of generating a dose-response curve and identifying an $IC_{50}$ value associated with a DsiRNA/dsRNA).

Glycolate Oxidase inhibitory levels and/or Glycolate Oxidase levels may also be assessed indirectly, e.g., measurement of a reduction of primary hyperoxaluria 1 phenotype(s) in a subject may be used to assess Glycolate Oxidase levels and/or Glycolate Oxidase inhibitory efficacy of a double-stranded nucleic acid of the instant invention.

In certain embodiments, the phrase "consists essentially of" is used in reference to the anti-Glycolate Oxidase dsRNAs of the invention. In some such embodiments, "consists essentially of" refers to a composition that comprises a dsRNA of the invention which possesses at least a certain level of Glycolate Oxidase inhibitory activity (e.g., at least 50% Glycolate Oxidase inhibitory activity) and that also comprises one or more additional components and/or modifications that do not significantly impact the Glycolate Oxidase inhibitory activity of the dsRNA. For example, in certain embodiments, a composition "consists essentially of" a dsRNA of the invention where modifications of the dsRNA of the invention and/or dsRNA-associated components of the composition do not alter the Glycolate Oxidase inhibitory activity (optionally including potency or duration of Glycolate Oxidase inhibitory activity) by greater than 3%, greater than 5%, greater than 10%, greater than 15%, greater than 20%, greater than 25%, greater than 30%, greater than 35%, greater than 40%, greater than 45%, or greater than 50% relative to the dsRNA of the invention in isolation. In certain embodiments, a composition is deemed to consist essentially of a dsRNA of the invention even if more dramatic reduction of Glycolate Oxidase inhibitory activity (e.g., 80% reduction, 90% reduction, etc. in efficacy, duration and/or potency) occurs in the presence of additional components or modifications, yet where Glycolate Oxidase inhibitory activity is not significantly elevated (e.g., observed levels of Glycolate Oxidase inhibitory activity are within 10% those observed for the isolated dsRNA of the invention) in the presence of additional components and/or modifications.

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs) and unlocked nucleic acids (UNAs; see, e.g., Jensen et al. *Nucleic Acids Symposium Series* 52: 133-4), and derivatives thereof.

As used herein, "nucleotide" is used as recognized in the art to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g., Usman and McSwiggen, supra; Eckstein, et al., International PCT Publication No. WO 92/07065; Usman et al, International PCT Publication No. WO 93/15187; Uhlman & Peyman, supra, all are hereby incorporated by reference herein). There are several examples of modified nucleic acid bases known in the art as summarized by Limbach, et al, *Nucleic Acids Res.* 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine and uracil at 1' position or their equivalents.

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-methoxyethoxy, 2'-fluoro, 2'-allyl, 2'-O-[2-(methylamino)-2-oxoethyl], 4'-thio, 4'-CH$_2$—O-2'-bridge, 4'-(CH$_2$)$_2$—O-2'-bridge, 2'-LNA or other bicyclic or "bridged" nucleoside analog, and 2'-O—(N-methylcarbamate) or those comprising base analogs. In connection with 2'-modified nucleotides as described for the present disclosure, by "amino" is meant 2'-NH$_2$ or 2'-O—NH$_2$, which can be modified or unmodified. Such modified groups are described. e.g., in Eckstein et al., U.S. Pat. No. 5,672,695 and Matulic-Adamic et al., U.S. Pat. No. 6,248,878. "Modified nucleotides" of the instant invention can also include nucleotide analogs as described above.

In reference to the nucleic acid molecules of the present disclosure, modifications may exist upon these agents in patterns on one or both strands of the double stranded ribonucleic acid (dsRNA). As used herein, "alternating positions" refers to a pattern where every other nucleotide is a modified nucleotide or there is an unmodified nucleotide (e.g., an unmodified ribonucleotide) between every modified nucleotide over a defined length of a strand of the dsRNA (e.g., 5'-MNMNMN-3'; 3'-MNMNMN-5'; where M is a modified nucleotide and N is an unmodified nucleotide). The modification pattern starts from the first nucleotide position at either the 5' or 3' terminus according to a position numbering convention, e.g., as described herein (in certain embodiments, position 1 is designated in reference to the terminal residue of a strand following a projected Dicer cleavage event of a DsiRNA agent of the invention; thus, position 1 does not always constitute a 3' terminal or 5' terminal residue of a pre-processed agent of the invention). The pattern of modified nucleotides at alternating positions may run the full length of the strand, but in certain embodiments includes at least 4, 6, 8, 10, 12, 14 nucleotides containing at least 2, 3, 4, 5, 6 or 7 modified nucleotides, respectively. As used herein, "alternating pairs of positions" refers to a pattern where two consecutive modified nucleotides are separated by two consecutive unmodified nucleotides over a defined length of a strand of the dsRNA (e.g., 5'-MMNNMMNNMMNN-3'; 3'-MMNNMMNNMMNN-5'; where M is a modified nucleotide and N is an unmodified nucleotide). The modification pattern starts from the first nucleotide position at either the 5' or 3' terminus according to a position numbering convention such as those described herein. The pattern of modified nucleotides at alternating positions may run the full length of the strand, but preferably includes at least 8, 12, 16, 20, 24, 28 nucleotides containing at least 4, 6, 8, 10, 12 or 14 modified nucleotides, respectively. It is emphasized that the above modification patterns are exemplary and are not intended as limitations on the scope of the invention.

As used herein, "base analog" refers to a heterocyclic moiety which is located at the 1' position of a nucleotide sugar moiety in a modified nucleotide that can be incorporated into a nucleic acid duplex (or the equivalent position in a nucleotide sugar moiety substitution that can be incorporated into a nucleic acid duplex). In the dsRNAs of the invention, a base analog is generally either a purine or pyrimidine base excluding the common bases guanine (G), cytosine (C), adenine (A), thymine (T), and uracil (U). Base analogs can duplex with other bases or base analogs in dsRNAs. Base analogs include those useful in the compounds and methods of the invention, e.g., those disclosed in U.S. Pat. Nos. 5,432,272 and 6,001,983 to Benner and US Patent Publication No. 20080213891 to Manoharan, which are herein incorporated by reference. Non-limiting examples of bases include hypoxanthine (I), xanthine (X), 3β-D-ribofuranosyl-(2,6-diaminopyrimidine) (K), 3-β-D-ribofuranosyl-(1-methyl-pyrazolo[4,3-d]pyrimidine-5,7(4H,6H)-dione) (P), iso-cytosine (iso-C), iso-guanine (iso-G), 1-β-D-ribofuranosyl-(5-nitroindole), 1-β-D-ribofuranosyl-(3-nitropyrrole), 5-bromouracil, 2-aminopurine, 4-thio-dT, 7-(2-thienyl)-imidazo[4,5-b]pyridine (Ds) and pyrrole-2-carbaldehyde (Pa), 2-amino-6-(2-thienyl)purine (S), 2-oxopyridine (Y), difluorotolyl, 4-fluoro-6-methylbenzimidazole, 4-methylbenzimidazole, 3-methyl isocarbostyrilyl, 5-methyl isocarbostyrilyl, and 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivates thereof (Schweitzer et al., J. Org. Chem., 59:7238-7242 (1994); Berger et al., Nucleic Acids Research, 28(15):2911-2914 (2000); Moran et al., J. Am. Chem. Soc., 119:2056-2057 (1997); Morales et al., J. Am. Chem. Soc., 121:2323-2324 (1999); Guckian et al., J. Am. Chem. Soc., 118:8182-8183 (1996); Morales et al., J. Am. Chem. Soc., 122(6):1001-1007 (2000); McMinn et al., J. Am. Chem. Soc., 121:11585-11586 (1999): Guckian et al., J. Org. Chem., 63:9652-9656 (1998); Moran et al., Proc. Natl. Acad. Sci., 94:10506-10511 (1997); Das et al., J. Chem. Soc., Perkin Trans., 1:197-206 (2002); Shibata et al., J. Chem. Soc., Perkin Trans., 1: 1605-1611 (2001); Wu et al., J. Am. Chem. Soc., 122(32):7621-7632 (2000); O'Neill et al., J. Org. Chem., 67:5869-5875 (2002); Chaudhuri et al., J. Am. Chem. Soc., 117:10434-10442 (1995); and U.S. Pat. No. 6,218,108.). Base analogs may also be a universal base.

As used herein, "universal base" refers to a heterocyclic moiety located at the 1' position of a nucleotide sugar moiety in a modified nucleotide, or the equivalent position in a nucleotide sugar moiety substitution, that, when present in a nucleic acid duplex, can be positioned opposite more than one type of base without altering the double helical structure (e.g., the structure of the phosphate backbone). Additionally, the universal base does not destroy the ability of the single stranded nucleic acid in which it resides to duplex to a target nucleic acid. The ability of a single stranded nucleic acid containing a universal base to duplex a target nucleic can be assayed by methods apparent to one in the art (e.g., UV absorbance, circular dichroism, gel shift, single stranded nuclease sensitivity, etc.). Additionally, conditions under which duplex formation is observed may be varied to determine duplex stability or formation, e.g., temperature, as melting temperature (Tm) correlates with the stability of nucleic acid duplexes. Compared to a reference single stranded nucleic acid that is exactly complementary to a target nucleic acid, the single stranded nucleic acid containing a universal base forms a duplex with the target nucleic acid that has a lower Tm than a duplex formed with the complementary nucleic acid. However, compared to a reference single stranded nucleic acid in which the universal base has been replaced with a base to generate a single mismatch, the single stranded nucleic acid containing the universal base forms a duplex with the target nucleic acid that has a higher Tm than a duplex formed with the nucleic acid having the mismatched base.

Some universal bases are capable of base pairing by forming hydrogen bonds between the universal base and all of the bases guanine (G), cytosine (C), adenine (A), thymine (T), and uracil (U) under base pair forming conditions. A universal base is not a base that forms a base pair with only one single complementary base. In a duplex, a universal base may form no hydrogen bonds, one hydrogen bond, or more than one hydrogen bond with each of G, C, A, T, and U opposite to it on the opposite strand of a duplex. Preferably, the universal bases does not interact with the base opposite to it on the opposite strand of a duplex. In a duplex, base pairing between a universal base occurs without altering the double helical structure of the phosphate backbone. A universal base may also interact with bases in adjacent nucleotides on the same nucleic acid strand by stacking interactions. Such stacking interactions stabilize the duplex, especially in situations where the universal base does not form any hydrogen bonds with the base positioned opposite to it on the opposite strand of the duplex. Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11:22(20):4039-43).

As used herein. "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length. Examples of loops include the unpaired nucleotides present in such structures as hairpins, stem loops, or extended loops.

As used herein, "extended loop" in the context of a dsRNA refers to a single stranded loop and in addition 1, 2, 3, 4, 5, 6 or up to 20 base pairs or duplexes flanking the loop. In an extended loop, nucleotides that flank the loop on the 5' side form a duplex with nucleotides that flank the loop on the 3' side. An extended loop may form a hairpin or stem loop.

As used herein. "tetraloop" in the context of a dsRNA refers to a loop (a single stranded region) consisting of four nucleotides that forms a stable secondary structure that contributes to the stability of adjacent Watson-Crick hybridized nucleotides. Without being limited to theory, a tetraloop may stabilize an adjacent Watson-Crick base pair by stacking interactions. In addition, interactions among the four nucleotides in a tetraloop include but are not limited to non-Watson-Crick base pairing, stacking interactions, hydrogen bonding, and contact interactions (Cheong et al., *Nature* 1990 Aug. 16; 346(6285):680-2; Heus and Pardi, *Science* 1991 July 12; 253(5016):191-4). A tetraloop confers an increase in the melting temperature (Tm) of an adjacent duplex that is higher than expected from a simple model loop sequence consisting of four random bases. For example, a tetraloop can confer a melting temperature of at least 55° C. in 10 mM $NaHPO_4$ to a hairpin comprising a duplex of at least 2 base pairs in length. A tetraloop may contain ribonucleotides, deoxyribonucleotides, modified nucleotides, and combinations thereof. Examples of RNA tetraloops include the UNCG family of tetraloops (e.g., UUCG), the GNRA family of tetraloops (e.g., GAAA), and the CUUG tetraloop. (Woese et al., Proc Natl Acad Sci USA. 1990 November; 87(21):8467-71; Antao et al., Nucleic Acids Res. 1991 Nov. 11:19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, the d(TNCG) family of tetraloops (e.g., d(TTCG)). (Nakano et al. Biochemistry, 41 (48), 14281-14292, 2002.; SHINJI et al. Nippon Kagakkai Koen Yokoshu VOL. 78th; NO. 2; PAGE. 731 (2000).)

As used herein, the term "siRNA" refers to a double stranded nucleic acid in which each strand comprises RNA, RNA analog(s) or RNA and DNA. The siRNA comprises between 19 and 23 nucleotides or comprises 21 nucleotides. The siRNA typically has 2 bp overhangs on the 3' ends of each strand such that the duplex region in the siRNA comprises 17-21 nucleotides, or 19 nucleotides. Typically, the antisense strand of the siRNA is sufficiently complementary with the target sequence of the Glycolate Oxidase gene/RNA.

In certain embodiments, an anti-Glycolate Oxidase DsiRNA of the instant invention possesses strand lengths of at least 25 nucleotides. Accordingly, in certain embodiments, an anti-Glycolate Oxidase DsiRNA contains one oligonucleotide sequence, a first sequence, that is at least 25 nucleotides in length and no longer than 35 or up to 50 or more nucleotides. This sequence of RNA can be between 26 and 35, 26 and 34, 26 and 33, 26 and 32, 26 and 31, 26 and 30, and 26 and 29 nucleotides in length. This sequence can be 27 or 28 nucleotides in length or 27 nucleotides in length. The second sequence of the DsiRNA agent can be a sequence that anneals to the first sequence under biological conditions, such as within the cytoplasm of a eukaryotic cell. Generally, the second oligonucleotide sequence will have at least 19 complementary base pairs with the first oligonucleotide sequence, more typically the second oligonucleotide sequence will have 21 or more complementary base pairs, or 25 or more complementary base pairs with the first oligonucleotide sequence. In one embodiment, the second sequence is the same length as the first sequence, and the DsiRNA agent is blunt ended. In another embodiment, the ends of the DsiRNA agent have one or more overhangs.

In certain embodiments, the first and second oligonucleotide sequences of the DsiRNA agent exist on separate oligonucleotide strands that can be and typically are chemically synthesized. In some embodiments, both strands are between 26 and 35 nucleotides in length. In other embodiments, both strands are between 25 and 30 or 26 and 30 nucleotides in length. In one embodiment, both strands are 27 nucleotides in length, are completely complementary and have blunt ends. In certain embodiments of the instant invention, the first and second sequences of an anti-Glycolate Oxidase DsiRNA exist on separate RNA oligonucleotides (strands). In one embodiment, one or both oligonucleotide strands are capable of serving as a substrate for Dicer. In other embodiments, at least one modification is present that promotes Dicer to bind to the double-stranded RNA structure in an orientation that maximizes the double-stranded RNA structure's effectiveness in inhibiting gene expression. In certain embodiments of the instant invention, the anti-Glycolate Oxidase DsiRNA agent is comprised of two oligonucleotide strands of differing lengths, with the anti-Glycolate Oxidase DsiRNA possessing a blunt end at the 3' terminus of a first strand (sense strand) and a 3' overhang at the 3' terminus of a second strand (antisense strand). The DsiRNA can also contain one or more deoxyribonucleic acid (DNA) base substitutions.

Suitable DsiRNA compositions that contain two separate oligonucleotides can be chemically linked outside their annealing region by chemical linking groups. Many suitable chemical linking groups are known in the art and can be used. Suitable groups will not block Dicer activity on the DsiRNA and will not interfere with the directed destruction of the RNA transcribed from the target gene. Alternatively, the two separate oligonucleotides can be linked by a third oligonucleotide such that a hairpin structure is produced upon annealing of the two oligonucleotides making up the DsiRNA composition. The hairpin structure will not block Dicer activity on the DsiRNA and will not interfere with the directed destruction of the target RNA.

The dsRNA molecule can be designed such that every residue of the antisense strand is complementary to a residue in the target molecule. Alternatively, substitutions can be made within the molecule to increase stability and/or enhance processing activity of said molecule. Substitutions can be made within the strand or can be made to residues at the ends of the strand. In certain embodiments, substitutions and/or modifications are made at specific residues within a DsiRNA agent. Such substitutions and/or modifications can include, e.g., deoxy-modifications at one or more residues of positions 1, 2 and 3 when numbering from the 3' terminal position of the sense strand of a DsiRNA agent; and introduction of 2'-O-alkyl (e.g., 2'-O-methyl) modifications at the 3' terminal residue of the antisense strand of DsiRNA agents, with such modifications also being performed at overhang positions of the 3' portion of the antisense strand and at alternating residues of the antisense strand of the DsiRNA that are included within the region of a DsiRNA agent that is processed to form an active siRNA agent. The preceding modifications are offered as exemplary, and are not intended to be limiting in any manner. Further consideration of the structure of preferred DsiRNA agents, including further description of the modifications and substitutions that can be performed upon the anti-Glycolate Oxidase DsiRNA agents of the instant invention, can be found below.

Where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where separate RNA molecules, such dsRNA are often referred to as siRNA ("short interfering RNA") or DsiRNA ("Dicer substrate siRNAs"). Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop", "short hairpin RNA" or "shRNA". Where the two strands are connected covalently by means other than an uninterrupted chain of nucleotides between the 3'-end of one strand and the 5'end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. In addition, as used herein, "dsRNA" may include chemical modifications to ribonucleotides, internucleoside linkages, end-groups, caps, and conjugated moieties, including substantial modifications at multiple nucleotides and including all types of modifications disclosed herein or known in the art. Any such modifications, as used in an siRNA- or DsiRNA-type molecule, are encompassed by "dsRNA" for the purposes of this specification and claims.

The phrase "duplex region" refers to the region in two complementary or substantially complementary oligonucleotides that form base pairs with one another, either by Watson-Crick base pairing or other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

Single-stranded nucleic acids that base pair over a number of bases are said to "hybridize." Hybridization is typically determined under physiological or biologically relevant conditions (e.g., intracellular: pH 7.2, 140 mM potassium ion; extracellular pH 7.4, 145 mM sodium ion). Hybridization conditions generally contain a monovalent cation and biologically acceptable buffer and may or may not contain a divalent cation, complex anions, e.g. gluconate from potassium gluconate, uncharged species such as sucrose, and inert polymers to reduce the activity of water in the sample, e.g. PEG. Such conditions include conditions under which base pairs can form.

Hybridization is measured by the temperature required to dissociate single stranded nucleic acids forming a duplex, i.e., (the melting temperature; Tm). Hybridization conditions are also conditions under which base pairs can form. Various conditions of stringency can be used to determine hybridization (see, e.g., Wahl, G. M. and S. L. Berger (1987) Methods Enzymol. 152:399; Kimmel, A. R. (1987) Methods Enzymol. 152:507). Stringent temperature conditions will ordinarily include temperatures of at least about 30° C., more preferably of at least about 37° C., and most preferably of at least about 42° C. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41 (% G+C)−(600/N), where N is the number of bases in the hybrid, and [Na+] is the concentration of sodium ions in the hybridization buffer ([Na+] for 1×SSC=0.165 M). For example, a hybridization determination buffer is shown in Table 1.

TABLE 1

| | final conc. | Vender | Cat# | Lot# | m.w./Stock | To make 50 mL solution |
|---|---|---|---|---|---|---|
| NaCl | 100 mM | Sigma | S-5150 | 41K8934 | 5M | 1 mL |
| KCl | 80 mM | Sigma | P-9541 | 70K0002 | 74.55 | 0.298 g |
| MgCl₂ | 8 mM | Sigma | M-1028 | 120K8933 | 1M | 0.4 g |
| sucrose | 2% w/v | Fisher | BP220-212 | 907105 | 342.3 | 1 g |
| Tris-HCl | 16 mM | Fisher | BP1757-500 | 12419 | 1M | 0.8 mL |
| NaH₂PO₄ | 1 mM | Sigma | S-3193 | 52H-029515 | 120.0 | 0.006 g |
| EDTA | 0.02 mM | Sigma | E-7879 | 110K89271 | 0.5M | 2 μL |
| H₂O | | Sigma | W-4502 | 51K2359 | | to 50 ml |
| pH = 7.0 at 20° C. | | | | adjust with HCl | | |

Useful variations on hybridization conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Antisense to Molecular Cloning Techniques, 1987, Academic Press, New York); and Sambrook et al., Molecular Cloning: A Laboratory Manual, Cold Spring Harbor Laboratory Press, New York.

As used herein, "oligonucleotide strand" is a single stranded nucleic acid molecule. An oligonucleotide may comprise ribonucleotides, deoxyribonucleotides, modified nucleotides (e.g., nucleotides with 2' modifications, synthetic base analogs, etc.) or combinations thereof. Such modified oligonucleotides can be preferred over native forms because of properties such as, for example, enhanced cellular uptake and increased stability in the presence of nucleases.

As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide. As used herein, the term "ribonucleotide" specifically excludes a deoxyribonucleotide, which is a nucleotide possessing a single proton group at the 2' ribose ring position.

As used herein, the term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide. As used herein, the term "deoxyribonucleotide" also includes a modified ribonucleotide that does not permit Dicer cleavage of a dsRNA agent, e.g., a 2'-O-methyl ribonucleotide, a phosphorothioate-modified ribonucleotide residue, etc., that does not permit Dicer cleavage to occur at a bond of such a residue.

As used herein, the term "PS-NA" refers to a phosphorothioate-modified nucleotide residue. The term "PS-NA" therefore encompasses both phosphorothioate-modified ribonucleotides ("PS-RNAs") and phosphorothioate-modified deoxyribonucleotides ("PS-DNAs").

As used herein, "Dicer" refers to an endoribonuclease in the RNase III family that cleaves a dsRNA or dsRNA-containing molecule, e.g., double-stranded RNA (dsRNA) or pre-microRNA (miRNA), into double-stranded nucleic acid fragments 19-25 nucleotides long, usually with a two-base overhang on the 3' end. With respect to certain dsRNAs of the invention (e.g., "DsiRNAs"), the duplex formed by a dsRNA region of an agent of the invention is recognized by Dicer and is a Dicer substrate on at least one strand of the duplex. Dicer catalyzes the first step in the RNA interference pathway, which consequently results in the degradation of a target RNA. The protein sequence of human Dicer is provided at the NCBI database under accession number NP_085124, hereby incorporated by reference.

Dicer "cleavage" can be determined as follows (e.g., see Collingwood et al., Oligonucleotides 18:187-200 (2008)). In a Dicer cleavage assay, RNA duplexes (100 pmol) are incubated in 20 µL of 20 mM Tris pH 8.0, 200 mM NaCl, 2.5 mM MgCl2 with or without 1 unit of recombinant human Dicer (Stratagene, La Jolla, Calif.) at 37° C. for 18-24 hours. Samples are desalted using a Performa SR 96-well plate (Edge Biosystems, Gaithersburg, Md.). Electrospray-ionization liquid chromatography mass spectroscopy (ESI-LCMS) of duplex RNAs pre- and post-treatment with Dicer is done using an Oligo HTCS system (Novatia, Princeton, N.J.; Hail et al., 2004), which consists of a ThermoFinnigan TSQ7000, Xcalibur data system, ProMass data processing software and Paradigm MS4 HPLC (Michrom BioResources, Auburn, Calif.). In this assay, Dicer cleavage occurs where at least 5%, 10%, 20%, 30%, 40%, 50%, 60%, 70%, 80%, 90%, 95%, or even 100% of the Dicer substrate dsRNA, (i.e., 25-30 bp, dsRNA, preferably 26-30 bp dsRNA) is cleaved to a shorter dsRNA (e.g., 19-23 bp dsRNA, preferably, 21-23 bp dsRNA).

As used herein. "Dicer cleavage site" refers to the sites at which Dicer cleaves a dsRNA (e.g., the dsRNA region of a DsiRNA agent of the invention). Dicer contains two RNase III domains which typically cleave both the sense and antisense strands of a dsRNA. The average distance between the RNase III domains and the PAZ domain determines the length of the short double-stranded nucleic acid fragments it produces and this distance can vary (Macrae et al. (2006) Science 311: 195-8). As shown in FIG. 1, Dicer is projected to cleave certain double-stranded ribonucleic acids of the instant invention that possess an antisense strand having a 2 nucleotide 3' overhang at a site between the $21^{st}$ and $22^{nd}$ nucleotides removed from the 3' terminus of the antisense strand, and at a corresponding site between the $21^{st}$ and $22^{nd}$ nucleotides removed from the 5' terminus of the sense strand. The projected and/or prevalent Dicer cleavage site(s) for dsRNA molecules distinct from those depicted in FIG. 1 may be similarly identified via art-recognized methods, including those described in Macrae et al. While the Dicer cleavage events depicted in FIG. 1 generate 21 nucleotide siRNAs, it is noted that Dicer cleavage of a dsRNA (e.g., DsiRNA) can result in generation of Dicer-processed siRNA lengths of 19 to 23 nucleotides in length. Indeed, in certain embodiments, a double-stranded DNA region may be included within a dsRNA for purpose of directing prevalent Dicer excision of a typically non-preferred 19mer or 20mer siRNA, rather than a 21 mer.

As used herein, "overhang" refers to unpaired nucleotides, in the context of a duplex having one or more free ends at the 5' terminus or 3' terminus of a dsRNA. In certain embodiments, the overhang is a 3' or 5' overhang on the antisense strand or sense strand. In some embodiments, the overhang is a 3' overhang having a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. "Blunt" or "blunt end" means that there are no unpaired nucleotides at that end of the dsRNA, i.e., no nucleotide overhang. For clarity, chemical caps or non-nucleotide chemical moieties conjugated to the 3' end or 5' end of an siRNA are not considered in determining whether an siRNA has an overhang or is blunt ended. In certain embodiments, the invention provides a dsRNA molecule for inhibiting the expression of the Glycolate Oxidase target gene in a cell or mammal, wherein the dsRNA comprises an antisense strand comprising a region of complementarity which is complementary to at least a part of an mRNA formed in the expression of the Glycolate Oxidase target gene, and wherein the region of complementarity is less than 35 nucleotides in length, optionally 19-24 nucleotides in length or 25-30 nucleotides in length, and wherein the dsRNA, upon contact with a cell expressing the Glycolate Oxidase target gene, inhibits the expression of the Glycolate Oxidase target gene by at least 10%, 25%, or 40%.

A dsRNA of the invention comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of the Glycolate Oxidase target gene, the other strand (the sense strand) comprises a region which is complementary to the antisense strand, such that the two strands hybridize and form a duplex structure when combined under suitable conditions. Generally, the duplex structure is between 15 and 80, or between 15 and 53, or between 15 and 35, optionally between 25 and 30, between 26 and 30, between 18 and 25, between 19 and 24, or between 19 and 21 base pairs in length. Similarly, the region of complementarity to the target sequence is between 15 and 35, optionally between 18 and 30, between 25 and 30, between 19 and 24, or between 19 and 21 nucleotides in length. The dsRNA of the invention may further comprise one or more single-stranded nucleotide overhang(s). It has been identified that dsRNAs comprising duplex structures of between 15 and 35 base pairs in length can be effective in inducing RNA interference, including DsiRNAs (generally of at least 25 base pairs in length) and siRNAs (in certain embodiments, duplex structures of siRNAs are between 20 and 23, and optionally, specifically 21 base pairs (Elbashir et al., *EMBO* 20: 6877-6888)). It has also been identified that dsRNAs possessing duplexes shorter than 20 base pairs can be effective as well (e.g., 15, 16, 17, 18 or 19 base pair duplexes). In certain embodiments, the dsRNAs of the invention can comprise at least one strand of a length of 19 nucleotides or more. In certain embodiments, it can be reasonably expected that shorter dsRNAs comprising a sequence complementary to one of the sequences of Tables 4, 6, 8 or 10, minus only a few nucleotides on one or both ends may be similarly effective as compared to the dsRNAs described above and in Tables 2, 3, 5, 7 and 9. Hence, dsRNAs comprising a partial sequence of at least 15, 16, 17, 18, 19, 20, or more contiguous nucleotides sufficiently complementary to one of the sequences of Tables 4, 6, 8 or 10, and differing in their ability to inhibit the expression of the Glycolate Oxidase target gene in an assay as described herein by not more than 5, 10, 15, 20, 25, or 30% inhibition from a dsRNA comprising the full sequence, are contemplated by the invention. In one embodiment, at least one end of the dsRNA has a single-stranded nucleotide overhang of 1 to 5, optionally 1 to 4, in certain embodiments, 1 or 2 nucleotides. Certain dsRNA structures having at least one nucleotide overhang possess superior inhibitory properties as compared to counterparts possessing base-paired blunt ends at both ends of the dsRNA molecule.

As used herein, the term "RNA processing" refers to processing activities performed by components of the siRNA, miRNA or RNase H pathways (e.g., Drosha, Dicer, Argonaute2 or other RISC endoribonucleases, and RNaseH), which are described in greater detail below (see "RNA Processing" section below). The term is explicitly distinguished from the post-transcriptional processes of 5' capping of RNA and degradation of RNA via non-RISC- or non-RNase H-mediated processes. Such "degradation" of an RNA can take several forms, e.g. deadenylation (removal of a 3' poly(A) tail), and/or nuclease digestion of part or all of the body of the RNA by one or more of several endo- or exo-nucleases (e.g., RNase III, RNase P, RNase T1, RNase A (1, 2, 3, 4/5), oligonucleotidase, etc.).

By "homologous sequence" is meant a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., 99%, 98%, 97%, 96%, 95%, 94%, 93%, 92%, 91%, 90%, 89%, 88%, 87%, 86%, 85%, 84%, 83%, 82%, 81%, 80% etc.). Indeed, design and use of the dsRNA agents of the instant invention contemplates the possibility of using such dsRNA agents not only against target RNAs of Glycolate Oxidase possessing perfect complementarity with the presently described dsRNA agents, but also against target Glycolate Oxidase RNAs possessing sequences that are, e.g., only 99%, 98%, 97%, 96%, 95%, 94%, 93%, 92%, 91%, 90%, 89%, 88%, 87%, 86%, 85%, 84%, 83%, 82%, 81%, 80% etc. complementary to said dsRNA agents. Similarly, it is contemplated that the presently described dsRNA agents of the instant invention might be readily altered by the skilled artisan to enhance the extent of complementarity between said dsRNA agents and a target Glycolate Oxidase RNA, e.g., of a specific allelic variant of Glycolate Oxidase (e.g., an allele of enhanced therapeutic interest). Indeed, dsRNA agent sequences with insertions, deletions, and single point mutations relative to the target Glycolate Oxidase sequence can also be effective for inhibition. Alternatively, dsRNA agent sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul. et al. (1990) *J. Mol. Biol.* 215:403-10.

In another embodiment, a gapped alignment, the alignment is optimized by introducing appropriate gaps, and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, a global alignment the alignment is optimized by introducing appropriate gaps, and percent identity is determined over the entire length of the sequences aligned. (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the dsRNA antisense strand and the portion of the Glycolate Oxidase RNA sequence is preferred. Alternatively, the dsRNA may be defined functionally as a nucleotide sequence (or oligonucleotide sequence) that is capable of hybridizing with a portion of the Glycolate Oxidase RNA (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41 (% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4. The length of the identical nucleotide sequences may be at least 10, 12, 15, 17, 20, 22, 25, 27 or 30 bases.

By "conserved sequence region" is meant, a nucleotide sequence of one or more regions in a polynucleotide does not vary significantly between generations or from one biological system, subject, or organism to another biological system, subject, or organism. The polynucleotide can include both coding and non-coding DNA and RNA.

By "sense region" is meant a nucleotide sequence of a dsRNA molecule having complementarity to an antisense region of the dsRNA molecule. In addition, the sense region of a dsRNA molecule can comprise a nucleic acid sequence having homology with a target nucleic acid sequence.

By "antisense region" is meant a nucleotide sequence of a dsRNA molecule having complementarity to a target nucleic acid sequence. In addition, the antisense region of a dsRNA molecule comprises a nucleic acid sequence having complementarity to a sense region of the dsRNA molecule.

As used herein, "antisense strand" refers to a single stranded nucleic acid molecule which has a sequence complementary to that of a target RNA. When the antisense strand contains modified nucleotides with base analogs, it is not necessarily complementary over its entire length, but must at least hybridize with a target RNA.

As used herein, "sense strand" refers to a single stranded nucleic acid molecule which has a sequence complementary to that of an antisense strand. When the antisense strand contains modified nucleotides with base analogs, the sense strand need not be complementary over the entire length of the antisense strand, but must at least duplex with the antisense strand.

As used herein, "guide strand" refers to a single stranded nucleic acid molecule of a dsRNA or dsRNA-containing molecule, which has a sequence sufficiently complementary to that of a target RNA to result in RNA interference. After cleavage of the dsRNA or dsRNA-containing molecule by Dicer, a fragment of the guide strand remains associated with RISC, binds a target RNA as a component of the RISC complex, and promotes cleavage of a target RNA by RISC.

As used herein, the guide strand does not necessarily refer to a continuous single stranded nucleic acid and may comprise a discontinuity, preferably at a site that is cleaved by Dicer. A guide strand is an antisense strand.

As used herein, "passenger strand" refers to an oligonucleotide strand of a dsRNA or dsRNA-containing molecule, which has a sequence that is complementary to that of the guide strand. As used herein, the passenger strand does not necessarily refer to a continuous single stranded nucleic acid and may comprise a discontinuity, preferably at a site that is cleaved by Dicer. A passenger strand is a sense strand.

By "target nucleic acid" is meant a nucleic acid sequence whose expression, level or activity is to be modulated. The target nucleic acid can be DNA or RNA. For agents that target Glycolate Oxidase, in certain embodiments, the target nucleic acid is Glycolate Oxidase (HAO1) RNA, e.g., in certain embodiments, Glycolate Oxidase (HAO1) mRNA. Glycolate Oxidase RNA target sites can also interchangeably be referenced by corresponding cDNA sequences. Levels of Glycolate Oxidase may also be targeted via targeting of upstream effectors of Glycolate Oxidase, or the effects of modulated or misregulated Glycolate Oxidase may also be modulated by targeting of molecules downstream of Glycolate Oxidase in the Glycolate Oxidase signalling pathway.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence. In one embodiment, a dsRNA molecule of the invention comprises 19 to 30 (e.g., 19, 20, 21, 22, 23, 24, 25, 26, 27, 28, 29, or 30 or more) nucleotides that are complementary to one or more target nucleic acid molecules or a portion thereof.

As used herein, a dsNA. e.g., DsiRNA or siRNA, having a sequence "sufficiently complementary" to a target RNA or cDNA sequence (e.g., glycolate oxidase (HAO1) mRNA) means that the dsNA has a sequence sufficient to trigger the destruction of the target RNA (where a cDNA sequence is recited, the RNA sequence corresponding to the recited cDNA sequence) by the RNAi machinery (e.g., the RISC complex) or process. For example, a dsNA that is "sufficiently complementary" to a target RNA or cDNA sequence to trigger the destruction of the target RNA by the RNAi machinery or process can be identified as a dsNA that causes a detectable reduction in the level of the target RNA in an appropriate assay of dsNA activity (e.g., an in vitro assay as described in Example 2 below), or, in further examples, a dsNA that is sufficiently complementary to a target RNA or cDNA sequence to trigger the destruction of the target RNA by the RNAi machinery or process can be identified as a dsNA that produces at least a 5%, at least a 10%, at least a 15%, at least a 20%, at least a 25%, at least a 30%, at least a 35%, at least a 40%, at least a 45%, at least a 50%, at least a 55%, at least a 60%, at least a 65%, at least a 70%, at least a 75%, at least a 80%, at least a 85%, at least a 90%, at least a 95%, at least a 98% or at least a 99% reduction in the level of the target RNA in an appropriate assay of dsNA activity. In additional examples, a dsNA that is sufficiently complementary to a target RNA or cDNA sequence to trigger the destruction of the target RNA by the RNAi machinery or process can be identified based upon assessment of the duration of a certain level of inhibitory activity with respect to the target RNA or protein levels in a cell or organism. For example, a dsNA that is sufficiently complementary to a target RNA or cDNA sequence to trigger the destruction of the target RNA by the RNAi machinery or process can be identified as a dsNA capable of reducing target mRNA levels by at least 20% at least 48 hours post-administration of said dsNA to a cell or organism. Preferably, a dsNA that is sufficiently complementary to a target RNA or cDNA sequence to trigger the destruction of the target RNA by the RNAi machinery or process is identified as a dsNA capable of reducing target mRNA levels by at least 40% at least 72 hours post-administration of said dsNA to a cell or organism, by at least 40% at least four, five or seven days post-administration of said dsNA to a cell or organism, by at least 50% at least 48 hours post-administration of said dsNA to a cell or organism, by at least 50% at least 72 hours post-administration of said dsNA to a cell or organism, by at least 50% at least four, five or seven days post-administration of said dsNA to a cell or organism, by at least 80% at least 48 hours post-administration of said dsNA to a cell or organism, by at least 80% at least 72 hours post-administration of said dsNA to a cell or organism, or by at least 80% at least four, five or seven days post-administration of said dsNA to a cell or organism.

In certain embodiments, a nucleic acid of the invention (e.g., a DsiRNA or siRNA) possesses a sequence "sufficiently complementary to hybridize" to a target RNA or cDNA sequence, thereby achieving an inhibitory effect upon the target RNA. Hybridization, and conditions available for determining whether one nucleic acid is sufficiently complementary to another nucleic acid to allow the two sequences to hybridize, is described in greater detail below.

As will be clear to one of ordinary skill in the art, "sufficiently complementary" (contrasted with, e.g., "100% complementary") allows for one or more mismatches to exist between a dsNA of the invention and the target RNA or cDNA sequence (e.g., glycolate oxidase (HAO1) mRNA), provided that the dsNA possesses complementarity sufficient to trigger the destruction of the target RNA by the RNAi machinery (e.g., the RISC complex) or process. In certain embodiments, a "sufficiently complementary" dsNA of the invention can harbor one, two, three or even four or more mismatches between the dsNA sequence and the target RNA or cDNA sequence (e.g., in certain such embodiments, the antisense strand of the dsRNA harbors one, two, three, four, five or even six or more mismatches when aligned with the target RNA or cDNA sequence for maximum complementarity). Additional consideration of the preferred location of such mismatches within certain dsRNAs of the instant invention is considered in greater detail below.

In one embodiment, dsRNA molecules of the invention that down regulate or reduce Glycolate Oxidase gene expression are used for treating, preventing or reducing Glycolate Oxidase-related diseases or disorders (e.g., PH1) in a subject or organism.

In one embodiment of the present invention, each sequence of a DsiRNA molecule of the invention is independently 25 to 35 nucleotides in length, in specific embodiments 25, 26, 27, 28, 29, 30, 31, 32, 33, 34 or 35 nucleotides in length. In another embodiment, the DsiRNA duplexes of the invention independently comprise 25 to 30 base pairs (e.g., 25, 26, 27, 28, 29, or 30). In another embodiment, one or more strands of the DsiRNA molecule of the invention independently comprises 19 to 35 nucleotides (e.g., 19, 20, 21, 22, 23, 24, 25, 26, 27, 28, 29, 30, 31, 32, 33, 34 or 35) that are complementary to a target (Glycolate Oxidase) nucleic acid molecule. In certain embodiments, a DsiRNA molecule of the invention possesses a length of duplexed nucleotides between 25 and 66 nucleotides, optionally between 25 and 49 nucleotides in length (e.g., 25, 26, 27, 28, 29, 30, 31, 32, 33, 34, 35, 36, 37, 38, 39, 40, 41, 42, 43, 44, 45, 46, 47, 48 or 49, 50, 51, 52, 53, 54, 55, 56, 57, 58, 59, 60, 61, 62, 63, 64, 65, 66 nucleotides in length; optionally, all such nucleotides base pair with cognate nucleotides of the opposite strand). In related embodiments, a dsNA of the invention possesses strand lengths that are, independently, between 19 and 66 nucleotides in length, optionally between 25 and 53 nucleotides in length, e.g., 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49, 50, 51, 52, 53, 54, 55, 56, 57, 58, 59, 60, 61, 62, 63, 64, 65, 66 nucleotides in length. In certain embodiments, one strand length is 19-35 nucleotides in length, while the other strand length is 30-66 nucleotides in length and at least one strand has a 5' overhang of at least 5 nucleotides in length relative to the other strand. In certain related embodiments, the 3' end of the first strand and the 5' end of the second strand form a structure that is a blunt end or a 1-6 nucleotide 3' overhang, while the 5' end of the first strand forms a 5-35 nucleotide overhang with respect to the 3' end of the second strand. Optionally, between one and all nucleotides of the 5-35 nucleotide overhang are modified nucleotides (optionally, deoxyribonucleotides and/or modified ribonucleotides).

In some embodiments, a dsNA of the invention has a first or second strand that has at least 8 contiguous ribonucleotides. In certain embodiments, a dsNA of the invention has 9, 10, 11, 12, 13, 14, 15, 16, 17, 18, 19, 20, 21, 22, 23 or more (e.g., 24, 25, 26, 27, 28, 29, 30, 31, 32, 33, 34, 35, 26, or more, up to the full length of the strand) ribonucleotides, optionally including modified ribonucleotides (2'-O-methyl ribonucleotides, phosphorothioate linkages, etc.). In certain embodiments, the ribonucleotides or modified ribonucleotides are contiguous.

In certain embodiments of the invention, tetraloop- and modified nucleotide-containing dsNAs are contemplated as described, e.g., in US 2011/0288147. In certain such embodiments, a dsNA of the invention possesses a first strand and a second strand, where the first strand and the second strand form a duplex region of 19-25 nucleotides in length, wherein the first strand comprises a 3' region that extends beyond the first strand-second strand duplex region and comprises a tetraloop, and the dsNA comprises a discontinuity between the 3' terminus of the first strand and the 5' terminus of the second strand. Optionally, the discontinuity is positioned at a projected dicer cleavage site of the tetraloop-containing dsNA. It is contemplated that, as for any of the other duplexed oligonucleotides of the invention, tetraloop-containing duplexes of the invention can possess any range of modifications disclosed herein or otherwise known in the art, including, e.g., 2'-O-methyl, 2'-fluoro, inverter basic, GalNAc moieties, etc.

In certain embodiments, a dsNA comprising a first strand and a second strand, each strand, independently, having a 5' terminus and a 3' terminus, and having, independently, respective strand lengths of 25-53 nucleotides in length, is sufficiently highly modified (e.g., at least 10% or more, at least 20% or more, at least 30% or more, at least 40% or more, at least 50% or more, at least 60% or more, at least 70% or more, at least 80% or more, at least 90% or more, at least 95% or more residues of one and/or both strands are modified such that dicer cleavage of the dsNA is prevented (optionally, modified residues occur at and/or flanking one or all predicted dicer cleavage sites of the dsNA). Such non-dicer-cleaved dsNAs retain glycolate oxidase (HAO1) inhibition activity and are optionally cleaved by non-dicer nucleases to yield, e.g., 15-30, or in particular embodiments, 19-23 nucleotide strand length dsNAs capable of inhibiting glycolate oxidase (HAO1) in a mammalian cell. In certain related embodiments, dsNAs possessing sufficiently extensive modification to block dicer cleavage of such dsNAs optionally possess regions of unmodified nucleotide residues (e.g., one or two or more consecutive nucleotides, forming a "gap" or "window" in a modification pattern) that allow for and/or promote cleavage of such dsNAs by non-Dicer nucleases. In other embodiments, Dicer-cleaved dsNAs of the invention can include extensive modification patterns that possess such "windows" or "gaps" in modification such that Dicer cleavage preferentially occurs at such sites (as compared to heavily modified regions within such dsNAs).

In certain embodiments of the present invention, an oligonucleotide is provided (optionally, as a free antisense oligonucleotide or as an oligonucleotide of a double-stranded or other multiple-stranded structure) that includes a sequence complementary to the HAO1 target as described elsewhere herein and that is 15 to 80 nucleotides in length, e.g., in specific embodiments 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 nucleotides in length.

In certain additional embodiments of the present invention, each oligonucleotide of a DsiRNA molecule of the invention is independently 25 to 53 nucleotides in length, in specific embodiments 25, 26, 27, 28, 29, 30, 31, 32, 33, 34, 35, 36, 37, 38, 39, 40, 41, 42, 43, 44, 45, 46, 47, 48, 49, 50, 51, 52 or 53 nucleotides in length. For DsiRNAs possessing a strand that exceeds 30 nucleotides in length, available structures include those where only one strand exceeds 30 nucleotides in length (see, e.g., U.S. Pat. No. 8,349,809), or those where both strands exceed 30 nucleotides in length (see, e.g., WO 2010/080129). Stabilizing modifications (e.g., 2'-O-Methyl, phosphorothioate, deoxyribonucleotides, including dNTP base pairs, 2'-F, etc.) can be incorporated within any double stranded nucleic acid of the invention, and can be used in particular, and optionally in abundance, especially within DsiRNAs possessing one or both strands exceeding 30 nucleotides in length. While the guide strand of a double stranded nucleic acid of the invention must possess a sequence of, e.g., 15, 16, 17, 18 or 19 nucleotides that are complementary to a target RNA (e.g., mRNA), additional sequence(s) of the guide strand need not be complementary to the target RNA. The end structures of double stranded nucleic acids possessing at least one strand length in excess of 30 nucleotides can also be varied while continuing to yield functional dsNAs—e.g. the 5' end of the guide strand and the 3' end of the passenger strand may form a 5'-overhang, a blunt end or a 3' overhang (for certain dsNAs, e.g., "single strand extended" dsNAs, the length of such a 5' or 3' overhang can be 1-4, 1-5, 1-6, 1-10, 1-15, 1-20 or even 1-25 or more nucleotides): similarly, the 3' end of the guide strand and the 5' end of the passenger strand may form a 5'-overhang, a blunt end or a 3' overhang (for certain dsNAs, e.g., "single strand extended" dsNAs, the length of such a 5' or 3' overhang can be 1-4, 1-5, 1-6, 1-10, 1-15, 1-20 or even 1-25 or more nucleotides). In certain embodiments, the 5' end of the passenger strand includes a 5'-overhang relative to the 3' end of the guide strand, such that a one to fifteen or more nucleotide single strand extension exists. Optionally, such single strand extensions of the dsNAs of the invention (whether present on the passenger or the guide strand) can be modified, e.g., with phosphorothioate (PS), 2'-F, 2'-O-methyl and/or other forms of modification contemplated herein or known in the art, including conjugation to, e.g., GalNAc moieties, inverted abasic residues, etc. In some embodiments, the guide strand of a single-strand extended duplex of the invention is between 35 and 50 nucleotides in length, while the duplex presents a single-strand extension that is seven to twenty nucleotides in length. In certain embodiments, the guide strand of a duplex is between 37 and 42 nucleotides in length and the duplex possesses a 5' single-stranded overhang of the passenger strand that is approximately five to fifteen single-stranded nucleotides in length (optionally, 6, 7, 8, 9, 10, 11, 12, 13, or 14 nucleotides in length). In related embodiments, the passenger strand of the duplex is about 25 to about 30 nucleotides in length. In certain embodiments, the extended region of the duplex can optionally be extensively modified, e.g., with one or more of 2'-O-methyl, 2'-Fluoro, GalNAc moieties, phosphorothioate internucleotide linkages, inverted abasic residues, etc. In certain embodiments, the length of the passenger strand is 31-49 nucleotides while the length of the guide strand is 31-53 nucleotides, optionally while the 5' end of the guide strand forms a blunt end (optionally, a base-paired blunt end) with the 3' end of the passenger strand, optionally, with the 3' end of the guide strand and the 5' end of the passenger strand forming a 3' overhang of 1-4 nucleotides in length. Exemplary "extended" Dicer substrate structures are set forth, e.g., in US 2010/01739748,513,207 and U.S. Pat. No. 8,349,809, both of which are incorporated herein by reference. In certain embodiments, one or more strands of the dsNA molecule of the invention independently comprises 19 to 35 nucleotides (e.g., 19, 20, 21, 22, 23, 24, 25, 26, 27, 28, 29, 30, 31, 32, 33, 34 or 35) that are complementary to a target (Glycolate Oxidase) nucleic acid molecule. In certain embodiments, a DsiRNA molecule of the invention possesses a length of duplexed nucleotides between 25 and 49 nucleotides in length (e.g., 25, 26, 27, 28, 29, 30, 31, 32, 33, 34, 35, 36, 37, 38, 39, 40, 41, 42, 43, 44, 45, 46, 47, 48 or 49 nucleotides in length; optionally, all such nucleotides base pair with cognate nucleotides of the opposite strand).

In a further embodiment of the present invention, each oligonucleotide of a DsiRNA molecule of the invention is independently 19 to 66 nucleotides in length, in specific embodiments 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 or 66 nucleotides in length. For dsNAs possessing a strand that exceeds 30 nucleotides in length, available structures include those where only one strand exceeds 30 nucleotides in length (see, e.g., U.S. Pat. No. 8,349,809, where an exemplary double stranded nucleic acid possesses a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the first strand (or the second strand) is 25-30 nucleotide residues in length, where starting from the 5' terminal nucleotide (position 1) positions 1 to 23 of the first strand (or the second strand) include at least 8 ribonucleotides; the second strand (or the first strand) is 36-66 nucleotide residues in length and, starting from the 3' terminal nucleotide, includes at least 8 ribonucleotides in the positions paired with positions 1-23 of the first strand to form a duplex: where at least the 3' terminal nucleotide of the second strand (or the first strand) is unpaired with the first strand (or the second strand), and up to 6 consecutive 3' terminal nucleotides are unpaired with the first strand (or the second strand), thereby forming a 3' single stranded overhang of 1-6 nucleotides; where the 5' terminus of the second strand (or the first strand) includes from 10-30 consecutive nucleotides which are unpaired with the first strand (or the second strand), thereby forming a 10-30 nucleotide single stranded 5' overhang; where at least the first strand (or the second strand) 5' terminal and 3' terminal nucleotides are base paired with nucleotides of the second strand (or first strand) when the first and second strands are aligned for maximum complementarity, thereby forming a substantially duplexed region between the first and second strands; and the second strand is sufficiently complementary to a target RNA along at least 19 ribonucleotides of the second strand length to reduce target gene expression when the double stranded nucleic acid is introduced into a mammalian cell), or those where both strands exceed 30 nucleotides in length (see, e.g., U.S. Pat. No. 8,513,207, where an exemplary double stranded nucleic acid (dsNA) possesses a first oligonucleotide strand having a 5' terminus and a 3' terminus and a second oligonucleotide strand having a 5' terminus and a 3' terminus, where the first strand is 31 to 49 nucleotide residues in length, where starting from the first nucleotide (position 1) at the 5' terminus of the first strand, positions 1 to 23 of the first strand are ribonucleotides; the second strand is 31 to 53 nucleotide residues in length and includes 23 consecutive ribonucleotides that base pair with the ribonucleotides of positions 1 to 23 of the first strand to form a duplex; the 5' terminus of the first strand and the 3' terminus of said second strand form a blunt end or a 1-4 nucleotide 3' overhang; the 3' terminus of the first strand and the 5' terminus of said second strand form a duplexed blunt end, a 5' overhang or a 3' overhang; optionally, at least one of positions 24 to the 3' terminal nucleotide residue of the first strand is a deoxyribonucleotide, optionally, that base pairs with a deoxyribonucleotide of said second strand; and the second strand is sufficiently complementary to a target RNA along at least 19 ribonucleotides of the second strand length to reduce target gene expression when the double stranded nucleic acid is introduced into a mammalian cell).

In certain embodiments, an active dsNA of the invention can possess a 5' overhang of the first strand (optionally, the passenger strand) with respect to the second strand (optionally, the guide strand) of 2-50 nucleotides (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) or more in length. In related embodiments, the duplex region formed by the first and second strands of such a dsNA is 15, 16, 17, 18, 19, 20, 21, 22, 23, 24, 25 or more base pairs in length. The 5' overhang "extended" region of the first strand is optionally modified at one or more residues (optionally, at alternating residues, all residues, or any other selection of residues).

In certain embodiments, an active dsNA of the invention can possess a 3' overhang of the first strand (optionally, the passenger strand) with respect to the second strand (optionally, the guide strand) of 2-50 nucleotides (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) or more in length. In related embodiments, the duplex region formed by the first and second strands of such a dsNA is 15, 16, 17, 18, 19, 20, 21, 22, 23, 24, 25 or more base pairs in length. The 3' overhang "extended" region of the first strand is optionally modified at one or more residues (optionally, at alternating residues, all residues, or any other selection of residues).

In additional embodiments, an active dsNA of the invention can possess a 5' overhang of the second strand (optionally, the guide strand) with respect to the first strand (optionally, the passenger strand) of 2-50 nucleotides (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) or more in length. In related embodiments, the duplex region formed by the first and second strands of such a dsNA is 15, 16, 17, 18, 19, 20, 21, 22, 23, 24, 25 or more base pairs in length. The 5' overhang "extended" region of the second strand is optionally modified at one or more residues (optionally, at alternating residues, all residues, or any other selection of residues).

In further embodiments, an active dsNA of the invention can possess a 3' overhang of the second strand (optionally, the guide strand) with respect to the first strand (optionally, the passenger strand) of 2-50 nucleotides (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) or more in length. In related embodiments, the duplex region formed by the first and second strands of such a dsNA is 15, 16, 17, 18, 19, 20, 21, 22, 23, 24, 25 or more base pairs in length. The 3' overhang "extended" region of the second strand is optionally modified at one or more residues (optionally, at alternating residues, all residues, or any other selection of residues).

In another embodiment of the present invention, each sequence of a DsiRNA molecule of the invention is independently 25 to 35 nucleotides in length, in specific embodiments 25, 26, 27, 28, 29, 30, 31, 32, 33, 34 or 35 nucleotides in length. In another embodiment, the DsiRNA duplexes of the invention independently comprise 25 to 30 base pairs (e.g., 25, 26, 27, 28, 29, or 30). In another embodiment, one or more strands of the DsiRNA molecule of the invention independently comprises 19 to 35 nucleotides (e.g., 19, 20, 21, 22, 23, 24, 25, 26, 27, 28, 29, 30, 31, 32, 33, 34 or 35) that are complementary to a target (HAO1) nucleic acid molecule. In certain embodiments, a DsiRNA molecule of the invention possesses a length of duplexed nucleotides between 25 and 34 nucleotides in length (e.g., 25, 26, 27, 28, 29, 30, 31, 32, 33 or 34 nucleotides in length; optionally, all such nucleotides base pair with cognate nucleotides of the opposite strand). (Exemplary DsiRNA molecules of the invention are shown in FIG. 1, and below.)

In certain embodiments, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more of the nucleotide residues of a nucleic acid of the instant invention are modified residues. For a dsNA of the invention, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more of the nucleotide residues of the first strand are modified residues. Additionally and/or alternatively for a dsNA of the invention, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more of the nucleotide residues of the second strand are modified residues. For the dsNAs of the invention, modifications of both duplex (double-stranded) regions and overhang (single-stranded) regions are contemplated. Thus, in certain embodiments, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more (e.g., all) duplex nucleotide residues are modified residues. Additionally and/or alternatively, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more (e.g., all) overhang nucleotide residues of one or both strands are modified residues. Optionally, the modifications of the dsNAs of the invention do not include an inverted abasic (e.g., inverted deoxy abasic) or inverted dT end-protecting group. Alternatively, a dsNA of the invention includes a terminal cap moiety (e.g., an inverted deoxy abasic and/or inverted dT end-protecting group). Optionally, such a terminal cap moiety is located at the 5' end, at the 3' end, or at both the 5' end and the 3' end of the first strand, of the second strand, or of both first and second strands.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell. Within certain aspects, the term "cell" refers specifically to mammalian cells, such as human cells, that contain one or more isolated dsRNA molecules of the present disclosure. In particular aspects, a cell processes dsRNAs or dsRNA-containing molecules resulting in RNA interference of target nucleic acids, and contains proteins and protein complexes required for RNAi, e.g., Dicer and RISC.

In certain embodiments, dsRNAs of the invention are Dicer substrate siRNAs ("DsiRNAs"). DsiRNAs can possess certain advantages as compared to inhibitory nucleic acids that are not dicer substrates ("non-DsiRNAs"). Such advantages include, but are not limited to, enhanced duration of effect of a DsiRNA relative to a non-DsiRNA, as well as enhanced inhibitory activity of a DsiRNA as compared to a non-DsiRNA (e.g., a 19-23mer siRNA) when each inhibitory nucleic acid is suitably formulated and assessed for inhibitory activity in a mammalian cell at the same concentration (in this latter scenario, the DsiRNA would be identified as more potent than the non-DsiRNA). Detection of the enhanced potency of a DsiRNA relative to a non-DsiRNA is often most readily achieved at a formulated concentration (e.g., transfection concentration of the dsRNA) that results in the DsiRNA eliciting approximately 30-70% knockdown activity upon a target RNA (e.g., a mRNA). For active DsiRNAs, such levels of knockdown activity are most often achieved at in vitro mammalian cell DsiRNA transfection concentrations of 1 nM or less of as suitably formulated, and in certain instances are observed at DsiRNA transfection concentrations of 200 pM or less, 100 pM or less, 50 pM or less, 20 pM or less, 10 pM or less, 5 pM or less, or even 1 pM or less. Indeed, due to the variability among DsiRNAs of the precise concentration at which 30-70% knockdown of a target RNA is observed, construction of an $IC_{50}$ curve via assessment of the inhibitory activity of DsiRNAs and non-DsiRNAs across a range of effective concentrations is a preferred method for detecting the enhanced potency of a DsiRNA relative to a non-DsiRNA inhibitory agent.

In certain embodiments, a DsiRNA (in a state as initially formed, prior to dicer cleavage) is more potent at reducing Glycolate Oxidase target gene expression in a mammalian cell than a 19, 20, 21, 22 or 23 base pair sequence that is contained within it. In certain such embodiments, a DsiRNA prior to dicer cleavage is more potent than a 19-21mer contained within it. Optionally, a DsiRNA prior to dicer cleavage is more potent than a 19 base pair duplex contained within it that is synthesized with symmetric dTdT overhangs (thereby forming a siRNA possessing 21 nucleotide strand lengths having dTdT overhangs). In certain embodiments, the DsiRNA is more potent than a 19-23mer siRNA (e.g., a 19 base pair duplex with dTdT overhangs) that targets at least 19 nucleotides of the 21 nucleotide target sequence that is recited for a DsiRNA of the invention (without wishing to be bound by theory, the identity of a such a target site for a DsiRNA is identified via identification of the Ago2 cleavage site for the DsiRNA; once the Ago2 cleavage site of a DsiRNA is determined for a DsiRNA, identification of the Ago2 cleavage site for any other inhibitory dsRNA can be performed and these Ago2 cleavage sites can be aligned, thereby determining the alignment of projected target nucleotide sequences for multiple dsRNAs). In certain related embodiments, the DsiRNA is more potent than a 19-23mer siRNA that targets at least 20 nucleotides of the 21 nucleotide target sequence that is recited for a DsiRNA of the invention. Optionally, the DsiRNA is more potent than a 19-23mer siRNA that targets the same 21 nucleotide target sequence that is recited for a DsiRNA of the invention. In certain embodiments, the DsiRNA is more potent than any 21mer siRNA that targets the same 21 nucleotide target sequence that is recited for a DsiRNA of the invention. Optionally, the DsiRNA is more potent than any 21 or 22mer siRNA that targets the same 21 nucleotide target sequence that is recited for a DsiRNA of the invention. In certain embodiments, the DsiRNA is more potent than any 21, 22 or 23mer siRNA that targets the same 21 nucleotide target sequence that is recited for a DsiRNA of the invention. As noted above, such potency assessments are most effectively performed upon dsRNAs that are suitably formulated (e.g., formulated with an appropriate transfection reagent) at a concentration of 1 nM or less. Optionally, an $IC_{50}$ assessment is performed to evaluate activity across a range of effective inhibitory concentrations, thereby allowing for robust comparison of the relative potencies of dsRNAs so assayed.

The dsRNA molecules of the invention are added directly, or can be complexed with lipids (e.g., cationic lipids), packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers. In particular embodiments, the nucleic acid molecules of the invention comprise sequences shown in FIG. 1, and the below exemplary structures. Examples of such nucleic acid molecules consist essentially of sequences defined in these figures and exemplary structures. Furthermore, where such agents are modified in accordance with the below description of modification patterning of DsiRNA agents, chemically modified forms of constructs described in FIG. 1, and the below exemplary structures can be used in all uses described for the DsiRNA agents of FIG. 1, and the below exemplary structures.

In another aspect, the invention provides mammalian cells containing one or more dsRNA molecules of this invention. The one or more dsRNA molecules can independently be targeted to the same or different sites.

By "RNA" is meant a molecule comprising at least one, and preferably at least 4, 8 and 12 ribonucleotide residues. The at least 4, 8 or 12 RNA residues may be contiguous. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the dsRNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the dsRNA agents of the invention can be administered. A subject can be a mammal or mammalian cells, including a human or human cells.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA compositions may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Various methodologies of the instant invention include step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent (e.g., DsiRNA) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

The term "in vitro" has its art recognized meaning. e.g., involving purified reagents or extracts, e.g., cell extracts. The term "in vivo" also has its art recognized meaning, e.g., involving living cells, e.g., immortalized cells, primary cells, cell lines, and/or cells in an organism.

"Treatment", or "treating" as used herein, is defined as the application or administration of a therapeutic agent (e.g., a dsRNA agent or a vector or transgene encoding same) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

Structures of Anti-Glycolate Oxidase DsiRNA Agents

In certain embodiments, the anti-Glycolate Oxidase DsiRNA agents of the invention can have the following structures:

In one such embodiment, the DsiRNA comprises:

```
5'-XXXXXXXXXXXXXXXXXXXXXXXXX-3'

3'-YXXXXXXXXXXXXXXXXXXXXXXXXX-5'
``` wherein "X"=RNA and "Y" is an overhang domain comprised of 1-4 RNA monomers that are optionally 2'-O- methyl RNA monomers. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand.

DsiRNAs of the invention can carry a broad range of modification patterns (e.g., 2'-O-methyl RNA patterns, e.g., within extended DsiRNA agents). Certain modification patterns of the second strand of DsiRNAs of the invention are presented below.

In one embodiment, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers, and "D"=DNA. The top strand is the sense strand, and the bottom strand is the antisense strand.

In another such embodiment, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In another such embodiment, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In further embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M7" or "M7" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

```
5'-XXXXXXXXXXXXXXXXXXXXXXXXXDD-3'
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. The top strand is the sense strand, and the bottom strand is the antisense strand.

In another related embodiment, the DsiRNA comprises:

```
5'-XXXXXXXXXXXXXXXXXXXXXXXXX-3'
3'-XX̲XXXXXXXXXXXXXXX̲XXXXXXXXXX̲X̲-5'
``` wherein "X"=RNA and "X̲"=2'-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XX̲XXXXXXXXXXXXXXX̲XXXXXXXXXX̲X̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M6" or "M6" modification pattern.

In other embodiments, the DsiRNA comprises:

```
5'-XXXXXXXXXXXXXXXXXXXXXXXXX-3'
3'-YX̲XXXXXXXXXXXXXXX̲XXXXXXXXXX̲X̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXXXDD-3'
3'-YX̲XXXXXXXXXXXXXXX̲XXXXXXXXXX̲X̲-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

```
5'-XXXXXXXXXXXXXXXXXXXXXXXXX-3'
3'-X̲XXXXXXXXXXXXXXX̲XXXXXXXXXXX̲-5'
``` wherein "X"=RNA and "X̲"=2'-O-methyl RNA. The top strand is the sense strand, and the bottom strand is the antisense strand. In another related embodiment, the DsiRNA comprises:

```
5'-XXXXXXXXXXXXXXXXXXXXXXXXXDD-3'
3'-X̲XXXXXXXXXXXXXXX̲XXXXXXXXXXX̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M5" or "M5" modification pattern.

In further embodiments, the DsiRNA comprises:

```
5'-XXXXXXXXXXXXXXXXXXXXXXXXX-3'
3'-YX̲XXXXXXXXXXXXXXX̲XXXXXXXXXX̲X̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXXXDD-3'
3'-YX̲XXXXXXXXXXXXXXX̲XXXXXXXXXXX̲-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

```
5'-XXXXXXXXXXXXXXXXXXXXXXXXX-3'
3'-X̲XXXX̲XXXXXXXXXXX̲XXXXXXXXXXX̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-X̲XXXX̲XXXXXXXXXXX̲XXXXXXXXXXX̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M4" or "M4" modification pattern.

In additional embodiments, the DsiRNA comprises:

```
5'-XXXXXXXXXXXXXXXXXXXXXXXXX-3'
3'-YX̲XX̲XXXXXXXXXXXX̲XXXXXXXXXXX̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

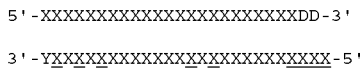

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

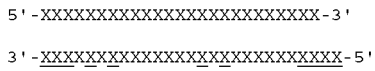

wherein "X"=RNA and "X"=2'-O-methyl RNA. The top strand is the sense strand, and the bottom strand is the antisense strand. In a further related embodiment, the DsiRNA comprises:

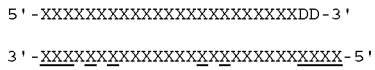

wherein "X"=RNA, "X"=2'-O-methyl RNA, and "D"=DNA. The top strand is the sense strand, and the bottom strand is the antisense strand. This modification pattern is also referred to herein as the "AS-M8" or "M8" modification pattern.

In other embodiments, the DsiRNA comprises:

wherein "X"=RNA. "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

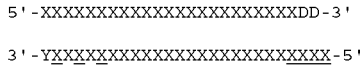

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

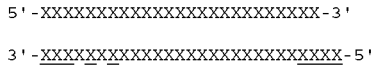

wherein "X"=RNA and "X"=2'-O-methyl RNA. The top strand is the sense strand, and the bottom strand is the antisense strand. In a further related embodiment, the DsiRNA comprises:

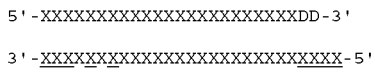

wherein "X"=RNA, "X"=2'-O-methyl RNA, and "D"=DNA. The top strand is the sense strand, and the bottom strand is the antisense strand. This modification pattern is also referred to herein as the "AS-M3" or "M3" modification pattern.

In additional embodiments, the DsiRNA comprises:

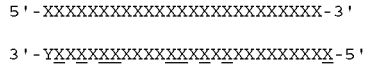

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

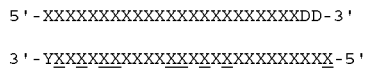

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

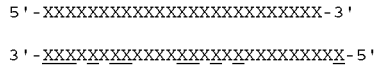

wherein "X"=RNA and "X"=2'-O-methyl RNA. The top strand is the sense strand, and the bottom strand is the antisense strand. In a further related embodiment, the DsiRNA comprises:

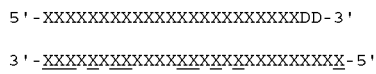

wherein "X"=RNA, "X"=2'-O-methyl RNA, and "D"=DNA. The top strand is the sense strand, and the bottom strand is the antisense strand. This modification pattern is also referred to herein as the "AS-M2" or "M2" modification pattern.

In further embodiments, the DsiRNA comprises:

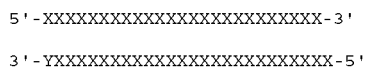

wherein "X"=RNA. "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

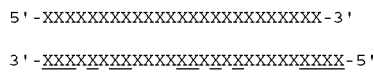

wherein "X"=RNA and "X"=2'-O-methyl RNA. The top strand is the sense strand, and the bottom strand is the antisense strand. In a further related embodiment, the DsiRNA comprises:

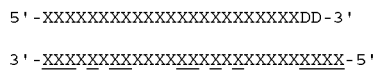

wherein "X"=RNA, "X"=2'-O-methyl RNA, and "D"=DNA. The top strand is the sense strand, and the bottom strand is the antisense strand. This modification pattern is also referred to herein as the "AS-M1" or "M1" modification pattern.

In additional embodiments, the DsiRNA comprises:

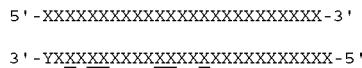

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

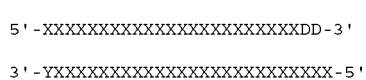

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

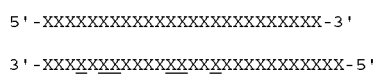

wherein "X"=RNA and "X"=2'-O-methyl RNA. The top strand is the sense strand, and the bottom strand is the antisense strand. In a further related embodiment, the DsiRNA comprises:

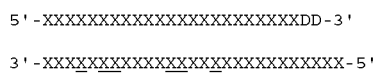

wherein "X"=RNA, "X"=2'-O-methyl RNA, and "D"=DNA. The top strand is the sense strand, and the bottom strand is the antisense strand. This modification pattern is also referred to herein as the "AS-M9" or "M9" modification pattern.

In other embodiments, the DsiRNA comprises:

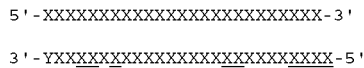

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

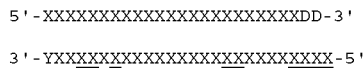

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

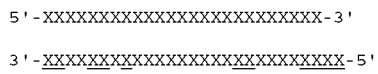

wherein "X"=RNA and "X"=2'-O-methyl RNA. The top strand is the sense strand, and the bottom strand is the antisense strand. In a further related embodiment, the DsiRNA comprises:

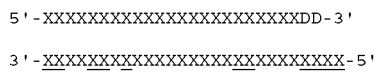

wherein "X"=RNA, "X"=2'-O-methyl RNA, and "D"=DNA. The top strand is the sense strand, and the bottom strand is the antisense strand. This modification pattern is also referred to herein as the "AS-M10" or "M10" modification pattern.

In further embodiments, the DsiRNA comprises:

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

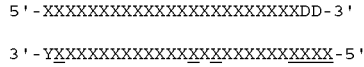

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M11" or "M11" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M12" or "M12" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA, "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M13" or "M13" modification pattern.

In other embodiments, the DsiRNA comprises:

```
5'-XXXXXXXXXXXXXXXXXXXXXXXXX-3'

3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In another related embodiment, the DsiRNA comprises:

```
5'-XXXXXXXXXXXXXXXXXXXXXXXDD-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

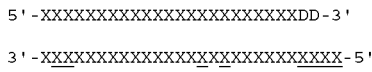

wherein "X"=RNA, "X̲"=2'-O-methyl RNA, and "D"=DNA. The top strand is the sense strand, and the bottom strand is the antisense strand. This modification pattern is also referred to herein as the "AS-M21" or "M21" modification pattern.

In further embodiments, the DsiRNA comprises:

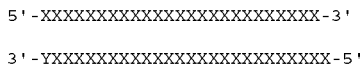

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

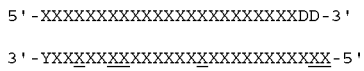

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

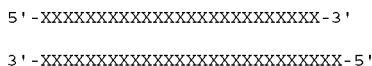

wherein "X"=RNA and "X̲"=2'-O-methyl RNA. The top strand is the sense strand, and the bottom strand is the antisense strand. In a further related embodiment, the DsiRNA comprises:

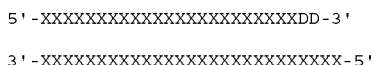

wherein "X"=RNA, "X̲"=2'-O-methyl RNA, and "D"=DNA. The top strand is the sense strand, and the bottom strand is the antisense strand. This modification pattern is also referred to herein as the "AS-M14" or "M14" modification pattern.

In additional embodiments, the DsiRNA comprises:

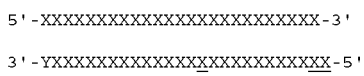

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

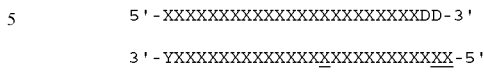

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

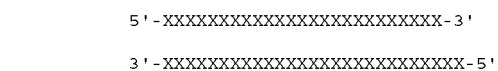

wherein "X"=RNA and "X̲"=2'-O-methyl RNA. The top strand is the sense strand, and the bottom strand is the antisense strand. In a further related embodiment, the DsiRNA comprises:

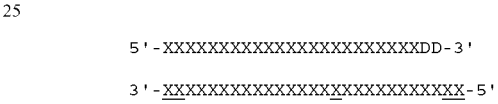

wherein "X"=RNA, "X̲"=2'-O-methyl RNA, and "D"=DNA. The top strand is the sense strand, and the bottom strand is the antisense strand. This modification pattern is also referred to herein as the "AS-M15" or "M15" modification pattern.

In further embodiments, the DsiRNA comprises:

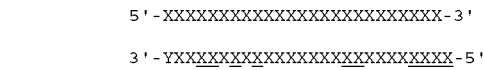

wherein "X"=RNA, "X̲"=2-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

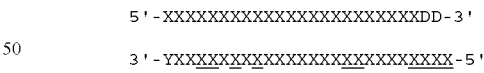

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

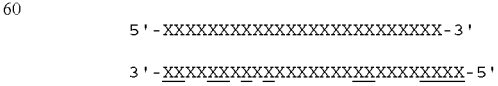

wherein "X"=RNA and "X̲"=2'-O-methyl RNA. The top strand is the sense strand, and the bottom strand is the antisense strand. In a further related embodiment, the DsiRNA comprises:

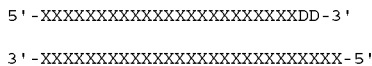

wherein "X"=RNA. "X"=2'-O-methyl RNA, and "D"=DNA. The top strand is the sense strand, and the bottom strand is the antisense strand. This modification pattern is also referred to herein as the "AS-M16" or "M16" modification pattern.

In additional embodiments, the DsiRNA comprises:

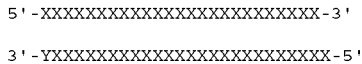

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

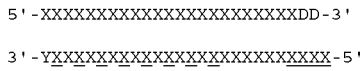

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

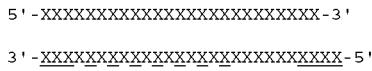

wherein "X"=RNA and "X"=2'-O-methyl RNA. The top strand is the sense strand, and the bottom strand is the antisense strand. In a further related embodiment, the DsiRNA comprises:

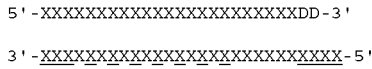

wherein "X"=RNA, "X"=2'-O-methyl RNA, and "D"=DNA. The top strand is the sense strand, and the bottom strand is the antisense strand. This modification pattern is also referred to herein as the "AS-M17" or "M17" modification pattern.

In further embodiments, the DsiRNA comprises:

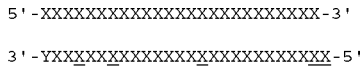

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand.

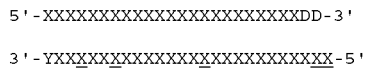

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

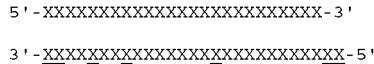

wherein "X"=RNA and "X"=2'-O-methyl RNA. The top strand is the sense strand, and the bottom strand is the antisense strand. In a further related embodiment, the DsiRNA comprises:

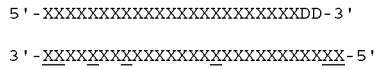

wherein "X"=RNA, "X"=2'-O-methyl RNA, and "D"=DNA. The top strand is the sense strand, and the bottom strand is the antisense strand. This modification pattern is also referred to herein as the "AS-M18" or "M18" modification pattern.

In additional embodiments, the DsiRNA comprises:

wherein "X"=RNA. "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

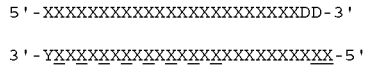

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

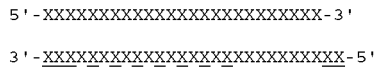

wherein "X"=RNA and "X"=2'-O-methyl RNA. The top strand is the sense strand, and the bottom strand is the antisense strand. In a further related embodiment, the DsiRNA comprises:

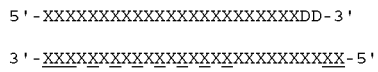

wherein "X"=RNA, "X̲"=2'-O-methyl RNA, and "D"=DNA. The top strand is the sense strand, and the bottom strand is the antisense strand. This modification pattern is also referred to herein as the "AS-M19" or "M19" modification pattern.

In further embodiments, the DsiRNA comprises:

```
5'-XXXXXXXXXXXXXXXXXXXXXXXXX-3'
3'-YX̲XXXX̲X̲X̲XXXXX̲X̲XXXXXXXXXXX̲X̲-5'
``` wherein "X"=RNA. "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YX̲XXXX̲X̲X̲XXXXX̲X̲XXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-X̲XXXX̲X̲X̲XXXXX̲X̲XXXXXXXXXXX̲X̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-X̲XXXX̲X̲X̲XXXXX̲X̲XXXXXXXXXXXX̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M20" or "M20" modification pattern.

In additional embodiments, the DsiRNA comprises:

```
5'-XXXXXXXXXXXXXXXXXXXXXXXXX-3'
3'-YXXXXXXXXXXXXXXXXXXXXXXX̲X̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXX̲X̲-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-X̲XXXXXXXXXXXXX̲XXXXXXXXXX̲X̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-X̲XXXXXXXXXXXXX̲XXXXXXXXXX̲X̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M22" or "M22" modification pattern.

In further embodiments, the DsiRNA comprises:

```
5'-XXXXXXXXXXXXXXXXXXXXXXXXX-3'
3'-YX̲XXX̲XXXXXXXX̲X̲XXXXXXXXXX̲X̲-5'
``` wherein "X"=RNA. "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YX̲XX̲X̲XXXXXXXX̲X̲XXXXXXXXXXX̲-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-X̲XXXX̲XXXXXXXX̲X̲XXXXXXXXXXX̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-X̲XXXX̲XXXXXXXX̲X̲XXXXXXXXXXX̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M24" or "M24" modification pattern.

In additional embodiments, the DsiRNA comprises:

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

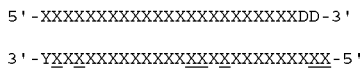

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

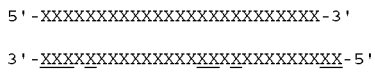

wherein "X"=RNA and "X"=2'-O-methyl RNA. The top strand is the sense strand, and the bottom strand is the antisense strand. In a further related embodiment, the DsiRNA comprises:

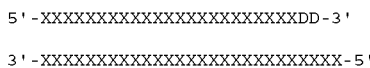

wherein "X"=RNA, "X"=2'-O-methyl RNA, and "D"=DNA. The top strand is the sense strand, and the bottom strand is the antisense strand. This modification pattern is also referred to herein as the "AS-M25" or "M25" modification pattern.

In further embodiments, the DsiRNA comprises:

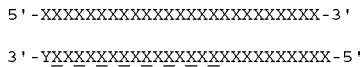

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

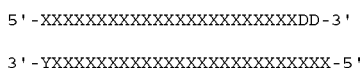

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

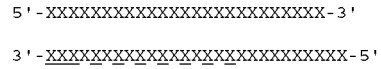

wherein "X"=RNA and "X"=2'-O-methyl RNA. The top strand is the sense strand, and the bottom strand is the antisense strand. In a further related embodiment, the DsiRNA comprises:

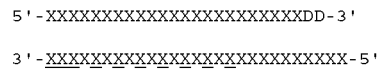

wherein "X"=RNA, "X"=2'-O-methyl RNA, and "D"=DNA. The top strand is the sense strand, and the bottom strand is the antisense strand. This modification pattern is also referred to herein as the "AS-M26" or "M26" modification pattern.

In additional embodiments, the DsiRNA comprises:

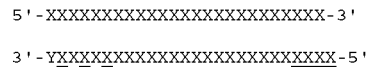

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

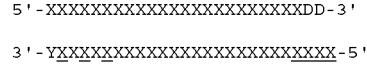

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

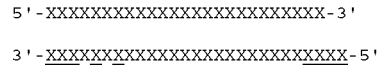

wherein "X"=RNA and "X"=2'-O-methyl RNA. The top strand is the sense strand, and the bottom strand is the antisense strand. In a further related embodiment, the DsiRNA comprises:

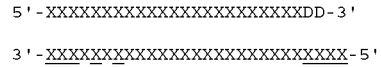

wherein "X"=RNA, "X"=2'-O-methyl RNA, and "D"=DNA. The top strand is the sense strand, and the bottom strand is the antisense strand. This modification pattern is also referred to herein as the "AS-M27" or "M27" modification pattern.

In further embodiments, the DsiRNA comprises:

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YX̲XX̲XX̲XXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-X̲X̲X̲X̲X̲X̲XXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-X̲X̲X̲X̲X̲X̲XXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M28" or "M28" modification pattern.

In further embodiments, the DsiRNA comprises:

```
5'-XXXXXXXXXXXXXXXXXXXXXXXXX-3'
3'-YX̲XXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YX̲XXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-X̲XXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XX̲XXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M29" or "M29" modification pattern.

In additional embodiments, the DsiRNA comprises:

```
5'-XXXXXXXXXXXXXXXXXXXXXXXXX-3'
3'-XXX̲XX̲X̲X̲XXXXXXXXXXXXXXXXX̲X̲X̲X̲X̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXX̲XX̲X̲X̲XXXXXXXXXXXXXXXXX̲X̲X̲X̲X̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M30" or "M30" modification pattern.

In further embodiments, the DsiRNA comprises:

```
5'-XXXXXXXXXXXXXXXXXXXXXXXXX-3'
3'-XX̲X̲X̲X̲X̲XXXXXXXXXXXXXXXXXX̲X̲X̲X̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XX̲X̲X̲X̲X̲XXXXXXXXXXXXXXXXXX̲X̲X̲X̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M31" or "M31" modification pattern.

In additional embodiments, the DsiRNA comprises:

```
5'-XXXXXXXXXXXXXXXXXXXXXXXXX-3'
3'-XXX̲XXXXXXXXX̲XXXXXXXXXX̲X̲X̲X̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXX̲XXXXXXXXX̲XXXXXXXXXX̲X̲X̲X̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M32" or "M32" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M34" or "M34" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M35" or "M35" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M37" or "M37" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

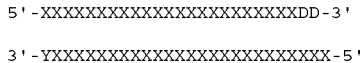

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

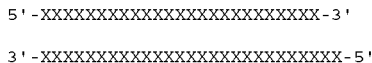

wherein "X"=RNA and "X"=2'-O-methyl RNA. The top strand is the sense strand, and the bottom strand is the antisense strand. In a further related embodiment, the DsiRNA comprises:

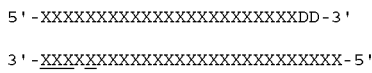

wherein "X"=RNA, "X"=2'-O-methyl RNA, and "D"=DNA. The top strand is the sense strand, and the bottom strand is the antisense strand. This modification pattern is also referred to herein as the "AS-M38" or "M38" modification pattern.

In further embodiments, the DsiRNA comprises:

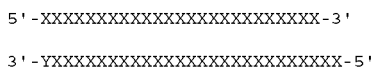

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

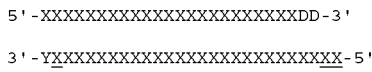

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

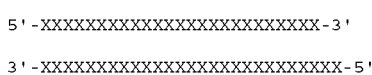

wherein "X"=RNA and "X"=2'-O-methyl RNA. The top strand is the sense strand, and the bottom strand is the antisense strand. In a further related embodiment, the DsiRNA comprises:

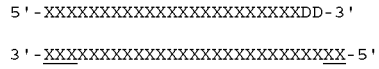

wherein "X"=RNA, "X"=2'-O-methyl RNA, and "D"=DNA. The top strand is the sense strand, and the bottom strand is the antisense strand. This modification pattern is also referred to herein as the "AS-M40" or "M40" modification pattern.

In additional embodiments, the DsiRNA comprises:

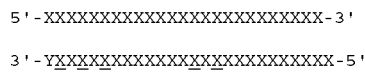

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

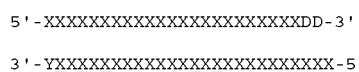

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

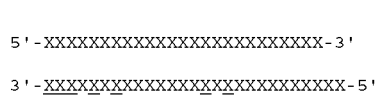

wherein "X"=RNA and "X"=2'-O-methyl RNA. The top strand is the sense strand, and the bottom strand is the antisense strand. In a further related embodiment, the DsiRNA comprises:

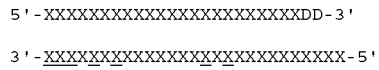

wherein "X"=RNA, "X"=2'-O-methyl RNA, and "D"=DNA. The top strand is the sense strand, and the bottom strand is the antisense strand. This modification pattern is also referred to herein as the "AS-M41" or "M41" modification pattern.

In further embodiments, the DsiRNA comprises:

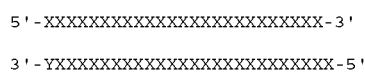

wherein "X"=RNA. "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

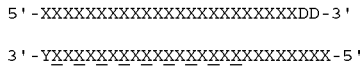

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

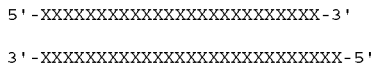

wherein "X"=RNA and "X"=2'-O-methyl RNA. The top strand is the sense strand, and the bottom strand is the antisense strand. In a further related embodiment, the DsiRNA comprises:

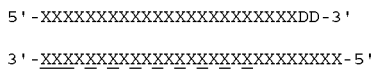

wherein "X"=RNA, "X"=2'-O-methyl RNA, and "D"=DNA. The top strand is the sense strand, and the bottom strand is the antisense strand. This modification pattern is also referred to herein as the "AS-M36" or "M36" modification pattern.

In additional embodiments, the DsiRNA comprises:

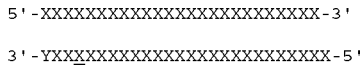

wherein "X"=RNA. "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

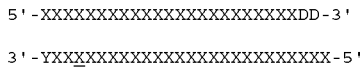

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

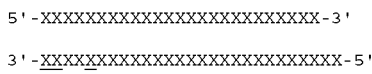

wherein "X"=RNA and "X"=2'-O-methyl RNA. The top strand is the sense strand, and the bottom strand is the antisense strand. In a further related embodiment, the DsiRNA comprises:

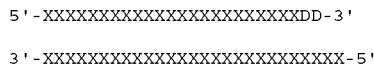

wherein "X"=RNA, "X"=2'-O-methyl RNA, and "D"=DNA. The top strand is the sense strand, and the bottom strand is the antisense strand. This modification pattern is also referred to herein as the "AS-M42" or "M42" modification pattern.

In further embodiments, the DsiRNA comprises:

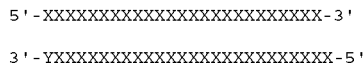

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

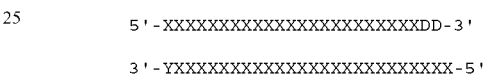

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

wherein "X"=RNA and "X"=2'-O-methyl RNA. The top strand is the sense strand, and the bottom strand is the antisense strand. In a further related embodiment, the DsiRNA comprises:

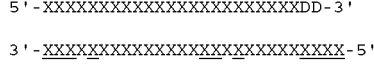

wherein "X"=RNA, "X"=2'-O-methyl RNA, and "D"=DNA. The top strand is the sense strand, and the bottom strand is the antisense strand. This modification pattern is also referred to herein as the "AS-M43" or "M43" modification pattern.

In additional embodiments, the DsiRNA comprises:

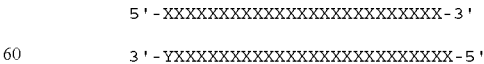

wherein "X"=RNA. "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M44" or "M44" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M45" or "M45" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M46" or "M46" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

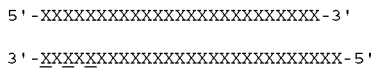

wherein "X"=RNA and "X"=2'-O-methyl RNA. The top strand is the sense strand, and the bottom strand is the antisense strand. In a further related embodiment, the DsiRNA comprises:

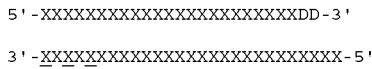

wherein "X"=RNA, "X"=2'-O-methyl RNA, and "D"=DNA. The top strand is the sense strand, and the bottom strand is the antisense strand. This modification pattern is also referred to herein as the "AS-M47" or "M47" modification pattern.

In additional embodiments, the DsiRNA comprises:

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

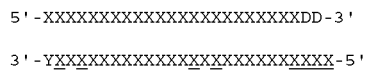

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

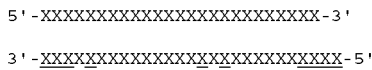

wherein "X"=RNA and "X"=2'-O-methyl RNA. The top strand is the sense strand, and the bottom strand is the antisense strand. In a further related embodiment, the DsiRNA comprises:

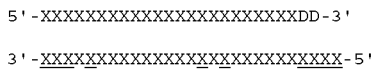

wherein "X"=RNA, "X"=2'-O-methyl RNA, and "D"=DNA. The top strand is the sense strand, and the bottom strand is the antisense strand. This modification pattern is also referred to herein as the "AS-M48" or "M48" modification pattern.

In further embodiments, the DsiRNA comprises:

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

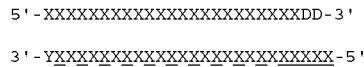

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

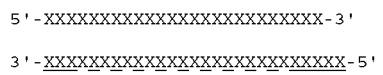

wherein "X"=RNA and "X"=2'-O-methyl RNA. The top strand is the sense strand, and the bottom strand is the antisense strand. In a further related embodiment, the DsiRNA comprises:

wherein "X"=RNA, "X"=2'-O-methyl RNA, and "D"=DNA. The top strand is the sense strand, and the bottom strand is the antisense strand. This modification pattern is also referred to herein as the "AS-M52" or "M52" modification pattern.

In further embodiments, the DsiRNA comprises:

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

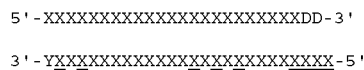

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M54" or "M54" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M56" or "M56" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-X̲X̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M57" or "M57" modification pattern.

In further embodiments, the DsiRNA comprises:

```
5'-XXXXXXXXXXXXXXXXXXXXXXXXX-3'
3'-YX̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YX̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-X̲X̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-X̲X̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M58" or "M58" modification pattern.

In additional embodiments, the DsiRNA comprises:

```
5'-XXXXXXXXXXXXXXXXXXXXXXXXX-3'
3'-YX̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YX̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-X̲X̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-X̲X̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M59" or "M59" modification pattern.

In further embodiments, the DsiRNA comprises:

```
5'-XXXXXXXXXXXXXXXXXXXXXXXXX-3'
3'-YX̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YX̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-X̲X̲X̲X̲X̲X̲X̲X̲X̲X̲X̲X̲X̲X̲X̲X̲X̲X̲X̲X̲X̲X̲X̲X̲X̲X̲X̲-5'
``` wherein "X"=RNA and "X̲"=2'-O-methyl RNA. The top strand is the sense strand, and the bottom strand is the antisense strand. In a further related embodiment, the DsiRNA comprises:

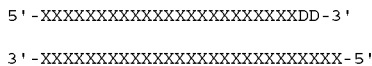

wherein "X"=RNA, "X"=2'-O-methyl RNA, and "D"=DNA. The top strand is the sense strand, and the bottom strand is the antisense strand. This modification pattern is also referred to herein as the "AS-M60" or "M60" modification pattern.

In additional embodiments, the DsiRNA comprises:

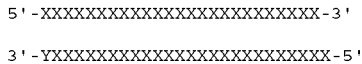

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

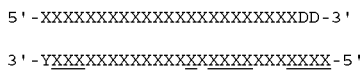

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

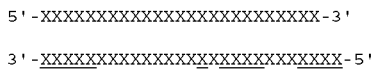

wherein "X"=RNA and "X"=2'-O-methyl RNA. The top strand is the sense strand, and the bottom strand is the antisense strand. In a further related embodiment, the DsiRNA comprises:

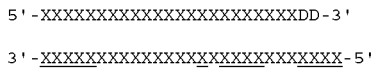

wherein "X"=RNA, "X"=2'-O-methyl RNA, and "D"=DNA. The top strand is the sense strand, and the bottom strand is the antisense strand. This modification pattern is also referred to herein as the "AS-M61" or "M61" modification pattern.

In further embodiments, the DsiRNA comprises:

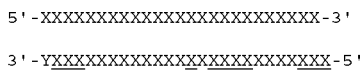

wherein "X"=RNA, "X"=2-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

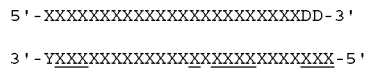

wherein "X"=RNA. "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

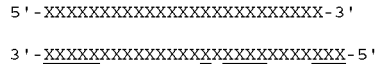

wherein "X"=RNA and "X"=2'-O-methyl RNA. The top strand is the sense strand, and the bottom strand is the antisense strand. In a further related embodiment, the DsiRNA comprises:

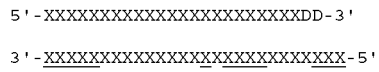

wherein "X"=RNA, "X"=2'-O-methyl RNA, and "D"=DNA. The top strand is the sense strand, and the bottom strand is the antisense strand. This modification pattern is also referred to herein as the "AS-M62" or "M62" modification pattern.

In additional embodiments, the DsiRNA comprises:

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

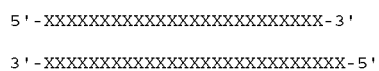

wherein "X"=RNA and "X"=2'-O-methyl RNA. The top strand is the sense strand, and the bottom strand is the antisense strand. In a further related embodiment, the DsiRNA comprises:

wherein "X"=RNA, "X̲"=2'-O-methyl RNA, and "D"=DNA. The top strand is the sense strand, and the bottom strand is the antisense strand. This modification pattern is also referred to herein as the "AS-M63" or "M63" modification pattern.

In further embodiments, the DsiRNA comprises:

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

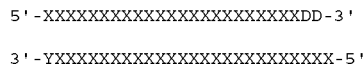

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

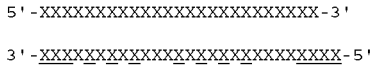

wherein "X"=RNA and "X̲"=2'-O-methyl RNA. The top strand is the sense strand, and the bottom strand is the antisense strand. In a further related embodiment, the DsiRNA comprises:

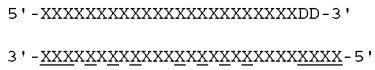

wherein "X"=RNA, "X̲"=2'-O-methyl RNA, and "D"=DNA. The top strand is the sense strand, and the bottom strand is the antisense strand. This modification pattern is also referred to herein as the "AS-M64" or "M64" modification pattern.

In additional embodiments, the DsiRNA comprises:

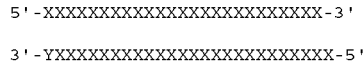

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

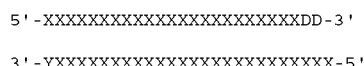

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

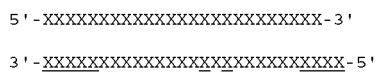

wherein "X"=RNA and "X̲"=2'-O-methyl RNA. The top strand is the sense strand, and the bottom strand is the antisense strand. In a further related embodiment, the DsiRNA comprises:

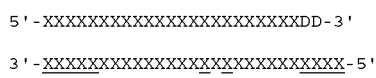

wherein "X"=RNA, "X̲"=2'-O-methyl RNA, and "D"=DNA. The top strand is the sense strand, and the bottom strand is the antisense strand. This modification pattern is also referred to herein as the "AS-M65" or "M65" modification pattern.

In further embodiments, the DsiRNA comprises:

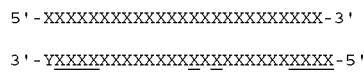

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

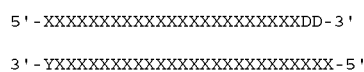

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

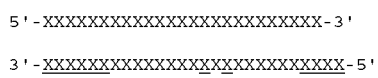

wherein "X"=RNA and "X̲"=2'-O-methyl RNA. The top strand is the sense strand, and the bottom strand is the antisense strand. In a further related embodiment, the DsiRNA comprises:

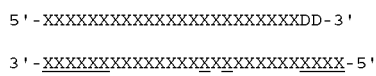

wherein "X"=RNA, "X̲"=2'-O-methyl RNA, and "D"=DNA. The top strand is the sense strand, and the bottom strand is the antisense strand. This modification pattern is also referred to herein as the "AS-M66" or "M66" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M67" or "M67" modification pattern.

In further embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M68" or "M68" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M69" or "M69" modification pattern.

In further embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

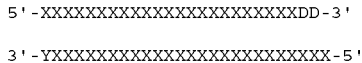

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

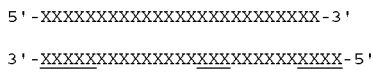

wherein "X"=RNA and "X"=2'-O-methyl RNA. The top strand is the sense strand, and the bottom strand is the antisense strand. In a further related embodiment, the DsiRNA comprises:

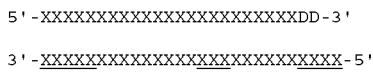

wherein "X"=RNA. "X"=2'-O-methyl RNA, and "D"=DNA. The top strand is the sense strand, and the bottom strand is the antisense strand. This modification pattern is also referred to herein as the "AS-M70" or "M70" modification pattern.

In additional embodiments, the DsiRNA comprises:

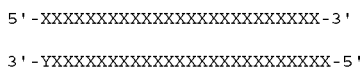

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

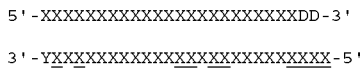

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

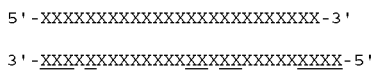

wherein "X"=RNA and "X"=2'-O-methyl RNA. The top strand is the sense strand, and the bottom strand is the antisense strand. In a further related embodiment, the DsiRNA comprises:

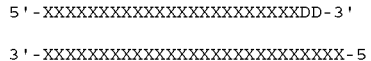

wherein "X"=RNA, "X"=2'-O-methyl RNA, and "D"=DNA. The top strand is the sense strand, and the bottom strand is the antisense strand. This modification pattern is also referred to herein as the "AS-M71" or "M71" modification pattern.

In further embodiments, the DsiRNA comprises:

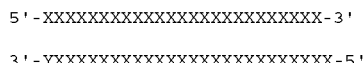

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

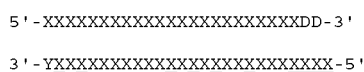

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

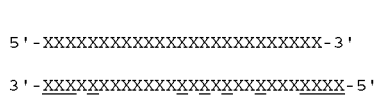

wherein "X"=RNA and "X"=2'-O-methyl RNA. The top strand is the sense strand, and the bottom strand is the antisense strand. In a further related embodiment, the DsiRNA comprises:

wherein "X"=RNA, "X"=2'-O-methyl RNA, and "D"=DNA. The top strand is the sense strand, and the bottom strand is the antisense strand. This modification pattern is also referred to herein as the "AS-M72" or "M72" modification pattern.

In additional embodiments, the DsiRNA comprises:

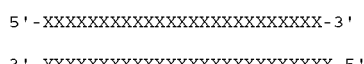

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M73" or "M73" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M7*" or "M7*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA. "X"=2'-O-methyl RNA, and "D"=DNA. The top strand is the sense strand, and the bottom strand is the antisense strand. This modification pattern is also referred to herein as the "AS-M6*" or "M6*" modification pattern.

In other embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In another related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M5*" or "M5*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M4*" or "M4*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA. "X"=2'-O-methyl RNA, and "D"=DNA. The top strand is the sense strand, and the bottom strand is the antisense strand. This modification pattern is also referred to herein as the "AS-M8*" or "M8*" modification pattern.

In additional embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M2*" or "M2*" modification pattern.

In other embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M10*" or "M10*" modification pattern.

In further embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M11*" or "M11*" modification pattern.

In further embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M13*" or "M13*" modification pattern.

In further embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M14*" or "M14*" modification pattern.

In additional embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA. "X"=2'-O-methyl RNA, and "D"=DNA. The top strand is the sense strand, and the bottom strand is the antisense strand. This modification pattern is also referred to herein as the "AS-M15*" or "M15*" modification pattern.

In further embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M16*" or "M16*" modification pattern.

In additional embodiments, the DsiRNA comprises:

5'-XXXXXXXXXXXXXXXXXXXXXXXXX-3'

3'-X<u>XXXXXXXXXXXXXXXXXXXXXXXX</u>-5' wherein "X"=RNA and "<u>X</u>"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X<u>XXXXXXXXXXXXXXXXXXXXXXXX</u>-5' wherein "X"=RNA, "<u>X</u>"=2'-O-methyl RNA, and "D"=DNA. The top strand is the sense strand, and the bottom strand is the antisense strand. This modification pattern is also referred to herein as the "AS-M17*" or "M17*" modification pattern.

In further embodiments, the DsiRNA comprises:

5'-XXXXXXXXXXXXXXXXXXXXXXXXX-3'

3'-X<u>XXXXXXXXXXXXXXXXXXXXXXXX</u>-5' wherein "X"=RNA and "<u>X</u>"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X<u>XXXXXX</u>X<u>XXXXXXXXXXXXXXXXXX</u>-5' wherein "X"=RNA. "<u>X</u>"=2'-O-methyl RNA, and "D"=DNA. The top strand is the sense strand, and the bottom strand is the antisense strand. This modification pattern is also referred to herein as the "AS-M18*" or "M18*" modification pattern.

In additional embodiments, the DsiRNA comprises:

5'-XXXXXXXXXXXXXXXXXXXXXXXXX-3'

3'-X<u>XXXXXXXXXXXXXXXXXXXXXXXX</u>-5' wherein "X"=RNA and "<u>X</u>"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X<u>XXXXXXXXXXXXXXXXXXXXXXXX</u>-5' wherein "X"=RNA, "<u>X</u>"=2'-O-methyl RNA, and "D"=DNA. The top strand is the sense strand, and the bottom strand is the antisense strand. This modification pattern is also referred to herein as the "AS-M19*" or "M19*" modification pattern.

In further embodiments, the DsiRNA comprises:

5'-XXXXXXXXXXXXXXXXXXXXXXXDD-3'

3'-Y<u>XXXXXXXXXXXXXXXXXXXXXXXX</u>-5' wherein "X"=RNA. "<u>X</u>"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXXX-3'

3'-X<u>XXXXXXXXXX</u>X<u>XXXXXXXXXXXX</u>XX-5' wherein "X"=RNA and "<u>X</u>"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X<u>XXXXXXXXXX</u>X<u>XXXXXXXXXXXXXX</u>-5' wherein "X"=RNA, "<u>X</u>"=2'-O-methyl RNA, and "D"=DNA. The top strand is the sense strand, and the bottom strand is the antisense strand. This modification pattern is also referred to herein as the "AS-M20*" or "M20*" modification pattern.

In additional embodiments, the DsiRNA comprises:

5'-XXXXXXXXXXXXXXXXXXXXXXXXX-3'

3'-X<u>XXXXXXXXXXXXXXXXXXXXXXX</u>XXX-5' wherein "X"=RNA and "<u>X</u>"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X<u>XXXXXXXXXXXXXXXXXXXXXX</u>XXX-5' wherein "X"=RNA, "<u>X</u>"=2'-O-methyl RNA, and "D"=DNA. The top strand is the sense strand, and the bottom strand is the antisense strand. This modification pattern is also referred to herein as the "AS-M22*" or "M22*" modification pattern.

In further embodiments, the DsiRNA comprises:

5'-XXXXXXXXXXXXXXXXXXXXXXXXX-3'

3'-X<u>XXXX</u>X<u>XXXXXXXX</u>X<u>XXXXXXXXX</u>XX-5' wherein "X"=RNA and "<u>X</u>"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X<u>XXXX</u>X<u>XXXXXXXX</u>X<u>XXXXXXXXX</u>XX-5' wherein "X"=RNA, "<u>X</u>"=2'-O-methyl RNA, and "D"=DNA. The top strand is the sense strand, and the bottom strand is the antisense strand. This modification pattern is also referred to herein as the "AS-M24*" or "M24*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA. "X"=2'-O-methyl RNA, and "D"=DNA. The top strand is the sense strand, and the bottom strand is the antisense strand. This modification pattern is also referred to herein as the "AS-M25*" or "M25*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M26*" or "M26*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M27*" or "M27*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA. "X"=2'-O-methyl RNA, and "D"=DNA. The top strand is the sense strand, and the bottom strand is the antisense strand. This modification pattern is also referred to herein as the "AS-M28*" or "M28*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M29*" or "M29*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M34*" or "M34*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M35*" or "M35*" modification pattern.

In additional embodiments, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M37*" or "M37*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M38*" or "M38*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M40*" or "M40*" modification pattern.

In additional embodiments, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M41*" or "M41*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M36*" or "M36*" modification pattern.

In additional embodiments, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M42*" or "M42*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M43*" or "M43*" modification pattern.

In additional embodiments, the DsiRNA comprises:

5'-XXXXXXXXXXXXXXXXXXXXXXXXX-3'

3'-X̲XXXXXXXXXXXXXXXX̲XXXXXXXXX̲X̲X̲X̲-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X̲XXXXXXXXXXXXXXXX̲XXXXXXXXX̲X̲X̲X̲-5' wherein "X"=RNA, "X̲"=2'-O-methyl RNA, and "D"=DNA. The top strand is the sense strand, and the bottom strand is the antisense strand. This modification pattern is also referred to herein as the "AS-M44*" or "M44*" modification pattern.

In further embodiments, the DsiRNA comprises:

5'-XXXXXXXXXXXXXXXXXXXXXXXXX-3'

3'-X̲XXXXXXXXXXXXXXXXX̲XXXXXXXX̲X̲X̲X̲-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X̲XXXXXXXXXXXXXXXXX̲XXXXXXXX̲X̲X̲X̲-5' wherein "X"=RNA, "X̲"=2'-O-methyl RNA, and "D"=DNA. The top strand is the sense strand, and the bottom strand is the antisense strand. This modification pattern is also referred to herein as the "AS-M46*" or "M46*" modification pattern.

In additional embodiments, the DsiRNA comprises:

5'-XXXXXXXXXXXXXXXXXXXXXXXXX-3'

3'-XX̲XXXXXXXXXXXXXXXXXXXXXXXX-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XX̲XXXXXXXXXXXXXXXXXXXXXXXX-3' wherein "X"=RNA, "X̲"=2'-O-methyl RNA, and "D"=DNA. The top strand is the sense strand, and the bottom strand is the antisense strand. This modification pattern is also referred to herein as the "AS-M47*" or "M47*" modification pattern.

In further embodiments, the DsiRNA comprises:

5'-XXXXXXXXXXXXXXXXXXXXXXXXX-3'

3'-X̲XXXXXXXXXXXXXXX̲XXXXXXXXXXX-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X̲XXXXXXXXXXXXXXX̲XXXXXXXXXXX-3' wherein "X"=RNA, "X̲"=2'-O-methyl RNA, and "D"=DNA. The top strand is the sense strand, and the bottom strand is the antisense strand. This modification pattern is also referred to herein as the "AS-M48*" or "M48*" modification pattern.

In additional embodiments, the DsiRNA comprises:

5'-XXXXXXXXXXXXXXXXXXXXXXXXX-3'

3'-X̲XXXXXXXXXXXXXXXX̲XXXXXXXXXX-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X̲XXXXXXXXXXXXXXXX̲XXXXXXXXXX-5' wherein "X"=RNA, "X̲"=2'-O-methyl RNA, and "D"=DNA. The top strand is the sense strand, and the bottom strand is the antisense strand. This modification pattern is also referred to herein as the "AS-M52*" or "M52*" modification pattern.

In further embodiments, the DsiRNA comprises:

5'-XXXXXXXXXXXXXXXXXXXXXXXXX-3'

3'-X̲XXXXXXXXXXXXXXXXX̲XXXXXXXXX-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X̲XXXXXXXXXXXXXXXXX̲XXXXXXXXX-5' wherein "X"=RNA, "X̲"=2'-O-methyl RNA, and "D"=DNA. The top strand is the sense strand, and the bottom strand is the antisense strand. This modification pattern is also referred to herein as the "AS-M54*" or "M54*" modification pattern.

In additional embodiments, the DsiRNA comprises:

5'-XXXXXXXXXXXXXXXXXXXXXXXXX-3'

3'-X̲XXXXXXXXXXXXXXXXXX̲XXXXXXXX-5' wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M55*" or "M55*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M56*" or "M56*" modification pattern.

In additional embodiments, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M57*" or "M57*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M58*" or "M58*" modification pattern.

In additional embodiments, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M59*" or "M59*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M60*" or "M60*" modification pattern.

In additional embodiments, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M61*" or "M61*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M62*" or "M62*" modification pattern.

In additional embodiments, the DsiRNA comprises:

```
5'-XXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M63*" or "M63*" modification pattern.

In further embodiments, the DsiRNA comprises:

```
5'-XXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
3'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M64*" or "M64*" modification pattern.

In additional embodiments, the DsiRNA comprises:

```
5'-XXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M65*" or "M65*" modification pattern.

In further embodiments, the DsiRNA comprises:

```
5'-XXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M66*" or "M66*" modification pattern.

In additional embodiments, the DsiRNA comprises:

```
5'-XXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
3'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M67*" or "M67*" modification pattern.

In further embodiments, the DsiRNA comprises:

```
5'-XXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M68*" or "M68*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M69*" or "M69*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
3'-XXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M70*" or "M70*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M71*" or "M71*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M72*" or "M72*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
3'-XXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M73*" or "M73*" modification pattern.

Additional exemplary antisense strand modifications include the following:

```
"AS-M74"
3'-XXXXXXXXXXXXXXXXXXXXXXXXXXX-5'

"AS-M75"
3'-XXXXXXXXXXXXXXXXXXXXXXXXXXX-5'

"AS-M76"
3'-XXXXXXXXXXXXXXXXXXXXXXXXXXX-5'

"AS-M77"
3'-XXXXXXXXXXXXXXXXXXXXXXXXXXX-5'

"AS-M78"
3'-XXXXXXXXXXXXXXXXXXXXXXXXXXX-5'

"AS-M79"
3'-XXXXXXXXXXXXXXXXXXXXXXXXXXX-5'

"AS-M80"
3'-XXXXXXXXXXXXXXXXXXXXXXXXXXX-5'

"AS-M81"
3'-XXXXXXXXXXXXXXXXXXXXXXXXXXX-5'

"AS-M82"
3'-XpXXXXXXXXXXXXXXXXXXXXXXXXXXX-5'

"AS-M83"
3'-XpXXXXXXXXXXXXXXXXXXXXXXXXXXX-5'

"AS-M84"
3'-XXXXXXXXXXXXXXXXXXXXXXXXXXX-5'

"AS-M85"
3'-XXXXXXXXXXXXXXXXXXXXXXXXXXX-5'
```

```
"AS-M88"
3'-FFFXXXXXXXXXXXXXXXXXXXXFFFF-5'

"AS-M89"
3'-XXXXFXXXFXFXXXXXXXXXXXXXXX-5'

"AS-M90"
3'-FFFXFXFXFXFXFXFXFXXXXXXFFFF-5'

"AS-M91"
3'-FFFXXXXXXXXXXXXXXXXXXXXXFF-5'

"AS-M92"
3'-XXXXXFXXXXXFXFXXXXXXXXXXX-5'

"AS-M93"
3'-FFFXFXXXXXXXXXXXFXXXXXXXX-5'

"AS-M94"
3'-FFFXFXFXXXXXFXFXFXFXXXXFFFF-5'

"AS-M95"
3'-FFFXFXFXFXFXFXFXFXXXXXXFFFF-5'

"AS-M96"
3'-FFFXFXFXFXFXFXFXFXXXXXXFFFpF-5'

"AS-M210"
3'-XXXXXXXXXXXXXXXXXXXXXXXXXX-5'

"AS-M74*"
3'-XXXXXXXXXXXXXXXXXXXXXXXXXX-5'

"AS-M75*"
3'-XXXXXXXXXXXXXXXXXXXXXXXXXX-5'

"AS-M76*"
3'-XXXXXXXXXXXXXXXXXXXXXXXXXX-5'

"AS-M77*"
3'-XXXXXXXXXXXXXXXXXXXXXXXXXX-5'

"AS-M78*"
3'-XXXXXXXXXXXXXXXXXXXXXXXXXX-5'

"AS-M79*"
3'-XXXXXXXXXXXXXXXXXXXXXXXXXX-5'

"AS-M80*"
3'-XXXXXXXXXXXXXXXXXXXXXXXXXX-5'

"AS-M82*"
3'-XpXXXXXXXXXXXXXXXXXXXXXXXXX-5'

"AS-M83*"
3'-XpXXXXXXXXXXXXXXXXXXXXXXXXX-5'

"AS-M84*"
3'-XXXXXXXXXXXXXXXXXXXXXXXXXX-5'

"AS-M88*"
3'-XFFXXXXXXXXXXXXXXXXXXFFFF-5'

"AS-M89*"
3'-XXXXFXXXFXFXXXXXXXXXXXXXX-5'

"AS-M90*"
3'-XFFXFXFXFXFXFXFXFXXXXXXFFFF-5'

"AS-M91*"
3'-XFFXXXXXXXXXXXXXXXXXXXXFF-5'

"AS-M92*"
3'-XXXXXFXXXXXFXFXXXXXXXXXXX-5'

"AS-M93*"
3'-XFFXFXXXXXXXXXXXFXXXXXXXX-5'

"AS-M94*"
3'-XFFXFXXXXXXFXFXFXFXXXXFFFF-5'

"AS-M95*"
3'-XFFXFXFXFXFXFXFXXXXXXFFFF-5'

"AS-M96*"
3'-XFFXFXFXFXFXFXFXXXXXXFFFpF-5'

"AS-M210*"
3'-XXXXXXXXXXXXXXXXXXXXXXXXXX-5'

"AS-M101"
3'-XpXXXXXXXXXXXXXXXXXXXXXpX-5'

"AS-M104"
3'-XpXXXXXXXXXXXXXXXXXXXXXpX-5'

"AS-M104*"
3'-XpXXXXXXXXXXXXXXXXXXXXXXpX-5'

"AS-M105"
3'-XpFpXFXFXFXFXFXFXFXFXFFXXXpX-5'

"AS-M105*"
3'-XpFpXFXFXFXFXFXFXFXFXFFXXXpX-5'

"AS-M106"
3'-XpXXXXXXXXXXXXXXXXXXXXXXpX-5'

"AS-M106*"
3'-XpXXXXXXXXXXXXXXXXXXXXXXpX-5'

"AS-M107"
3'-XXpXXXXXXXXXXXXXXXXXXXXXX-5'

"AS-M107*"
3'-XXpXXXXXXXXXXXXXXXXXXXXXX-5'

"AS-M108"
3'-ba-XXXXXXXXXXXXXXXXXXXXXXXX-5' (ba = inverted abasic for F7 stabilizaton at 3' end)

"As-M108*"
3'-ba-XXXXXXXXXXXXXXXXXXXXXXXXX-5' (ba = inverted abasic for F7 stabilization at 3' end)

"AS-M109"
3'-XDXXXXXXXXXXXXXXXXXXXXXXX-5'

"AS-M110"
3'-XpXXFXFXXXXXXXXXXXXXXXXpX-5'

"AS-M110*"
3'-XpXXFXFXXXXXXXXXXXXXXXXXpX-5'

"AS-M111"
3'-XpXXFXFXFXXXXXFXFXFXXXXXXpX-5'

"AS-M112"
3'-XpXXFXFXFFXXXXXXXXFXXXXXXpX-5'

"AS-M113"
3'-XpXXFXFXFFXXFXXXXXFXXXXXXpX-5'

"AS-M114"
3'-XpXXFXFXFFFFFXXXXXXFXXXXXXpX-5'

"AS-M115"
3'-XpXXFXFFFFFFXXXXXXFXXFXXXpX-5'

"AS-M116"
3'-XpXXFXFXFFFFFXXXXXXFFFFXXXpX-5'

"AS-M117"
3'-XpFXFXFXFXFXFXFXFXFXFXFpX-5'

"AS-M111*"
3'-XpXXFXFXFXXXXXFXFXFXXXXXXpX-5'

"AS-M112*"
3'-XpXXFXFXFFXXXXXXXXFXXXXXXpX-5'
```

"AS-M113*"
3'-XpXXFXFXFFXXFXXXXXXXFXXXXXXpX-5'

"AS-M114*"
3'-XpXXFXFXFFFFXXXXXXXFXXXXXXpX-5'

"AS-M115*"
3'-XpXXFXFXFFFFFXXXXXXXFXXXXXpX-5'

"AS-M116*"
3'-XpXXFXFXFFFFFFXXXXXXXFFFFXXXpX-5'

"AS-M117*"
3'-XpFXFXFXFXFXFXFXFXFXFXFpX-5'

"AS-M120"
3'-XpXXXXXXXXXXXXXXXXXXXXXXXXXpX-5'

"AS-M121"
3'-XpXXXXXXXXXXXXXXXXXXXXXXXXXpX-5'

"AS-M122"
3'-XpXXXXXXXXXXXXXXXXXXXXXXXXXpX-5'

"AS-M123"
3'-XpXXXXXXXXXXXXXXXXXXXXXXXXXpX-5'

"AS-M124"
3'-XpXXXXXXXXXXXXXXXXXXXXXXXXXpX-5'

"AS-M125"
3'-XpXXXXXXXXXXXXXXXXXXXXXXXXXpX-5'

"AS-M126"
3'-XpFpXFXFXXXXXFXFXFXXXFXFpX-5'

"AS-M127"
3'-XpFpXFXFXFXXXXXFXFXFXXXFXFpX-5'

"AS-M128"
3'-XpFpXFXFXFXFXFXFXFXFXFFXXXpX-5'

"AS-M129"
3'-XpFpXFXFXFXFXFXFXFXFXFFFFFpF-5'

"AS-M130"
3'-XpFpXFXFXFXFXFXFXFXFXFXXXFXFpX-5'

"AS-M131"
3'-XpFDXFXFXFXFXFXFXFXFXFXFXFpX-5'

"AS-M132"
3'-XpFpXFXFXFXFXFXFXFXFXFXFXXXXpX-5'

"AS-M133"
3'-XpFpXFXFXFXFXFXFXFXFXFXFXXXXpX-5'

"AS-M134"
3'-XpFpXFXFXFXFXFXFXFXFXFXFFFpF-5'

"AS-M135"
3'-XXXXXXXXXXXXXXXXXXXXXXXXX-5'

"AS-M136"
3'-XXXXXXXXXXXXXXXXXXXXXXXXX-5'

"AS-M137"
3'-XXXXXXXXXXXXXXXXXXXXXXXXX-5'

"AS-M138"
3'-XXXFXFXFXXXXXFXFXFXFXXXXXXX-5'

"AS-M139"
3'-XXXFXFXFFXXXXXXXXXFXXXXX-5'

"AS-M140"
3'-XpXXFXFXFXXXXFXFXFFFXXXXXXpX-5'

"AS-M141"
3'-XpXXFXFXFXFFXXXFFXFXFFFFXXXXXpX-5'

"AS-M142"
3'-XpXXFXFXFXFXFXFXFFFXXXXXpX-5'

"AS-M143"
3'-XpXXFXFFFFFFFFXFXFFFXXXXXXpX-5'

"AS-M144"
3'-XpXXFXFXFXFXFXFXFpXpFpXXXXXpX-5'

"AS-M145"
3'-XXXXXXXXXXXXXXXXFXXXXXXXXXXX-5'

"AS-M146"
3'-XXXXXXXXXXXXXXXFXXXXXXXXXXX-5'

"AS-M147"
3'-XXXXXXFXXXXXXXXXXXXXXXXXXXX-5'

"AS-M148"
3'-XXXXXXXXXFXXXXXXXXXXXXXXXXX-5'

"AS-M149"
3'-XXXXXXXXXXXFXXXXXXXXXXXXXXX-5'

"AS-M150"
3'-XXXXXXXXXXFXFXXXXXXXXXXXXXX-5'

"AS-M151"
3'-XXXXXXXXXXXFXXXFXXXXXXXXXXX-5'

"AS-M152"
3'-XXXXXXXXXXFXXFXXXXXXXXXXXXX-5'

"AS-M153"
3'-XXXXXXXXFXXXXXXXXXXXXXXXXXX-5'

"AS-M154"
3'-XXXXXXXXFXXXXXXXXXXXXXXXXXX-5'

"AS-M155"
3'-XXXXXFXXXXXXXXXXXXXXXXXXXXX-5'

"AS-M156"
3'-XpXXXXXXXXXXXXXXXXXXXXXXXXpX-5'

"AS-M157"
3'-XpXXXXXXXXXXXXXXXXXXXXXXXXpX-5'

"AS-M158"
3'-XpXXFXFFFFXXXFXXFXXFXXXXXXpX-5'

"AS-M159"
3'-XpXXFXFFFFFFFFXXFXXFXXXXXXpX-5'

"AS-M160"
3'-XpXXFXXXFXXXXXFXXFFXXXXXXpX-5'

"AS-M161"
3'-XpXXFXXXFXFXFXFXXFFXXXXXXpX-5'

"AS-M162"
3'-XXXXXXXXFXFXFXXXXXXXXXXXXX-5'

"AS-M163"
3'-XXXXXXXXXXXXXXXXXXXXXXXXX-5'

"AS-M164"
3'-XXXXXXXDXXXXXXXXXXXXXXXXX-5'

"AS-M120*"
3'-XpXXXXXXXXXXXXXXXXXXXXXXXXXpX-5'

"AS-M121*"
3'-XpXXXXXXXXXXXXXXXXXXXXXXXXXpX-5'

"AS-M122*"
3'-XpXXXXXXXXXXXXXXXXXXXXXXXXXpX-5'

"AS-M123*"
3'-XpXXXXXXXXXXXXXXXXXXXXXXXXXpX-5'

```
"AS-M124*"
3'-XpXXXXXXXXXXXXXXXXXXXXXXXXXpX-5'

"AS-M125*"
3'-XpXXXXXXXXXXXXXXXXXXXXXXXXXpX-5'

"AS-M126*"
3'-XpFpXFXFXFXXXXXFXFXFXXXXFXFpX-5'

"AS-M127*"
3'-XpFpXFXFXFXXXXXFXFXFXXXXFXFpX-5'

"AS-M128*"
3'-XpFpXFXFXFXFXFXFXFXFXFFXXXpX-5'

"AS-M129*"
3'-XpFpXFXFXFXFXFXFXFXFXFFFFFF-5'

"AS-M130*"
3'-XpFpXFXFXFXFXFXFXFXFXXXXFXFpX-5'

"AS-M131*"
3'-XpFpXFXFXFXFXFXFXFXFXFXFXFpX-5'

"AS-M132*"
3'-XpFpXFXFXFXFXFXFXFXFXFXXXXpX-5'

"AS-M133*"
3'-XpFpXFXFXFXFXFXFXFXFXFXXXXpX-5'

"AS-M134*"
3'-XpFpXFXFXFXFXFXFXFXFXFXFFFpF-5'

"AS-M135*"
3'-XXXXXXXXXXXXXXXXXXXXXXXXXXXX-5'

"AS-M136*"
3'-XXXXXXXXXXXXXXXXXXXXXXXXXXX-5'

"AS-M137*"
3'-XXXXXXXXXXXXXXXXXXXXXXXXXXX-5'

"AS-M138*"
3'-XXXFXFXFXXXXXFXFXFXFXXXXXXX-5'

"AS-M139*"
3'-XXXFXFXFFXXXXXXXXXFXXXXXXX-5'

"AS-M140*"
3'-XpXXFXFXFXXXXXFXFXFFFXXXXXXpX-5'

"AS-M141*"
3'-XpXXFXFXFFXXXFFXFXFFFXXXXXXpX-5'

"AS-M142*"
3'-XpXXFXFXFXFXFXFXFXFFFXXXXXXpX-5'

"AS-M143*"
3'-XpXXFXFXFFFFFFFXFXFYFXXXXXXpX-5'

"AS-M144*"
3'-XpXXFXFXFXFXFXFXFXFXFpXpFpXXXXXXpX-5'

"AS-M145*"
3'-XXXXXXXXXXXXXXXXFXXXXXXXXXX-5'

"AS-M146*"
3'-XXXXXXXXXXXXXFXXXXXXXXXXXX-5'

"AS-M147*"
3'-XXXXXXFXXXXXXXXXXXXXXXXXXX-5'

"AS-M148*"
3'-XXXXXXXXXFXXXXXXXXXXXXXXXX-5'

"AS-M149*"
3'-XXXXXXXXXFXXXXXXXXXXXXXXXX-5'

"AS-M150*"
3f-XXXXXXXXFXFXXXXXXXXXXXXXX-5'

"AS-M151*"
3'-XXXXXXXXXXXFXXXFXXXXXXXXXXX-5'

"AS-M152*"
3'-XXXXXXXXXXFXXXFXXXXXXXXXXX-5'

"AS-M153*"
3'-XXXXXXXXFXXXXXXXXXXXXXXXXX-5'

"AS-M154*"
3'-XXXXXXXXFXXXXXXXXXXXXXXXXX-5'

"AS-M155*"
3'-XXXXXXFXXXXXXXXXXXXXXXXXXX-5'

"AS-M156*"
3'-XpXXXXXXXXXXXXXXXXXXXXXXXXpX-5'

"AS-M157*"
3'-XpXXXXXXXXXXXXXXXXXXXXXXXXXpX-5'

"AS-M158*"
3'-XpXXFXFFFFXXXFXXFFXXXXXXpX-5'

"AS-M159*"
3'-XpXXFXFFFFFFFFXXFXXFFXXXXXXpX-5'

"AS-M160*"
3'-XpXXFXXXFXXXXXFXFXXFXXXXXXpX-5'

"AS-M161*"
3'-XpXXFXXXFXFXFXFXXFXXFXXXXXXpX-5'

"AS-M162*"
3'-XXXXXXXXFXFXFXXXXXXXXXXXXX-5'

"AS-M163*"
3'-XXXXXXXXXXXXXXXXXXXXXXXXXXX-5'

"AS-M164*"
3'-XXXXXXXDXXXXXXXXXXXXXXXXXX-5'

"AS-M211"
3'-XXXXXXXXXXXXXXXXXXXXXXXXXX-5'

"AS-M212"
3'-XXXXXXXXXXXXXXXXXXXXXXXXXX-5'

"AS-M215"
3'-XXXXXXXXXXXXXXXXXXXXXXXXXX-5'

"AS-M216"
3'-XXXXXXXXXXXXXXXXXXXXXXXXXX-5'

"AS-M217"
3'-XXXXXXXXXXXXXXXXXXXXXXXXXX-5'

"AS-M218"
3'-XXXXXXXXXXXXXXXXXXXXXXXXXX-5'

"AS-M219"
3'-XXXXXXXXXXXXXXXXXXXXXXXXXX-5'

"AS-M220"
3'-XXXXXXXXXXXXXXXXXXXXXXXXXX-5'

"AS-M221"
3'-XXXXXXXXXXXXXXXXXXXXXXXXXX-5'

"AS-M222"
3'-XXXXXXXXXXXXXXXXXXXXXXXXXX-5'

"AS-M223"
3'-XXXXXXXXXXXXXXXXXXXXXXXXXX-5'

"AS-M224"
3'-XXXXXXXXXXXXXXXXXXXXXXXXXX-5'

"AS-M225"
3'-XXXXXXXXXXXXXXXXXXXXXXXXXX-5'
```

"AS-M226"
3'-XXXXXXXXXXXXXXXXXXXXXXXXX-5'

"AS-M230"
3'-XXXXXXXXXXXXXXXXXXXXXXXXX-5'

"AS-M231"
3'-XXXXXXXXXXXXXXXXXXXXXXXXX-5'

"AS-M232"
3'-XXXXXXXXXXXXXXXXXXXXXXXXX-5'

"AS-M233"
3'-XXXXXXXXXXXXXXXXXXXXXXXXX-5'

"AS-M234"
3'-XXXXXXXXXXXXXXXXXXXXXXXXX-5'

"AS-M235"
3'-XXXXXXXXXXXXXXXXXXXXXXXXX-5'

"AS-M236"
3'-XXXXXXXXXXXXXXXXXXXXXXXXX-5'

"AS-M237"
3'-XXXXXXXXXXXXXXXXXXXXXXXXX-5'

"AS-M238"
3'-XXXXXXXXXXXXXXXXXXXXXXXXX-5'

"AS-M239"
3'-XXXXXXXXXXXXXXXXXXXXXXXXX-5'

"AS-M240"
3'-XXXXXXXXXXXXXXXXXXXXXXXXX-5'

"AS-M241"
3'-XXXXXXXXXXXXXXXXXXXXXXXXX-5'

"AS-M242"
3'-XXXXXXXXXXXXXXXXXXXXXXXXX-5'

"AS-M243"
3'-XpXXXXXXXXXXXXXXXXXXXXXXXpX-5'

"AS-M244"
3'-XpXXXXXXXXXXXXXXXXXXXXXXXpX-5'

"AS-M245"
3'-XpXXXXXXXXXXXXXXXXXXXXXXXpX-5'

"AS-M246"
3'-XpXXXXXXXXXXXXXXXXXXXXXXXpX-5'

"AS-M247"
3'-XpXXXXXXXXXXXXXXXXXXXXXXXpX-5'

"AS-M248"
3'-XpXXXXXXXXXXXXXXXXXXXXXXXpX-5'

"AS-M249"
3'-XpXXXXXXXXXXXXXXXXXXXXXXXpX-5'

"AS-M250"
3'-XpXXXXXXXXXXXXXXXXXXXXXXXpX-5'

"AS-M251"
3'-XpXXXXXXXXXXXXXXXXXXXXXXXpX-5'

"AS-M252"
3'-XpXXXXXXXXXXXXXXXXXXXXXXXpX-5'

"AS-M253"
3'-XpXXXXXXXXXXXXXXXXXXXXXXXpX-5'

"AS-M254"
3'-XpXXXXXXXXXXXXXXXXXXXXXXXpX-5'

"AS-M255"
3'-XpXXXXXXXXXXXXXXXXXXXXXXXpX-5'

"AS-M211*"
3'-XXXXXXXXXXXXXXXXXXXXXXXXX-5'

"AS-M212*"
3'-XXXXXXXXXXXXXXXXXXXXXXXXX-5'

"AS-M215*"
3'-XXXXXXXXXXXXXXXXXXXXXXXXX-5'

"AS-M216*"
3'-XXXXXXXXXXXXXXXXXXXXXXXXX-5'

"AS-M217*"
3'-XXXXXXXXXXXXXXXXXXXXXXXXX-5'

"AS-M218*"
3'-XXXXXXXXXXXXXXXXXXXXXXXXX-5'

"AS-M219*"
3'-XXXXXXXXXXXXXXXXXXXXXXXXX-5'

"AS-M220*"
3'-XXXXXXXXXXXXXXXXXXXXXXXXX-5'

"AS-M221*"
3'-XXXXXXXXXXXXXXXXXXXXXXXXX-5'

"AS-M222*"
3'-XXXXXXXXXXXXXXXXXXXXXXXXX-5'

"AS-M223*"
3'-XXXXXXXXXXXXXXXXXXXXXXXXX-5'

"AS-M224*"
3'-XXXXXXXXXXXXXXXXXXXXXXXXX-5'

"AS-M225*"
3'-XXXXXXXXXXXXXXXXXXXXXXXXX-5'

"AS-M226*"
3'-XXXXXXXXXXXXXXXXXXXXXXXXX-5'

"AS-M230*"
3'-XXXXXXXXXXXXXXXXXXXXXXXXX-5'

"AS-M231*"
3'-XXXXXXXXXXXXXXXXXXXXXXXXX-5'

"AS-M232*"
3'-XXXXXXXXXXXXXXXXXXXXXXXXX-5'

"AS-M233*"
3'-XXXXXXXXXXXXXXXXXXXXXXXXX-5'

"AS-M234*"
3'-XXXXXXXXXXXXXXXXXXXXXXXXX-5'

"AS-M235*"
3'-XXXXXXXXXXXXXXXXXXXXXXXXX-5'

"AS-M236*"
3'-XXXXXXXXXXXXXXXXXXXXXXXXX-5'

"AS-M237*"
3'-XXXXXXXXXXXXXXXXXXXXXXXXX-5'

"AS-M238*"
3'-XXXXXXXXXXXXXXXXXXXXXXXXX-5'

"AS-M239*"
3'-XXXXXXXXXXXXXXXXXXXXXXXXX-5'

"AS-M240*"
3'-XXXXXXXXXXXXXXXXXXXXXXXXX-5'

"AS-M241*"
3'-XXXXXXXXXXXXXXXXXXXXXXXXX-5'

"AS-M242*"
3'-XXXXXXXXXXXXXXXXXXXXXXXXX-5'

```
"AS-M243*"
3'-XpXXXXXXXXXXXXXXXXXXXXXXXXXpX-5'

"AS-M244*"
3'-XpXXXXXXXXXXXXXXXXXXXXXXXXXpX-5'

"AS-M245*"
3'-XpXXXXXXXXXXXXXXXXXXXXXXXXXpX-5'

"AS-M246*"
3'-XpXXXXXXXXXXXXXXXXXXXXXXXXXpX-5'

"AS-M247*"
3'-XpXXXXXXXXXXXXXXXXXXXXXXXXXpX-5'

"AS-M248*"
3'-XpXXXXXXXXXXXXXXXXXXXXXXXXXpX-5'

"AS-M249*"
3'-XpXXXXXXXXXXXXXXXXXXXXXXXXXpX-5'

"AS-M250*"
3'-XpXXXXXXXXXXXXXXXXXXXXXXXXXpX-5'

"AS-M251*"
3'-XpXXXXXXXXXXXXXXXXXXXXXXXXXpX-5'

"AS-M252*"
3'-XpXXXXXXXXXXXXXXXXXXXXXXXXXpX-5'

"AS-M253*"
3'-XpXXXXXXXXXXXXXXXXXXXXXXXXXpX-5'

"AS-M254*"
3'-XpXXXXXXXXXXXXXXXXXXXXXXXXXpX-5'

"AS-M255*"
3'-XpXXXXXXXXXXXXXXXXXXXXXXXXXpX-5'
``` where "X"=RNA, "X"=2'-O-methyl RNA, "D"=DNA, "F"=2'-Fluoro NA and "p"=Phosphorothioate linkage.

In certain additional embodiments, the antisense strand of selected dsRNAs of the invention are extended, optionally at the 5' end, with an exemplary 5' extension of base "AS-M8". "AS-M17" and "AS-M48" modification patterns respectively represented as follows:

```
"AS-M8, extended"
                                  (SEQ ID NO: 14860)
3'-XXXXXXXXXXXXXXXXXXXXXXXXXXXUAGCUAUCGT-5'

"AS-M17, extended"
                                  (SEQ ID NO: 14860)
3'-XXXXXXXXXXXXXXXXXXXXXXXXXXXUAGCUAUCGT-5'

"AS-M48, extended"
                                  (SEQ ID NO: 14860)
3'-XXXXXXXXXXXXXXXXXXXXXXXXXXXUAGCUAUCGT-5'
``` where "X"=RNA; "X"=2'-O-methyl RNA; "F"=2'-Fluoro NA and "A" in bold, italics indicates a 2'-Fluoro-adenine residue.

In certain embodiments, the sense strand of a DsiRNA of the invention is modified-specific exemplary forms of sense strand modifications are shown below, and it is contemplated that such modified sense strands can be substituted for the sense strand of any of the DsiRNAs shown above to generate a DsiRNA comprising a below-depicted sense strand that anneals with an above-depicted antisense strand. Exemplary sense strand modification patterns include:

```
"SM1"
5'-XXXXXXXXXXXXXXXXXXXXXXXDD-3'

"SM2"
5'-XXXXXXXXXXXXXXXXXXXXXXXDD-3'

"SM3"
5'-XXXXXXXXXXXXXXXXXXXXXXXDD-3'

"SM4"
5'-XXXXXXXXXXXXXXXXXXXXXXXDD-3'

"SM5"
5'-XXXXXXXXXXXXXXXXXXXXXXXDD-3'

"SM6"
5'-XXXXXXXXXXXXXXXXXXXXXXXDD-3'

"SM7"
5'-XXXXXXXXXXXXXXXXXXXXXXXDD-3'

"SM8"
5'-XXXXXXXXXXXXXXXXXXXXXXXDD-3'

"SM9"
5'-XXXXXXXXXXXXXXXXXXXXXXXDD-3'

"SM10"
5'-XXXXXXXXXXXXXXXXXXXXXXXDD-3'

"SM11"
5'-XXXXXXXXXXXXXXXXXXXXXXXDD-3'

"SM12"
5'-XXXXXXXXXXXXXXXXXXXXXXXDD-3'

"SM13"
5'-XXXXXXXXXXXXXXXXXXXXXXXDD-3'

"SM14"
5'-XXXXXXXXXXXXXXXXXXXXXXXDD-3'

"SM15"
5'-XXXXXXXXXXXXXXXXXXXXXXXDD-3'

"SM16"
5'-XXXXXXXXXXXXXXXXXXXXXXXDD-3'

"SM17"
5'-XXXXXXXXXXXXXXXXXXXXXXXDD-3'

"SM18"
5'-XXXXXXXXXXXXXXXXXXXXXXXDD-3'

"SM19"
5'-XXXXXXXXXXXXXXXXXXXXXXXDD-3'

"SM20"
5'-XXXXXXXXXXXXXXXXXXXXXXXDD-3'

"SM21"
5'-XXXXXXXXXXXXXXXXXXXXXXXDD-3'

"SM23"
5'-XXXXXXXXXXXXXXXXXXXXXXXDD-3'

"SM24"
5'-XXXXXXXXXXXXXXXXXXXXXXXDD-3'

"SM25"
5'-XXXXXXXXXXXXXXXXXXXXXXXDD-3'

"SM30"
5'-XXXXXXXXXXXXXXXXXXXXXXXDD-3'

"SM31"
5'-XXXXXXXXXXXXXXXXXXXXXXXDD-3'

"SM32"
5'-XXXXXXXXXXXXXXXXXXXXXXXDD-3'

"SM33"
5'-XXXXXXXXXXXXXXXXXXXXXXXDD-3'
```

"SM34"
5'-XXXXXXXXXXXXXXXXXXXXXXXXXDD-3'

"SM35"
5'-XXXXXXXXXXXXXXXXXXXXXXXXXDD-3'

"SM36"
5'-XXXXXXXXXXXXXXXXXXXXXXXXXDD-3'

"SM37"
5'-XXXXXXXXXXXXXXXXXXXXXXXXXDD-3'

"SM38"
5'-XXXXXXXXXXXXXXXXXXXXXXXXXDD-3'

"SM39"
5'-XXXXXXXXXXXXXXXXXXXXXXXXXDD-3'

"SM40"
5'-XXXXXXXXXXXXXXXXXXXXXXXXXDD-3'

"SM41"
5'-XXXXXXXXXXXXXXXXXXXXXXXXXDD-3'

"SM42"
5'-XXXXXXXXXXXXXXXXXXXXXXXXXDD-3'

"SM43"
5'-XXXXXXXXXXXXXXXXXXXXXXXXXDD-3'

"SM44"
5'-XXXXXXXXXXXXXXXXXXXXXXXXXDD-3'

"SM45", "SM47"
5'-XXXXXXXXXXXXXXXXXXXXXXXXXDD-3'

"SM46"
5'-XXXXXXXXXXXXXXXXXXXXXXXXXDD-3'

"SM48"
5'-XXXXXXXXXXXXXXXXXXXXXXXXXDD-3'

"SM49"
5'-XXXXXXXXXXXXXXXXXXXXXXXXXDD-3'

"SM50"
5'-XXXXXXXXXXXXXXXXXXXXXXXXXDD-3'

"SM51"
5'-XXXXXXXXXXXXXXXXXXXXXXXXXDD-3'

"SM52"
5'-XXXXXXXXXXXXXXXXXXXXXXXXXDD-3'

"SM53"
5'-XXXXXXXXXXXXXXXXXXXXXXXXXDD-3'

"SM54"
5'-XXXXXXXXXXXXXXXXXXXXXXXXXDD-3'

"SM55"
5'-XXXXXXXXXXXXXXXXXXXXXXXXXDD-3'

"SM56"
5'-XXXXXXXXXXXXXXXXXXXXXXXXXDD-3'

"SM57"
5'-XXXXXXXXXXXXXXXXXXXXXXXXXDD-3'

"SM58"
5'-XXXXXXXXXXXXXXXXXXXXXXXXXDD-3'

"SM59"
5'-XXXXXXXXXXXXXXXXXXXXXXXXXDD-3'

"SM60"
5'-XXXXXXXXXXXXXXXXXXXXXXXXXDD-3'

"SM61"
5'-XXXXXXXXXXXXXXXXXXXXXXXXXDD-3'

"SM62"
5'-XXXXXXXXXXXXXXXXXXXXXXXXXDD-3'

"SM63"
5'-XXXXXXXXXXXXXXXXXXXXXXXXXDD-3'

"SM64"
5'-XXXXXXXXXXXXXXXXXXXXXXXXXDD-3'

"SM65"
5'-XXXXXXXXXXXXXXXXXXXXXXXXXDD-3'

"SM66"
5'-XXXXXXXXXXXXXXXXXXXXXXXXXpDpD-3'

"SM67"
5'-XpXXXXXXXXXXXXXXXXXXXXXXXXXDD-3'

"SM68"
5'-XpXXXXXXXXXXXXXXXXXXXXXXXXXpDpD-3'

"SM69"
5'-DXXXXXXXXXXXXXXXXXXXXXXXXXDD-3'

"SM70"
5'-DpXXXXXXXXXXXXXXXXXXXXXXXXXpDpD-3'

"SM71"
5'-DXDXXXXXXXXXXXXXXXXXXXXXXXDD-3'

"SM72"
5'-DpXDXXXXXXXXXXXXXXXXXXXXXXXDD-3'

"SM73"
5'-XDXXXXXXXXXDXXXXXXXXXXXXDD-3'

"SM74"
5'-XpXDXXXXXXXXDXXXXXXXXXXXDD-3'

"SM75"
5'-DXDXXXXXXXXXDXXXXXDXXXXDD-3'

"SM76"
5'-DpXDXXXXXXXXXDXXXXXDXXXXDD-3

"SM77"
5'-XpXpXXXXXXXXXXXXXXXXXXXXXXXDD-3'

"SM78"
5'-XpXpXXXXXXXXXXXXXXXXXXXXXXXpDpD-3'

"SM79"
5'-DpXpDXXXXXXXXXXXXXXXXXXXXXXDD-3'

"SM80"
5'-XpXpDXXXXXXXXXDXXXXXXXXXXDD-3'

"SM81"
5'-DXDXXXDXXXXXDXXXXXDXXXXDD-3'

"SM82"
5'-DpXDXXXDXXXXXDXXXXXDXXXXpDpD-3'

"SM83"
5' C3 spacer-XXXXXXXXXXXXXXXXXXXXXXXXXDD-3'

"SM84"
5' C3 spacer-XDXXXXXXXXXDXXXXXXXXXXXDD-3'

"SM85"
5' C3 spacer-XXXXXXXXXXXXXXXXXXXXXXXXXpDpD-3'

"SM86"
5'-XXXXXXXXXXXXXXXXXXXXXXXXXpDpD-3'

"SM87"
5'-XpXXXXXXXXXXXXXXXXXXXXXXXXXDD-3'

"SM88"
5'-XpXXXXXXXXXXXXXXXXXXXXXXXXXpDpD-3'

"SM89"
5'-DXXXXXXXXXXXXXXXXXXXXXXDD-3'

"SM90"
5'-DpXXXXXXXXXXXXXXXXXXXXXXpDpD-3'

"SM91"
5'-DXDXXXXXXXXXXXXXXXXXXXXDD-3'

"SM92"
5'-DpXDXXXXXXXXXXXXXXXXXXXXDD-3'

"SM93"
5'-XXDXXXXXXXXXDXXXXXXXXXXDD-3'

"SM94"
5'-XpXDXXXXXXXXXDXXXXXXXXXXDD-3'

"SM95"
5'-DXDXXXXXXXXXDXXXXXDXXXXDD-3'

"SM96"
5'-DpXDXXXXXXXXXDXXXXXDXXXXDD-3'

"SM97"
5'-XpXpXXXXXXXXXXXXXXXXXXXXXDD-3'

"SM98"
5'-XpXpXXXXXXXXXXXXXXXXXXXXXpDpD-3'

"SM99"
5'-DpXpDXXXXXXXXXXXXXXXXXXXXDD-3'

"SM100"
5'-XpXpDXXXXXXXXXDXXXXXXXXXXDD-3'

"SM101"
5'-DXDXXXXXXXXXDXDXXXDDXXDDD-3'

"SM102"
5'-DpXDXXXDXXXXXDXXXXXDXXXXpDpD-3'

"SM103"
5' C3 spacer-XXXXXXXXXXXXXXXXXXXXXXDD-3'

"SM104"
5' C3 spacer-XXDXXXXXXXXXDXXXXXXXXXXDD-3'

"SM105"
5' C3 spacer-XXXXXXXXXXXXXXXXXXXXXXXpDpD-3'

"SM106"
5'-XXXXXXXXXXXXXXXXXXXXXXXDD-3'

"SM107"
5'-XXXXXXXXXXXXXXXXXXXXXXXDD-3'

"SM108"
5'-XXXXXXXXXXXXXXXXXXXXXXXDD-3'

"SM110"
5'-XFXXXXXXXXXXXXXXXFXXXXXDD-3'

"SM111"
5'-XXXFXFXXXXXXXFXXXXXXXXXDD-3'

"SM112"
5'-XFXFXFXFXXXFXFXFXFXXXXXDD-3'

"SM113"
5'-XpFXFXFXFXXXXFXFXFXFXXXXXpDpD-3'

"SM114"
5'-XFXXXXXXXXXXXXXXXXXXXXXDD-3'

"SM115"
5'-XXXXFFXFXXXXFXFXXXXXXXXDD-3'

"SM116"
5'-XFXFXXXXXXXXXXXXFXXXXXXDD-3'

"SM117"
5'-XFXFFFXFXXXFXFXFFFXXXXXDD-3'

"SM118"
5'-XFXFXFXFXXXXFXFXFXFXXXXXDD-3'

"SM119"
5'-XpFXFXFXFXXXXFXFXFXFXXXXXpDpD-3'

"SM250"
5'-XXXXXXXXXXXXXXXXXXXXXXXDD-3'

"SM251"
5'-XXXXXXXXXXXXXXXXXXXXXXXDD-3'

"SM252"
5'-XXXXXXXXXXXXXXXXXXXXXXXDD-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

-continued
5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

5'-XXXXXXXXXXXXXXXXXXXXXXXXX-3'

"SM22"
5'-XXXXXXXXXXXXXXXXXXXXXXXXX-3'

5'-XXXXXXXXXXXXXXXXXXXXXXXXX-3

5'-XXXXXXXXXXXXXXXXXXXXXXXXX-3'

5'-XXXXXXXXXXXXXXXXXXXXXXXXX-3'

"SM120"
5'-XpXXXXXXXXXXXXXXXXXXXXXXXDpD-3

"SM121"
5'-FpXFXFXFXFXFXFXFXFXFXXDpD-3'

"SM122"
5'-XpXXXXXXXXXXXXXXXXXXXXXXXDpD-3'

"SM123"
5'-XpXXXXXXXXXXXXXXXXXXXXXXXDpD-3'

"SM124"
5'-FpXFXXXFXXXXXXXXXXXXXXXXpDpD-3'

"SM125"
5'-FpXFXXXFXXXXXFXFXXXXXXXXpDpD-3'

"SM126"
5'-FpXFXXXFXFFFXFXFXXXXXXXXpDpD-3'

"SM127"
5'-FpXFXXXFXFFFXFXFXXXFFXXXpDpD-3'

"SM128"
5'-FpXFXXXFXFFFXFXFXXXFFXXFpDpD-3'

"SM129"
5'-FpXFXXXFXFFFXFXFXXXFFFFpDpD-3'

"SM130"
5'-FpXFXFXFXFXFXFXFXFXFXFpDpD-3'

5'-XpXXXXXXXXXXXXXXXXXXXXXXXpX-3'

5'-FpXFXFXFXFXFXFXFXFXFXXXXpX-3'

5'-XpXXXXXXXXXXXXXXXXXXXXXXXpX-3'

5'-XpXXXXXXXXXXXXXXXXXXXXXXXpX-3'

5'-FpXFXXXFXXXXXXXXXXXXXXXXpXpX-3'

5'-FpXFXXXFXXXXFXFXXXXXXXXpXpX-3'

-continued
5'-FpXFXXXFXFFFXFXFXXXXXXXXpXpX-3'

5'-FpXFXXXFXFFFXFXFXXXFFXXXpXpX-3'

5'-FpXFXXXFXFFFXFXFXXXFFXXFpXpX-3'

5'-FpXFXXXFXFFFXFXFXXXFFFETpXpX-3'

5'-FpXFXFXFXFXFXFXFXFXFXFpXpX-3'

"SM133"
5'-XpXXXXXXXXXXXXXXXXXXXXXXXpDpD-3'

"SM134"
5'-XpXXXXXXXXXXXXXXXXXXXXXXXpDpD-3'

"SM135"
5'-XpXXXXXXXXXXXXXXXXXXXXXXXpDpD-3'

"SM136"
5'-XpXXXXXXXXXXXXXXXXXXXXXXXpDpD-3'

"SM137"
5'-XpXXXXXXXXXXXXXXXXXXXXXXXpDpD-3'

"SM138"
5'-XpXXXXXXXXXXXXXXXXXXXXXXXpDpD-3'

5'-XpXXXXXXXXXXXXXXXXXXXXXXXpXpX-3'

5'-XpXXXXXXXXXXXXXXXXXXXXXXXpXpX-3'

5'-XpXXXXXXXXXXXXXXXXXXXXXXXpXpX-3'

5'-XpXXXXXXXXXXXXXXXXXXXXXXXpXpX-3'

5'-XpXXXXXXXXXXXXXXXXXXXXXXXpXpX-3'

5'-XpXXXXXXXXXXXXXXXXXXXXXXXpXpX-3'

"SM140"
5'-XpXXXXXXXXXXXXXXXXXXXXXXXDpD-3'

"SM141"
5'-XpXXXXXXXXXXXXXXXXXXXXXXXDpD-3

"SM142"
5'-XpXXXXXXXXXXXXXXXXXXXXXXXDpD-3'

"SM143"
5'-FpXFXFXFXFXFXFXFXFXFXXXFDpD-3'

"SM144"
5'-FpXFXFXFXFXFXFXFXFXFFFFFDpD-3'

"SM145"
5'-FpXFXFXFXFXFXFXFXFXFXXXXDpD-3'

"SM146"
5'-FpXFXFXFXFXFXFXFXFXFXFXFDpD-3'

"SM147"
5'-FXFXXXFXFFFXFXFXXXXXXXXDD-3'

"SM148"
5'-FXFXXXFXFFFXFXFXXXFFXXXDD-3'

"SM149"
5'-FXFXXXFXFFFXFXFXXXFFXXFDD-3'

"SM150"
5'-FXFXXXFXFFFXFXFXXXFFFFFDD-3'

"SM151"
5'-FpXFXFXFXFFFXFXFXFXFFXXFDpD-3'

"SM152"
5'-FpXFXFXFXFXFXXXFXFXFXXXXDpD-3'

"SM153"
5'-FpXFXFXXFFFFFXXFXTXXFXXXDpD-3'

"SM154"
5'-ab-XXFXXFFFXXFFXXXFFFFXpXXXDD-3' (ab = abasic for F7 stabilization at 5' end)

"SM155"
5'-XpXXXXXXXXXXXXXXXXXXXXXXXXpX-3'

"SM156"
5'-XpXXXXXXXXXXXXXXXXXXXXXXpX-3'

"SM151"
5'-FpXFXXXFFFFFFFXXXFXXFXXFXpX-3'

"SM158"
5'-XpXFXFXXFFFFXFXFXFXXFXXXXpX-3'

"SM159"
5'-FpXFXXXFXFFXFXXXFXXXFXXXXXpX-3'

"SN160"
5'-FDXFXFXFFFFXFXFXFXXXXXXX-3'

5'-XpXXXXXXXXXXXXXXXXXXXXXXXpX-3'

5'-XpXXXXXXXXXXXXXXXXXXX_XXpX-3'

5'-XpXXXXXXXXXXXXXXXXXXXXXXpX-3'

5'-FpXFXFXFXFXFXFXFXFXXXXFXpX-3'

5'-FpXFXFXFXFXFXFXFXFXFFFFFXpX-3'

5'-FpXFXFXFXFXFXFXFXFXFXXXXXpX-3'

5'-FpXFXFXFXFXFXFXFXFXTXFXFXpX-3'

5'-FXFXXXFXFFFXFXFXXXXXXXXXX-3'

5'-FXFXXXFXFFFXFXFXXXFFXXXXXX-3'

5'-FXFXXXFXFFFXFXFXXXFFXXFXX-3'

5'-FXFXXXFXFFFXFXFXXXFFFFFXX-3'

5'-FpXFXFXFFFXFXFXFXFFXXXFXpX-3'

5'-FpXFXFXFFFXFXFXFXFXXXXXpX-3'

5'-FpXFXXFFFFFXXXFXFXXFXXXXpX-3'

5'-ab-XXFXXFFFXXFFXXXFFFFXpXXXXX-3' (ab = abasic for F7 stabilization at 5' end)

5'-XpXXXXXXXXXXXXXXXXXXXXXXXpX-3'

5'-XpXXXXXXXXXXXXXXXXXXXXXXXpX-3'

5'-FpXFXXXFFFFFFFXXXFXXFXXFXpX-3'

5'-XpXFXXFFFFXFXFXFXXFXXXXpX-3'

5'-FpXFXXXFXFFXFXXFXXXFXXXXpX-3'

5'-FDXFXFXFFFXFXFXFXFXXXXXXX-3'

"SM253"
5'-XXXXXXXXXXXXXXXXXXXXXXXDD-3'

"SM255"
5'-XXXXXXXXXXXXXXXXXXXXXXXDD-3'

"SM256"
5'-XXXXXXXXXXXXXXXXXXXXXXXDD-3

"SM257"
5'-XXXXXXXXXXXXXXXXXXXXXXXDD-3'

"SM258"
5'-XXXXXXXXXXXXXXXXXXXXXXXDD-3'

"SM259"
5'-XXXXXXXXXXXXXXXXXXXXXXXDD-3'

"SM260"
5'-XXXXXXXXXXXXXXXXXXXXXXXDD-3'

"SM261"
5'-XXXXXXXXXXXXXXXXXXXXXXXDD-3'

"SM262"
5'-XXXXXXXXXXXXXXXXXXXXXXXDD-3'

"SM263"
5'-XXXXXXXXXXXXXXXXXXXXXXXDD-3'

"SM264"
5'-XXXXXXXXXXXXXXXXXXXXXXXDD-3'

"SM265"
5'-XXXXXXXXXXXXXXXXXXXXXXXDD-3'

"SM266"
5'-XXXXXXXXXXXXXXXXXXXXXXXDD-3'

"SM267"
5'-XXXXXXXXXXXXXXXXXXXXXXXDD-3'

"SM268"
5'-XXXXXXXXXXXXXXXXXXXXXXXDD-3'

"SM269"
5'-XXXXXXXXXXXXXXXXXXXXXXXDD-3'

"SM270"
5'-XXXXXXXXXXXXXXXXXXXXXXXDD-3'

"SM271"
5'-XXXXXXXXXXXXXXXXXXXXXXXDD-3'

"SM275"
5'-XXXXXXXXXXXXXXXXXXXXXXXDD-3'

"SM276"
5'-XXXXXXXXXXXXXXXXXXXXXXXDD-3'

"SM277"
5'-XXXXXXXXXXXXXXXXXXXXXXXDD-3'

"SM278"
5'-XXXXXXXXXXXXXXXXXXXXXXXDD-3'

"SM279"
5'-XXXXXXXXXXXXXXXXXXXXXXXDD-3'

"SM280"
5'-XXXXXXXXXXXXXXXXXXXXXXXDD-3'

"SM281"
5'-XXXXXXXXXXXXXXXXXXXXXXXDD-3'

"SM282"
5'-XXXXXXXXXXXXXXXXXXXXXXXDD-3'

"SM283"
5'-XXXXXXXXXXXXXXXXXXXXXXXDD-3'

"SM284"
5'-XXXXXXXXXXXXXXXXXXXXXXXDD-3'

"SM285"
5'-XXXXXXXXXXXXXXXXXXXXXXXDD-3'

"SM286"
5'-XXXXXXXXXXXXXXXXXXXXXXXDD-3'

"SM287"
5'-XXXXXXXXXXXXXXXXXXXXXXXDD-3'

"SM288"
5'-XXXXXXXXXXXXXXXXXXXXXXXDD-3'

"SM289"
5'-XXXXXXXXXXXXXXXXXXXXXXXXXDD-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

5'-XXXXXXXXXXXXXXXXXXXXXXXXXX-3'

"SM300"
5'-XXXXXXXXXXXXXXXXXXXXXXXXXDD-3'

"SM301"
5'-XpXXXXXXXXXXXXXXXXXXXXXXXXDpD-3'

"SM302"
5'-XpXXXXXXXXXXXXXXXXXXXXXXXXDpD-3'

"SM303"
5'-XpXXXXXXXXXXXXXXXXXXXXXXXXDpD-3'

"SM304"
5'-XpXXXXXXXXXXXXXXXXXXXXXXXXDpD-3'

"SM305"
5'-XpXXXXXXXXXXXXXXXXXXXXXXXXDpD-3

"SM306"
5'-XpXXXXXXXXXXXXXXXXXXXXXXXXDpD-3'

"SM301"
5'-XpXXXXXXXXXXXXXXXXXXXXXXXXDpD-3'

"SM308"
5'-XpXXXXXXXXXXXXXXXXXXXXXXXXDpD-3'

"SM309"
5'-XpXXXXXXXXXXXXXXXXXXXXXXXXDpD-3'

"SM310"
5'-XpXXXXXXXXXXXXXXXXXXXXXXXXDpD-3'

5'-XXXXXXXXXXXXXXXXXXXXXXXXXXX-3'

5'-XpXXXXXXXXXXXXXXXXXXXXXXXXpX-3'

5'-XpXXXXXXXXXXXXXXXXXXXXXXXXpX-3'

5'-XpXXXXXXXXXXXXXXXXXXXXXXXXpX-3'

5'-XpXXXXXXXXXXXXXXXXXXXXXXXXpX-3'

5'-XpXXXXXXXXXXXXXXXXXXXXXXXXpX-3'

5'-XpXXXXXXXXXXXXXXXXXXXXXXXXpX-3'

5'-XpXXXXXXXXXXXXXXXXXXXXXXXXpX-3'

5'-XpXXXXXXXXXXXXXXXXXXXXXXXXpX-3'

5'-XpXXXXXXXXXXXXXXXXXXXXXXXXpX-3'

5'-XpXXXXXXXXXXXXXXXXXXXXXXXXpX-3' where "X"=RNA, "$\underline{X}$"=2'-O-methyl RNA, "D"=DNA, "F"=2'-Fluoro NA and "p"=Phosphorothioate linkage.

It is contemplated that in certain embodiments of the invention, for all 2'-O-methyl modification patterns disclosed herein, any or all sites of 2'-O-methyl modification can optionally be replaced by a 2'-Fluoro modification. The above modification patterns can also be incorporated into, e.g., the extended DsiRNA structures and mismatch and/or frayed DsiRNA structures described below.

In another embodiment, the DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary 27mer DsiRNA agent with two terminal mismatched residues is shown:

5'-XXXXXXXXXXXXXXXXXXXXXXXXXXX$X^M M^{M-3'}$

3'-XXXXXXXXXXXXXXXXXXXXXXXXXXX$M_{M-5'}$ wherein "X"=RNA, "M"=Nucleic acid residues (RNA, DNA or non-natural or modified nucleic acids) that do not base pair (hydrogen bond) with corresponding "M" residues of otherwise complementary strand when strands are annealed. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand is the sense strand, and the bottom strand is the antisense strand. Alternatively, the bottom strand is the sense strand and the top strand is the antisense strand.

In certain additional embodiments, the present invention provides compositions for RNA interference (RNAi) that possess one or more base paired deoxyribonucleotides within a region of a double stranded ribonucleic acid (dsRNA) that is positioned 3' of a projected sense strand Dicer cleavage site and correspondingly 5' of a projected antisense strand Dicer cleavage site. The compositions of the invention comprise a dsRNA which is a precursor molecule. i.e., the dsRNA of the present invention is processed in vivo to produce an active small interfering nucleic acid (siRNA). The dsRNA is processed by Dicer to an active siRNA which is incorporated into RISC.

In certain embodiments, the DsiRNA agents of the invention can have the following exemplary structures (noting that any of the following exemplary structures can be combined, e.g., with the bottom strand modification patterns of the above-described structures—in one specific example, the bottom strand modification pattern shown in any of the above structures is applied to the 27 most 3' residues of the bottom strand of any of the following structures; in another specific example, the bottom strand modification pattern shown in any of the above structures upon the 23 most 3' residues of the bottom strand is applied to the 23 most 3' residues of the bottom strand of any of the following structures):

In one such embodiment, the DsiRNA comprises the following (an exemplary "right-extended", "DNA extended" DsiRNA):

5'-XXXXXXXXXXXXXXXXXXXXXXXX$_{N*}$D$_N$DD-3'

3'-YXXXXXXXXXXXXXXXXXXXXXXXX$_{N*}$D$_N$XX-5' wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

5'-XXXXXXXXXXXXXXXXXXXXXXXX$_{N*}$D$_N$DD-3'

3'-YXXXXXXXXXXXXXXXXXXXXXXXX$_{N*}$D$_N$DD-5' wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In an additional embodiment, the DsiRNA comprises:

5'-XXXXXXXXXXXXXXXXXXXXXXXX$_{N*}$D$_N$DD-3'

3'-Y$\underline{XXXXXXXXXXXXXXXXXXXXXXXX}$$_{N*}$D$_N$ZZ-5' wherein "X"=RNA, "$\underline{X}$"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

5'-XXXXXXXXXXXXXXXXXXXXXXXX$_{N*}$D$_N$DD-3'

3'-Y$\underline{XXXXXXXXXXXXXXXXXXXXXXXX}$$_{N*}$D$_N$ZZ-5' wherein "X"=RNA, "$\underline{X}$"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

5'-XXXXXXXXXXXXXXXXXXXXXXXX$_{N*}$D$_N$DD-3'

3'-Y$\underline{XXXXXXXXXXXXXXXXXXXXXXXX}$$_{N*}$D$_N$ZZ-5' wherein "X"=RNA, "$\underline{X}$"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

5'-XXXXXXXXXXXXXXXXXXXXXXXX$_{N*}$[X1/D1]$_N$DD-3'

3'-YXXXXXXXXXXXXXXXXXXXXXXXX$_{N*}$[X2/D2]$_N$ZZ-5' wherein "X"=RNA, "Y" is an optional overhang domain comprised of 0-10 RNA monomers that are optionally 2'-O-methyl RNA monomers—in certain embodiments. "Y"

is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In the structures depicted herein, the 5' end of either the sense strand or antisense strand can optionally comprise a phosphate group.

In another embodiment, a DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

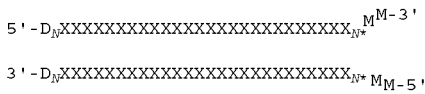

wherein "X"=RNA. "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-15 or, optionally, 1-8. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA:DNA extension patterns paralleling those shown above for asymmetric/overhang agents can also be incorporated into such "blunt/frayed" agents.

In one embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsRNA structure. An exemplary structure for such a molecule is shown:

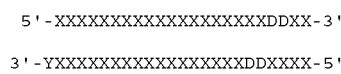

wherein "X"=RNA, "Y" is an optional overhang domain comprised of 0-10 RNA monomers that are optionally 2'-O-methyl RNA monomers—in certain embodiments. "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand. The above structure is modeled to force Dicer to cleave a minimum of a 21mer duplex as its primary post-processing form. In embodiments where the bottom strand of the above structure is the antisense strand, the positioning of two deoxyribonucleotide residues at the ultimate and penultimate residues of the 5' end of the antisense strand will help reduce off-target effects (as prior studies have shown a 2'-O-methyl modification of at least the penultimate position from the 5' terminus of the antisense strand to reduce off-target effects; see, e.g., US 2007/0223427).

In one embodiment, the DsiRNA comprises the following (an exemplary "left-extended", "DNA extended" DsiRNA):

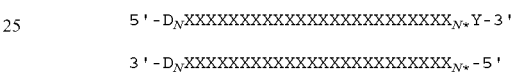

wherein "X"=RNA. "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

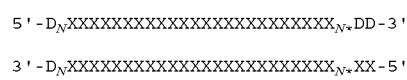

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In an additional embodiment, the DsiRNA comprises:

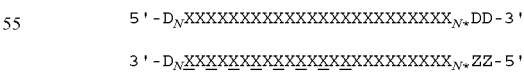

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. "Z"=DNA or RNA. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

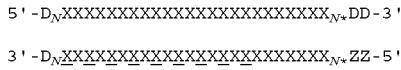

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. "Z"=DNA or RNA. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

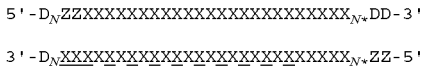

wherein "X"=RNA, "$\underline{X}$"=2'-O-methyl RNA, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

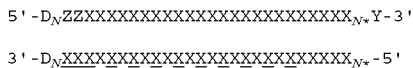

wherein "X"=RNA, "$\underline{X}$"=2'-O-methyl RNA, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

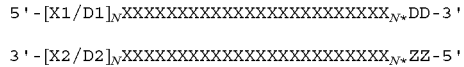

wherein "X"=RNA, "D"=DNA, "Z"=DNA or RNA, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In a related embodiment, the DsiRNA comprises:

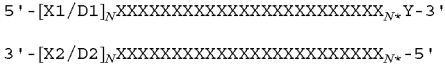

wherein "X"=RNA, "D"=DNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

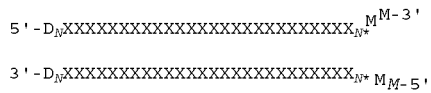

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-8 or 1-10. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA: DNA extension patterns paralleling those shown above for asymmetric/overhang agents can also be incorporated into such "blunt/frayed" agents.

In another embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsRNA structure. Exemplary structures for such a molecule are shown:

5'-XXDDXXXXXXXXXXXXXXXXXXXXX$_{N*}$Y-3'

3'-DDXXXXXXXXXXXXXXXXXXXXXX$_{N*}$-5' or

5'-XDXDXXXXXXXXXXXXXXXXXXXXX$_{N*}$Y-3'

3'-DXDXXXXXXXXXXXXXXXXXXXXX$_{N*}$-5' wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "D"=DNA. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In any of the above embodiments where the bottom strand of the above structure is the antisense strand, the positioning of two deoxyribonucleotide residues at the ultimate and penultimate residues of the 5' end of the antisense strand will help reduce off-target effects (as prior studies have shown a 2'-O-methyl modification of at least the penultimate position from the 5' terminus of the antisense strand to reduce off-target effects; see, e.g., US 2007/0223427).

In certain embodiments, the "D" residues of the above structures include at least one PS-DNA or PS-RNA. Optionally, the "D" residues of the above structures include at least one modified nucleotide that inhibits Dicer cleavage.

While the above-described "DNA-extended" DsiRNA agents can be categorized as either "left extended" or "right extended", DsiRNA agents comprising both left- and right-extended DNA-containing sequences within a single agent (e.g., both flanks surrounding a core dsRNA structure are dsDNA extensions) can also be generated and used in similar manner to those described herein for "right-extended" and "left-extended" agents.

In some embodiments, the DsiRNA of the instant invention further comprises a linking moiety or domain that joins the sense and antisense strands of a DNA:DNA-extended DsiRNA agent. Optionally, such a linking moiety domain joins the 3' end of the sense strand and the 5' end of the antisense strand. The linking moiety may be a chemical (non-nucleotide) linker, such as an oligomethylenediol linker, oligoethylene glycol linker, or other art-recognized linker moiety. Alternatively, the linker can be a nucleotide linker, optionally including an extended loop and/or tetraloop.

In one embodiment, the DsiRNA agent has an asymmetric structure, with the sense strand having a 25-base pair length, and the antisense strand having a 27-base pair length with a 1-4 base 3'-overhang (e.g., a one base 3'-overhang, a two base 3'-overhang, a three base 3'-overhang or a four base 3'-overhang). In another embodiment, this DsiRNA agent has an asymmetric structure further containing 2 deoxynucleotides at the 3' end of the sense strand.

In another embodiment, the DsiRNA agent has an asymmetric structure, with the antisense strand having a 25-base pair length, and the sense strand having a 27-base pair length with a 1-4 base 3'-overhang (e.g., a one base 3'-overhang, a two base 3'-overhang, a three base 3'-overhang or a four base 3'-overhang). In another embodiment, this DsiRNA agent has an asymmetric structure further containing 2 deoxyribonucleotides at the 3' end of the antisense strand.

Exemplary Glycolate Oxidase targeting DsiRNA agents of the invention, and their associated Glycolate Oxidase target sequences, include the following, presented in the below series of tables:

Table Number:

(2) Selected Human Anti-Glycolate Oxidase DsiRNA Agents (Asymmetrics);

(3) Selected Human Anti-Glycolate Oxidase DsiRNAs, Unmodified Duplexes (Asymmetrics);

(4) DsiRNA Target Sequences (21mers) in Glycolate Oxidase mRNA;

(5) Selected Human Anti-Glycolate Oxidase "Blunt/Blunt" DsiRNAs; and (6) DsiRNA Component 19 Nucleotide Target Sequences in Glycolate Oxidase mRNA (7) Human Anti-Glycolate Oxidase DsiRNAs Predicted to have >50% Knockdown Efficacy (Asymmetrics);

(8) DsiRNA Target Sequences (21mers) of Human Anti-Glycolate Oxidase DsiRNAs Predicted to have >50% Knockdown Efficacy;

(9) "Blunt/Blunt" DsiRNAs Corresponding to Human Anti-Glycolate Oxidase DsiRNAs Predicted to have >50% Knockdown Efficacy; and

(10) DsiRNA Component 19 Nucleotide Target Sequences of Human Anti-Glycolate Oxidase DsiRNAs Predicted to have >50% Knockdown Efficacy Lengthy table referenced here

US10435692-20191008-T00001

Please refer to the end of the specification for access instructions.

Lengthy table referenced here

US10435692-20191008-T00002

Please refer to the end of the specification for access instructions.

Lengthy table referenced here

US10435692-20191008-T00003

Please refer to the end of the specification for access instructions.

Lengthy table referenced here

US10435692-20191008-T00004

Please refer to the end of the specification for access instructions.

Lengthy table referenced here

US10435692-20191008-T00005

Please refer to the end of the specification for access instructions.

Lengthy table referenced here

US10435692-20191008-T00006

Please refer to the end of the specification for access instructions.

Lengthy table referenced here

US10435692-20191008-T00007

Please refer to the end of the specification for access instructions.

Lengthy table referenced here

US10435692-20191008-T00008

Please refer to the end of the specification for access instructions.

Lengthy table referenced here

US10435692-20191008-T00009

Please refer to the end of the specification for access instructions.

Within Tables 2, 3, 5, 7 and 9 above, underlined residues indicate 2'-O-methyl residues, UPPER CASE indicates ribonucleotides, and lower case denotes deoxyribonucleotides. The DsiRNA agents of Tables 2, 3 and 7 above are 25/27mer agents possessing a blunt end. The structures and/or modification patterning of the agents of Tables 2, 3 and 7 above can be readily adapted to the above generic sequence structures, e.g., the 3' overhang of the second strand can be extended or contracted, 2'-O-methylation of the second strand can be expanded towards the 5' end of the second strand, optionally at alternating sites, etc. Such further modifications are optional, as 25/27mer DsiRNAs with such modifications can also be readily designed from the above DsiRNA agents and are also expected to be functional inhibitors of Glycolate Oxidase expression. Similarly, the 27mer "blunt/blunt" DsiRNA structures and/or modification patterns of the agents of Tables 5 and 9 above can also be readily adapted to the above generic sequence structures, e.g., for application of modification patterning of the antisense strand to such structures and/or adaptation of such sequences to the above generic structures.

In certain embodiments, 27mer DsiRNAs possessing independent strand lengths each of 27 nucleotides are designed and synthesized for targeting of the same sites within the Glycolate Oxidase transcript as the asymmetric "25/27" structures shown in Tables 2, 3 and 7 herein. Exemplary "27/27" DsiRNAs are optionally designed with a "blunt/blunt" structure as shown for the DsiRNAs of Tables 5 and 9 above.

In certain embodiments, the dsRNA agents of the invention require, e.g., at least 15, at least 16, at least 17, at least 18, at least 19, at least 20, at least 21, at least 22, at least 23, at least 24, at least 25 or at least 26 residues of the first strand to be complementary to corresponding residues of the second strand. In certain related embodiments, these first strand residues complementary to corresponding residues of the second strand are optionally consecutive residues.

As used herein "DsiRNAmm" refers to a DisRNA having a "mismatch tolerant region" containing one, two, three or four mismatched base pairs of the duplex formed by the sense and antisense strands of the DsiRNA, where such mismatches are positioned within the DsiRNA at a location(s) lying between (and thus not including) the two terminal base pairs of either end of the DsiRNA. The mismatched base pairs are located within a "mismatch-tolerant region" which is defined herein with respect to the location of the projected Ago2 cut site of the corresponding target nucleic acid. The mismatch tolerant region is located "upstream of" the projected Ago2 cut site of the target strand. "Upstream" in this context will be understood as the 5'-most portion of the DsiRNAmm duplex, where 5' refers to the orientation of the sense strand of the DsiRNA duplex. Therefore, the mismatch tolerant region is upstream of the base on the sense (passenger) strand that corresponds to the projected Ago2 cut site of the target nucleic acid (see FIG. 1); alternatively, when referring to the antisense (guide) strand of the DsiRNAmm, the mismatch tolerant region can also be described as positioned downstream of the base that is complementary to the projected Ago2 cut site of the target nucleic acid, that is, the 3'-most portion of the antisense strand of the DsiRNAmm (where position 1 of the antisense strand is the 5' terminal nucleotide of the antisense strand, see FIG. 1).

In one embodiment, for example with numbering as depicted in FIG. 1, the mismatch tolerant region is positioned between and including base pairs 3-9 when numbered from the nucleotide starting at the 5' end of the sense strand of the duplex. Therefore, a DsiRNAmm of the invention possesses a single mismatched base pair at any one of positions 3, 4, 5, 6, 7, 8 or 9 of the sense strand of a right-hand extended DsiRNA (where position 1 is the 5' terminal nucleotide of the sense strand and position 9 is the nucleotide residue of the sense strand that is immediately 5' of the projected Ago2 cut site of the target Glycolate Oxidase RNA sequence corresponding to the sense strand sequence). In certain embodiments, for a DsiRNAmm that possesses a mismatched base pair nucleotide at any of positions 3, 4, 5, 6, 7, 8 or 9 of the sense strand, the corresponding mismatched base pair nucleotide of the antisense strand not only forms a mismatched base pair with the DsiRNAmm sense strand sequence, but also forms a mismatched base pair with a DsiRNAmm target Glycolate Oxidase RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target Glycolate Oxidase RNA sequence). In alternative embodiments, the mismatch base pair nucleotide of the antisense strand of a DsiRNAmm only form a mismatched base pair with a corresponding nucleotide of the sense strand sequence of the DsiRNAmm, yet base pairs with its corresponding target Glycolate Oxidase RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target Glycolate Oxidase RNA sequence).

A DsiRNAmm of the invention that possesses a single mismatched base pair within the mismatch-tolerant region (mismatch region) as described above (e.g., a DsiRNAmm harboring a mismatched nucleotide residue at any one of positions 3, 4, 5, 6, 7, 8 or 9 of the sense strand) can further include one, two or even three additional mismatched base pairs. In preferred embodiments, these one, two or three additional mismatched base pairs of the DsiRNAmm occur at position(s) 3, 4, 5, 6, 7, 8 and/or 9 of the sense strand (and at corresponding residues of the antisense strand). In one embodiment where one additional mismatched base pair is present within a DsiRNAmm, the two mismatched base pairs of the sense strand can occur, e.g., at nucleotides of both position 4 and position 6 of the sense strand (with mismatch also occurring at corresponding nucleotide residues of the antisense strand).

In DsiRNAmm agents possessing two mismatched base pairs, mismatches can occur consecutively (e.g., at consecutive positions along the sense strand nucleotide sequence). Alternatively, nucleotides of the sense strand that form mismatched base pairs with the antisense strand sequence can be interspersed by nucleotides that base pair with the antisense strand sequence (e.g., for a DsiRNAmm possessing mismatched nucleotides at positions 3 and 6, but not at positions 4 and 5, the mismatched residues of sense strand positions 3 and 6 are interspersed by two nucleotides that form matched base pairs with corresponding residues of the antisense strand). For example, two residues of the sense strand (located within the mismatch-tolerant region of the sense strand) that form mismatched base pairs with the corresponding antisense strand sequence can occur with zero, one, two, three, four or five matched base pairs located between these mismatched base pairs.

For certain DsiRNAmm agents possessing three mismatched base pairs, mismatches can occur consecutively (e.g., in a triplet along the sense strand nucleotide sequence). Alternatively, nucleotides of the sense strand that form mismatched base pairs with the antisense strand sequence can be interspersed by nucleotides that form matched base pairs with the antisense strand sequence (e.g., for a DsiRNAmm possessing mismatched nucleotides at positions 3, 4 and 8, but not at positions 5, 6 and 7, the mismatched residues of sense strand positions 3 and 4 are adjacent to one another, while the mismatched residues of sense strand positions 4 and 8 are interspersed by three nucleotides that form matched base pairs with corresponding residues of the antisense strand). For example, three residues of the sense strand (located within the mismatch-tolerant region of the sense strand) that form mismatched base pairs with the corresponding antisense strand sequence can occur with zero, one, two, three or four matched base pairs located between any two of these mismatched base pairs.

For certain DsiRNAmm agents possessing four mismatched base pairs, mismatches can occur consecutively (e.g., in a quadruplet along the sense strand nucleotide sequence). Alternatively, nucleotides of the sense strand that form mismatched base pairs with the antisense strand sequence can be interspersed by nucleotides that form matched base pairs with the antisense strand sequence (e.g., for a DsiRNAmm possessing mismatched nucleotides at positions 3, 5, 7 and 8, but not at positions 4 and 6, the mismatched residues of sense strand positions 7 and 8 are adjacent to one another, while the mismatched residues of sense strand positions 3 and 5 are interspersed by one nucleotide that forms a matched base pair with the corresponding residue of the antisense strand—similarly, the the mismatched residues of sense strand positions 5 and 7 are also interspersed by one nucleotide that forms a matched base pair with the corresponding residue of the antisense strand). For example, four residues of the sense strand (located within the mismatch-tolerant region of the sense strand) that form mismatched base pairs with the corresponding antisense strand sequence can occur with zero, one, two or three matched base pairs located between any two of these mismatched base pairs.

In another embodiment, for example with numbering also as depicted in FIG. 1, a DsiRNAmm of the invention comprises a mismatch tolerant region which possesses a single mismatched base pair nucleotide at any one of positions 17, 18, 19, 20, 21, 22 or 23 of the antisense strand of the DsiRNA (where position 1 is the 5' terminal nucleotide of the antisense strand and position 17 is the nucleotide residue of the antisense strand that is immediately 3' (downstream) in the antisense strand of the projected Ago2 cut site of the target Glycolate Oxidase RNA sequence sufficiently complementary to the antisense strand sequence). In certain embodiments, for a DsiRNAmm that possesses a mismatched base pair nucleotide at any of positions 17, 18, 19, 20, 21, 22 or 23 of the antisense strand with respect to the sense strand of the DsiRNAmm, the mismatched base pair nucleotide of the antisense strand not only forms a mismatched base pair with the DsiRNAmm sense strand sequence, but also forms a mismatched base pair with a DsiRNAmm target Glycolate Oxidase RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target Glycolate Oxidase RNA sequence). In alternative embodiments, the mismatch base pair nucleotide of the antisense strand of a DsiRNAmm only forms a mismatched base pair with a corresponding nucleotide of the sense strand sequence of the DsiRNAmm, yet base pairs with its corresponding target Glycolate Oxidase RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target Glycolate Oxidase RNA sequence).

A DsiRNAmm of the invention that possesses a single mismatched base pair within the mismatch-tolerant region as described above (e.g., a DsiRNAmm harboring a mismatched nucleotide residue at positions 17, 18, 19, 20, 21, 22 or 23 of the antisense strand) can further include one, two or even three additional mismatched base pairs. In preferred embodiments, these one, two or three additional mismatched base pairs of the DsiRNAmm occur at position(s) 17, 18, 19, 20, 21, 22 and/or 23 of the antisense strand (and at corresponding residues of the sense strand). In one embodiment where one additional mismatched base pair is present within a DsiRNAmm, the two mismatched base pairs of the antisense strand can occur, e.g., at nucleotides of both position 18 and position 20 of the antisense strand (with mismatch also occurring at corresponding nucleotide residues of the sense strand).

In DsiRNAmm agents possessing two mismatched base pairs, mismatches can occur consecutively (e.g., at consecutive positions along the antisense strand nucleotide sequence). Alternatively, nucleotides of the antisense strand that form mismatched base pairs with the sense strand sequence can be interspersed by nucleotides that base pair with the sense strand sequence (e.g., for a DsiRNAmm possessing mismatched nucleotides at positions 17 and 20, but not at positions 18 and 19, the mismatched residues of antisense strand positions 17 and 20 are interspersed by two nucleotides that form matched base pairs with corresponding residues of the sense strand). For example, two residues of the antisense strand (located within the mismatch-tolerant region of the sense strand) that form mismatched base pairs with the corresponding sense strand sequence can occur with zero, one, two, three, four, five, six or seven matched base pairs located between these mismatched base pairs.

For certain DsiRNAmm agents possessing three mismatched base pairs, mismatches can occur consecutively (e.g., in a triplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 17, 18 and 22, but not at positions 19, 20 and 21, the mismatched residues of antisense strand positions 17 and 18 are adjacent to one another, while the mismatched residues of antisense strand positions 18 and 122 are interspersed by three nucleotides that form matched base pairs with corresponding residues of the sense strand). For example, three residues of the antisense strand (located within the mismatch-tolerant region of the antisense strand) that form mismatched base pairs with the corresponding sense strand sequence can occur with zero, one, two, three, four, five or six matched base pairs located between any two of these mismatched base pairs.

For certain DsiRNAmm agents possessing four mismatched base pairs, mismatches can occur consecutively (e.g., in a quadruplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 18, 20, 22 and 23, but not at positions 19 and 21, the mismatched residues of antisense strand positions 22 and 23 are adjacent to one another, while the mismatched residues of antisense strand positions 18 and 20 are interspersed by one nucleotide that forms a matched base pair with the corresponding residue of the sense strand—similarly, the the mismatched residues of antisense strand positions 20 and 22 are also interspersed by one nucleotide that forms a matched base pair with the corresponding residue of the sense strand). For example, four residues of the antisense strand (located within the mismatch-tolerant region of the antisense strand) that form mismatched base pairs with the corresponding sense strand sequence can occur with zero, one, two, three, four or five matched base pairs located between any two of these mismatched base pairs.

For reasons of clarity, the location(s) of mismatched nucleotide residues within the above DsiRNAmm agents are numbered in reference to the 5' terminal residue of either sense or antisense strands of the DsiRNAmm. The numbering of positions located within the mismatch-tolerant region (mismatch region) of the antisense strand can shift with variations in the proximity of the 5' terminus of the sense or antisense strand to the projected Ago2 cleavage site. Thus, the location(s) of preferred mismatch sites within either antisense strand or sense strand can also be identified as the permissible proximity of such mismatches to the projected Ago2 cut site. Accordingly, in one preferred embodiment, the position of a mismatch nucleotide of the sense strand of a DsiRNAmm is the nucleotide residue of the sense strand that is located immediately 5' (upstream) of the projected Ago2 cleavage site of the corresponding target Glycolate Oxidase RNA sequence. In other preferred embodiments, a mismatch nucleotide of the sense strand of a DsiRNAmm is positioned at the nucleotide residue of the sense strand that is located two nucleotides 5' (upstream) of the projected Ago2 cleavage site, three nucleotides 5' (upstream) of the projected Ago2 cleavage site, four nucleotides 5' (upstream) of the projected Ago2 cleavage site, five nucleotides 5' (upstream) of the projected Ago2 cleavage site, six nucleotides 5' (upstream) of the projected Ago2 cleavage site, seven nucleotides 5' (upstream) of the projected Ago2 cleavage site, eight nucleotides 5' (upstream) of the projected Ago2 cleavage site, or nine nucleotides 5' (upstream) of the projected Ago2 cleavage site.

Exemplary single mismatch-containing 25/27mer DsiRNAs (DsiRNAmm) include the following structures (such mismatch-containing structures may also be incorporated into other exemplary DsiRNA structures shown herein).

wherein "X"=RNA, "D"=DNA and "M"=Nucleic acid residues (RNA, DNA or non-natural or modified nucleic acids) that do not base pair (hydrogen bond) with corresponding "M" residues of otherwise complementary strand when strands are annealed. Any of the residues of such agents can optionally be 2'-O-methyl RNA monomers—alternating positioning of 2'-O-methyl RNA monomers that commences from the 3'-terminal residue of the bottom (second) strand, as shown above, can also be used in the above DsiRNAmm agents. For the above mismatch structures, the top strand is the sense strand, and the bottom strand is the antisense strand.

In certain embodiments, a DsiRNA of the invention can contain mismatches that exist in reference to the target Glycolate Oxidase RNA sequence yet do not necessarily exist as mismatched base pairs within the two strands of the DsiRNA—thus, a DsiRNA can possess perfect complementarity between first and second strands of a DsiRNA, yet still possess mismatched residues in reference to a target Glycolate Oxidase RNA (which, in certain embodiments, may be advantageous in promoting efficacy and/or potency and/ or duration of effect). In certain embodiments, where mismatches occur between antisense strand and target Glycolate Oxidase RNA sequence, the position of a mismatch is located within the antisense strand at a position(s) that corresponds to a sequence of the sense strand located 5' of the projected Ago2 cut site of the target region—e.g., antisense strand residue(s) positioned within the antisense strand to the 3' of the antisense residue which is complementary to the projected Ago2 cut site of the target sequence.

Exemplary 25/27mer DsiRNAs that harbor a single mismatched residue in reference to target sequences include the following structures.

```
Target RNA Sequence:
5'-. . . AXXXXXXXXXXXXXXXXXXX . . .-3'

DsiRNAmm Sense Strand:
5'-XXXXXXXXXXXXXXXXXXXXXXXDD-3'

DsiRNAmm Antisense Strand:
3'-EXXXXXXXXXXXXXXXXXXXXXXXXX-5'

Target RNA Sequence:
5'-. . . XAXXXXXXXXXXXXXXXXXX . . .-3'

DsiRNAmm Sense Strand:
5'-XXXXXXXXXXXXXXXXXXXXXXXDD-3'

DsiRNAmm Antisense Strand:
3'-XEXXXXXXXXXXXXXXXXXXXXXXXX-5'

Target RNA Sequence:
5'-. . . AXXXXXXXXXXXXXXXXXX . . .-3'

DsiRNAmm Sense Strand:
5'-BXXXXXXXXXXXXXXXXXXXXXXXDD-3'

DsiRNAmm Antisense Strand:
3'-XXEXXXXXXXXXXXXXXXXXXXXXXX-5'

Target RNA Sequence:
5'-. . . XAXXXXXXXXXXXXXXXXX . . .-3'

DsiRNAmm Sense Strand.:
5'-XBXXXXXXXXXXXXXXXXXXXXXXDD-3'

DsiRNAmm Antisense Strand:
3'-XXXEXXXXXXXXXXXXXXXXXXXXXX-5'

Target RNA Sequence:
5'-. . . XXAXXXXXXXXXXXXXXXX . . .-3'

DsiRNAmm Sense Strand:
5'-XXBXXXXXXXXXXXXXXXXXXXXDD-3'

DsiRNAmm Antisense Strand:
3'-XXXXEXXXXXXXXXXXXXXXXXXXXX-5'

Target RNA Sequence:
5'-. . . XXXAXXXXXXXXXXXXXXX . . .-3'

DsiRNAmm Sense Strand:
5'-XXXBXXXXXXXXXXXXXXXXXXXDD-3'

DsiRNAmm Antisense Strand:
3'-XXXXXEXXXXXXXXXXXXXXXXXXXX-5'

Target RNA Sequence:
5'-. . . XXXXAXXXXXXXXXXXXXX . . .-3'

DsiRNAmm Sense Strand:
5'-XXXXBXXXXXXXXXXXXXXXXXXDD-3'

DsiRNAmm Antisense Strand:
3'-XXXXXXEXXXXXXXXXXXXXXXXXXX-5'

Target RNA Sequence:
5'-. . . XXXXXAXXXXXXXXXXXXX . . .-3'

DsiRNAmm Sense Strand:
5'-XXXXXBXXXXXXXXXXXXXXXXXDD-3'

DsiRNAmm Antisense Strand:
3'-XXXXXXXEXXXXXXXXXXXXXXXXXX-5'

Target RNA Sequence:
5'-. . . XXXXXXAXXXXXXXXXXXX . . .-3'

DsiRNAmm Sense Strand:
5'-XXXXXXBXXXXXXXXXXXXXXXXDD-3'

DsiRNAmm Antisense Strand:
3'-XXXXXXXXEXXXXXXXXXXXXXXXXX-5'

Target RNA Sequence:
5'-. . . XXXXXXXAXXXXXXXXXXX . . .-3'

DsiRNAmm Sense Strand:
5'-XXXXXXXBXXXXXXXXXXXXXXXDD-3'

DsiRNAmm Antisense Strand:
3'-XXXXXXXXXEXXXXXXXXXXXXXXXX-5'

Target RNA Sequence:
5'-. . . XXXXXXXXAXXXXXXXXXX . . .-3'

DsiRNAmm Sense Strand:
5'-XXXXXXXXBXXXXXXXXXXXXXXDD-3'

DsiRNAmm Antisense Strand:
3'-XXXXXXXXXXEXXXXXXXXXXXXXXX-5'
``` wherein "X"=RNA, "D"=DNA and "E"=Nucleic acid residues (RNA, DNA or non-natural or modified nucleic acids) that do not base pair (hydrogen bond) with corresponding "A" RNA residues of otherwise complementary (target) strand when strands are annealed, yet optionally do base pair with corresponding "B" residues ("B" residues are also RNA, DNA or non-natural or modified nucleic acids). Any of the residues of such agents can optionally be 2'-O-methyl RNA monomers—alternating positioning of 2'-O-methyl RNA monomers that commences from the 3'-terminal residue of the bottom (second) strand, as shown above, can also be used in the above DsiRNA agents.

In certain embodiments, the guide strand of a dsRNA of the invention that is sufficiently complementary to a target RNA (e.g., mRNA) along at least 19 nucleotides of the target gene sequence to reduce target gene expression is not perfectly complementary to the at least 19 nucleotide long target gene sequence. Rather, it is appreciated that the guide strand of a dsRNA of the invention that is sufficiently complementary to a target mRNA along at least 19 nucleotides of a target RNA sequence to reduce target gene expression can have one, two, three, or even four or more nucleotides that are mismatched with the 19 nucleotide or longer target strand sequence. Thus, for a 19 nucleotide target RNA sequence, the guide strand of a dsRNA of the invention can be sufficiently complementary to the target RNA sequence to reduce target gene levels while possessing, e.g., only 15/19, 16/19, 17/19 or 18/19 matched nucleotide residues between guide strand and target RNA sequence.

In addition to the above-exemplified structures, dsRNAs of the invention can also possess one, two or three additional residues that form further mismatches with the target Glycolate Oxidase RNA sequence. Such mismatches can be consecutive, or can be interspersed by nucleotides that form matched base pairs with the target Glycolate Oxidase RNA sequence. Where interspersed by nucleotides that form matched base pairs, mismatched residues can be spaced apart from each other within a single strand at an interval of one, two, three, four, five, six, seven or even eight base paired nucleotides between such mismatch-forming residues.

As for the above-described DsiRNAmm agents, a preferred location within dsRNAs (e.g., DsiRNAs) for antisense strand nucleotides that form mismatched base pairs with target Glycolate Oxidase RNA sequence (yet may or may not form mismatches with corresponding sense strand nucleotides) is within the antisense strand region that is located 3' (downstream) of the antisense strand sequence which is complementary to the projected Ago2 cut site of the DsiRNA (e.g., in FIG. 1, the region of the antisense strand which is 3' of the projected Ago2 cut site is preferred for mismatch-forming residues and happens to be located at positions 17-23 of the antisense strand for the 25/27mer agent shown in FIG. 1). Thus, in one embodiment, the position of a mismatch nucleotide (in relation to the target Glycolate Oxidase RNA sequence) of the antisense strand of a DsiRNAmm is the nucleotide residue of the antisense strand that is located immediately 3' (downstream) within the antisense strand sequence of the projected Ago2 cleavage site of the corresponding target Glycolate Oxidase RNA sequence. In other preferred embodiments, a mismatch nucleotide of the antisense strand of a DsiRNAmm (in relation to the target Glycolate Oxidase RNA sequence) is positioned at the nucleotide residue of the antisense strand that is located two nucleotides 3' (downstream) of the corresponding projected Ago2 cleavage site, three nucleotides 3' (downstream) of the corresponding projected Ago2 cleavage site, four nucleotides 3' (downstream) of the corresponding projected Ago2 cleavage site, five nucleotides 3' (downstream) of the corresponding projected Ago2 cleavage site, six nucleotides 3' (downstream) of the projected Ago2 cleavage site, seven nucleotides 3' (downstream) of the projected Ago2 cleavage site, eight nucleotides 3' (downstream) of the projected Ago2 cleavage site, or nine nucleotides 3' (downstream) of the projected Ago2 cleavage site.

In dsRNA agents possessing two mismatch-forming nucleotides of the antisense strand (where mismatch-forming nucleotides are mismatch forming in relation to target Glycolate Oxidase RNA sequence), mismatches can occur consecutively (e.g., at consecutive positions along the antisense strand nucleotide sequence). Alternatively, nucleotides of the antisense strand that form mismatched base pairs with the target Glycolate Oxidase RNA sequence can be interspersed by nucleotides that base pair with the target Glycolate Oxidase RNA sequence (e.g., for a DsiRNA possessing mismatch-forming nucleotides at positions 17 and 20 (starting from the 5' terminus (position 1) of the antisense strand of the 25/27mer agent shown in FIG. 1), but not at positions 18 and 19, the mismatched residues of sense strand positions 17 and 20 are interspersed by two nucleotides that form matched base pairs with corresponding residues of the target Glycolate Oxidase RNA sequence). For example, two residues of the antisense strand (located within the mismatch-tolerant region of the antisense strand) that form mismatched base pairs with the corresponding target Glycolate Oxidase RNA sequence can occur with zero, one, two, three, four or five matched base pairs (with respect to target Glycolate Oxidase RNA sequence) located between these mismatch-forming base pairs.

For certain dsRNAs possessing three mismatch-forming base pairs (mismatch-forming with respect to target Glycolate Oxidase RNA sequence), mismatch-forming nucleotides can occur consecutively (e.g., in a triplet along the antisense strand nucleotide sequence). Alternatively, nucleotides of the antisense strand that form mismatched base pairs with the target Glycolate Oxidase RNA sequence can be interspersed by nucleotides that form matched base pairs with the target Glycolate Oxidase RNA sequence (e.g., for a DsiRNA possessing mismatched nucleotides at positions 17, 18 and 22, but not at positions 19, 20 and 21, the mismatch-forming residues of antisense strand positions 17 and 18 are adjacent to one another, while the mismatch-forming residues of antisense strand positions 18 and 22 are interspersed by three nucleotides that form matched base pairs with corresponding residues of the target Glycolate Oxidase RNA). For example, three residues of the antisense strand (located within the mismatch-tolerant region of the antisense strand) that form mismatched base pairs with the corresponding target Glycolate Oxidase RNA sequence can occur with zero, one, two, three or four matched base pairs located between any two of these mismatch-forming base pairs.

For certain dsRNAs possessing four mismatch-forming base pairs (mismatch-forming with respect to target Glycolate Oxidase RNA sequence), mismatch-forming nucleotides can occur consecutively (e.g., in a quadruplet along the sense strand nucleotide sequence). Alternatively, nucleotides of the antisense strand that form mismatched base pairs with the target Glycolate Oxidase RNA sequence can be interspersed by nucleotides that form matched base pairs with the target Glycolate Oxidase RNA sequence (e.g., for a DsiRNA possessing mismatch-forming nucleotides at positions 17, 19, 21 and 22, but not at positions 18 and 20, the mismatch-forming residues of antisense strand positions 21 and 22 are adjacent to one another, while the mismatch-forming residues of antisense strand positions 17 and 19 are interspersed by one nucleotide that forms a matched base pair with the corresponding residue of the target Glycolate Oxidase RNA sequence—similarly, the mismatch-forming residues of antisense strand positions 19 and 21 are also interspersed by one nucleotide that forms a matched base pair with the corresponding residue of the target Glycolate Oxidase RNA sequence). For example, four residues of the antisense strand (located within the mismatch-tolerant region of the antisense strand) that form mismatched base pairs with the corresponding target Glycolate Oxidase RNA sequence can occur with zero, one, two or three matched base pairs located between any two of these mismatch-forming base pairs.

The above DsiRNAmm and other dsRNA structures are described in order to exemplify certain structures of DsiRNAmm and dsRNA agents. Design of the above DsiRNAmm and dsRNA structures can be adapted to generate. e.g., DsiRNAmm forms of other DsiRNA structures shown infra. As exemplified above, dsRNAs can also be designed that possess single mismatches (or two, three or four mismatches) between the antisense strand of the dsRNA and a target sequence, yet optionally can retain perfect complementarity between sense and antisense strand sequences of a dsRNA.

It is further noted that the dsRNA agents exemplified infra can also possess insertion/deletion (in/del) structures within their double-stranded and/or target Glycolate Oxidase RNA-aligned structures. Accordingly, the dsRNAs of the invention can be designed to possess in/del variations in, e.g., antisense strand sequence as compared to target Glycolate Oxidase RNA sequence and/or antisense strand sequence as compared to sense strand sequence, with preferred location(s) for placement of such in/del nucleotides corresponding to those locations described above for positioning of mismatched and/or mismatch-forming base pairs.

It is also noted that the DsiRNAs of the instant invention can tolerate mismatches within the 3'-terminal region of the sense strand/5'-terminal region of the antisense strand, as this region is modeled to be processed by Dicer and liberated from the guide strand sequence that loads into RISC. Exemplary DsiRNA structures of the invention that harbor such mismatches include the following:

```
Target RNA Sequence:
5'-. . . XXXXXXXXXXXXXXXXXXXXHXXX . . .-3'

DsiRNA Sense Strand:
5'-XXXXXXXXXXXXXXXXXXXXXIXDD-3'

DsiRNA Antisense Strand.:
3'-XXXXXXXXXXXXXXXXXXXXXXXJXXX-5'

Target RNA Sequence:
5'-. . . XXXXXXXXXXXXXXXXXXXXHXX . . .-3'

DsiRNA Sense Strand:
5'-XXXXXXXXXXXXXXXXXXXXXXIDD-3'

DsiRNA Antisense Strand:
3'-XXXXXXXXXXXXXXXXXXXXXXXJXX-5'

Target RNA Sequence:
5'-. . . XXXXXXXXXXXXXXXXXXXXHX . . .-3'

DsiRNA Sense Strand:
5'-XXXXXXXXXXXXXXXXXXXXXXXID-3'

DsiRNA Antisense Strand:
3'-XXXXXXXXXXXXXXXXXXXXXXXJX-5'

Target RNA Sequence:
5'-. . . XXXXXXXXXXXXXXXXXXXXH . . .-3'

DsiRNA Sense Strand:
5'-XXXXXXXXXXXXXXXXXXXXXXXDI-3'

DsiRNA Antisense Strand:
3'-XXXXXXXXXXXXXXXXXXXXXXXXJ-5'
``` wherein "X"=RNA, "D"=DNA and "I" and "J"=Nucleic acid residues (RNA, DNA or non-natural or modified nucleic acids) that do not base pair (hydrogen bond) with one another, yet optionally "J" is complementary to target RNA sequence nucleotide "H". Any of the residues of such agents can optionally be 2'-O-methyl RNA monomers—alternating positioning of 2'-O-methyl RNA monomers that commences from the 3'-terminal residue of the bottom (second) strand, as shown above—or any of the above-described methylation patterns—can also be used in the above DsiRNA agents. The above mismatches can also be combined within the DsiRNAs of the instant invention.

In the below structures, such mismatches are introduced within the asymmetric HAO1-1171 DsiRNA (newly-introduced mismatch residues are italicized): HAO1-1171 25/27mer DsiRNA, mismatch position=19 of sense strand (from 5'-terminus)

```
                                    (SEQ ID NO: 3460)
5'-AUAUUUCCCAUCUGUAU^AUUUtt-3'
                                    (SEQ ID NO: 580)
3'-GUUAUAAAAGGGUAGACAUA_AUAAAAA-5'
```

Optionally, the mismatched 'A' residue of position 19 of the sense strand is alternatively 'C' or 'G'.

HAO1-1171 25/27mer DsiRNA, mismatch position=20 of sense strand (from 5'-terminus)

```
                                    (SEQ ID NO: 3461)
5'-AUAUUUCCCAUCUGUAUU^UUUtt-3'
                                    (SEQ ID NO: 580)
3'-GUUAUAAAAGGGUAGACAUAA_UAAAAA-3'
```

Optionally, the mismatched 'U' residue of position 20 of the sense strand is alternatively 'C' or 'G'.

HAO1-1171 25/27mer DsiRNA, mismatch position=21 of sense strand (from 5'-terminus)

```
                                    (SEQ ID NO: 3462)
5'-AUAUUUCCCAUCUGUAUUA^AUUtt-3'
                                    (SEQ ID NO: 580)
3'-GUUAUAAAAGGGUAGACAUAAU_AAAAA-5'
```

Optionally, the mismatched 'A' residue of position 21 of the sense strand is alternatively 'C' or 'G'.

HAO1-1171 25/27mer DsiRNA, mismatch position=22 of sense strand (from 5'-terminus)

```
                                    (SEQ ID NO: 3463)
5'-AUAUUUCCCAUCUGUAUUAU^GUtt-3'
                                    (SEQ ID NO: 580)
3'-GUUAUAAAAGGGUAGACAUAAUA_AAA-5'
```

Optionally, the mismatched 'G' residue of position 22 of the sense strand is alternatively 'A' or 'C'.

HAO1-1171 25/27mer DsiRNA, mismatch position=23 of sense strand (from 5'-terminus)

```
                                    (SEQ ID NO: 3464)
5'-AUAUUUCCCAUCUGUAUUAUU^Att-3'
                                    (SEQ ID NO: 580)
3'-GUUAUAAAAGGGUAGACAUAAUAA_AA-5'
```

Optionally, the mismatched 'A' residue of position 23 of the sense strand is alternatively 'C' or 'G'.

HAO1-1171 25/27mer DsiRNA, mismatch position=24 of sense strand (from 5'-terminus)

```
                                    (SEQ ID NO: 3465)
5'-AUAUUUCCCAUCUGUAUUAUUU^gt-3'
                                    (SEQ ID NO: 580)
3'-GUUAUAAAAGGGUAGACAUAAUAAA_A-5'
```

Optionally, the mismatched 'g' residue of position 24 of the sense strand is alternatively 'a' or 'c'.

HAO1-1171 25/27mer DsiRNA, mismatch position=25 of sense strand (from 5'-terminus)

(SEQ ID NO: 3466)
5'-AUAUUUCCCAUCUGUAUUAUUUt$^a$-3'
(SEQ ID NO: 580)
3'-GUUAUAAAAGGGUAGACAUAAUAAAA$_A$-3'

Optionally, the mismatched 'a' residue of position 25 of the sense strand is alternatively 'c' or 'g'.

HAO1-1171 25/27mer DsiRNA, mismatch position=1 of antisense strand (from 5'-terminus)

(SEQ ID NO: 196)
5'-AUAUUUCCCAUCUGUAUUAUUU$^t$t-3'
(SEQ ID NO: 3467)
3'-GUUAUAAAAGGGUAGACAUAAUAAAA$_U$-5'

Optionally, the mismatched 'U' residue of position 1 of the antisense strand is alternatively 'G' or 'C'.

HAO1-1171 25/27mer DsiRNA, mismatch position=2 of antisense strand (from 5'-terminus)

(SEQ ID NO: 196)
5'-AUAUUUCCCAUCUGUAUUAUUU$^c$t-3'
(SEQ ID NO: 3468)
3'-GUUAUAAAAGGGUAGACAUAAUAAA$_C$A-5'

Optionally, the mismatched 'C' residue of position 2 of the antisense strand is alternatively 'U' or 'G'.

HAO1-1171 25/27mer DsiRNA, mismatch position=3 of antisense strand (from 5'-terminus)

(SEQ ID NO: 196)
5'-AUAUUUCCCAUCUGUAUUAUU$^U$tt-3'
(SEQ ID NO: 3469)
3'-GUUAUAAAAGGGUAGACAUAAUAA$_U$AA-5'

Optionally, the mismatched 'U' residue of position 3 of the antisense strand is alternatively 'C' or 'G'.

HAO1-1171 25/27mer DsiRNA, mismatch position=4 of antisense strand (from 5'-terminus)

(SEQ ID NO: 196)
5'-AUAUUUCCCAUCUGUAUUAU$^U$Utt-3'
(SEQ ID NO: 3470)
3'-GUUAUAAAAGGGUAGACAUAAUA$_C$AAA-5'

Optionally, the mismatched 'C' residue of position 4 of the antisense strand is alternatively 'U' or 'G'.

HAO1-1171 25/27mer DsiRNA, mismatch position=5 of antisense strand (from 5'-terminus)

(SEQ ID NO: 196)
5'-AUAUUUCCCAUCUGUAUUA$^U$UUtt-3'
(SEQ ID NO: 3471)
3'-GUUAUAAAAGGGUAGACAUAAU$_U$AAAA-5'

Optionally, the mismatched 'U' residue of position 5 of the antisense strand is alternatively 'C' or 'G'.

HAO1-1171 25/27mer DsiRNA, mismatch position=6 of antisense strand (from 5'-terminus)

(SEQ ID NO: 196)
5'-AUAUUUCCCAUCUGUAUU$^A$UUUtt-3'
(SEQ ID NO: 3472)
3'-GUUAUAAAAGGGUAGACAUAA$_A$AAAAA-5'

Optionally, the mismatched 'A' residue of position 6 of the antisense strand is alternatively 'C' or 'G'.

HAO1-1171 25/27mer DsiRNA, mismatch position=7 of antisense strand (from 5'-terminus)

(SEQ ID NO: 196)
5'-AUAUUUCCCAUCUGUAU$^U$AUUUtt-3'
(SEQ ID NO: 3473)
3'-GUUAUAAAAGGGUAGACAUA$_U$UAAAAA-5'

Optionally, the mismatched 'U' residue of position 7 of the antisense strand is alternatively 'C' or 'G'.

As another example, in the below structures, such mismatches are introduced within the asymmetric HAO1-1378 DsiRNA (newly-introduced mismatch residues are italicized): HAO1-1378 25/27mer DsiRNA, mismatch position=19 of sense strand (from 5'-terminus)

(SEQ ID NO: 3474)
5'-UGGAAAUAUAUUAACUGU$^A$AAAAag-3'
(SEQ ID NO: 680)
3'-GGACCUUUAUAUAAUUGACA$_A$UUUUUC-5'

Optionally, the mismatched 'A' residue of position 19 of the sense strand is alternatively 'C' or 'G'.

HAO1-1378 25/27mer DsiRNA, mismatch position=20 of sense strand (from 5'-terminus)

(SEQ ID NO: 3475)
5'-UGGAAAUAUAUUAACUGUU$^U$AAAag-3'
(SEQ ID NO: 680)
3'-GGACCUUUAUAUAAUUGACAA$_U$UUUUC-5'

Optionally, the mismatched 'U' residue of position 20 of the sense strand is alternatively 'C' or 'G'.

HAO1-1378 25/27mer DsiRNA, mismatch position=21 of sense strand (from 5'-terminus)

(SEQ ID NO: 3476)
5'-UGGAAAUAUAUUAACUGUUA$^U$AAag-3'
(SEQ ID NO: 680)
3'-GGACCUUUAUAUAAUUGACAAU$_U$UUUC-5'

Optionally, the mismatched 'U' residue of position 21 of the sense strand is alternatively 'G' or 'C'.

HAO1-1378 25/27mer DsiRNA, mismatch position=22 of sense strand (from 5'-terminus)

(SEQ ID NO: 3477)
5'-UGGAAAUAUAUUAACUGUUAA$^G$Aag-3'
(SEQ ID NO: 680)
3'-GGACCUUUAUAUAAUUGACAAUU$_U$UUC-5'

Optionally, the mismatched 'G' residue of position 22 of the sense strand is alternatively 'U' or 'C'.

HAO1-1378 25/27mer DsiRNA, mismatch position=23 of sense strand (from 5'-terminus)

(SEQ ID NO: 3478)
5'-UGGAAAUAUAUUAACUGUUAAA$^U$ag-3'
(SEQ ID NO: 680)
3'-GGACCUUUAUAUAAUUGACAAUUU$_U$UC-5'

Optionally, the mismatched 'U' residue of position 23 of the sense strand is alternatively 'C' or 'G'.

HAO1-1378 25/27mer DsiRNA, mismatch position=24 of sense strand (from 5'-terminus)

(SEQ ID NO: 3479)
5'-UGGAAAUAUAUUAACUGUUAAAA$^g$g-3'
(SEQ ID NO: 680)
3'-GGACCUUUAUAUAAUUGACAAUUUU$_U$C-5'

Optionally, the mismatched 'g' residue of position 24 of the sense strand is alternatively 't' or 'c'.

HAO1-1378 25/27mer DsiRNA, mismatch position=25 of sense strand (from 5'-terminus)

(SEQ ID NO: 3480)
5'-UGGAAAUAUAUUAACUGUUAAAAa$^a$-3'
(SEQ ID NO: 680)
3'-GGACCUUUAUAUAAUUGACAAUUUUU$_C$-5'

Optionally, the mismatched 'a' residue of position 25 of the sense strand is alternatively 't' or 'c'.

HAO1-1378 25/27mer DsiRNA, mismatch position=1 of antisense strand (from 5'-terminus)

(SEQ ID NO: 296)
5'-UGGAAAUAUAUUAACUGUUAAAAa$^g$-3'
(SEQ ID NO: 3481)
3'-GGACCUUUAUAUAAUUGACAAUUUUU$_U$-5'

Optionally, the mismatched 'U' residue of position 1 of the antisense strand is alternatively 'A' or 'G'.

HAO1-1378 25/27mer DsiRNA, mismatch position=2 of antisense strand (from 5'-terminus)

(SEQ ID NO: 296)
5'-UGGAAAUAUAUUAACUGUUAAAA$^a$g-3'
(SEQ ID NO: 3482)
3'-GGACCUUUAUAUAAUUGACAAUUUU$_C$C-5'

Optionally, the mismatched 'C' residue of position 2 of the antisense strand is alternatively 'A' or 'G'.

HAO1-1378 25/27mer DsiRNA, mismatch position=3 of antisense strand (from 5'-terminus)

(SEQ ID NO: 296)
5'-UGGAAAUAUAUUAACUGUUAAA$^A$ag-3'
(SEQ ID NO: 3483)
3'-GGACCUUUAUAUAAUUGACAAUUU$_A$UC-5'

Optionally, the mismatched 'A' residue of position 3 of the antisense strand is alternatively 'C' or 'G'.

HAO1-1378 25/27mer DsiRNA, mismatch position=4 of antisense strand (from 5'-terminus)

(SEQ ID NO: 296)
5'-UGGAAAUAUAUUAACUGUUAA$^A$Aag-3'
(SEQ ID NO: 3484)
3'-GGACCUUUAUAUAAUUGACAAUU$_C$UUC-5'

Optionally, the mismatched 'C' residue of position 4 of the antisense strand is alternatively 'A' or 'G'.

HAO1-1378 25/27mer DsiRNA, mismatch position=5 of antisense strand (from 5'-terminus)

(SEQ ID NO: 296)
5'-UGGAAAUAUAUUAACUGUUA$^A$AAag-3'
(SEQ ID NO: 3485)
3'-GGACCUUUAUAUAAUUGACAAU$_A$UUUC-5'

Optionally, the mismatched 'A' residue of position 5 of the antisense strand is alternatively 'C' or 'G'.

HAO1-1378 25/27mer DsiRNA, mismatch position=6 of antisense strand (from 5'-terminus)

```
                                          (SEQ ID NO: 296)
5'-UGGAAAUAUAUUAACUGUUᴬAAAag-3'
                                         (SEQ ID NO: 3486)
3'-GGACCUUUAUAUAAUUGACAAₐUUUUC-5'
```

Optionally, the mismatched 'A' residue of position 6 of the antisense strand is alternatively 'C' or 'G'.
HAO1-1378 25/27mer DsiRNA, mismatch position=7 of antisense strand (from 5'-terminus)

```
                                          (SEQ ID NO: 296)
5'-UGGAAAUAUAUUAACUGUᵁAAAag-3'
                                         (SEQ ID NO: 3487)
3'-GGACCUUUAUAUAAUUGACAᵤUUUUUC-5'
```

Optionally, the mismatched 'U' residue of position 7 of the antisense strand is alternatively 'C' or 'G'.

For the above oligonucleotide strand sequences, it is contemplated that the sense strand sequence of one depicted duplex can be combined with an antisense strand of another depicted duplex, thereby forming a distinct duplex—in certain instances, such duplexes contain a mismatched residue with respect to the Glycolate Oxidase target transcript sequence, while such sense and antisense strand sequences do not present a mismatch at this residue with respect to one another (e.g., duplexes comprising SEQ ID NOs: 3466 and 3467; SEQ ID NOs: 3465 and 3468; SEQ ID NOs: 3464 and 3469, etc., are contemplated as exemplary of such duplexes).

As noted above, introduction of mismatches can be performed upon any of the DsiRNAs described herein.

The mismatches of such DsiRNA structures can be combined to produce a DsiRNA possessing, e.g., two, three or even four mismatches within the 3'-terminal four to seven nucleotides of the sense strand/5'-terminal four to seven nucleotides of the antisense strand.

Indeed, in view of the flexibility of sequences which can be incorporated into DsiRNAs at the 3'-terminal residues of the sense strand/5'-terminal residues of the antisense strand, in certain embodiments, the sequence requirements of an asymmetric DsiRNA of the instant invention can be represented as the following (minimalist) structure (shown for an exemplary HAO1-1171 DsiRNA sequence):

```
                                         (SEQ ID NO: 3488)
5'-AUAUUUCCCAUCUGUAUXXXXXX[X]ₙ-3'
                                         (SEQ ID NO: 3489)
3'-GUUAUAAAAGGGUAGACAUAXXXXXX[X]ₙ-5'
``` where n=1 to 5, 1 to 10, 1 to 20, 1 to 30, 1 to 50, or 1 to 80 or more.
HAO1-1171 mRNA Target: 5'-CAAUAUUUCCCAUCU-GUAUXXXXXXX-3' (SEQ ID NO: 3490).

The Glycolate Oxidase target site may also be a site which is targeted by one or more of several oligonucleotides whose complementary target sites overlap with a stated target site. For example, for an exemplary HAO1-1315 DsiRNA, it is noted that certain DsiRNAs targeting overlapping and only slightly offset Glycolate Oxidase sequences could exhibit activity levels similar to that of HAO1-1315 (e.g., HAO1-1314 to HAO1-1317 of Table 2 above). Thus, in certain embodiments, a designated target sequence region might be effectively targeted by a series of DsiRNAs possessing largely overlapping sequences. (E.g., if considering DsiRNAs of the HAO1-1314 to HAO1-1317 target site(s), a more encompassing Glycolate Oxidase transcript target sequence might be recited as, e.g., 5'-TTTCATGCTTT-GACTTTTCAATGGGTGT-3' (SEQ ID NO: 3491), wherein any given DsiRNA (e.g., a DsiRNA selected from HAO1-1314 to HAO1-1317) only targets a sub-sequence within such a sequence region, yet the entire sequence can be considered a viable target for such a series of DsiRNAs).

Additionally and/or alternatively, mismatches within the 3'-terminal seven nucleotides of the sense strand/5'-terminal seven nucleotides of the antisense strand can be combined with mismatches positioned at other mismatch-tolerant positions, as described above.

In view of the present identification of the above-described Dicer substrate agents (DsiRNAs) as inhibitors of Glycolate Oxidase levels via targeting of specific Glycolate Oxidase sequences, it is also recognized that dsRNAs having structures similar to those described herein can also be synthesized which target other sequences within the Glycolate Oxidase sequence of NM_017545.2, or within variants thereof (e.g., target sequences possessing 80% identity, 90% identity, 95% identity, 96% identity, 97% identity, 98% identity, 99% or more identity to a sequence of NM_017545.2).

Anti-Glycolate Oxidase DsiRNA Design/Synthesis

It has been found empirically that longer dsRNA species of from 25 to 35 nucleotides (DsiRNAs) and especially from 25 to 30 nucleotides give unexpectedly effective results in terms of potency and duration of action, as compared to 19-23mer siRNA agents. Without wishing to be bound by the underlying theory of the dsRNA processing mechanism, it is thought that the longer dsRNA species serve as a substrate for the Dicer enzyme in the cytoplasm of a cell. In addition to cleaving the dsRNA of the invention into shorter segments, Dicer is thought to facilitate the incorporation of a single-stranded cleavage product derived from the cleaved dsRNA into the RISC complex that is responsible for the destruction of the cytoplasmic RNA (e.g., Glycolate Oxidase RNA) of or derived from the target gene, Glycolate Oxidase (or other gene associated with a Glycolate Oxidase-associated disease or disorder). Prior studies (Rossi et al., U.S. Patent Application No. 2007/0265220) have shown that the cleavability of a dsRNA species (specifically, a DsiRNA agent) by Dicer corresponds with increased potency and duration of action of the dsRNA species.

Certain anti-Glycolate Oxidase DsiRNA agents were selected from a pre-screened population. Design of DsiRNAs can optionally involve use of predictive scoring algorithms that perform in silico assessments of the projected activity/efficacy of a number of possible DsiRNA agents spanning a region of sequence. Information regarding the design of such scoring algorithms can be found, e.g., in Gong et al. (*BMC Bioinformatics* 2006, 7:516), though a more recent "v4.3" algorithm represents a theoretically improved algorithm relative to siRNA scoring algorithms previously available in the art. (E.g., "v3" and "v4" scoring algorithms are machine learning algorithms that are not reliant upon any biases in human sequence. In addition, the "v3" and "v4" algorithms derive from data sets that are many-fold larger than that from which an older "v2" algorithm such as that described in Gong et al. derives.)

The first and second oligonucleotides of the DsiRNA agents of the instant invention are not required to be completely complementary. In fact, in one embodiment, the 3'-terminus of the sense strand contains one or more mismatches. In one aspect, two mismatches are incorporated at the 3' terminus of the sense strand. In another embodiment, the DsiRNA of the invention is a double stranded RNA molecule containing two RNA oligonucleotides each of which is 27 nucleotides in length and, when annealed to each other, have blunt ends and a two nucleotide mismatch on the 3'-terminus of the sense strand (the 5'-terminus of the antisense strand). The use of mismatches or decreased thermodynamic stability (specifically at the 3'-sense/5'-antisense position) has been proposed to facilitate or favor entry of the antisense strand into RISC (Schwarz et al., 2003, Cell 115: 199-208: Khvorova et al., 2003. Cell 115: 209-216), presumably by affecting some rate-limiting unwinding steps that occur with entry of the siRNA into RISC. Thus, terminal base composition has been included in design algorithms for selecting active 21mer siRNA duplexes (Ui-Tei et al., 2004, Nucleic Acids Res 32: 936-948; Reynolds et al., 2004, Nat Biotechnol 22: 326-330). With Dicer cleavage of the dsRNA of this embodiment, the small end-terminal sequence which contains the mismatches will either be left unpaired with the antisense strand (become part of a 3'-overhang) or be cleaved entirely off the final 21-mer siRNA. These "mismatches", therefore, do not persist as mismatches in the final RNA component of RISC. The finding that base mismatches or destabilization of segments at the 3'-end of the sense strand of Dicer substrate improved the potency of synthetic duplexes in RNAi, presumably by facilitating processing by Dicer, was a surprising finding of past works describing the design and use of 25-30mer dsRNAs (also termed "DsiRNAs" herein; Rossi et al., U.S. Patent Application Nos. 2005/0277610, 2005/0244858 and 2007/0265220).

Modification of Anti-Glycolate Oxidase dsRNAs

One major factor that inhibits the effect of double stranded RNAs ("dsRNAs") is the degradation of dsRNAs (e.g., siRNAs and DsiRNAs) by nucleases. A 3'-exonuclease is the primary nuclease activity present in serum and modification of the 3'-ends of antisense DNA oligonucleotides is crucial to prevent degradation (Eder et al., 1991, Antisense Res Dev, 1: 141-151). An RNase-T family nuclease has been identified called ERI-1 which has 3' to 5' exonuclease activity that is involved in regulation and degradation of siRNAs (Kennedy et al., 2004. Nature 427: 645-649; Hong et al., 2005, Biochem J, 390: 675-679). This gene is also known as Thex1 (NM_026067) in mice or THEX1 (NM_153332) in humans and is involved in degradation of histone mRNA; it also mediates degradation of 3'-overhangs in siRNAs, but does not degrade duplex RNA (Yang et al., 2006, J Biol Chem, 281: 30447-30454). It is therefore reasonable to expect that 3'-end-stabilization of dsRNAs, including the DsiRNAs of the instant invention, will improve stability.

XRN1 (NM_019001) is a 5' to 3' exonuclease that resides in P-bodies and has been implicated in degradation of mRNA targeted by miRNA (Rehwinkel et al., 2005. RNA 11: 1640-1647) and may also be responsible for completing degradation initiated by internal cleavage as directed by a siRNA. XRN2 (NM_012255) is a distinct 5' to 3' exonuclease that is involved in nuclear RNA processing.

RNase A is a major endonuclease activity in mammals that degrades RNAs. It is specific for ssRNA and cleaves at the 3'-end of pyrimidine bases. SiRNA degradation products consistent with RNase A cleavage can be detected by mass spectrometry after incubation in serum (Turner et al., 2007, Mol Biosyst 3: 43-50). The 3'-overhangs enhance the susceptibility of siRNAs to RNase degradation. Depletion of RNase A from serum reduces degradation of siRNAs; this degradation does show some sequence preference and is worse for sequences having poly A/U sequence on the ends (Haupenthal et al., 2006 Biochem Pharmacol 71: 702-710). This suggests the possibility that lower stability regions of the duplex may "breathe" and offer transient single-stranded species available for degradation by RNase A. RNase A inhibitors can be added to serum and improve siRNA longevity and potency (Haupenthal el al., 2007, bht J. Cancer 121: 206-210).

In 21mers, phosphorothioate or boranophosphate modifications directly stabilize the internucleoside phosphate linkage. Boranophosphate modified RNAs are highly nuclease resistant, potent as silencing agents, and are relatively non-toxic. Boranophosphate modified RNAs cannot be manufactured using standard chemical synthesis methods and instead are made by in vitro transcription (IVT) (Hall et al., 2004, Nucleic Acids Res 32: 5991-6000; Hall et al., 2006, Nucleic Acids Res 34: 2773-2781). Phosphorothioate (PS) modifications can be easily placed in the RNA duplex at any desired position and can be made using standard chemical synthesis methods. The PS modification shows dose-dependent toxicity, so most investigators have recommended limited incorporation in siRNAs, favoring the 3'-ends where protection from nucleases is most important (Harborth et al., 2003, Antisense Nucleic Acid Drug Dev 13: 83-105; Chiu and Rana, 2003, Mol Cell 10: 549-561: Braasch et al., 2003. Biochemistry 42: 7967-7975; Amarzguioui et al., 2003, Nucleic Acids Research 31: 589-595). More extensive PS modification can be compatible with potent RNAi activity; however, use of sugar modifications (such as 2'-O-methyl RNA) may be superior (Choung et al., 2006, Biochem Biophys Res Commun 342: 919-927).

A variety of substitutions can be placed at the 2'-position of the ribose which generally increases duplex stability ($T_m$) and can greatly improve nuclease resistance. 2'-O-methyl RNA is a naturally occurring modification found in mammalian ribosomal RNAs and transfer RNAs. 2'-O-methyl modification in siRNAs is known, but the precise position of modified bases within the duplex is important to retain potency and complete substitution of 2'-O-methyl RNA for RNA will inactivate the siRNA. For example, a pattern that employs alternating 2'-O-methyl bases can have potency equivalent to unmodified RNA and is quite stable in serum (Choung el al., 2006, Biochem Biophys Res Commun 342: 919-927; Czauderna et al., 2003, Nucleic Acids Research 31: 2705-2716).

The 2'-fluoro (2'-F) modification is also compatible with dsRNA (e.g., siRNA and DsiRNA) function; it is most commonly placed at pyrimidine sites (due to reagent cost and availability) and can be combined with 2'-O-methyl modification at purine positions; 2'-F purines are available and can also be used. Heavily modified duplexes of this kind can be potent triggers of RNAi in vitro (Allerson et al., 2005. J Med Chem 48: 901-904; Prakash et al., 2005, J Med Chem 48: 4247-4253; Kraynack and Baker, 2006, RNA 12: 163-176) and can improve performance and extend duration of action when used in vivo (Morrissey et al., 2005, Hepatology 41: 1349-1356; Morrissey et al., 2005, Nat Biotechnol 23: 1002-1007). A highly potent, nuclease stable, blunt 19mer duplex containing alternative 2'-F and 2'-O-Me bases is taught by Allerson. In this design, alternating 2'-O-Me residues are positioned in an identical pattern to that employed by Czauderna, however the remaining RNA residues are converted to 2'-F modified bases. A highly potent, nuclease resistant siRNA employed by Morrissey employed a highly potent, nuclease resistant siRNA in vivo. In addition to 2'-O-Me RNA and 2'-F RNA, this duplex includes DNA. RNA, inverted abasic residues, and a 3'-terminal PS internucleoside linkage. While extensive modification has certain benefits, more limited modification of the duplex can also improve in vivo performance and is both simpler and less costly to manufacture. Soutschek et al. (2004, Nature 432: 173-178) employed a duplex in vivo and was mostly RNA with two 2'-O-Me RNA bases and limited 3'-terminal PS internucleoside linkages.

Locked nucleic acids (LNAs) are a different class of 2'-modification that can be used to stabilize dsRNA (e.g., siRNA and DsiRNA). Patterns of LNA incorporation that retain potency are more restricted than 2'-O-methyl or 2'-F bases, so limited modification is preferred (Braasch et al., 2003, Biochemistry 42: 7967-7975; Grunweller et al., 2003, Nucleic Acids Res 31: 3185-3193; Elmen et al., 2005, Nucleic Acids Res 33: 439-447). Even with limited incorporation, the use of LNA modifications can improve dsRNA performance in vivo and may also alter or improve off target effect profiles (Mook el al., 2007, Mol Cancer Ther 6: 833-843).

Synthetic nucleic acids introduced into cells or live animals can be recognized as "foreign" and trigger an immune response. Immune stimulation constitutes a major class of off-target effects which can dramatically change experimental results and even lead to cell death. The innate immune system includes a collection of receptor molecules that specifically interact with DNA and RNA that mediate these responses, some of which are located in the cytoplasm and some of which reside in endosomes (Marques and Williams, 2005. Nat Biotechnol 23: 1399-1405; Schlee et al., 2006, Mol Ther 14: 463-470). Delivery of siRNAs by cationic lipids or liposomes exposes the siRNA to both cytoplasmic and endosomal compartments, maximizing the risk for triggering a type 1 interferon (IFN) response both in vitro and in vivo (Morrissey et al., 2005, Nat Biotechnol 23: 1002-1007; Sioud and Sorensen, 2003, Biochem Biophys Res Commun 312: 1220-1225; Sioud, 2005, J Mol Biol 348: 1079-1090; Ma et al., 2005, Biochem Biophys Res Commun 330: 755-759). RNAs transcribed within the cell are less immunogenic (Robbins et al., 2006, Nat Biotechnol 24: 566-571) and synthetic RNAs that are immunogenic when delivered using lipid-based methods can evade immune stimulation when introduced unto cells by mechanical means, even in vivo (Heidel et al., 2004, Nat Biotechnol 22: 1579-1582). However, lipid based delivery methods are convenient, effective, and widely used. Some general strategy to prevent immune responses is needed, especially for in vivo application where all cell types are present and the risk of generating an immune response is highest. Use of chemically modified RNAs may solve most or even all of these problems.

In certain embodiments, modifications can be included in the anti-Glycolate Oxidase dsRNA agents of the present invention so long as the modification does not prevent the dsRNA agent from possessing Glycolate Oxidase inhibitory activity. In one embodiment, one or more modifications are made that enhance Dicer processing of the DsiRNA agent (an assay for determining Dicer processing of a DsiRNA is described elsewhere herein). In a second embodiment, one or more modifications are made that result in more effective Glycolate Oxidase inhibition (as described herein, Glycolate Oxidase inhibition/Glycolate Oxidase inhibitory activity of a dsRNA can be assayed via art-recognized methods for determining RNA levels, or for determining Glycolate Oxidase polypeptide levels, should such levels be assessed in lieu of or in addition to assessment of, e.g., Glycolate Oxidase mRNA levels). In a third embodiment, one or more modifications are made that support greater Glycolate Oxidase inhibitory activity (means of determining Glycolate Oxidase inhibitory activity are described supra). In a fourth embodiment, one or more modifications are made that result in greater potency of Glycolate Oxidase inhibitory activity per each dsRNA agent molecule to be delivered to the cell (potency of Glycolate Oxidase inhibitory activity is described supra). Modifications can be incorporated in the 3'-terminal region, the 5'-terminal region, in both the 3'-terminal and 5'-terminal region or in some instances in various positions within the sequence. With the restrictions noted above in mind, numbers and combinations of modifications can be incorporated into the dsRNA agent. Where multiple modifications are present, they may be the same or different. Modifications to bases, sugar moieties, the phosphate backbone, and their combinations are contemplated. Either 5'-terminus can be phosphorylated.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003, Nucleic Acids Research 31: 589-595). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988 and 6,291.438 and in U.S. published patent application No. 2004/0203145 A1. Other modifications are disclosed in Herdewijn (2000, Antisense Nucleic Acid Drug Dev 10: 297-310), Eckstein (2000. Antisense Nucleic Acid Drug Dev 10: 117-21), Rusckowski et al. (2000. Antisense Nucleic Acid Drug Dev 10: 333-345), Stein et al. (2001, Antisense Nucleic Acid Drug Dev 11: 317-25): Vorobjev et al. (2001. Antisense Nucleic Acid Drug Dev 11: 77-85).

One or more modifications contemplated can be incorporated into either strand. The placement of the modifications in the dsRNA agent can greatly affect the characteristics of the dsRNA agent, including conferring greater potency and stability, reducing toxicity, enhance Dicer processing, and minimizing an immune response. In one embodiment, the antisense strand or the sense strand or both strands have one or more 2'-O-methyl modified nucleotides. In another embodiment, the antisense strand contains 2'-O-methyl modified nucleotides. In another embodiment, the antisense stand contains a 3' overhang that is comprised of 2'-O-methyl modified nucleotides. The antisense strand could also include additional 2'-O-methyl modified nucleotides.

In certain embodiments, the anti-Glycolate Oxidase DsiRNA agent of the invention has several properties which enhance its processing by Dicer. According to such embodiments, the DsiRNA agent has a length sufficient such that it is processed by Dicer to produce an siRNA and at least one of the following properties: (i) the DsiRNA agent is asymmetric, e.g., has a 3' overhang on the sense strand and (ii) the DsiRNA agent has a modified 3' end on the antisense strand to direct orientation of Dicer binding and processing of the dsRNA to an active siRNA. According to these embodiments, the longest strand in the DsiRNA agent comprises 25-30 nucleotides. In one embodiment, the sense strand comprises 25-30 nucleotides and the antisense strand comprises 25-28 nucleotides. Thus, the resulting dsRNA has an overhang on the 3' end of the sense strand. The overhang is 1-4 nucleotides, such as 2 nucleotides. The antisense strand may also have a 5' phosphate.

In certain embodiments, the sense strand of a DsiRNA agent is modified for Dicer processing by suitable modifiers located at the 3' end of the sense strand, i.e., the DsiRNA agent is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the sense strand in place of two ribonucleotides forming a blunt end of the duplex on the 5' end of the antisense strand and the 3' end of the sense strand, and a two-nucleotide RNA overhang is located on the 3'-end of the antisense strand. This is an asymmetric composition with DNA on the blunt end and RNA bases on the overhanging end.

In certain other embodiments, the antisense strand of a DsiRNA agent is modified for Dicer processing by suitable modifiers located at the 3' end of the antisense strand, i.e., the DsiRNA agent is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is also an asymmetric composition with DNA on the blunt end and RNA bases on the overhanging end.

The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3' end of antisense strand and are sufficiently complementary to a nucleotide sequence of the target Glycolate Oxidase RNA.

Additionally, the DsiRNA agent structure can be optimized to ensure that the oligonucleotide segment generated from Dicer's cleavage will be the portion of the oligonucleotide that is most effective in inhibiting gene expression. For example, in one embodiment of the invention, a 27-bp oligonucleotide of the DsiRNA agent structure is synthesized wherein the anticipated 21 to 22-bp segment that will inhibit gene expression is located on the 3'-end of the antisense strand. The remaining bases located on the 5'-end of the antisense strand will be cleaved by Dicer and will be discarded. This cleaved portion can be homologous (i.e., based on the sequence of the target sequence) or non-homologous and added to extend the nucleic acid strand.

US 2007/0265220 discloses that 27mer DsiRNAs showed improved stability in serum over comparable 21mer siRNA compositions, even absent chemical modification. Modifications of DsiRNA agents, such as inclusion of 2'-O-methyl RNA in the antisense strand, in patterns such as detailed above, when coupled with addition of a 5' Phosphate, can improve stability of DsiRNA agents. Addition of 5'-phosphate to all strands in synthetic RNA duplexes may be an inexpensive and physiological method to confer some limited degree of nuclease stability.

The chemical modification patterns of the dsRNA agents of the instant invention are designed to enhance the efficacy of such agents. Accordingly, such modifications are designed to avoid reducing potency of dsRNA agents; to avoid interfering with Dicer processing of DsiRNA agents; to improve stability in biological fluids (reduce nuclease sensitivity) of dsRNA agents; or to block or evade detection by the innate immune system. Such modifications are also designed to avoid being toxic and to avoid increasing the cost or impact the ease of manufacturing the instant dsRNA agents of the invention.

In certain embodiments of the present invention, an anti-Glycolate Oxidase DsiRNA agent has one or more of the following properties: (i) the DsiRNA agent is asymmetric, e.g., has a 3' overhang on the antisense strand and (ii) the DsiRNA agent has a modified 3' end on the sense strand to direct orientation of Dicer binding and processing of the dsRNA to an active siRNA. According to this embodiment, the longest strand in the dsRNA comprises 25-35 nucleotides (e.g., 25, 26, 27, 28, 29, 30, 31, 32, 33, 34 or 35 nucleotides). In certain such embodiments, the DsiRNA agent is asymmetric such that the sense strand comprises 25-34 nucleotides and the 3' end of the sense strand forms a blunt end with the 5' end of the antisense strand while the antisense strand comprises 26-35 nucleotides and forms an overhang on the 3' end of the antisense strand. In one embodiment, the DsiRNA agent is asymmetric such that the sense strand comprises 25-28 nucleotides and the antisense strand comprises 25-30 nucleotides. Thus, the resulting dsRNA has an overhang on the 3' end of the antisense strand. The overhang is 1-4 nucleotides, for example 2 nucleotides. The sense strand may also have a 5' phosphate.

The DsiRNA agent can also have one or more of the following additional properties: (a) the antisense strand has a right shift from the typical 21mer (e.g., the DsiRNA comprises a length of antisense strand nucleotides that extends to the 5' of a projected Dicer cleavage site within the DsiRNA, with such antisense strand nucleotides base paired with corresponding nucleotides of the sense strand extending 3' of a projected Dicer cleavage site in the sense strand), (b) the strands may not be completely complementary, i.e., the strands may contain simple mismatched base pairs (in certain embodiments, the DsiRNAs of the invention possess 1, 2, 3, 4 or even 5 or more mismatched base pairs, provided that Glycolate Oxidase inhibitory activity of the DsiRNA possessing mismatched base pairs is retained at sufficient levels (e.g., retains at least 50% Glycolate Oxidase inhibitory activity or more, at least 60% Glycolate Oxidase inhibitory activity or more, at least 70% Glycolate Oxidase inhibitory activity or more, at least 80% Glycolate Oxidase inhibitory activity or more, at least 90% Glycolate Oxidase inhibitory activity or more or at least 95% Glycolate Oxidase inhibitory activity or more as compared to a corresponding DsiRNA not possessing mismatched base pairs. In certain embodiments, mismatched base pairs exist between the antisense and sense strands of a DsiRNA. In some embodiments, mismatched base pairs exist (or are predicted to exist) between the antisense strand and the target RNA. In certain embodiments, the presence of a mismatched base pair(s) between an antisense strand residue and a corresponding residue within the target RNA that is located 3' in the target RNA sequence of a projected Ago2 cleavage site retains and may even enhance Glycolate Oxidase inhibitory activity of a DsiRNA of the invention) and (c) base modifications such as locked nucleic acid(s) may be included in the 5' end of the sense strand. A "typical" 21mer siRNA is designed using conventional techniques. In one technique, a variety of sites are commonly tested in parallel or pools containing several distinct siRNA duplexes specific to the same target with the hope that one of the reagents will be effective (Ji et al., 2003, FEBS Lett 552: 247-252). Other techniques use design rules and algorithms to increase the likelihood of obtaining active RNAi effector molecules (Schwarz et al., 2003, Cell 115: 199-208; Khvorova et al., 2003, Cell 115: 209-216; Ui-Tei et al., 2004, Nucleic Acids Res 32: 936-948: Reynolds et al., 2004, Nat Biotechnol 22: 326-330; Krol et al., 2004, J Biol Chem 279: 42230-42239; Yuan et al., 2004, Nucl Acids Res 32(Webserver issue):W 130-134; Boese et al., 2005, Methods Enzymol 392: 73-96). High throughput selection of siRNA has also been developed (U.S. published patent application No. 2005/0042641 A1). Potential target sites can also be analyzed by secondary structure predictions (Heale et al., 2005, Nucleic Acids Res 33(3): e30). This 21mer is then used to design a right shift to include 3-9 additional nucleotides on the 5' end of the 21 mer. The sequence of these additional nucleotides is not restricted. In one embodiment, the added ribonucleotides are based on the sequence of the target gene. Even in this embodiment, full complementarity between the target sequence and the antisense siRNA is not required.

The first and second oligonucleotides of a DsiRNA agent of the instant invention are not required to be completely complementary. They only need to be sufficiently complementary to anneal under biological conditions and to provide a substrate for Dicer that produces a siRNA sufficiently complementary to the target sequence. Locked nucleic acids, or LNA's, are well known to a skilled artisan (Elmen et al., 2005, Nucleic Acids Res 33: 439-447; Kurreck et al., 2002, Nucleic Acids Res 30: 1911-1918; Crinelli et al., 2002, Nucleic Acids Res 30: 2435-2443; Braasch and Corey, 2001, Chem Biol 8: 1-7; Bondensgaard et al., 2000. Chemistry 6: 2687-2695: Wahlestedt et al., 2000, Proc Natl Acad Sci USA 97: 5633-5638). In one embodiment, an LNA is incorporated at the 5' terminus of the sense strand. In another embodiment, an LNA is incorporated at the 5' terminus of the sense strand in duplexes designed to include a 3' overhang on the antisense strand.

In certain embodiments, the DsiRNA agent of the instant invention has an asymmetric structure, with the sense strand having a 25-base pair length, and the antisense strand having a 27-base pair length with a 2 base 3'-overhang. In other embodiments, this DsiRNA agent having an asymmetric structure further contains 2 deoxynucleotides at the 3' end of the sense strand in place of two of the ribonucleotides.

Certain DsiRNA agent compositions containing two separate oligonucleotides can be linked by a third structure. The third structure will not block Dicer activity on the DsiRNA agent and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the DsiRNA agent in a manner such that a hairpin structure is produced upon annealing of the two oligonucleotides making up the dsRNA composition. The hairpin structure will not block Dicer activity on the DsiRNA agent and will not interfere with the directed destruction of the Glycolate Oxidase RNA.

Glycolate Oxidase cDNA and Polypeptide Sequences

Known human and mouse Glycolate Oxidase (HAO1) cDNA and polypeptide sequences include the following: human Hydroxyacid Oxidase 1 (HAO1) NM_017545.2 and corresponding human HAO1 polypeptide sequence GenBank Accession No. NP_060015.1; and mouse wild-type HAO1 sequence GenBank Accession No. NM_010403.2 (Mus musculus C57BU6 HAO1) and corresponding mouse HAO1 sequence GenBank Accession No. NP_034533.1.

In Vitro Assay to Assess dsRNA Glycolate Oxidase Inhibitory Activity

An in vitro assay that recapitulates RNAi in a cell-free system can be used to evaluate dsRNA constructs targeting Glycolate Oxidase RNA sequence(s), and thus to assess Glycolate Oxidase-specific gene inhibitory activity (also referred to herein as Glycolate Oxidase inhibitory activity) of a dsRNA. The assay comprises the system described by Tuschl et al., 1999, Genes and Development, 13, 3191-3197 and Zamore et al., 2000, Cell, 101, 25-33 adapted for use with dsRNA (e.g., DsiRNA) agents directed against Glycolate Oxidase RNA. A Drosophila extract derived from syncytial blastoderm is used to reconstitute RNAi activity in vitro. Target RNA is generated via in vitro transcription from a selected Glycolate Oxidase expressing plasmid using T7 RNA polymerase or via chemical synthesis. Sense and antisense dsRNA strands (for example, 20 uM each) are annealed by incubation in buffer (such as 100 mM potassium acetate, 30 mM HEPES-KOH, pH 7.4, 2 mM magnesium acetate) for 1 minute at 90° C. followed by 1 hour at 37° C., then diluted in lysis buffer (for example 100 mM potassium acetate, 30 mM HEPES-KOH at pH 7.4, 2 mM magnesium acetate). Annealing can be monitored by gel electrophoresis on an agarose gel in TBE buffer and stained with ethidium bromide. The *Drosophila* lysate is prepared using zero to two-hour-old embryos from Oregon R flies collected on yeasted molasses agar that are dechorionated and lysed. The lysate is centrifuged and the supernatant isolated. The assay comprises a reaction mixture containing 50% lysate [vol/vol], RNA (10-50 pM final concentration), and 10% [vol/vol] lysis buffer containing dsRNA (10 nM final concentration). The reaction mixture also contains 10 mM creatine phosphate, 10 ug/ml creatine phosphokinase, 100 um GTP, 100 uM UTP, 100 uM CTP, 500 uM ATP, 5 mM DTT, 0.1 U/uL RNasin (Promega), and 100 uM of each amino acid. The final concentration of potassium acetate is adjusted to 100 mM. The reactions are pre-assembled on ice and pre-incubated at 25° C. for 10 minutes before adding RNA, then incubated at 25° C. for an additional 60 minutes. Reactions are quenched with 4 volumes of 1.25× Passive Lysis Buffer (Promega). Target RNA cleavage is assayed by RT-PCR analysis or other methods known in the art and are compared to control reactions in which dsRNA is omitted from the reaction.

Alternately, internally-labeled target RNA for the assay is prepared by in vitro transcription in the presence of [$\alpha$-$^{32}$P] CTP, passed over a G50 Sephadex column by spin chromatography and used as target RNA without further purification. Optionally, target RNA is 5'-$^{32}$P-end labeled using T4 polynucleotide kinase enzyme. Assays are performed as described above and target RNA and the specific RNA cleavage products generated by RNAi are visualized on an autoradiograph of a gel. The percentage of cleavage is determined by PHOSPHOR IMAGER® (autoradiography) quantitation of bands representing intact control RNA or RNA from control reactions without dsRNA and the cleavage products generated by the assay.

In one embodiment, this assay is used to determine target sites in the Glycolate Oxidase RNA target for dsRNA mediated RNAi cleavage, wherein a plurality of dsRNA constructs are screened for RNAi mediated cleavage of the Glycolate Oxidase RNA target, for example, by analyzing the assay reaction by electrophoresis of labeled target RNA, or by northern blotting, as well as by other methodology well known in the art.

In certain embodiments, a dsRNA of the invention is deemed to possess Glycolate Oxidase inhibitory activity if, e.g., a 50% reduction in Glycolate Oxidase RNA levels is observed in a system, cell, tissue or organism, relative to a suitable control. Additional metes and bounds for determination of Glycolate Oxidase inhibitory activity of a dsRNA of the invention are described supra.

Conjugation and Delivery of Anti-Glycolate Oxidase dsRNA Agents

In certain embodiments, the present invention relates to a method for treating a subject having or at risk of developing a disease or disorder for which inhibition of Glycolate Oxidase is predicted to or has been demonstrated to have therapeutic value (e.g., a liver disease such as primary hyperoxaluria 1 (PH1)). In such embodiments, the dsRNA can act as novel therapeutic agents for controlling the disease or disorder for which inhibition of Glycolate Oxidase is predicted to or has been demonstrated to have therapeutic value. The method comprises administering a pharmaceutical composition of the invention to the patient (e.g., human), such that the expression, level and/or activity of a Glycolate Oxidase (HAO1) RNA is reduced. The expression, level and/or activity of a polypeptide encoded by a Glycolate Oxidase (HAO1) RNA might also be reduced by a dsRNA of the instant invention, even where said dsRNA is directed against a non-coding region of the Glycolate Oxidase transcript (e.g., a targeted 5' UTR or 3' UTR sequence). Because of their high specificity, the dsRNAs of the present invention can specifically target Glycolate Oxidase (HAO1) sequences of cells and tissues, optionally even in an allele-specific manner where polymorphic alleles exist within an individual and/or population.

In the treatment of a disease or disorder for which inhibition of Glycolate Oxidase is predicted to or has been demonstrated to have therapeutic value, the dsRNA can be brought into contact with the cells or tissue of a subject, e.g., the cells or tissue of a subject exhibiting disregulation of Glycolate Oxidase and/or otherwise targeted for reduction of Glycolate Oxidase levels. For example, dsRNA substantially identical to all or part of a Glycolate Oxidase RNA sequence may be brought into contact with or introduced into such a cell, either in vivo or in vitro. Similarly, dsRNA substantially identical to all or part of a Glycolate Oxidase RNA sequence may be administered directly to a subject having or at risk of developing a disease or disorder for which inhibition of Glycolate Oxidase is predicted to or has been demonstrated to have therapeutic value.

Therapeutic use of the dsRNA agents of the instant invention can involve use of formulations of dsRNA agents comprising multiple different dsRNA agent sequences. For example, two or more, three or more, four or more, five or more, etc. of the presently described agents can be combined to produce a formulation that, e.g., targets multiple different regions of the Glycolate Oxidase RNA, or that not only target Glycolate Oxidase RNA but also target, e.g., cellular target genes associated with a disease or disorder for which inhibition of Glycolate Oxidase is predicted to or has been demonstrated to have therapeutic value. A dsRNA agent of the instant invention may also be constructed such that either strand of the dsRNA agent independently targets two or more regions of Glycolate Oxidase RNA, or such that one of the strands of the dsRNA agent targets a cellular target gene of Glycolate Oxidase known in the art.

Use of multifunctional dsRNA molecules that target more then one region of a target nucleic acid molecule can also provide potent inhibition of Glycolate Oxidase RNA levels and expression. For example, a single multifunctional dsRNA construct of the invention can target both the HAO1-1171 and HAO1-1378 sites simultaneously; additionally and/or alternatively, single or multifunctional agents of the invention can be designed to selectively target one splice variant of Glycolate Oxidase over another.

Thus, the dsRNA agents of the instant invention, individually, or in combination or in conjunction with other drugs, can be used to treat, inhibit, reduce, or prevent a disease or disorder for which inhibition of Glycolate Oxidase is predicted to or has been demonstrated to have therapeutic value. For example, the dsRNA molecules can be administered to a subject or can be administered to other appropriate cells evident to those skilled in the art, individually or in combination with one or more drugs under conditions suitable for the treatment.

The dsRNA molecules also can be used in combination with other known treatments to treat, inhibit, reduce, or prevent a disease or disorder for which inhibition of Glycolate Oxidase is predicted to or has been demonstrated to have therapeutic value in a subject or organism. For example, the described molecules could be used in combination with one or more known compounds, treatments, or procedures to treat, inhibit, reduce, or prevent a disease or disorder for which inhibition of Glycolate Oxidase is predicted to or has been demonstrated to have therapeutic value in a subject or organism as are known in the art.

A dsRNA agent of the invention can be conjugated (e.g., at its 5' or 3' terminus of its sense or antisense strand) or unconjugated to another moiety (e.g. a non-nucleic acid moiety such as a peptide), an organic compound (e.g., a dye, cholesterol, or the like). Modifying dsRNA agents in this way may improve cellular uptake or enhance cellular targeting activities of the resulting dsRNA agent derivative as compared to the corresponding unconjugated dsRNA agent, are useful for tracing the dsRNA agent derivative in the cell, or improve the stability of the dsRNA agent derivative compared to the corresponding unconjugated dsRNA agent.

In certain embodiments, specific exemplary forms of dsRNA conjugates are contemplated. Notably, RNAi therapies, such as the dsRNAs that are specifically exemplified herein, have demonstrated particularly good ability to be delivered to the cells of the liver in vivo (via, e.g., lipid nanoparticles and/or conjugates such as dynamic polyconjugates or GalNAc conjugates—in certain exemplary embodiments, one or more GalNAc moieties can be conjugated to a 3'- and/or 5'-overhang region of a dsNA, optionally to an "extended" overhang region of a dsNA (e.g., to a 5 or more nucleotide, 8 or more nucleotide, etc. example of such an overhang): additionally and/or alternatively, one or more GalNAc moieties can be conjugated to ds extended regions of a dsNA, e.g., to the duplex region formed by the 5'-end region of the guide/antisense strand of a dsNA and the corresponding 3'-end region of the passenger/sense strand of a dsNA and/or to the duplex region formed by the 3'-end region of the guide/antisense strand of a dsNA and the corresponding 5'-end region of the passenger/sense strand of a dsNA). Thus, formulated RNAi therapies, such as those described herein, are attractive modalities for treating or preventing diseases or disorders that are present in, originate in or otherwise involve the liver.

Methods of Introducing Nucleic Acids, Vectors, and Host Cells dsRNA agents of the invention may be directly introduced into a cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The dsRNA agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target Glycolate Oxidase RNA.

A cell having a target Glycolate Oxidase RNA may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target Glycolate Oxidase RNA sequence and the dose of dsRNA agent material delivered, this process may provide partial or complete loss of function for the Glycolate Oxidase RNA. A reduction or loss of RNA levels or expression (either Glycolate Oxidase RNA expression or encoded polypeptide expression) in at least 50%, 60%, 70%, 80%, 90%, 95% or 99% or more of targeted cells is exemplary. Inhibition of Glycolate Oxidase RNA levels or expression refers to the absence (or observable decrease) in the level of Glycolate Oxidase RNA or Glycolate Oxidase RNA-encoded protein. Specificity refers to the ability to inhibit the Glycolate Oxidase RNA without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). Inhibition of target Glycolate Oxidase RNA sequence(s) by the dsRNA agents of the invention also can be measured based upon the effect of administration of such dsRNA agents upon development/progression of a disease or disorder for which inhibition of Glycolate Oxidase is predicted to or has been demonstrated to have therapeutic value, e.g., primary hyperoxaluria 1 (PH1) or other rare liver disease, either in vivo or in vitro. Treatment and/or reductions in PH1 and/or other rare liver disease can include halting or reduction of organ damage (e.g., kidney and/or liver damage) associated with PH1 or other rare liver disease (e.g., reduction of kidney damage, liver damage, calcium oxalate depositions, systemic oxalosis, osteolytic lesions, epiphysiolysis (e.g., in the bone of a subject), renal osteopathy, including renal calcification and/or calcification/calcium oxalate depositions of the skin, eye or other organs of, e.g., 10%, 20%, 30%, 40%, 50%, 60%, 70%, 80%, 90%, 95% or 99% or more, and can also be measured in logarithmic terms, e.g., 10-fold, 100-fold, 1000-fold, $10^5$-fold, $10^6$-fold, $10^7$-fold reduction in kidney damage, liver damage, calcium oxalate depositions, systemic oxalosis, osteolytic lesions, epiphysiolysis (e.g., in the bone of a subject), renal osteopathy, including renal calcification and calcification/calcium oxalate depositions of the skin, eye or other organs could be achieved via administration of the dsRNA agents of the invention to cells, a tissue, or a subject).

For RNA-mediated inhibition in a cell line or whole organism, expression of a reporter or drug resistance gene whose protein product is easily assayed can be measured. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention.

Lower doses of injected material and longer times after administration of RNA silencing agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target Glycolate Oxidase RNA or translation of target protein. As an example, the efficiency of inhibition may be determined by assessing the amount of gene product in the cell; RNA may be detected with a hybridization probe having a nucleotide sequence outside the region used for the inhibitory dsRNA, or translated polypeptide may be detected with an antibody raised against the polypeptide sequence of that region.

The dsRNA agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

Glycolate Oxidase Biology

Glycolate oxidase (the product of the HAO1 gene) is the enzyme responsible for converting glycolate to glyoxylate in the mitochondrial/peroxisomal glycine metabolism pathway. While glycolate is a harmless intermediate of the glycine metabolism pathway, accumulation of glyoxylate (via, e.g., AGT1 mutation) drives oxalate accumulation (as calcium precipitates in the kidney initially and other organs eventually), which ultimately results in the PH1 disease.

Pharmaceutical Compositions

In certain embodiments, the present invention provides for a pharmaceutical composition comprising the dsRNA agent of the present invention. The dsRNA agent sample can be suitably formulated and introduced into the environment of the cell by any means that allows for a sufficient portion of the sample to enter the cell to induce gene silencing, if it is to occur. Many formulations for dsRNA are known in the art and can be used so long as the dsRNA gains entry to the target cells so that it can act. See, e.g., U.S. published patent application Nos. 2004/0203145 A1 and 2005/0054598 A1. For example, the dsRNA agent of the instant invention can be formulated in buffer solutions such as phosphate buffered saline solutions, liposomes, micellar structures, and capsids. Formulations of dsRNA agent with cationic lipids can be used to facilitate transfection of the dsRNA agent into cells. For example, cationic lipids, such as lipofectin (U.S. Pat. No. 5,705,188), cationic glycerol derivatives, and polycationic molecules, such as polylysine (published PCT International Application WO 97/30731), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; cHuh7ting agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL.™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch: a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The compounds can also be administered by a method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals. e.g., for determining the $LD_{50}$, (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a nucleic acid molecule (i.e., an effective dosage) depends on the nucleic acid selected. For instance, single dose amounts of a dsRNA (or, e.g., a construct(s) encoding for such dsRNA) in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a nucleic acid (e.g., dsRNA), protein, polypeptide, or antibody can include a single treatment or, preferably, can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The expression constructs may be constructs suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or HI RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, e.g., Tuschl (2002, *Nature Biotechnol* 20: 500-505).

It can be appreciated that the method of introducing dsRNA agents into the environment of the cell will depend on the type of cell and the make up of its environment. For example, when the cells are found within a liquid, one preferable formulation is with a lipid formulation such as in lipofectamine and the dsRNA agents can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate dsRNA agents in a buffer or saline solution and directly inject the formulated dsRNA agents into cells, as in studies with oocytes. The direct injection of dsRNA agent duplexes may also be done. For suitable methods of introducing dsRNA (e.g., DsiRNA agents), see U.S. published patent application No. 2004/0203145 A1.

Suitable amounts of a dsRNA agent must be introduced and these amounts can be empirically determined using standard methods. Typically, effective concentrations of individual dsRNA agent species in the environment of a cell will be 50 nanomolar or less, 10 nanomolar or less, or compositions in which concentrations of 1 nanomolar or less can be used. In another embodiment, methods utilizing a concentration of 200 picomolar or less, 100 picomolar or less, 50 picomolar or less, 20 picomolar or less, and even a concentration of 10 picomolar or less, 5 picomolar or less, 2 picomolar or less or 1 picomolar or less can be used in many circumstances.

The method can be carried out by addition of the dsRNA agent compositions to an extracellular matrix in which cells can live provided that the dsRNA agent composition is formulated so that a sufficient amount of the dsRNA agent can enter the cell to exert its effect. For example, the method is amenable for use with cells present in a liquid such as a liquid culture or cell growth media, in tissue explants, or in whole organisms, including animals, such as mammals and especially humans.

The level or activity of a Glycolate Oxidase RNA can be determined by a suitable method now known in the art or that is later developed. It can be appreciated that the method used to measure a target RNA and/or the expression of a target RNA can depend upon the nature of the target RNA. For example, where the target Glycolate Oxidase RNA sequence encodes a protein, the term "expression" can refer to a protein or the Glycolate Oxidase RNA/transcript derived from the Glycolate Oxidase gene (either genomic or of exogenous origin). In such instances the expression of the target Glycolate Oxidase RNA can be determined by measuring the amount of Glycolate Oxidase RNA/transcript directly or by measuring the amount of Glycolate Oxidase protein. Protein can be measured in protein assays such as by staining or immunoblotting or, if the protein catalyzes a reaction that can be measured, by measuring reaction rates. All such methods are known in the art and can be used. Where target Glycolate Oxidase RNA levels are to be measured, art-recognized methods for detecting RNA levels can be used (e.g., RT-PCR, Northern Blotting, etc.). In targeting Glycolate Oxidase RNAs with the dsRNA agents of the instant invention, it is also anticipated that measurement of the efficacy of a dsRNA agent in reducing levels of Glycolate Oxidase RNA or protein in a subject, tissue, in cells, either in vitro or in vivo, or in cell extracts can also be used to determine the extent of reduction of Glycolate Oxidase-associated phenotypes (e.g., disease or disorders, e.g., PH1, PH1-associated biomarkers and/or phenotypes, other rare liver diseases and associated biomarkers and/or phenotypes, etc.). The above measurements can be made on cells, cell extracts, tissues, tissue extracts or other suitable source material.

The determination of whether the expression of a Glycolate Oxidase RNA has been reduced can be by a suitable method that can reliably detect changes in RNA levels. Typically, the determination is made by introducing into the environment of a cell undigested dsRNA such that at least a portion of that dsRNA agent enters the cytoplasm, and then measuring the level of the target RNA. The same measurement is made on identical untreated cells and the results obtained from each measurement are compared.

The dsRNA agent can be formulated as a pharmaceutical composition which comprises a pharmacologically effective amount of a dsRNA agent and pharmaceutically acceptable carrier. A pharmacologically or therapeutically effective amount refers to that amount of a dsRNA agent effective to produce the intended pharmacological, therapeutic or preventive result. The phrases "pharmacologically effective amount" and "therapeutically effective amount" or simply "effective amount" refer to that amount of an RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

Suitably formulated pharmaceutical compositions of this invention can be administered by means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general, a suitable dosage unit of dsRNA will be in the range of 0.001 to 0.25 milligrams per kilogram body weight of the recipient per day, or in the range of 0.01 to 20 micrograms per kilogram body weight per day, or in the range of 0.001 to 5 micrograms per kilogram of body weight per day, or in the range of 1 to 500 nanograms per kilogram of body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. A pharmaceutical composition comprising the dsRNA can be administered once daily. However, the therapeutic agent may also be dosed in dosage units containing two, three, four, five, six or more sub-doses administered at appropriate intervals throughout the day. In that case, the dsRNA contained in each sub-dose must be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. In this embodiment, the dosage unit contains a corresponding multiple of the daily dose. Regardless of the formulation, the pharmaceutical composition must contain dsRNA in a quantity sufficient to inhibit expression of the target gene in the animal or human being treated. The composition can be compounded in such a way that the sum of the multiple units of dsRNA together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

The pharmaceutical compositions can be included in a kit, container, pack, or dispenser together with instructions for administration.

Methods of Treatment

The present invention provides for both prophylactic and therapeutic methods of treating a subject at risk of (or susceptible to) a disease or disorder caused, in whole or in part, by Glycolate Oxidase (e.g., normal functioning or misregulation and/or elevation of HAO1 transcript and/or Glycolate Oxidase protein levels), or treatable via selective targeting of Glycolate Oxidase.

"Treatment", or "treating" as used herein, is defined as the application or administration of a therapeutic agent (e.g., a dsRNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above (including. e.g., prevention of the commencement of, e.g., PH1-forming events within a subject via inhibition of Glycolate Oxidase expression), by administering to the subject a therapeutic agent (e.g., a dsRNA agent or vector or transgene encoding same). Subjects at risk for the disease can be identified by, for example, one or a combination of diagnostic or prognostic assays as described herein. Administration of a prophylactic agent can occur prior to the detection of, e.g., PH1 in a subject, or the manifestation of symptoms characteristic of the disease or disorder, such that the disease or disorder is prevented or, alternatively, delayed in its progression.

Another aspect of the invention pertains to methods of treating subjects therapeutically, i.e., altering the onset of symptoms of the disease or disorder. These methods can be performed in vitro (e.g., by culturing the cell with the dsRNA agent) or, alternatively, in vivo (e.g., by administering the dsRNA agent to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target HAO1 RNA molecules of the present invention or target HAO1 RNA modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in a selected animal model. For example, a dsRNA agent (or expression vector or transgene encoding same) as described herein can be used in an animal model to determine the efficacy, toxicity, or side effects of treatment with said agent. Alternatively, an agent (e.g., a therapeutic agent) can be used in an animal model to determine the mechanism of action of such an agent.

Models Useful to Evaluate the Down-Regulation of HAO1 mRNA Levels and Expression Cell Culture The dsRNA agents of the invention can be tested for cleavage activity in vivo, for example, using the following procedure. The nucleotide sequences within the HAO1 cDNA targeted by the dsRNA agents of the invention are shown in the above HAO1 sequences.

The dsRNA reagents of the invention can be tested in cell culture using HeLa or other mammalian cells (e.g., human cell lines Hep3B, HepG2, DU145, Calu3, SW480, T84. PL45, etc., and mouse cell lines Hepa1-6, AML12, Neuro2a, etc.) to determine the extent of HAO1 RNA and/or Glycolate Oxidase protein inhibition. In certain embodiments, DsiRNA reagents (e.g., see FIG. 1, and above-recited structures) are selected against the HAO1 target as described herein. HAO1 RNA inhibition is measured after delivery of these reagents by a suitable transfection agent to, for example, cultured HeLa cells or other transformed or non-transformed mammalian cells in culture. Relative amounts of target HAO1 RNA are measured by reporter assay (e.g., as exemplified below) and/or versus HPRT1, actin or other appropriate control using real-time PCR monitoring of amplification (e.g., ABI 7700 TAQMAN®). A comparison is made to the activity of oligonucleotide sequences made to unrelated targets or to a randomized DsiRNA control with the same overall length and chemistry, or simply to appropriate vehicle-treated or untreated controls. Primary and secondary lead reagents are chosen for the target and optimization performed.

TAQMAN® (Real-Time PCR Monitoring of Amplification) and Lightcycler Quantification of mRNA For RT-qPCR assays, total RNA is prepared from cells following DsiRNA delivery, for example, using Ambion Rnaqueous 4-PCR purification kit for large scale extractions, or Promega SV96 for 96-well assays. For Taqman analysis, dual-labeled probes are synthesized with, for example, the reporter dyes FAM or VIC covalently linked at the 5'-end and the quencher dye TAMRA conjugated to the 3'-end. PCR amplifications are performed on, for example, an ABI PRISM 7700 Sequence detector using 50 uL reactions consisting of 10 uL total RNA, 100 nM forward primer, 100 mM reverse primer, 100 nM probe, 1×TaqMan PCR reaction buffer (PE-Applied Biosystems), 5.5 mM MgCl2, 100 uM each dATP, dCTP, dGTP and dTTP, 0.2U RNase Inhibitor (Promega), 0.025U AmpliTaq Gold (PE-Applied Biosystems) and 0.2U M-MLV Reverse Transcriptase (Promega). The thermal cycling conditions can consist of 30 minutes at 48° C., 10 minutes at 95° C., followed by 40 cycles of 15 seconds at 95° C. and 1 minute at 60° C. Quantitation of target HAO1 mRNA level is determined relative to standards generated from serially diluted total cellular RNA (300, 100, 30, 10 ng/rxn) and normalizing to, for example, HPRT1 mRNA in either parallel or same tube TaqMan reactions.

Western Blotting

Cellular protein extracts can be prepared using a standard micro preparation technique (for example using RIPA buffer). Cellular protein extracts are run on Tris-Glycine polyacrylamide gel and transferred onto membranes. Non-specific binding can be blocked by incubation, for example, with 5% non-fat milk for 1 hour followed by primary antibody for 16 hours at 4° C. Following washes, the secondary antibody is applied, for example (1:10,000 dilution) for 1 hour at room temperature and the signal detected on a VersaDoc imaging system In several cell culture systems, cationic lipids have been shown to enhance the bioavailability of oligonucleotides to cells in culture (Bennet, et al., 1992, Mol. Pharmacology, 41, 1023-1033). In one embodiment, dsRNA molecules of the invention are complexed with cationic lipids for cell culture experiments, dsRNA and cationic lipid mixtures are prepared in serum-free OptimMEM (InVitrogen) immediately prior to addition to the cells. OptiMEM is warmed to room temperature (about 20-25° C.) and cationic lipid is added to the final desired concentration, dsRNA molecules are added to OptiMEM to the desired concentration and the solution is added to the diluted dsRNA and incubated for 15 minutes at room temperature. In dose response experiments, the RNA complex is serially diluted into OptiMEM prior to addition of the cationic lipid.

Animal Models

The efficacy of anti-HAO1 dsRNA agents may be evaluated in an animal model. Animal models of PH1 as are known in the art can be used for evaluation of the efficacy, potency, toxicity, etc. of anti-HAO1 dsRNAs. Exemplary animal models useful for assessment of anti-HAO1 dsRNAs include mouse models of glycolate challenge and genetically engineered mouse models of PH1 disease. Such animal models may also be used as source cells or tissue for assays of the compositions of the invention. Such models can additionally be used or adapted for use for pre-clinical evaluation of the efficacy of dsRNA compositions of the invention in modulating HAO1 gene expression toward therapeutic use.

Such models and/or wild-type mice can be used in evaluating the efficacy of dsRNA molecules of the invention to inhibit HAO1 levels, expression, development of HAO1-associated phenotypes, diseases or disorders, etc. These models, wild-type mice and/or other models can similarly be used to evaluate the safety/toxicity and efficacy of dsRNA molecules of the invention in a pre-clinical setting.

Specific examples of animal model systems useful for evaluation of the HAO1-targeting dsRNAs of the invention include wild-type mice and genetically engineered alanine-glyoxylate aminotransferase-deficient model mice (see Salido et al. Proc. Natl. Acad. Sci. USA 103(48): 18249-54). In an exemplary in vivo experiment, dsRNAs of the invention are tail vein injected into such mouse models at doses ranging from 0.01 to 0.1 to 1 mg/kg or, alternatively, repeated doses are administered at single-dose $IC_{50}$ levels, and organ samples (e.g., liver, but may also include prostate, kidney, lung, pancreas, colon, skin, spleen, bone marrow, lymph nodes, mammary fat pad, etc.) are harvested 24 hours after administration of the final dose. Such organs are then evaluated for mouse and/or human HAO1 levels, depending upon the model used, and/or for impact upon PH1-related phenotypes. Duration of action can also be examined at, e.g., 1, 4, 7, 14, 21 or more days after final dsRNA administration.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory): Methods In Enzymology, Vols. 154 and 155 (Wu et al. eds.), Immunochemical Methods In Cell And Molecular Biology (Mayer and Walker, eds., Academic Press. London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The present invention is described by reference to the following Examples, which are offered by way of illustration and are not intended to limit the invention in any manner. Standard techniques well known in the art or the techniques specifically described below were utilized.

Example 1

Preparation of Double-Stranded RNA Oligonucleotides

Oligonucleotide Synthesis and Purification DsiRNA molecules were designed to interact with various sites in the RNA message, for example, target sequences within the RNA sequences described herein. In presently exemplified agents, 384 human target HAO1 sequences were selected for evaluation (a selection of the 384 human target HAO1 sites were predicted to be conserved with corresponding sites in the mouse HAO1 transcript sequence). The sequences of one strand of the DsiRNA molecules were complementary to the target HAO1 site sequences described above. The DsiRNA molecules were chemically synthesized using methods described herein. Generally, DsiRNA constructs were synthesized using solid phase oligonucleotide synthesis methods as described for 19-23mer siRNAs (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086).

Individual RNA strands were synthesized and HPLC purified according to standard methods (Integrated DNA Technologies. Coralville, Iowa). For example, RNA oligonucleotides were synthesized using solid phase phosphoramidite chemistry, deprotected and desalted on NAP-5 columns (Amersham Pharmacia Biotech, Piscataway, N.J.) using standard techniques (Damha and Olgivie, 1993, *Methods Mol Biol* 20: 81-114; Wincott et al., 1995, *Nucleic Acids Res* 23: 2677-84). The oligomers were purified using ion-exchange high performance liquid chromatography (IE-HPLC) on an Amersham Source 15Q column (1.0 cm×25 cm; Amersham Pharmacia Biotech, Piscataway, N.J.) using a 15 min step-linear gradient. The gradient varied from 90:10 Buffers A:B to 52:48 Buffers A:B, where Buffer A was 100 mM Tris pH 8.5 and Buffer B was 100 mM Tris pH 8.5, 1 M NaCl. Samples were monitored at 260 nm and peaks corresponding to the full-length oligonucleotide species were collected, pooled, desalted on NAP-5 columns, and lyophilized.

The purity of each oligomer was determined by capillary electrophoresis (CE) on a Beckman PACE 5000 (Beckman Coulter, Inc., Fullerton, Calif.). The CE capillaries had a 100 µm inner diameter and contained ssDNA 100R Gel (Beckman-Coulter). Typically, about 0.6 nmole of oligonucleotide was injected into a capillary, run in an electric field of 444 V/cm and detected by UV absorbance at 260 nm. Denaturing Tris-Borate-7 M-urea running buffer was purchased from Beckman-Coulter. Oligoribonucleotides were obtained that were at least 90% pure as assessed by CE for use in experiments described below. Compound identity was verified by matrix-assisted laser desorption ionization time-of-flight (MALDI-TOF) mass spectroscopy on a Voyager DE.™ Biospectometry Work Station (Applied Biosystems, Foster City, Calif.) following the manufacturer's recommended protocol. Relative molecular masses of all oligomers were obtained, often within 0.2% of expected molecular mass.

Preparation of Duplexes

Single-stranded RNA (ssRNA) oligomers were resuspended, e.g., at 100 µM concentration in duplex buffer consisting of 100 mM potassium acetate, 30 mM HEPES, pH 7.5. Complementary sense and antisense strands were mixed in equal molar amounts to yield a final solution of, e.g., 50 µM duplex. Samples were heated to 100° C. for 5' in RNA buffer (IDT) and allowed to cool to room temperature before use. Double-stranded RNA (dsRNA) oligomers were stored at −20° C. Single-stranded RNA oligomers were stored lyophilized or in nuclease-free water at −80° C.

Nomenclature

For consistency, the following nomenclature has been employed in the instant specification. Names given to duplexes indicate the length of the oligomers and the presence or absence of overhangs. A "25/27" is an asymmetric duplex having a 25 base sense strand and a 27 base antisense strand with a 2-base 3'-overhang. A "27/25" is an asymmetric duplex having a 27 base sense strand and a 25 base antisense strand.

Cell Culture and RNA Transfection

HeLa cells were obtained and maintained in DMEM (HyClone) supplemented with 10% fetal bovine serum (HyClone) at 37° C. under 5% CO2. For RNA transfections, cells were transfected with DsiRNAs at a final concentration of 1 nM or 0.1 nM using Lipofectamine™ RNAiMAX (Invitrogen) and following manufacturer's instructions. Briefly, for 0.1 nM transfections, e.g., of Example 3 below, an aliquot of stock solution of each DsiRNA was mixed with Opti-MEM I (Invitrogen) and Lipofectamine™ RNAiMAX to reach a volume of 150 µL (with 0.3 nM DsiRNA). The resulting 150 µL mix was incubated for 20 min at RT to allow DsiRNA:Lipofectamine™ RNAiMAX complexes to form. Meanwhile, target cells were trypsinized and resuspended in medium. At the end of the 20 min of complexation. 50 uL of the DsiRNA:RNAiMAX mixture was added per well into triplicate wells of 96 well plates. Finally, 100 µL of the cell suspension was added to each well (final volume 150 µL) and plates were placed into the incubator for 24 hours.

Assessment of Glycolate Oxidase Inhibition

HAO1 target gene knockdown in human HeLa cells was determined by reporter assay (HeLa cells were transformed with a Psi-Check-HsHAO1 plasmid and *Renilla* luciferase levels were then detected using a luminometer), while HAO1 target gene knockdown in mouse Hepa1-6 cells was determined by qRT-PCR, with values normalized to HPRT and RPL23 housekeeping genes, and to transfections with control DsiRNAs and/or mock transfection controls.

RNA Isolation and Analysis

Media was aspirated, and total RNA was extracted using the SV96 kit (Promega). Total RNA was reverse-transcribed using SuperscriptII, Oligo dT, and random hexamers following manufacturer's instructions. Typically, the resulting cDNA was analyzed by qPCR using primers and probes specific for both the HAO1 gene and for the mouse genes HPRT-1 and RPL23. An ABI 7700 was used for the amplification reactions. Each sample was tested in triplicate. Relative Glycolate Oxidase RNA levels were normalized to HPRT1 and RPL23 RNA levels and compared with RNA levels obtained in transfection control samples.

Example 2

DsiRNA Inhibition of Glycolate Oxidase

DsiRNA molecules targeting Glycolate Oxidase were designed and synthesized as described above and tested in human HeLa cells (alternatively, HepG2 or other human cells could have been used) for inhibitory efficacy. For transfection, annealed DsiRNAs were mixed with the transfection reagent (Lipofectamine™ RNAiMAX, Invitrogen) and incubated for 20 minutes at room temperature. The HeLa (human) or Hepa1-6 (mouse) cells (alternatively, mouse AML12 or other mouse cells could have been used) were trypsinized, resuspended in media, and added to wells (100 uL per well) to give a final DsiRNA concentration of 1 nM in a volume of 150 μl. Each DsiRNA transfection mixture was added to 3 wells for triplicate DsiRNA treatments. Cells were incubated at 37° C. for 24 hours in the continued presence of the DsiRNA transfection mixture. At 24 hours, human cells were subjected to luminometer assay for detection of *Renilla* luciferase levels or RNA was prepared from each well of treated mouse cells. For such mouse cells, the supernatants with the transfection mixtures were first removed and discarded, then the cells were lysed and RNA was prepared from each well. Target reporter luciferase levels (human) or HAO1 RNA levels (mouse) following treatment were evaluated by luminometer (human) or qRT-PCR (mouse) for the HAO1 target gene, with values normalized to those obtained for controls. Triplicate data was averaged and the % error was determined for each treatment. Normalized data were both tablulated and graphed, and the reduction of target mRNA by active DsiRNAs in comparison to controls was determined (see Table 11 below and FIGS. 2A to 2F).

TABLE 11

Glycolate Oxidase Inhibitory Efficacy of DsiRNAs Assayed at 1 nM in Human HeLa and Mouse HEPA1-6 Cells

| Duplex Name | Mm Location | Macaque* Location | Human - HeLa Human Psi-Check-HsHAO1 Plasmid RLuc Remaining vs. NC1, NC5, NC7 Hs HAO1 Reporter Assay % Remaining | Mouse - Hepa1-6 Normalized HPRT/Rpl23; vs NC1, NC5, NC7 Mm HAO1 476-611 (FAM) Assay % Remaining | Mm HAO1 1775-1888 (HEX) Assay % Remaining |
|---|---|---|---|---|---|
| HAO1-118 | 114 | | 30.5 ± 7.1 | 88.3 ± 3.4 | 87.9 ± 4.2 |
| HAO1-119 | 115 | | 47.5 ± 2.7 | 102.7 ± 5.6 | 97.5 ± 7.2 |
| HAO1-120 | 116 | | 29.8 ± 5.8 | 100.5 ± 3.9 | 91.6 ± 7.6 |
| HAO1-121 | 117 | | 44.8 ± 3.6 | 96.4 ± 7.0 | 106.2 ± 6.6 |
| HAO1-122 | 118 | | 21.9 ± 0.9 | 83.2 ± 4.1 | 95.2 ± 10.2 |
| HAO1-123 | 119 | | 22.1 ± 6.4 | 95.5 ± 2.7 | 103.6 ± 8.7 |
| HAO1-124 | 120 | | 20.2 ± 1.2 | 82.2 ± 3.0 | 88.8 ± 5.9 |
| HAO1-125 | 121 | | 22.7 ± 2.4 | 86.6 ± 9.5 | 86.4 ± 4.0 |
| HAO1-126 | 122 | | 27.9 ± 11.0 | 77.7 ± 4.6 | 75.7 ± 5.0 |
| HAO1-127 | 123 | | 21.8 ± 5.0 | 97.9 ± 4.3 | 83.7 ± 6.2 |
| HAO1-128 | 124 | | 26.2 ± 3.8 | 101.7 ± 12.0 | 97.2 ± 14.4 |
| HAO1-129 | 125 | | 27.0 ± 2.0 | 92.8 ± 7.0 | 96.2 ± 13.6 |
| HAO1-238 | 234 | 310 | 33.7 ± 4.8 | 89.7 ± 6.4 | 119.2 ± 7.7 |
| HAO1-239 | 235 | 311 | 57.3 ± 6.0 | 93.3 ± 2.6 | 110.7 ± 9.3 |
| HAO1-502 | 498 | 574 | 39.4 ± 5.8 | 72.5 ± 2.4 | 83.8 ± 1.9 |
| HAO1-503 | 499 | 575 | 40.0 ± 5.0 | 90.6 ± 7.3 | 82.3 ± 5.6 |
| HAO1-583 | 579 | 655 | 48.5 ± 12.6 | 42.5 ± 7.1 | 38.5 ± 7.1 |
| HAO1-584 | 580 | 656 | 76.1 ± 2.3 | 45.5 ± 5.7 | 38.3 ± 10.7 |
| HAO1-753 | 749 | 825 | 37.8 ± 2.8 | 85.6 ± 9.6 | 90.7 ± 10.2 |
| HAO1-754 | 750 | 826 | 24.1 ± 1.4 | 40.8 ± 2.3 | 48.7 ± 6.4 |
| HAO1-755 | 751 | 827 | 25.8 ± 6.2 | 40.6 ± 5.8 | 51.8 ± 7.4 |
| HAO1-756 | 752 | 828 | 38.6 ± 5.3 | 76.5 ± 5.3 | 85.5 ± 9.4 |
| HAO1-757 | 753 | 829 | 39.0 ± 3.6 | 70.0 ± 2.3 | 76.0 ± 3.4 |
| HAO1-758 | 754 | 830 | 32.6 ± 1.1 | 70.7 ± 8.3 | 65.5 ± 5.6 |
| HAO1-759 | 755 | 831 | 29.8 ± 2.7 | 40.0 ± 9.0 | 29.8 ± 13.2 |
| HAO1-760 | 756 | 832 | 36.4 ± 3.2 | 62.6 ± 10.7 | 60.7 ± 11.5 |
| HAO1-761 | 757 | 833 | 42.6 ± 15.0 | 104.0 ± 8.5 | 111.7 ± 10.2 |
| HAO1-762 | 758 | 834 | 40.8 ± 2.0 | 58.2 ± 4.5 | 74.6 ± 3.7 |
| HAO1-763 | 759 | 835 | 48.6 ± 19.9 | 81.5 ± 5.9 | 91.8 ± 14.1 |
| HAO1-806 | 802 | 878 | 22.9 ± 5.6 | 48.8 ± 2.4 | 53.6 ± 4.9 |
| HAO1-807 | 803 | 879 | 31.6 ± 7.3 | 42.4 ± 5.0 | 46.1 ± 2.4 |
| HAO1-808 | 804 | 880 | 53.2 ± 10.2 | 69.5 ± 6.0 | 61.3 ± 1.9 |
| HAO1-809 | 805 | 881 | 25.3 ± 6.4 | 24.8 ± 16.7 | 28.2 ± 19.1 |
| HAO1-810 | 806 | 882 | 31.2 ± 4.7 | 40.2 ± 5.4 | 45.0 ± 14.4 |
| HAO1-811 | 807 | 883 | 45.1 ± 5.6 | 64.6 ± 6.4 | 73.2 ± 3.3 |
| HAO1-812 | 808 | 884 | 53.7 ± 2.4 | 74.6 ± 3.5 | 85.5 ± 8.6 |
| HAO1-813 | 809 | 885 | 51.0 ± 2.1 | 86.7 ± 5.7 | 120.4 ± 11.2 |
| HAO1-814 | 810 | 886 | 36.0 ± 0.8 | 68.8 ± 7.4 | 72.2 ± 17.9 |
| HAO1-815 | 811 | 887 | 18.3 ± 5.9 | 22.8 ± 5.5 | 29.6 ± 4.9 |
| HAO1-886 | 882 | | 51.6 ± 4.9 | 87.4 ± 11.4 | 88.1 ± 7.5 |
| HAO1-887 | 883 | | 33.3 ± 6.5 | 37.1 ± 3.9 | 34.0 ± 7.2 |
| HAO1-1023 | 1019 | 1095 | 32.5 ± 7.9 | 41.4 ± 6.1 | 37.5 ± 2.5 |
| HAO1-1024 | 1020 | 1096 | 35.8 ± 7.4 | 53.7 ± 17.7 | 42.6 ± 22.0 |
| HAO1-1025 | 1021 | 1097 | 24.6 ± 5.4 | 27.8 ± 4.5 | 29.7 ± 9.7 |
| HAO1-1026 | 1022 | 1098 | 32.6 ± 4.6 | 48.1 ± 3.4 | 55.6 ± 11.8 |

TABLE 11-continued

Glycolate Oxidase Inhibitory Efficacy of DsiRNAs Assayed at 1 nM in Human HeLa and Mouse HEPA1-6 Cells

| | | | Human - HeLa Human Psi-Check-HsHAO1 Plasmid RLuc Remaining vs. NC1, NC5, NC7 | Mouse - Hepa1-6 Normalized HPRT/Rpl23; vs NC1, NC5, NC7 | |
|---|---|---|---|---|---|
| Duplex Name | Mm Location | Macaque* Location | Hs HAO1 Reporter Assay % Remaining | Mm HAO1 476-611 (FAM) Assay % Remaining | Mm HAO1 1775-1888 (HEX) Assay % Remaining |
| HAO1-1027 | 1023 | 1099 | 21.7 ± 1.9 | 33.3 ± 3.0 | 36.3 ± 1.8 |
| HAO1-1028 | 1024 | 1100 | 23.8 ± 2.5 | 32.1 ± 4.4 | 32.4 ± 8.6 |
| HAO1-1029 | 1025 | | 18.1 ± 3.6 | 48.4 ± 9.8 | 48.8 ± 16.6 |
| HAO1-1030 | 1026 | | 26.0 ± 4.6 | 30.4 ± 9.6 | 22.3 ± 26.6 |
| HAO1-1031 | 1027 | | 46.5 ± 1.1 | 47.8 ± 11.2 | 46.9 ± 15.0 |
| HAO1-1032 | 1028 | | 47.0 ± 3.3 | 32.4 ± 26.5 | 32.8 ± 23.0 |
| HAO1-1033 | 1029 | | 44.0 ± 6.7 | 51.2 ± 23.8 | 55.6 ± 14.2 |
| HAO1-1034 | 1030 | | 31.0 ± 7.2 | 28.7 ± 27.0 | 33.2 ± 24.5 |
| HAO1-1035 | 1031 | | 31.5 ± 0.7 | 41.1 ± 5.0 | 45.6 ± 9.9 |
| HAO1-1073 | 1069 | | 22.7 ± 2.9 | 90.8 ± 4.7 | 104.2 ± 12.2 |
| HAO1-1074 | 1070 | | 17.0 ± 1.6 | 125.5 ± 3.4 | 100.0 ± 3.4 |
| HAO1-1075 | 1071 | | 20.6 ± 2.9 | 59.2 ± 5.6 | 52.3 ± 3.3 |
| HAO1-1076 | 1072 | | 36.1 ± 1.1 | 41.0 ± 4.2 | 40.5 ± 8.3 |
| HAO1-1077 | 1073 | | 24.1 ± 3.3 | 88.5 ± 10.3 | 95.9 ± 7.7 |
| HAO1-1078 | 1074 | | 29.9 ± 6.6 | 83.1 ± 6.4 | 89.4 ± 9.5 |
| HAO1-1079 | 1075 | | 17.3 ± 2.1 | 41.5 ± 8.4 | 51.3 ± 7.6 |
| HAO1-1080 | 1076 | | 19.8 ± 3.1 | 93.6 ± 8.7 | 105.2 ± 2.7 |
| HAO1-1081 | 1077 | | 20.1 ± 1.4 | 73.7 ± 4.5 | 88.5 ± 4.2 |
| HAO1-1082 | 1078 | | 19.4 ± 4.0 | 131.0 ± 17.3 | 120.9 ± 7.0 |
| HAO1-1083 | 1079 | | 16.7 ± 5.3 | 42.8 ± 14.3 | 46.8 ± 16.5 |
| HAO1-1084 | 1080 | | 22.2 ± 1.8 | 47.7 ± 4.3 | 45.0 ± 3.6 |
| HAO1-1085 | 1081 | 1157 | 23.0 ± 6.7 | 52.4 ± 3.1 | 54.1 ± 2.6 |
| HAO1-1086 | 1082 | 1158 | 17.1 ± 3.4 | 35.8 ± 4.1 | 39.9 ± 4.1 |
| HAO1-1087 | 1083 | 1159 | 19.4 ± 3.3 | 25.3 ± 3.4 | 25.8 ± 7.7 |
| HAO1-1088 | 1084 | 1160 | 17.5 ± 2.1 | 46.7 ± 3.3 | 46.7 ± 4.4 |
| HAO1-1089 | 1085 | 1161 | 21.2 ± 2.5 | 44.8 ± 6.5 | 45.1 ± 8.1 |
| HAO1-1090 | 1086 | 1162 | 19.1 ± 2.8 | 67.8 ± 2.2 | 72.0 ± 4.0 |
| HAO1-1091 | 1087 | 1163 | 21.1 ± 11.9 | 40.8 ± 5.5 | 30.2 ± 9.6 |
| HAO1-1092 | 1088 | 1164 | 22.9 ± 2.5 | 43.2 ± 6.1 | 42.3 ± 7.6 |
| HAO1-1093 | 1089 | 1165 | 18.6 ± 3.5 | 31.2 ± 16.9 | 28.5 ± 15.2 |
| HAO1-1094 | 1090 | 1166 | 20.8 ± 3.3 | 24.4 ± 10.3 | 26.8 ± 4.7 |
| HAO1-1095 | 1091 | 1167 | 16.6 ± 4.1 | 37.6 ± 8.0 | 32.5 ± 18.5 |
| HAO1-1096 | 1092 | 1168 | 25.1 ± 4.3 | 19.0 ± 5.5 | 19.0 ± 7.5 |
| HAO1-1097 | 1093 | 1169 | 67.8 ± 4.1 | 19.8 ± 13.4 | 18.9 ± 2.5 |
| HAO1-1098 | 1094 | 1170 | 50.4 ± 2.6 | 33.3 ± 5.5 | 29.8 ± 1.8 |
| HAO1-1099 | 1095 | 1171 | 32.7 ± 1.4 | 24.6 ± 5.4 | 22.3 ± 4.8 |
| HAO1-1100 | 1096 | 1172 | 29.5 ± 1.0 | 30.3 ± 8.5 | 34.4 ± 9.2 |
| HAO1-1101 | 1097 | 1173 | 51.9 ± 3.4 | 32.5 ± 6.2 | 35.1 ± 6.8 |
| HAO1-1102 | 1098 | 1174 | 40.6 ± 1.4 | 84.1 ± 4.5 | 94.4 ± 8.3 |
| HAO1-1103 | 1099 | 1175 | 38.9 ± 1.7 | 22.6 ± 9.9 | 30.5 ± 12.3 |
| HAO1-1104 | 1100 | 1176 | 68.5 ± 3.8 | 47.6 ± 8.6 | 47.8 ± 8.1 |
| HAO1-1105 | 1101 | 1177 | 36.2 ± 3.8 | 20.1 ± 13.1 | 22.2 ± 25.5 |
| HAO1-1106 | 1102 | 1178 | 49.5 ± 5.9 | 73.7 ± 6.3 | 74.8 ± 4.2 |
| HAO1-1107 | 1103 | 1179 | 35.9 ± 2.5 | 44.9 ± 6.0 | 38.6 ± 18.4 |
| HAO1-1108 | 1104 | 1180 | 35.9 ± 3.0 | 69.0 ± 4.7 | 74.7 ± 10.4 |
| HAO1-1109 | 1105 | 1181 | 30.2 ± 1.9 | 52.0 ± 8.4 | 50.7 ± 7.5 |
| HAO1-1110 | 1106 | 1182 | 34.6 ± 4.6 | 25.1 ± 16.5 | 26.3 ± 7.1 |
| HAO1-1111 | 1107 | 1183 | 26.0 ± 2.3 | 28.5 ± 4.5 | 32.9 ± 5.9 |
| HAO1-1112 | 1108 | 1184 | 34.2 ± 2.3 | 59.4 ± 8.8 | 65.3 ± 7.1 |
| HAO1-1113 | 1109 | 1185 | 32.5 ± 2.1 | 29.3 ± 7.7 | 32.3 ± 12.1 |
| HAO1-1114 | 1110 | 1186 | 39.4 ± 0.7 | 47.6 ± 11.3 | 50.9 ± 10.3 |
| HAO1-1115 | 1111 | 1187 | 23.7 ± 1.6 | 45.0 ± 4.1 | 36.2 ± 5.3 |
| HAO1-1116 | 1112 | 1188 | 28.0 ± 7.1 | 48.3 ± 8.1 | 34.2 ± 5.8 |
| HAO1-1117 | 1113 | 1189 | 29.9 ± 1.4 | 34.3 ± 14.9 | 29.9 ± 13.2 |
| HAO1-1118 | 1114 | 1190 | 29.9 ± 2.8 | 29.1 ± 17.1 | 28.5 ± 15.6 |
| HAO1-1119 | 1115 | 1191 | 36.2 ± 5.1 | 55.9 ± 9.1 | 48.9 ± 14.9 |
| HAO1-1120 | 1116 | 1192 | 37.7 ± 4.0 | 54.1 ± 10.9 | 47.9 ± 6.8 |
| HAO1-1121 | 1117 | 1193 | 26.8 ± 4.3 | 33.4 ± 4.6 | 31.9 ± 14.4 |
| HAO1-1122 | 1118 | 1194 | 27.4 ± 3.0 | 41.3 ± 4.3 | 32.1 ± 4.8 |
| HAO1-1123 | 1119 | 1195 | 27.8 ± 5.4 | 36.4 ± 6.1 | 32.3 ± 3.2 |
| HAO1-1124 | 1120 | 1196 | 30.5 ± 5.2 | 64.6 ± 8.8 | 56.3 ± 9.1 |
| HAO1-1125 | 1121 | 1197 | 33.6 ± 4.2 | 37.6 ± 5.5 | 32.7 ± 12.1 |
| HAO1-1126 | 1122 | 1198 | 26.4 ± 6.7 | 40.9 ± 3.0 | 41.2 ± 2.4 |
| HAO1-1127 | 1123 | 1199 | 74.2 ± 5.1 | 78.6 ± 4.3 | 85.2 ± 5.7 |
| HAO1-1147 | 1143 | 1219 | 38.3 ± 4.1 | 56.8 ± 10.1 | 51.0 ± 13.8 |
| HAO1-1148 | 1144 | 1220 | 36.8 ± 3.9 | 61.0 ± 7.1 | 58.6 ± 7.9 |
| HAO1-1149 | 1145 | 1221 | 27.6 ± 1.5 | 33.6 ± 6.2 | 32.2 ± 0.3 |

TABLE 11-continued

Glycolate Oxidase Inhibitory Efficacy of DsiRNAs Assayed at 1 nM in Human HeLa and Mouse HEPA1-6 Cells

| | | | Human - HeLa Human Psi-Check-HsHAO1 Plasmid RLuc Remaining vs. NC1, NC5, NC7 | Mouse - Hepa1-6 Normalized HPRT/Rpl23; vs NC1, NC5, NC7 | |
|---|---|---|---|---|---|
| Duplex Name | Mm Location | Macaque* Location | Hs HAO1 Reporter Assay % Remaining | Mm HAO1 476-611 (FAM) Assay % Remaining | Mm HAO1 1775-1888 (HEX) Assay % Remaining |
| HAO1-1150 | 1146 | 1222 | 34.6 ± 1.1 | 60.2 ± 13.8 | 39.7 ± 8.2 |
| HAO1-1151 | 1147 | 1223 | 36.7 ± 1.3 | 51.3 ± 5.6 | 44.6 ± 5.9 |
| HAO1-1152 | 1148 | 1224 | 35.1 ± 2.5 | 42.7 ± 9.1 | 31.4 ± 10.7 |
| HAO1-1153 | 1149 | 1225 | 32.7 ± 1.6 | 23.3 ± 4.2 | 23.2 ± 11.9 |
| HAO1-1154 | 1150 | 1226 | 21.3 ± 8.3 | 23.2 ± 5.7 | 26.3 ± 5.1 |
| HAO1-1155 | 1151 | 1227 | 30.5 ± 0.9 | 42.0 ± 9.5 | 41.9 ± 7.8 |
| HAO1-1156 | 1152 | 1228 | 27.8 ± 4.0 | 36.4 ± 6.3 | 38.6 ± 10.1 |
| HAO1-1157 | 1153 | 1229 | 28.6 ± 0.9 | 36.8 ± 6.1 | 32.6 ± 5.6 |
| HAO1-1158 | 1154 | 1230 | 30.1 ± 9.0 | 45.3 ± 3.8 | 38.5 ± 8.4 |
| HAO1-1159 | 1155 | 1231 | 26.7 ± 1.5 | 43.8 ± 10.2 | 31.2 ± 4.9 |
| HAO1-1160 | 1156 | 1232 | 45.8 ± 4.1 | 81.7 ± 7.9 | 62.2 ± 14.4 |
| HAO1-1161 | 1157 | 1233 | 42.4 ± 4.2 | 58.7 ± 9.5 | 56.6 ± 10.2 |
| HAO1-1162 | 1158 | 1234 | 24.3 ± 1.9 | 27.4 ± 21.0 | 29.6 ± 16.6 |
| HAO1-1163 | 1159 | 1235 | 22.7 ± 5.2 | 44.7 ± 8.9 | 43.1 ± 9.1 |
| HAO1-1164 | 1160 | 1236 | 27.6 ± 2.5 | 40.3 ± 9.9 | 35.4 ± 10.2 |
| HAO1-1165 | 1161 | 1237 | 38.4 ± 2.1 | 61.6 ± 3.6 | 52.8 ± 7.7 |
| HAO1-1166 | 1162 | 1238 | 29.9 ± 3.4 | 46.9 ± 5.5 | 44.3 ± 4.8 |
| HAO1-1167 | 1163 | 1239 | 28.7 ± 3.6 | 41.3 ± 4.6 | 41.1 ± 5.7 |
| HAO1-1168 | 1164 | 1240 | 27.9 ± 2.4 | 19.5 ± 10.7 | 12.2 ± 12.8 |
| HAO1-1169 | 1165 | 1241 | 23.2 ± 4.0 | 21.1 ± 5.5 | 17.2 ± 7.4 |
| HAO1-1170 | 1166 | 1242 | 27.3 ± 5.0 | 23.9 ± 8.2 | 25.7 ± 17.1 |
| HAO1-1171 | 1167 | 1243 | 23.4 ± 4.1 | 16.3 ± 9.6 | 15.8 ± 3.2 |
| HAO1-1172 | 1168 | 1244 | 23.8 ± 0.6 | 23.1 ± 6.2 | 21.5 ± 7.8 |
| HAO1-1173 | 1169 | 1245 | 29.3 ± 0.8 | 35.7 ± 6.8 | 36.3 ± 9.4 |
| HAO1-1207 | 1204 | 1280 | 48.6 ± 5.3 | 86.7 ± 21.6 | 52.9 ± 5.6 |
| HAO1-1208 | 1205 | 1281 | 49.5 ± 2.7 | 47.3 ± 8.4 | 40.2 ± 5.8 |
| HAO1-1209 | 1206 | 1282 | 48.9 ± 5.1 | 35.5 ± 4.9 | 29.8 ± 3.9 |
| HAO1-1210 | 1207 | 1283 | 27.8 ± 1.6 | 17.3 ± 13.9 | 19.1 ± 9.6 |
| HAO1-1211 | 1208 | 1284 | 32.3 ± 2.3 | 17.3 ± 5.5 | 21.5 ± 8.1 |
| HAO1-1212 | 1209 | 1285 | 50.6 ± 5.1 | 47.0 ± 1.6 | 48.4 ± 5.7 |
| HAO1-1213 | 1210 | 1286 | 34.6 ± 3.1 | 35.9 ± 4.5 | 36.1 ± 1.9 |
| HAO1-1214 | 1211 | 1287 | 62.1 ± 3.4 | 66.8 ± 6.9 | 62.1 ± 7.6 |
| HAO1-1215 | 1212 | 1288 | 31.0 ± 1.9 | 44.4 ± 24.2 | 34.7 ± 13.4 |
| HAO1-1216 | 1213 | 1289 | 36.9 ± 4.3 | 41.3 ± 41.8 | 53.6 ± 42.5 |
| HAO1-1217 | 1214 | 1290 | 35.0 ± 2.8 | 36.6 ± N/A | 49.8 ± N/A |
| HAO1-1218 | 1215 | 1291 | 41.1 ± 4.0 | 68.6 ± 48.3 | 49.0 ± 11.2 |
| HAO1-1219 | 1216 | 1292 | 30.3 ± 0.6 | 20.3 ± 17.6 | 19.7 ± 26.5 |
| HAO1-1220 | 1217 | 1293 | 46.2 ± 2.9 | 74.7 ± 37.9 | 58.7 ± 20.3 |
| HAO1-1221 | 1218 | 1294 | 25.6 ± 5.1 | 12.2 ± 26.8 | 16.4 ± 9.8 |
| HAO1-1222 | 1219 | 1295 | 33.8 ± 8.7 | 25.7 ± 24.9 | 23.6 ± 1.8 |
| HAO1-1223 | 1220 | 1296 | 47.9 ± 3.7 | 59.1 ± 22.4 | 48.4 ± 5.4 |
| HAO1-1224 | 1221 | 1297 | 27.7 ± 3.5 | 32.8 ± 27.9 | 46.4 ± 25.0 |
| HAO1-1225 | 1222 | 1298 | 64.0 ± 3.0 | 51.3 ± N/A | 63.2 ± N/A |
| HAO1-1226 | 1223 | 1299 | 38.8 ± 6.2 | 14.0 ± 17.6 | 23.1 ± 5.6 |
| HAO1-1227 | 1224 | 1300 | 44.1 ± 3.8 | N/A ± N/A | N/A ± N/A |
| HAO1-1228 | 1225 | 1301 | 60.2 ± 5.5 | 24.2 ± 14.9 | 44.7 ± 15.4 |
| HAO1-1266 | 1263 | | 20.7 ± 4.9 | 20.4 ± 30.4 | 30.2 ± 7.1 |
| HAO1-1267 | 1264 | | 26.5 ± 7.3 | 20.0 ± 4.6 | 21.9 ± 6.2 |
| HAO1-1268 | 1265 | | 27.5 ± 5.0 | 23.4 ± 13.9 | 25.1 ± 11.0 |
| HAO1-1269 | 1266 | | 23.6 ± 2.8 | 86.3 ± 21.3 | 29.8 ± 7.7 |
| HAO1-1270 | 1267 | | 30.9 ± 0.7 | 100.0 ± 48.0 | 32.0 ± 10.7 |
| HAO1-1271 | 1268 | | 24.9 ± 5.9 | N/A ± N/A | N/A ± N/A |
| HAO1-1272 | 1269 | | 18.7 ± 1.3 | 8.0 ± N/A | 12.3 ± N/A |
| HAO1-1273 | 1270 | | 23.1 ± 1.7 | 9.0 ± 11.8 | 10.8 ± 27.6 |
| HAO1-1274 | 1271 | | 25.4 ± 4.5 | 38.3 ± 54.0 | 25.4 ± 6.4 |
| HAO1-1275 | 1272 | | 25.6 ± 2.9 | 17.2 ± 6.0 | 20.0 ± 6.3 |
| HAO1-1276 | 1273 | 1349 | 26.4 ± 3.2 | 29.2 ± 13.8 | 22.3 ± 9.5 |
| HAO1-1277 | 1274 | 1350 | 24.7 ± 4.6 | 35.4 ± 3.6 | 30.3 ± 9.3 |
| HAO1-1278 | 1275 | 1351 | 24.0 ± 1.3 | 24.7 ± 8.8 | 17.1 ± 17.3 |
| HAO1-1279 | 1276 | 1352 | 22.1 ± 2.2 | 19.3 ± 10.6 | 19.8 ± 9.1 |
| HAO1-1280 | 1277 | 1353 | 25.0 ± 2.5 | 35.5 ± 11.2 | 29.5 ± 5.9 |
| HAO1-1281 | 1278 | 1354 | 27.3 ± 1.7 | 37.7 ± 11.3 | 33.0 ± 18.2 |
| HAO1-1282 | 1279 | 1355 | 23.6 ± 3.3 | 32.2 ± 6.4 | 33.4 ± 10.4 |
| HAO1-1313 | 1310 | 1386 | 32.5 ± 7.9 | 47.6 ± 3.4 | 46.9 ± 3.5 |
| HAO1-1314 | 1311 | 1387 | 18.2 ± 2.1 | 24.3 ± 15.9 | 17.9 ± 15.4 |
| HAO1-1315 | 1312 | 1388 | 16.2 ± 0.6 | 24.9 ± 11.2 | 15.0 ± 11.1 |
| HAO1-1316 | 1313 | 1389 | 17.1 ± 5.3 | 18.9 ± 4.2 | 12.6 ± 20.2 |

TABLE 11-continued

Glycolate Oxidase Inhibitory Efficacy of DsiRNAs Assayed at 1 nM in Human HeLa and Mouse HEPA1-6 Cells

| Duplex Name | Mm Location | Macaque* Location | Human - HeLa Human Psi-Check- HsHAO1 Plasmid RLuc Remaining vs. NC1, NC5, NC7 Hs HAO1 Reporter Assay % Remaining | Mouse - Hepa1-6 Normalized HPRT/Rpl23; vs NC1, NC5, NC7 | |
|---|---|---|---|---|---|
| | | | | Mm HAO1 476-611 (FAM) Assay % Remaining | Mm HAO1 1775-1888 (HEX) Assay % Remaining |
| HAO1-1317 | 1314 | 1390 | 20.9 ± 4.0 | 20.2 ± 4.5 | 20.7 ± 7.2 |
| HAO1-1318 | 1315 | 1391 | 32.7 ± 1.6 | 44.2 ± 9.3 | 38.6 ± 3.0 |
| HAO1-1319 | 1316 | 1392 | 33.7 ± 5.3 | 42.1 ± 14.2 | 42.5 ± 18.8 |
| HAO1-1320 | 1317 | 1393 | 21.3 ± 3.0 | 24.0 ± 10.3 | 26.8 ± 8.4 |
| HAO1-1321 | 1318 | 1394 | 29.6 ± 4.7 | 47.3 ± 6.3 | 57.1 ± 6.4 |
| HAO1-1322 | 1319 | 1395 | 22.0 ± 1.4 | 27.9 ± 19.7 | 30.7 ± 4.5 |
| HAO1-1323 | 1320 | 1396 | 34.7 ± 3.2 | 61.3 ± 3.2 | 59.9 ± 3.6 |
| HAO1-1324 | 1321 | 1397 | 40.9 ± 1.6 | 65.7 ± 11.9 | 57.4 ± 17.9 |
| HAO1-1325 | 1322 | 1398 | 38.3 ± 2.2 | 45.5 ± 11.4 | 43.0 ± 26.3 |
| HAO1-1326 | 1323 | 1399 | 24.4 ± 2.5 | 19.0 ± 7.0 | 19.8 ± 4.0 |
| HAO1-1327 | 1324 | 1400 | 25.9 ± 2.9 | 19.1 ± 7.0 | 16.3 ± 10.0 |
| HAO1-1328 | 1325 | 1401 | 53.5 ± 6.4 | 46.6 ± 5.6 | 58.5 ± 5.7 |
| HAO1-1329 | 1326 | 1402 | 26.0 ± 4.1 | 23.3 ± 6.5 | 26.6 ± 2.9 |
| HAO1-1330 | 1327 | 1403 | 28.1 ± 10.3 | 27.5 ± 9.7 | 19.5 ± 11.5 |
| HAO1-1331 | 1328 | 1404 | 26.5 ± 2.9 | 34.6 ± 12.9 | 24.4 ± 6.6 |
| HAO1-1332 | 1329 | 1405 | 25.5 ± 3.3 | 28.6 ± 24.6 | 22.8 ± 18.7 |
| HAO1-1333 | 1330 | 1406 | 23.3 ± 1.7 | 22.4 ± 9.8 | 19.3 ± 17.6 |
| HAO1-1334 | 1331 | 1407 | 29.6 ± 3.4 | 25.8 ± 18.2 | 24.2 ± 17.6 |
| HAO1-1335 | 1332 | 1408 | 24.5 ± 0.4 | 21.2 ± 14.4 | 21.2 ± 14.0 |
| HAO1-1373 | 1370 | 1446 | 30.2 ± 6.0 | 36.4 ± 7.4 | 31.7 ± 12.2 |
| HAO1-1374 | 1371 | 1447 | 25.4 ± 2.4 | 25.6 ± 5.3 | 17.5 ± 13.3 |
| HAO1-1375 | 1372 | 1448 | 19.1 ± 4.9 | 20.7 ± 9.2 | 17.7 ± 14.4 |
| HAO1-1376 | 1373 | 1449 | 22.5 ± 1.7 | 20.6 ± 4.3 | 18.5 ± 2.6 |
| HAO1-1377 | 1374 | 1450 | 22.6 ± 7.0 | 23.8 ± 11.4 | 20.9 ± 19.7 |
| HAO1-1378 | 1375 | 1451 | 19.8 ± 4.3 | 13.9 ± 4.2 | 12.4 ± 8.5 |
| HAO1-1379 | 1376 | 1452 | 18.5 ± 3.2 | 14.6 ± 5.7 | 14.7 ± 4.1 |
| HAO1-1380 | 1377 | 1453 | 21.6 ± 5.8 | 22.9 ± 5.0 | 22.9 ± 3.7 |
| HAO1-1381 | 1378 | 1454 | 24.9 ± 3.4 | 26.8 ± 7.4 | 29.6 ± 10.0 |
| HAO1-1382 | 1379 | 1455 | 24.1 ± 4.6 | 26.1 ± 15.4 | 21.7 ± 9.3 |
| HAO1-1383 | 1380 | 1456 | 26.1 ± 1.1 | 45.1 ± 27.8 | 23.9 ± 16.7 |
| HAO1-1384 | 1381 | 1457 | 25.2 ± 8.3 | 36.9 ± 14.1 | 32.1 ± 8.3 |
| HAO1-1385 | 1382 | 1458 | 21.6 ± 2.7 | 23.7 ± 6.7 | 17.7 ± 9.1 |
| HAO1-1386 | 1383 | 1459 | 28.2 ± 4.2 | 31.7 ± 2.4 | 30.1 ± 18.3 |
| HAO1-1387 | 1384 | 1460 | 31.0 ± 1.4 | 37.6 ± 7.8 | 39.4 ± 1.8 |
| HAO1-1388 | 1385 | 1461 | 33.6 ± 1.6 | 40.2 ± 4.1 | 49.7 ± 10.3 |
| HAO1-1389 | 1386 | 1462 | 33.8 ± 1.3 | 40.0 ± 7.5 | 41.1 ± 3.7 |
| HAO1-1390 | 1387 | 1463 | 55.4 ± 6.1 | 69.1 ± 4.3 | 53.9 ± 10.0 |
| HAO1-1391 | 1388 | 1464 | 28.1 ± 10.3 | 32.0 ± 6.1 | 21.5 ± 5.8 |
| HAO1-1392 | 1389 | 1465 | 26.5 ± 2.9 | 28.7 ± 13.2 | 20.7 ± 25.5 |
| HAO1-1393 | 1390 | 1466 | 25.5 ± 3.3 | 23.0 ± 21.0 | 13.3 ± 35.8 |
| HAO1-1394 | 1391 | 1467 | 23.3 ± 1.7 | 32.7 ± 17.1 | 35.5 ± 21.3 |
| HAO1-1395 | 1392 | 1468 | 29.6 ± 3.4 | 42.7 ± 16.7 | 42.0 ± 5.0 |
| HAO1-1426 | 1423 | | 24.5 ± 0.4 | 79.5 ± 6.4 | 86.6 ± 5.4 |
| HAO1-1427 | 1424 | | 30.2 ± 6.0 | 88.6 ± 9.8 | 85.6 ± 21.4 |
| HAO1-1428 | 1425 | | 25.4 ± 2.4 | 84.3 ± 4.2 | 58.9 ± 17.0 |
| HAO1-1429 | 1426 | | 19.1 ± 4.9 | 69.0 ± 3.8 | 51.8 ± 6.6 |
| HAO1-1430 | 1427 | | 22.5 ± 1.7 | 92.6 ± 4.9 | 80.4 ± 8.6 |
| HAO1-1431 | 1428 | | 22.6 ± 7.0 | 49.2 ± 10.7 | 40.3 ± 23.4 |
| HAO1-1432 | 1429 | | 19.8 ± 4.3 | 108.3 ± 3.4 | 143.8 ± 5.0 |
| HAO1-1433 | 1430 | | 18.5 ± 3.2 | 47.7 ± 17.1 | 58.3 ± 25.2 |
| HAO1-1434 | 1431 | | 21.6 ± 5.8 | 88.3 ± 0.7 | 111.8 ± 10.3 |
| HAO1-1435 | 1432 | | 24.9 ± 3.4 | 102.7 ± 2.7 | 119.3 ± 3.2 |
| HAO1-1436 | 1433 | | 24.1 ± 4.6 | 106.3 ± 11.1 | 85.7 ± 6.0 |
| HAO1-1437 | 1434 | | 26.1 ± 1.1 | 60.6 ± 14.5 | 74.4 ± 39.2 |
| HAO1-1438 | 1435 | | 25.2 ± 8.3 | 87.4 ± 5.4 | 88.5 ± 1.7 |
| HAO1-59 | | 131 | 21.6 ± 2.7 | 92.2 ± 5.2 | 101.2 ± 12.5 |
| HAO1-60 | | 132 | 28.2 ± 4.2 | 105.6 ± 16.4 | 110.7 ± 16.4 |
| HAO1-61 | | 133 | 31.0 ± 1.4 | 104.8 ± 3.9 | 112.6 ± 3.7 |
| HAO1-62 | | 134 | 33.6 ± 1.6 | 113.9 ± 9.4 | 141.5 ± 11.6 |
| HAO1-63 | | 135 | 33.8 ± 1.3 | 116.1 ± 3.9 | 136.4 ± 10.3 |
| HAO1-64 | | 136 | 55.4 ± 6.1 | 133.5 ± 6.3 | 107.4 ± 8.6 |
| HAO1-65 | | | 8.1 ± 10.5 | | |
| HAO1-66 | | | 12.2 ± 3.5 | | |
| HAO1-67 | | | 11.0 ± 3.2 | | |
| HAO1-68 | | | 17.4 ± 5.0 | | |
| HAO1-70 | | | 14.6 ± 5.5 | | |
| HAO1-71 | | | 17.0 ± 1.0 | | |

TABLE 11-continued

Glycolate Oxidase Inhibitory Efficacy of DsiRNAs Assayed at 1 nM in Human HeLa and Mouse HEPA1-6 Cells

| Duplex Name | Mm Location | Macaque* Location | Human - HeLa Human Psi-Check-HsHAO1 Plasmid RLuc Remaining vs. NC1, NC5, NC7 Hs HAO1 Reporter Assay % Remaining | Mouse - Hepa1-6 Normalized HPRT/Rpl23; vs NC1, NC5, NC7 | |
|---|---|---|---|---|---|
| | | | | Mm HAO1 476-611 (FAM) Assay % Remaining | Mm HAO1 1775-1888 (HEX) Assay % Remaining |
| HAO1-72 | | | 13.4 ± 2.0 | | |
| HAO1-73 | | | 11.8 ± 1.0 | | |
| HAO1-74 | | | 19.6 ± 4.8 | | |
| HAO1-75 | | | 16.3 ± 2.3 | | |
| HAO1-76 | | | 20.5 ± 3.2 | | |
| HAO1-77 | | | 17.2 ± 3.0 | | |
| HAO1-80 | | | 14.0 ± 1.6 | | |
| HAO1-82 | | | 22.5 ± 1.3 | | |
| HAO1-83 | | | 13.7 ± 0.9 | | |
| HAO1-86 | | | 15.0 ± 1.5 | | |
| HAO1-95 | | | 18.1 ± 6.2 | | |
| HAO1-96 | | | 18.0 ± 5.0 | | |
| HAO1-98 | | | 21.3 ± 8.4 | | |
| HAO1-99 | | | 19.6 ± 5.3 | | |
| HAO1-100 | | | 21.7 ± 1.2 | | |
| HAO1-103 | | | 23.3 ± 0.5 | | |
| HAO1-106 | | | 22.9 ± 4.7 | | |
| HAO1-107 | | | 18.4 ± 11.5 | | |
| HAO1-109 | | | 8.1 ± 10.5 | | |
| HAO1-212 | | | 12.2 ± 3.5 | | |
| HAO1-585 | | | 11.0 ± 3.2 | | |
| HAO1-586 | | | 17.4 ± 5.0 | | |
| HAO1-587 | | | 14.6 ± 5.5 | | |
| HAO1-589 | | | 17.0 ± 1.0 | | |
| HAO1-590 | | | 13.4 ± 2.0 | | |
| HAO1-591 | | | 11.8 ± 1.0 | | |
| HAO1-592 | | | 19.6 ± 4.8 | | |
| HAO1-594 | | | 16.3 ± 2.3 | | |
| HAO1-595 | | | 20.5 ± 3.2 | | |
| HAO1-596 | | | 17.2 ± 3.0 | | |
| HAO1-597 | | | 14.0 ± 1.6 | | |
| HAO1-598 | | | 22.5 ± 1.3 | | |
| HAO1-599 | | | 13.7 ± 0.9 | | |
| HAO1-600 | | | 15.0 ± 1.5 | | |
| HAO1-601 | | | 18.1 ± 6.2 | | |
| HAO1-602 | | | 18.0 ± 5.0 | | |
| HAO1-603 | | | 21.3 ± 8.4 | | |
| HAO1-604 | | | 19.6 ± 5.3 | | |
| HAO1-605 | | | 21.7 ± 1.2 | | |
| HAO1-606 | | | 23.3 ± 0.5 | | |
| HAO1-607 | | | 22.9 ± 4.7 | | |
| HAO1-608 | | | 21.6 ± 15.8 | | |
| HAO1-609 | | | 27.7 ± 2.4 | | |
| HAO1-611 | | | 46.6 ± 1.5 | | |
| HAO1-612 | | | 47.5 ± 4.4 | | |
| HAO1-621 | | | 41.0 ± 2.8 | | |
| HAO1-716 | | | 30.0 ± 4.4 | | |
| HAO1-857 | | | 31.3 ± 2.1 | | |
| HAO1-860 | | | 21.4 ± 2.0 | | |
| HAO1-861 | | | 16.6 ± 2.8 | | |
| HAO1-1194 | | | 22.0 ± 2.2 | | |
| HAO1-1195 | | | 36.5 ± 0.8 | | |
| HAO1-1196 | | | 25.3 ± 5.7 | | |
| HAO1-1197 | | | 29.8 ± 5.3 | | |
| HAO1-1198 | | | 17.7 ± 0.4 | | |
| HAO1-1199 | | | 19.7 ± 4.3 | | |
| HAO1-1200 | | | 20.4 ± 2.3 | | |
| HAO1-1201 | | | 19.6 ± 2.9 | | |
| HAO1-1202 | | | 17.0 ± 2.1 | | |
| HAO1-1206 | | | 22.8 ± 1.5 | | |
| HAO1-1246 | | | 22.6 ± 6.0 | | |
| HAO1-1247 | | | 17.0 ± 2.3 | | |
| HAO1-1248 | | | 18.8 ± 2.3 | | |
| HAO1-1249 | | | 18.0 ± 2.4 | | |
| HAO1-1289 | | | 21.1 ± 2.7 | | |
| HAO1-1290 | | | 19.1 ± 2.2 | | |
| HAO1-1291 | | | 24.8 ± 5.1 | | |

TABLE 11-continued

Glycolate Oxidase Inhibitory Efficacy of DsiRNAs Assayed at 1 nM in Human HeLa and Mouse HEPA1-6 Cells

| Duplex Name | Mm Location | Macaque* Location | Human - HeLa Human Psi-Check-HsHAO1 Plasmid RLuc Remaining vs. NC1, NC5, NC7 Hs HAO1 Reporter Assay % Remaining | Mouse - Hepa1-6 Normalized HPRT/Rpl23; vs NC1, NC5, NC7 | |
|---|---|---|---|---|---|
| | | | | Mm HAO1 476-611 (FAM) Assay % Remaining | Mm HAO1 1775-1888 (HEX) Assay % Remaining |
| HAO1-1292 | | | 19.4 ± 3.4 | | |
| HAO1-1293 | | | 21.8 ± 2.7 | | |
| HAO1-1362 | | | 24.6 ± 1.8 | | |
| HAO1-1363 | | | 27.1 ± 4.7 | | |
| HAO1-1364 | | | 24.0 ± 1.0 | | |
| HAO1-1365 | | | 29.7 ± 1.5 | | |
| HAO1-1366 | | | 29.2 ± 4.4 | | |
| HAO1-1367 | | | 30.4 ± 3.9 | | |
| HAO1-1368 | | | 28.4 ± 4.3 | | |
| HAO1-1369 | | | 25.6 ± 2.9 | | |
| HAO1-1370 | | | 26.5 ± 4.6 | | |
| HAO1-1371 | | | 18.5 ± 4.6 | | |
| HAO1-1372 | | | 22.3 ± 3.3 | | |
| HAO1-1478 | | | 24.8 ± 3.1 | | |
| HAO1-1479 | | | 20.7 ± 3.5 | | |
| HAO1-1480 | | | 18.5 ± 2.3 | | |
| HAO1-1481 | | | 24.4 ± 3.3 | | |
| HAO1-1483 | | | 25.0 ± 3.7 | | |
| HAO1-1484 | | | 24.4 ± 2.2 | | |
| HAO1-1488 | | | 18.5 ± 2.7 | | |
| HAO1-1489 | | | 16.1 ± 1.7 | | |
| HAO1-1490 | | | 14.1 ± 3.6 | | |
| HAO1-1491 | | | 14.0 ± 8.6 | | |
| HAO1-1492 | | | 17.5 ± 1.5 | | |
| HAO1-1493 | | | 17.6 ± 2.9 | | |
| HAO1-1494 | | | 15.9 ± 7.5 | | |
| HAO1-1495 | | | 19.3 ± 2.4 | | |
| HAO1-1496 | | | 15.6 ± 4.8 | | |
| HAO1-1497 | | | 16.5 ± 6.0 | | |
| HAO1-1498 | | | 19.7 ± 2.2 | | |
| HAO1-1499 | | | 15.6 ± 4.4 | | |
| HAO1-1500 | | | 15.3 ± 0.2 | | |
| HAO1-1501 | | | 15.6 ± 2.6 | | |
| HAO1-1502 | | | 18.4 ± 1.3 | | |
| HAO1-1503 | | | 18.7 ± 2.3 | | |
| HAO1-1504 | | | 14.6 ± 1.7 | | |
| HAO1-1505 | | | 19.8 ± 2.1 | | |
| HAO1-1506 | | | 34.9 ± 3.4 | | |
| HAO1-1507 | | | 16.2 ± 1.6 | | |
| HAO1-1508 | | | 21.7 ± 2.5 | | |
| HAO1-1509 | | | 30.5 ± 4.2 | | |
| HAO1-1510 | | | 14.7 ± 1.1 | | |
| HAO1-1511 | | | 15.8 ± 0.8 | | |
| HAO1-1512 | | | 14.7 ± 2.9 | | |
| HAO1-1515 | | | 17.7 ± 3.4 | | |
| HAO1-1516 | | | 26.8 ± 4.4 | | |
| HAO1-1519 | | | 22.0 ± 1.5 | | |
| HAO1-1520 | | | 23.3 ± 4.2 | | |
| HAO1-1546 | | | 17.0 ± 3.9 | | |
| HAO1-1547 | | | 19.6 ± 1.8 | | |
| HAO1-1548 | | | 16.9 ± 3.0 | | |
| HAO1-1549 | | | 16.3 ± 2.3 | | |
| HAO1-1550 | | | 19.9 ± 4.6 | | |
| HAO1-1551 | | | 24.3 ± 0.3 | | |
| HAO1-1552 | | | 18.5 ± 0.8 | | |
| HAO1-1557 | | | 16.4 ± 1.3 | | |
| HAO1-1560 | | | 22.1 ± 3.7 | | |
| HAO1-1561 | | | 16.8 ± 3.4 | | |
| HAO1-1563 | | | 16.8 ± 2.4 | | |
| HAO1-1564 | | | 19.0 ± 2.1 | | |
| HAO1-1565 | | | 18.8 ± 1.7 | | |
| HAO1-1656 | | | 18.7 ± 0.4 | | |
| HAO1-1685 | | | 16.0 ± 2.9 | | |
| HAO1-1695 | | | 19.9 ± 5.2 | | |
| HAO1-1696 | | | 15.3 ± 2.1 | | |
| HAO1-1697 | | | 17.9 ± 5.9 | | |
| HAO1-1699 | | | 25.2 ± 1.6 | | |

TABLE 11-continued

Glycolate Oxidase Inhibitory Efficacy of DsiRNAs Assayed at 1 nM in Human HeLa and Mouse HEPA1-6 Cells

| Duplex Name | Mm Location | Macaque* Location | Human - HeLa Human Psi-Check-HsHAO1 Plasmid RLuc Remaining vs. NC1, NC5, NC7 Hs HAO1 Reporter Assay % Remaining | Mouse - Hepa1-6 Normalized HPRT/Rpl23; vs NC1, NC5, NC7 Mm HAO1 476-611 (FAM) Assay % Remaining | Mm HAO1 1775-1888 (HEX) Assay % Remaining |
|---|---|---|---|---|---|
| HAO1-1700 | | | 19.8 ± 1.8 | | |
| HAO1-1701 | | | 19.9 ± 5.6 | | |
| HAO1-1702 | | | 20.4 ± 1.0 | | |
| HAO1-1703 | | | 17.1 ± 0.7 | | |

*Macaca mulatta*

Example 3

Figure 3A:
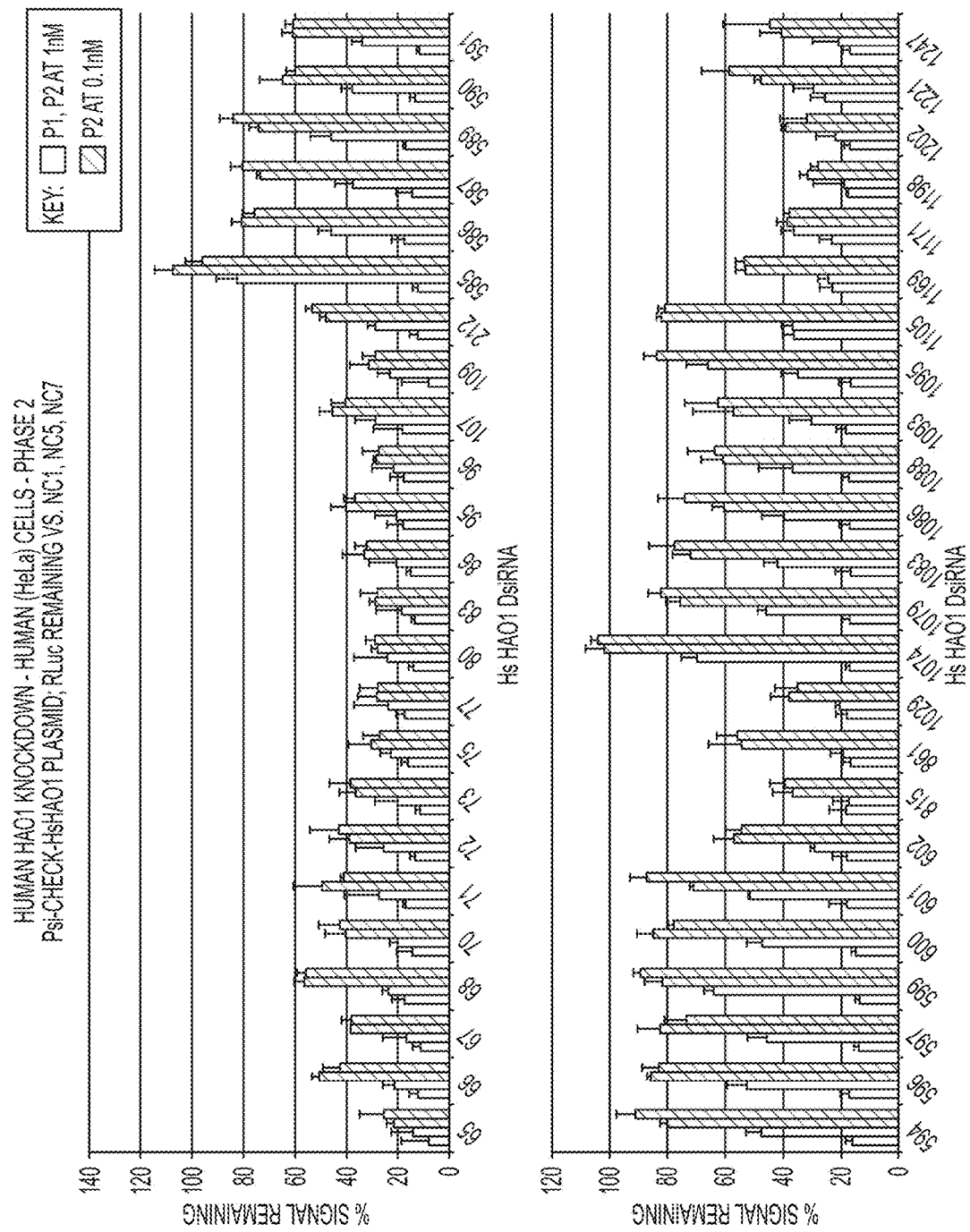
FIGS. 3A to 3F show histograms of human and mouse Glycolate Oxidase inhibitory efficacies observed for indicated DsiRNAs. "P1" indicates phase 1 (primary screen), while "P2" indicates phase 2. In phase 1, DsiRNAs were tested at 1 nM in the environment of HeLa cells (human cell assays.
Figure 3B:
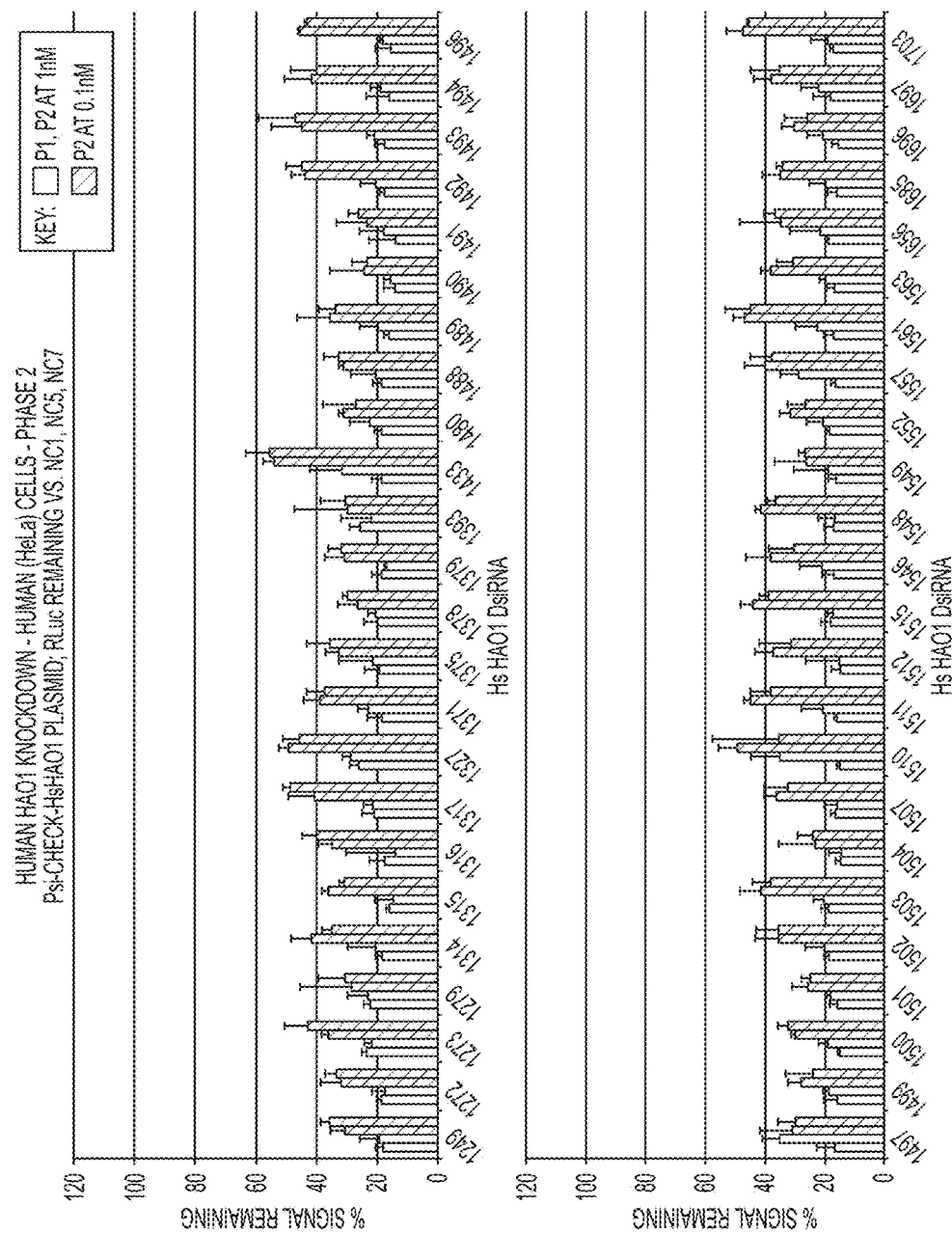
Figure 3C:
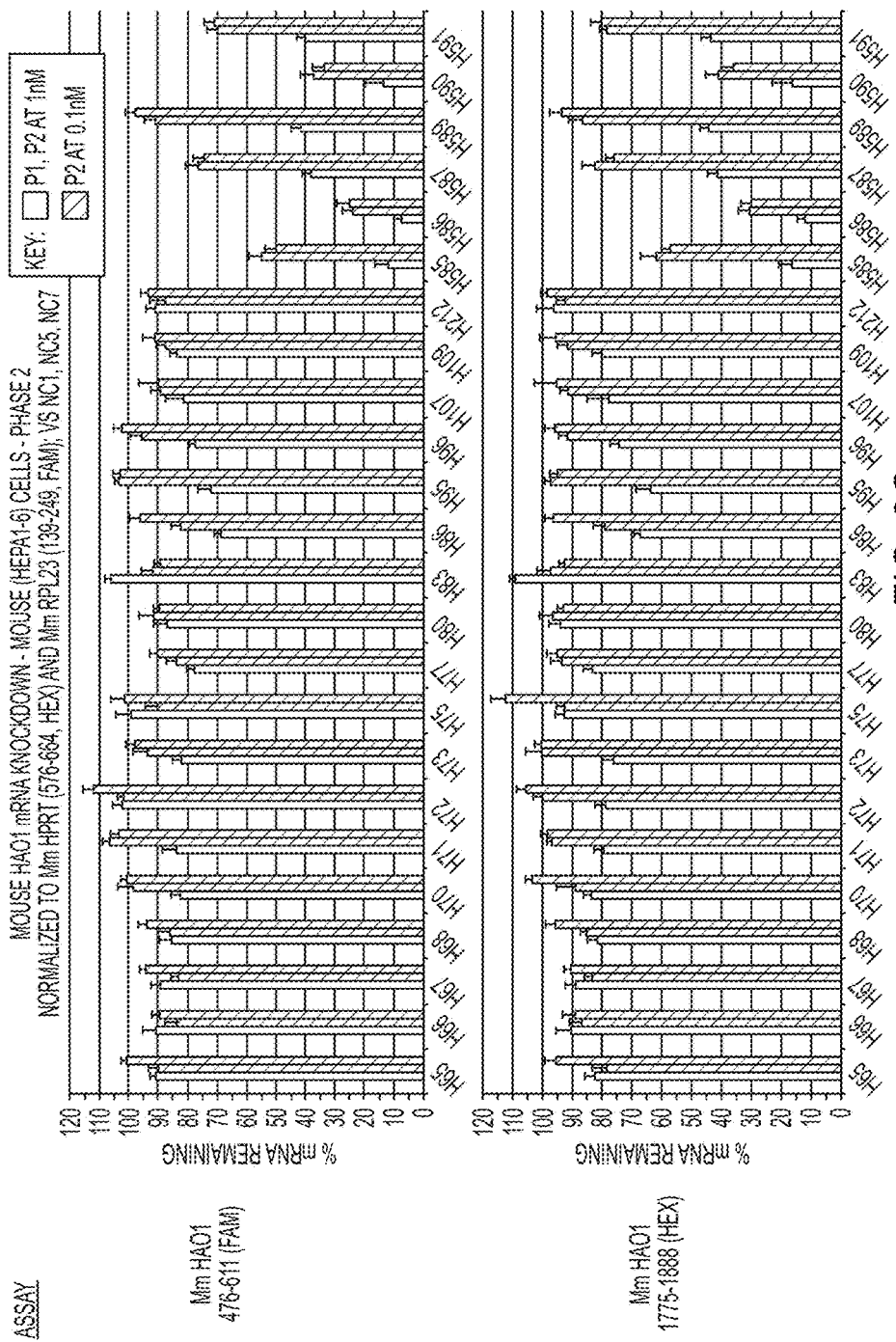
Figure 3D:
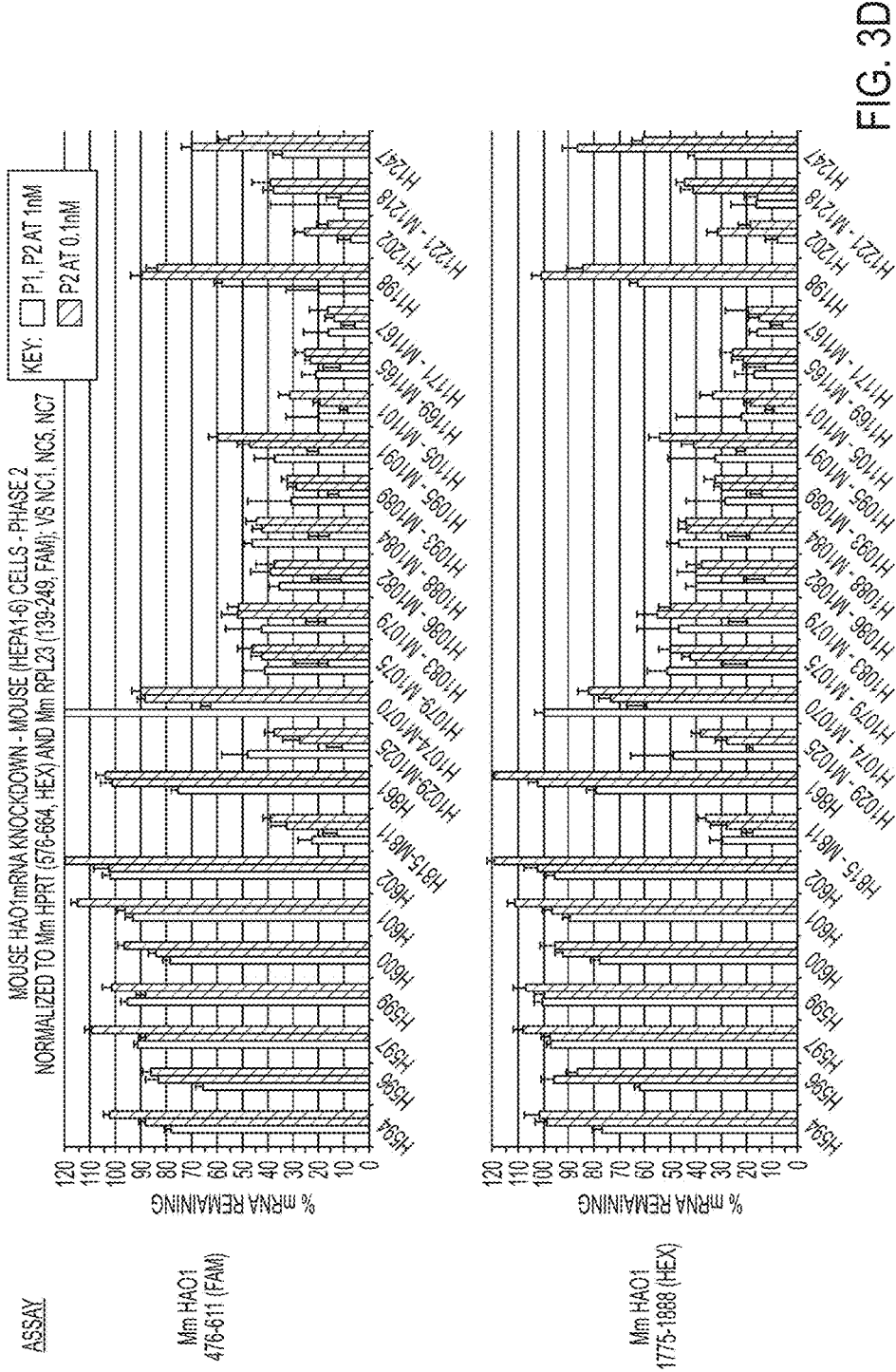
Figure 3E:
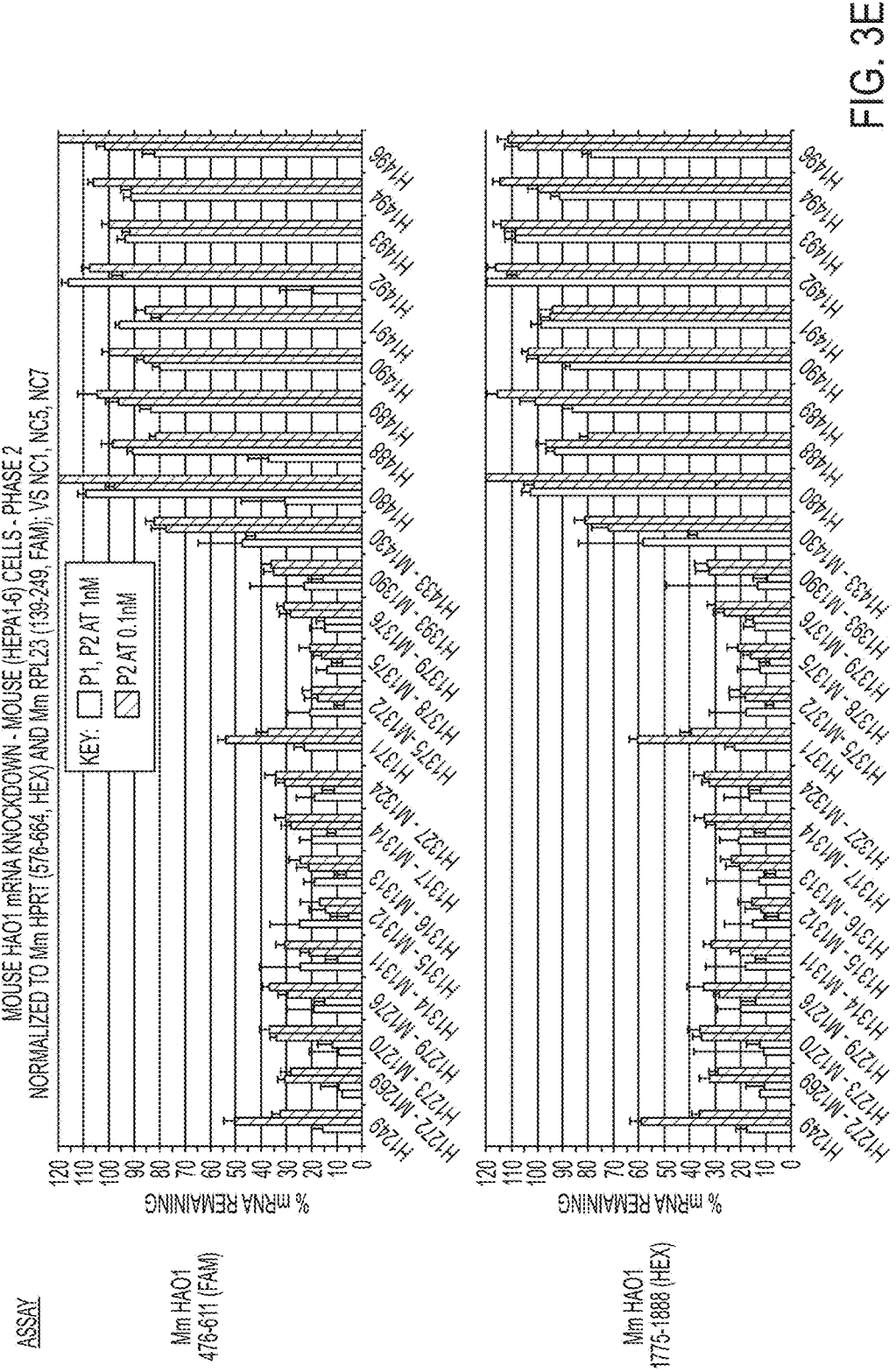
Figure 3F:
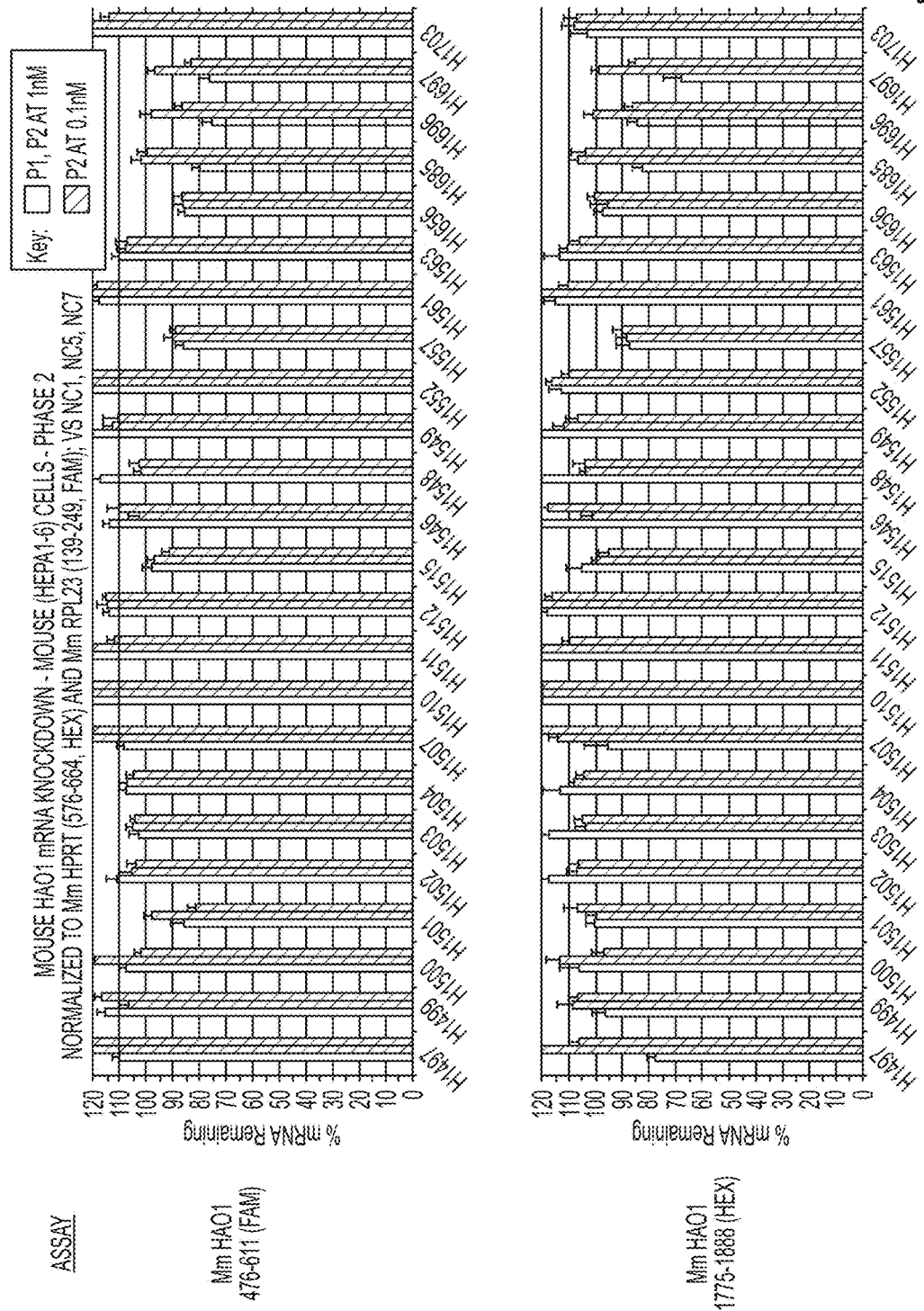

DsiRNA Inhibition of Glycolate Oxidase—Secondary Screen 96 asymmetric DsiRNAs (96 targeting Hs HAO1, 26 of which also targeted Mm HAO1) of the above experiment were then examined in a secondary assay ("Phase 2"), with results of such assays presented in histogram form in FIGS. 3A to 3F. Specifically, the 96 asymmetric DsiRNAs selected from those tested above were assessed for inhibition of human HAO1 at 1 nM or 0.1 nM (in duplicate assays) in the environment of human HeLa cells (FIGS. 3A and 3B). These 96 asymmetric DsiRNAs were also assessed for inhibition of mouse HAO1 at 1 nM or 0.1 nM (in duplicate) in the environment of mouse Hepa1-6 cells (FIGS. 3C to 3F). As shown in FIGS. 3A and 3B, most asymmetric DsiRNAs reproducibly exhibited significant human HAO1 inhibitory efficacies at sub-nanomolar concentrations when assayed in the environment of HeLa cells.

Without being bound by theory, it is noted that when using the RT-qPCR method to measure the amount of mRNA remaining after DsiRNA-mediated mRNA knockdown, the position of the qPCR assay within the mRNA can affect the detection of knockdown. The qPCR assay that is closer to the DsiRNA-directed mRNA cleavage point usually yields a more reliable measurement of mRNA level. For example, if a qPCR assay is located away from the cleavage point, slow degradation of the mRNA fragment resulting from DsiRNA-directed cleavage can yield an artifactual high qPCR signal (a 'false negative' for knockdown). A sign of this is high knockdown detected using a qPCR assay located near the DsiRNA site, and artifactual 'low' knockdown detected with a qPCR assay located away from the DsiRNA site. In this situation, the qPCR assay near the DsiRNA site is used for quantitation.

As shown in FIGS. 3C to 3F, a number of asymmetric DsiRNAs were also identified to possess significant mouse HAO1 inhibitory efficacies at sub-nanomolar concentrations when assayed in the environment of mouse Hepa1-6 cells.

Example 4

Assessment of In Vivo Efficacy of Glycolate Oxidase-Targeting DsiRNAs

Figure 4:
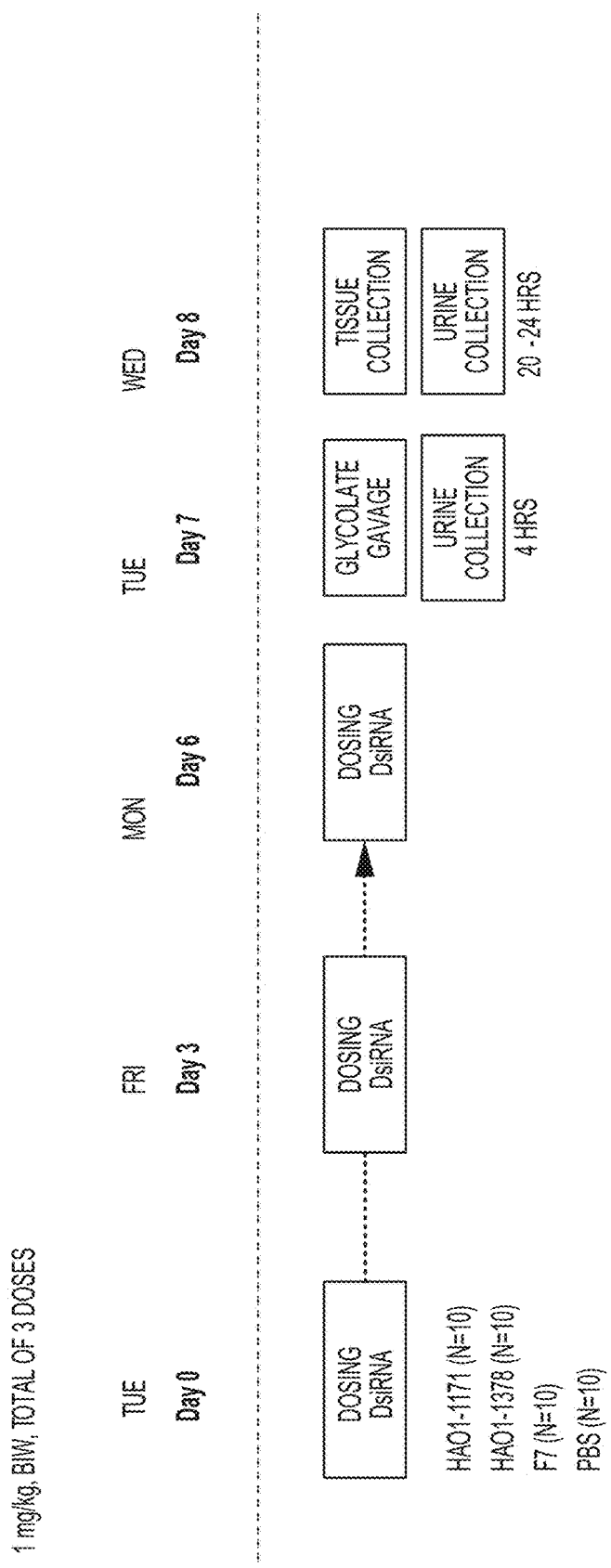
FIG. 4 shows a flow chart for initial in vivo mouse experiments, which included glycolate challenge.
Figure 5:
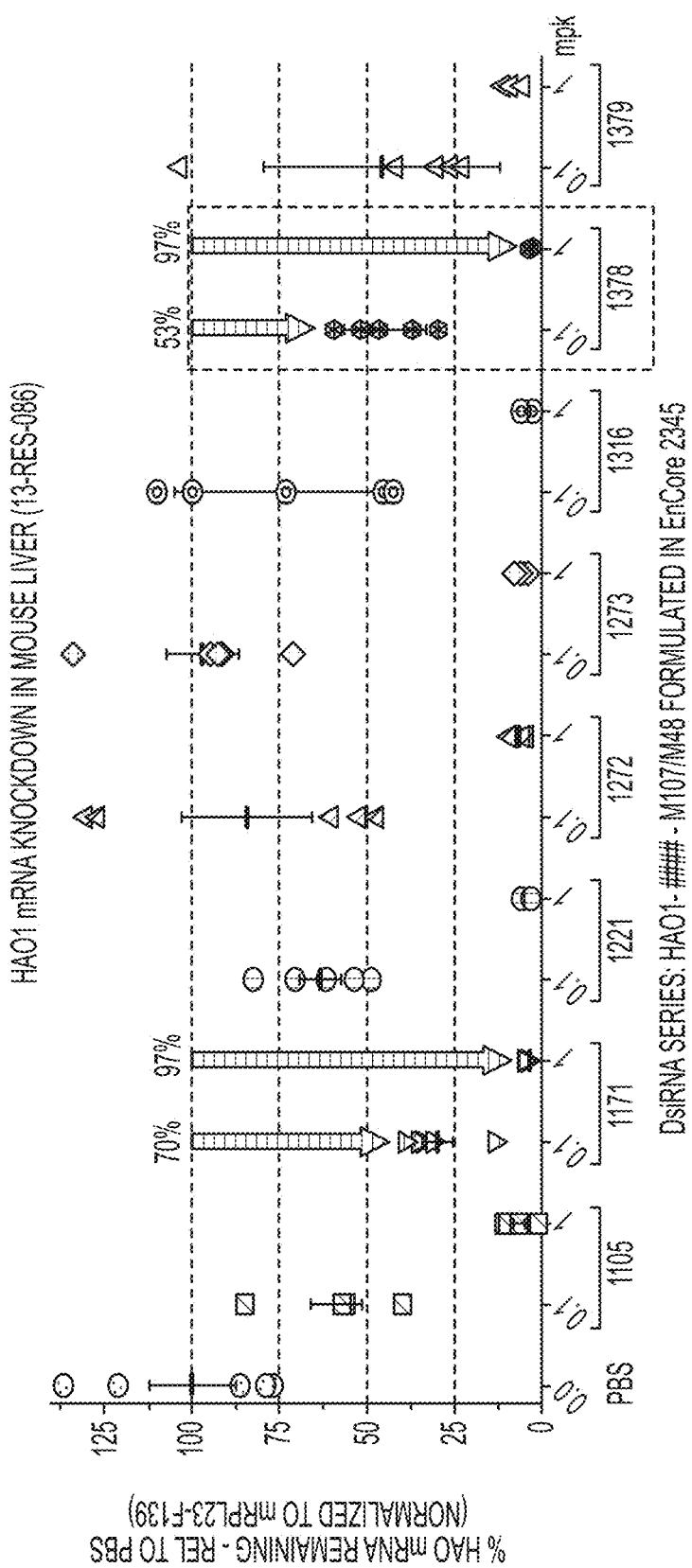
FIG. 5 shows HAO1 knockdown in mouse liver for animals administered 0.1 mg/kg or 1 mg/kg of indicated HAO1-targeting DsiRNAs formulated in LNP (here, LNP EnCore 2345).

The ability of certain, active HAO1-targeting DsiRNAs to reduce HAO1 levels within the liver of a mouse was examined. DsiRNAs employed in the study were: HAO1-1105, HAO1-1171. HAO1-1221, HAO1-1272, HAO1-1273. HAO1-1316, HAO1-1378 and HAO1-1379, each of which were synthesized with passenger (sense) strand modification pattern "SM107" and guide (antisense) strand modification pattern "M48" (patterns described above). To perform the study, a primary hyperoxaluria model was generated through oral gavage of 0.25 mL of 0.5 M glycolate to cause urine oxalate accumulation in C57BU6 female mice. Animals were randomized and assigned to groups based on body weight. Intravenous dosing of animals with lipid nanoparticles (LNPs; here, an LNP formulation named EnCore-2345 was employed) containing 1 mg/kg or 0.1 mg/kg of DsiRNA was initiated on day 0. Dosing continued BIW for a total of three doses in mice prior to glycolate challenge. Four hour and 24 h urine samples were collected after glycolate challenge for assessment of oxalate/creatinine levels (see FIG. 4 for experimental flow chart). Animals were then sacrificed at 24 hrs after glycolate challenge. Liver was dissected and weighed, and HAO1 levels were assessed using RT-qPCR, ViewRNA, western blot for glycolate oxidase and/or glycolate oxidase immunohistochemistry (ViewRNA, western blot for glycolate oxidase and glycolate oxidase immunohistochemistry data not shown). Serum samples were also subjected to ELISA for detection of glycolate oxidase (data not shown). Notably, all eight DsiRNAs showed robust knockdown of HAO1 when administered at 1 mg/kg (FIG. 5). At least two (HAO1-1171 and HAO1-1378) of the eight DsiRNAs tested in vivo also showed robust knockdown of HAO1 in all treated animals when administered at 0.1 mg/kg. As shown in FIG. 5, administration of the HAO1-1171-M107/M48 DsiRNA at 0.1 mg/kg caused an average knockdown of 70% in liver tissue of treated mice, while administration at 1 mg/kg produced an average knockdown of 97% in liver tissue of treated mice. Similarly, administration of the HAO1-1378-M107/M48 DsiRNA at 0.1 mg/kg caused an average knockdown of 53% in liver tissue of treated mice, while administration at 1 mg/kg produced an average knockdown of 97% in liver tissue of treated mice. HAO1-1171-induced knockdown at both 0.1 mg/kg and 1 mg/kg was further confirmed by ViewRNA in situ hybridization assays.

Figure 6:
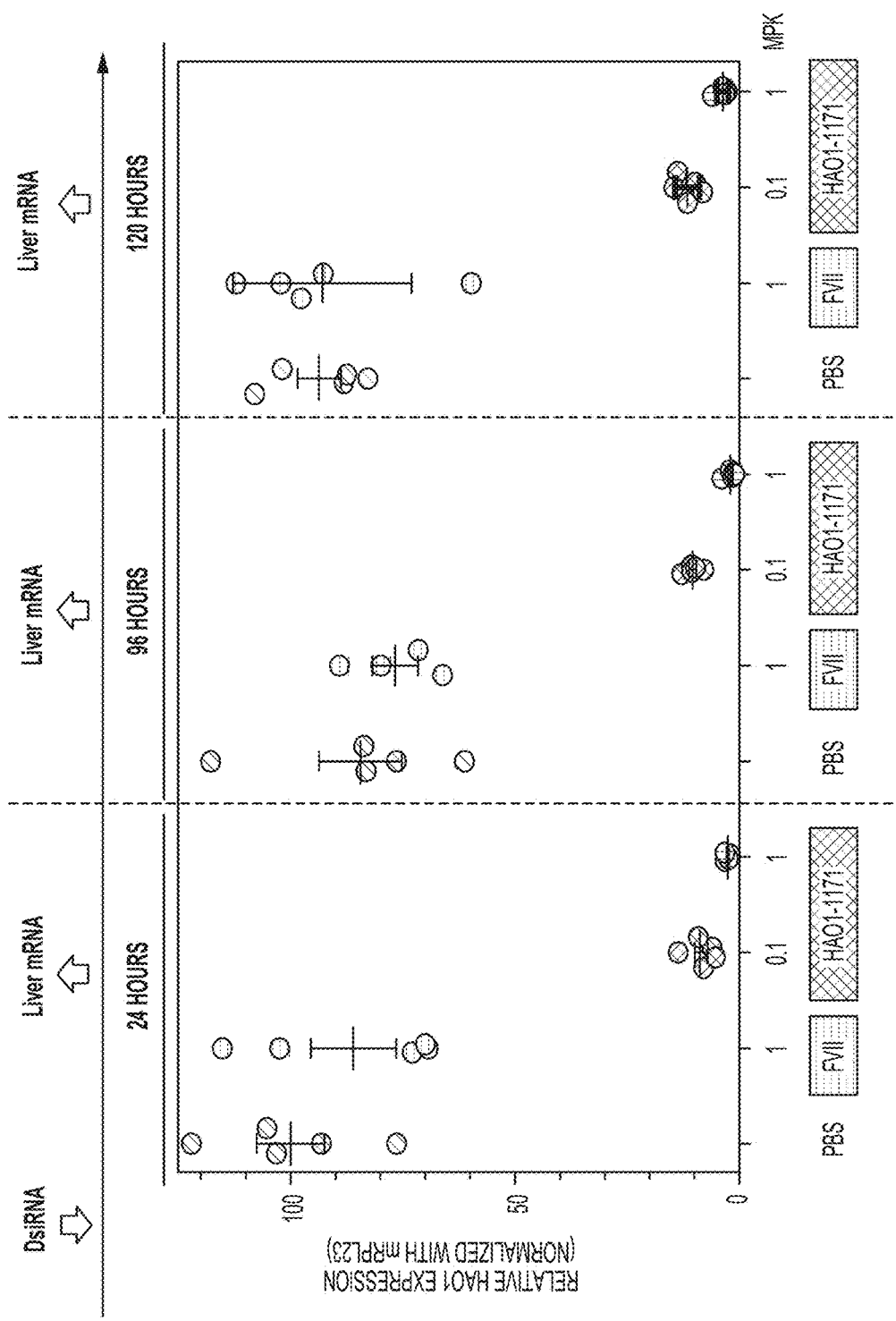
FIG. 6 shows that robust levels of HAO1 mRNA knockdown were observed in liver tissue of mice treated with 1 mg/kg and even 0.1 mg/kg amounts of HAO1-targeting DsiRNA HAO1-1171, with robust duration of efficacies observed (90% or greater levels of knockdown were observed at 120 hours post-administration for both 1 mg/kg and 0.1 mg/kg animals).

Robust levels of HAO1 mRNA knockdown were observed in liver tissue of mice treated with 1 mg/kg amounts of HAO1-targeting DsiRNAs HAO1-1171 and HAO1-1378 (FIG. 6 and data not shown), and even 0.1 mg/kg amounts of these HAO1-targeting DsiRNAs produced robust HAO1 knockdown. As shown in FIG. 6, single dose HAO1-1171 DsiRNA treatment achieved durable HAO1 mRNA target knockdown for at least 120 hours post-administration in the liver of treated animals. While robust HAO1 knockdown was achieved in liver, initial glycolate challenge experiments yielded inconclusive phenotypic results (data not shown).

In additional in vivo experiments, both HAO1 and oxalate levels were assessed in both control- and DsiRNA-treated genetically engineered PH1 model mice.

Example 5

Assessment of Modified Forms of Glycolate Oxidase-Targeting DsiRNAs In Vitro

Figure 7A:
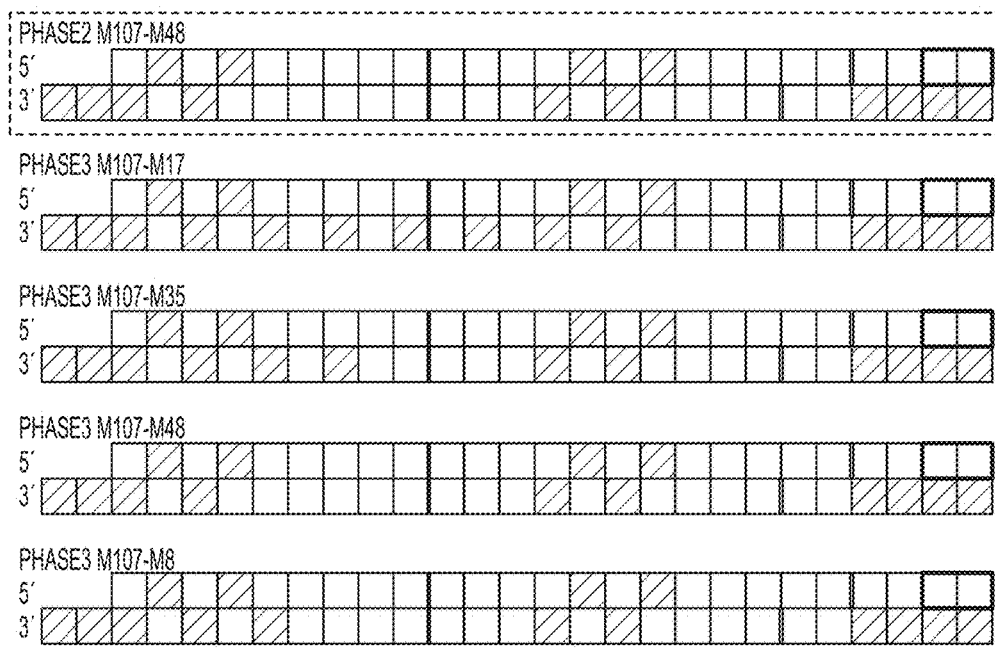
FIGS. 7A to 7E present modification pattern diagrams and histograms showing efficacy data for 24 independent HAO1-targeting DsiRNA sequences across four different guide (antisense) strand 2'-O-methyl modification patterns ("M17", "M35". "M48" and "M8", respectively, as shown in FIG. 7A and noting for FIGS. 7B to 7E that modification patterns are recited as passenger strand modification pattern (here, "M107")-guide strand modification pattern, e.g., "M107-M17", "M107-M35", "M107-M48" or "M107-M8") in human HeLa cells tested at 0.1 nM (duplicate assays) and 1 nM (FIGS. 7B and 7C) and mouse Hepa1-6 cells for a subset of 8 duplexes tested at 0.03 nM, 0.1 nM (duplicate assays) and 1 nM (FIGS. 7D and 7E).
Figure 7B:
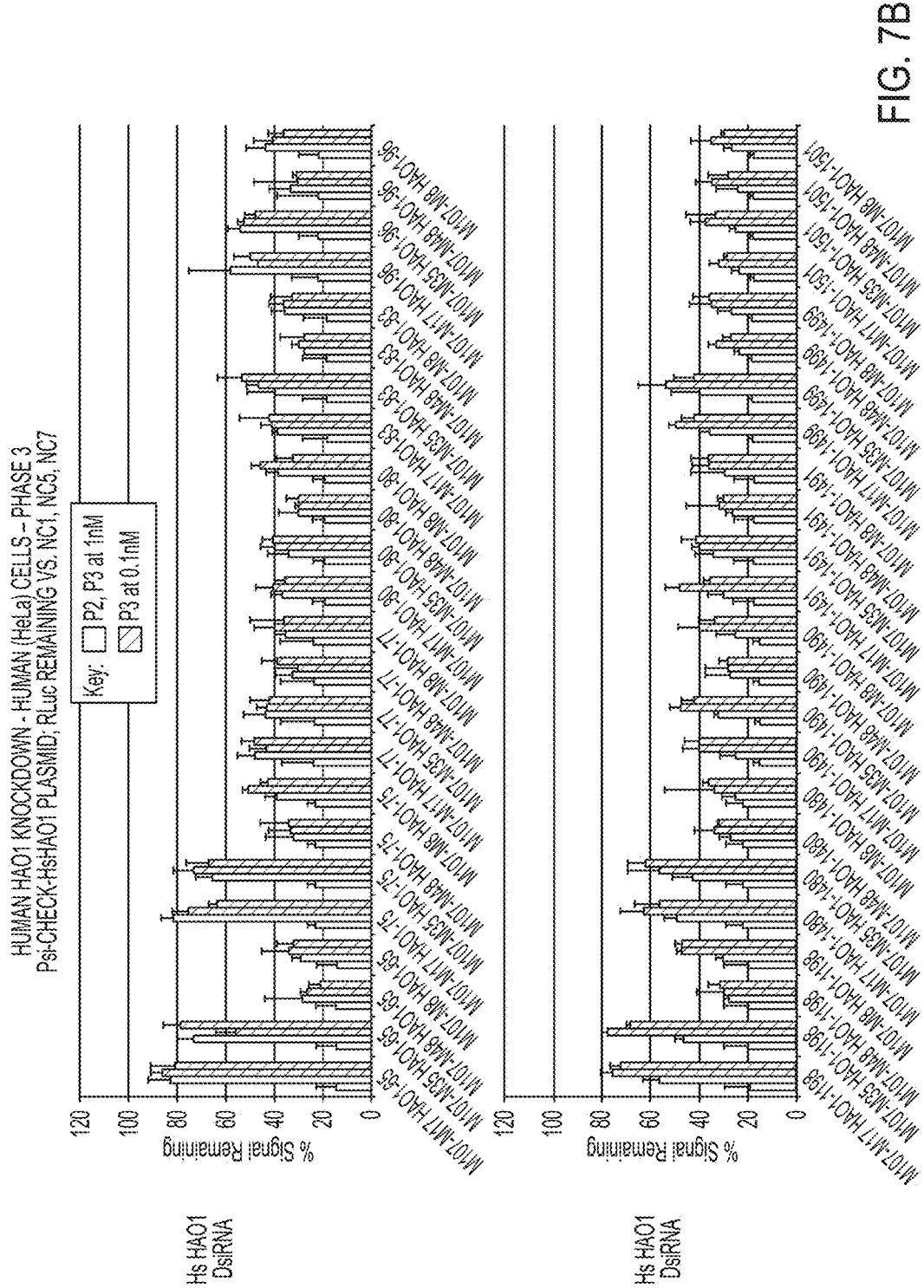
Figure 7C:
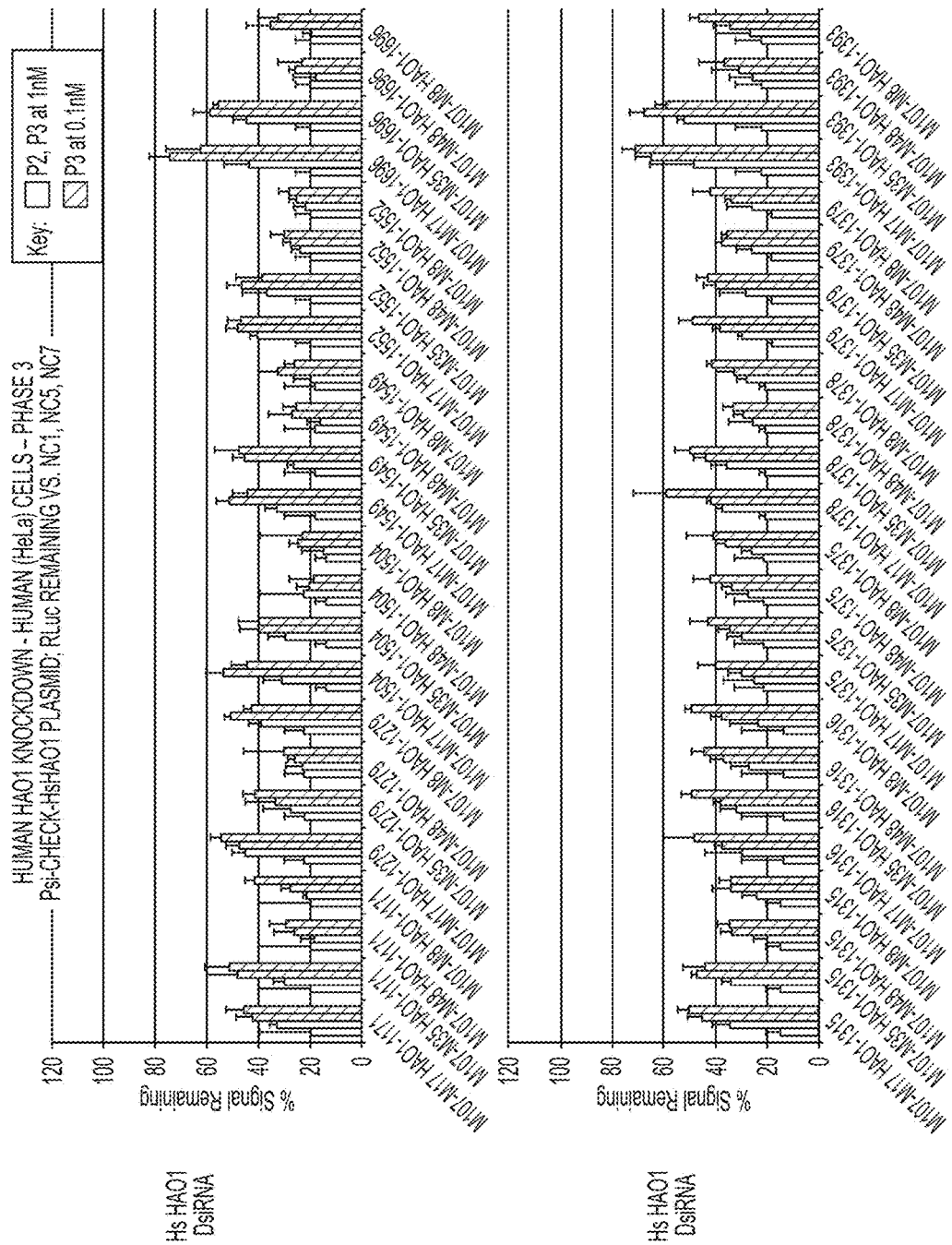

A selection of 24 DsiRNAs from Example 3 above were prepared with 2'-O-methyl guide strand modification patterns ("M17", "M35", "M48" and "M8" as shown above), paired with "M107" passenger strand modifications. For each of these DsiRNA sequences, DsiRNAs possessing each of the four guide strand modification patterns M17, M35, M48 and M8 coupled with the "M107" passenger strand modification pattern were assayed for HAO1 inhibition in human HeLa cells at 1.0 nM and 0.1 nM (in duplicate) concentrations in the environment of the HeLa cells. FIG. 7A shows specific modification patterns for such duplexes (with shaded residues indicating those possessing 2'-O-Methyl modifications), while FIGS. 7B and 7C show human HAO1 knockdown efficacy data for each of the four modified duplexes associated with the 24 duplex sequences examined (HAO1-65, 75, 77, 80, 83, 96, 1198, 1480, 1490, 1491, 1499, 1501, 1171, 1279, 1504, 1549, 1552, 1696, 1315, 1316, 1375, 1378, 1379 and 1393). As demonstrated in FIGS. 7B and 7C, many tested duplexes were demonstrated to possess robust HAO1 knockdown efficacy at even 0.1 nM concentrations across the full range of highly modified forms tested.

Figure 7D:
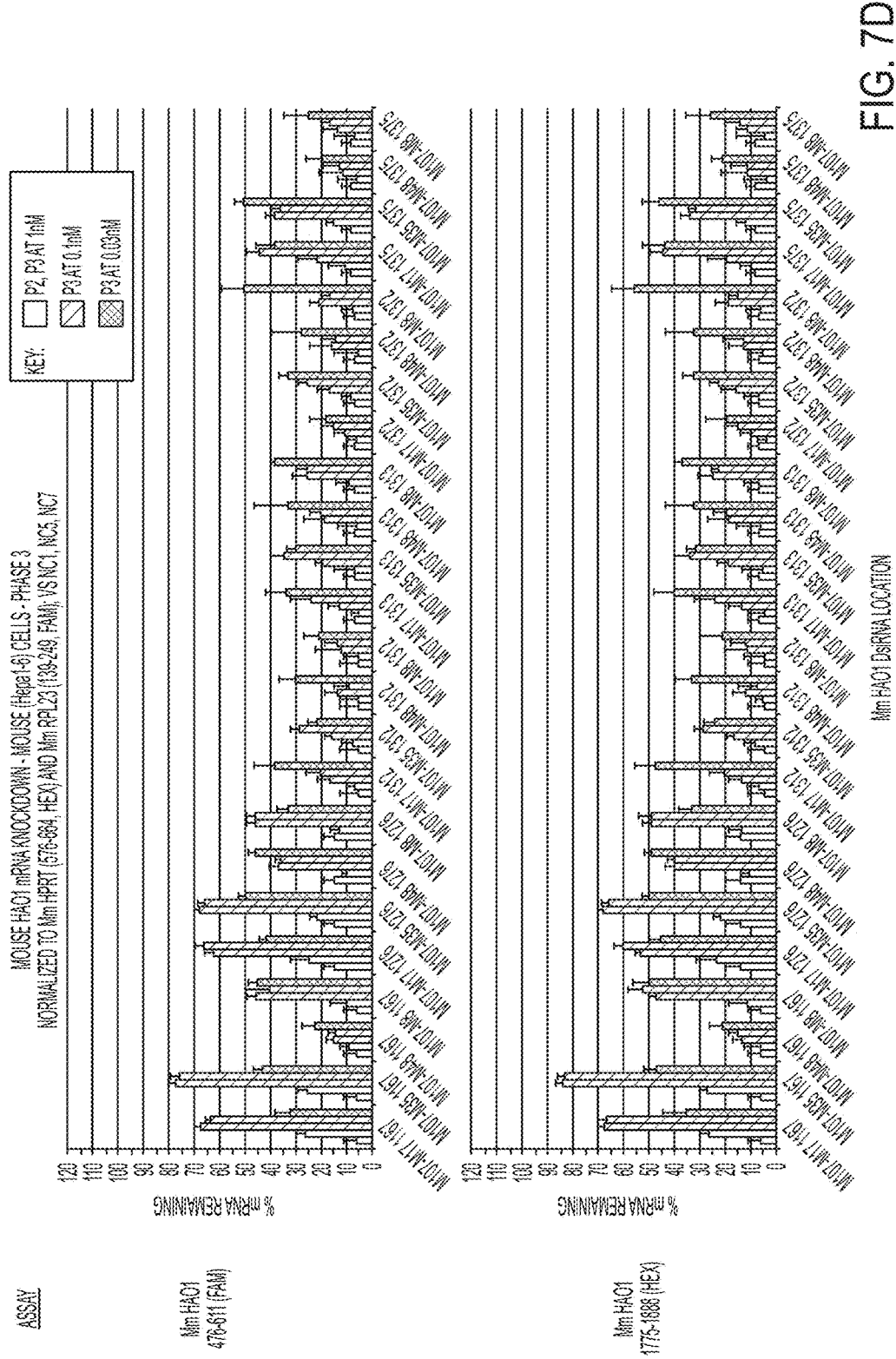
Figure 7E:
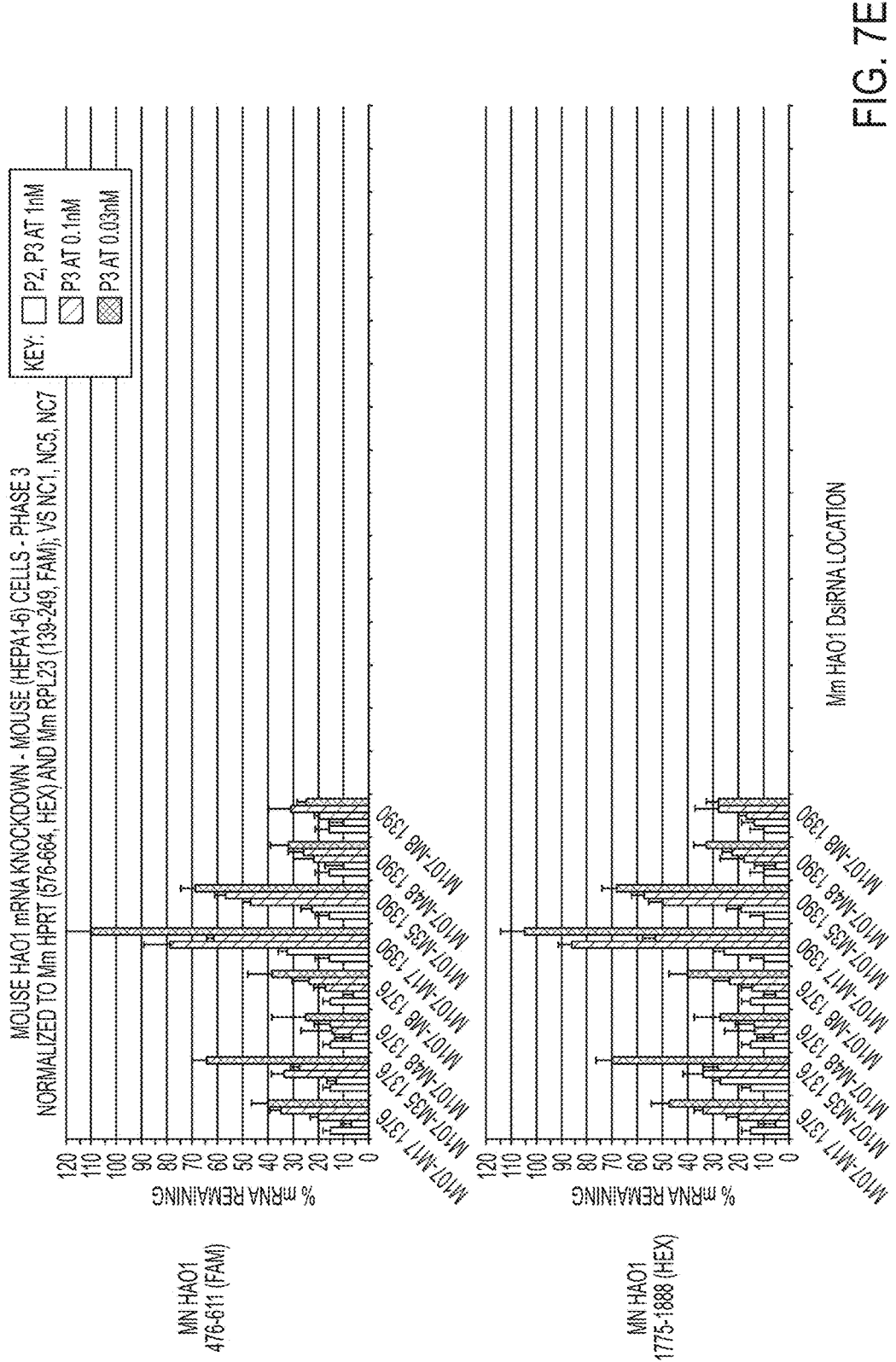

Eight duplex sequences (HAO1-m1167, m1276, m1312, m1313, m1372, m1375, m1376 and m1390, which correspond to human duplexes HAO1-1171, 1279, 1315, 1316, 1375, 1378, 1379 and 1393, respectively) were also examined for knockdown efficacy in mouse Hepa1-6 cells across the same range of four duplex modification patterns. As shown in FIGS. 7D and 7E, a majority of these duplexes showed robust HAO1 knockdown efficacy in mouse cells across a range of duplex modification patterns, at concentrations as low as 0.03 nM.

Example 6

Figure 8A:
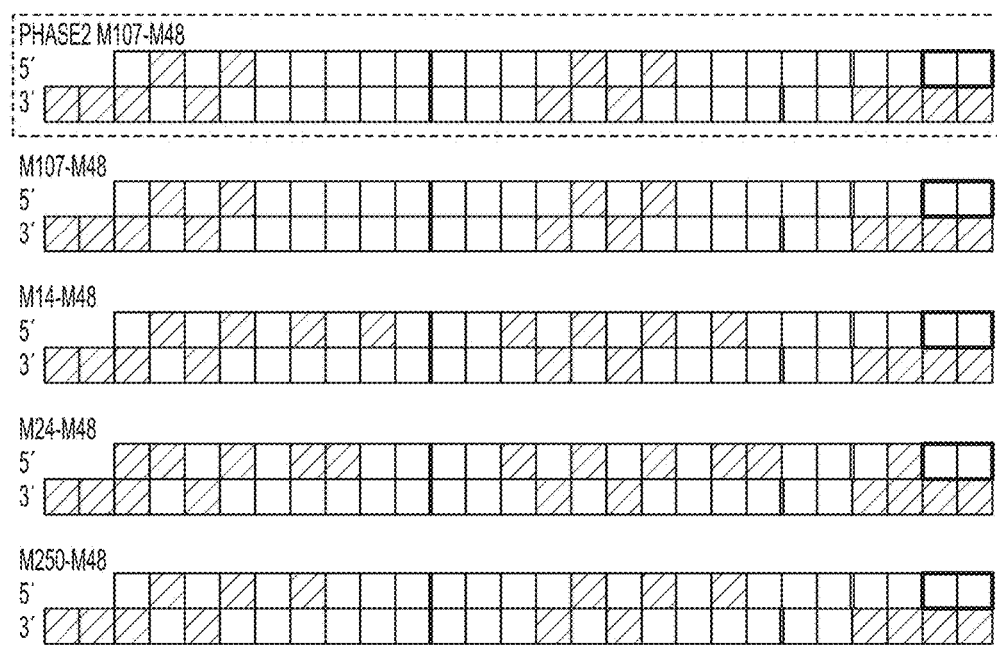
FIGS. 8A to 8E present modification pattern diagrams and histograms showing efficacy data for 24 independent HAO1-targeting DsiRNA sequences across four different passenger (sense) strand 2'-O-methyl modification patterns ("M107", "M14", "M24" and "M250", respectively, as shown in FIG. 8A and noting for FIGS. 8B to 8E that modification patterns are recited as passenger strand modification pattern-guide (here, "M48") strand modification pattern, e.g., "M107-M48", "M14-M48", "M24-M48" or "M250-M48") in human HeLa cells tested at 0.1 nM (duplicate assays) and 1 nM (FIGS. 8B and 8C) and mouse Hepa1-6 cells for a subset of 8 duplexes tested at 0.03 nM, 0.1 nM (duplicate assays) and 1 nM (FIGS. 8D and 8E).
Figure 8B:
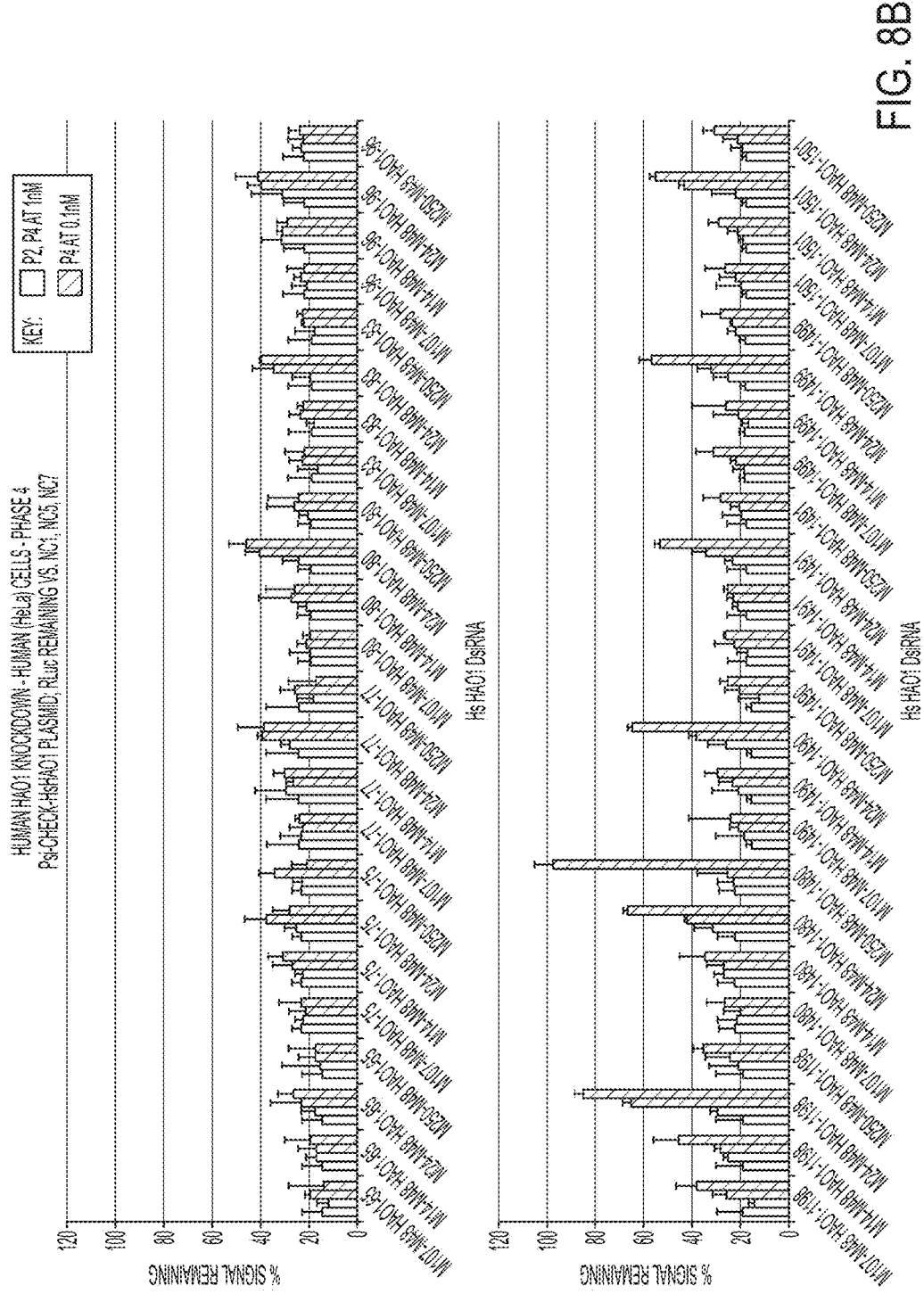
Figure 8C:
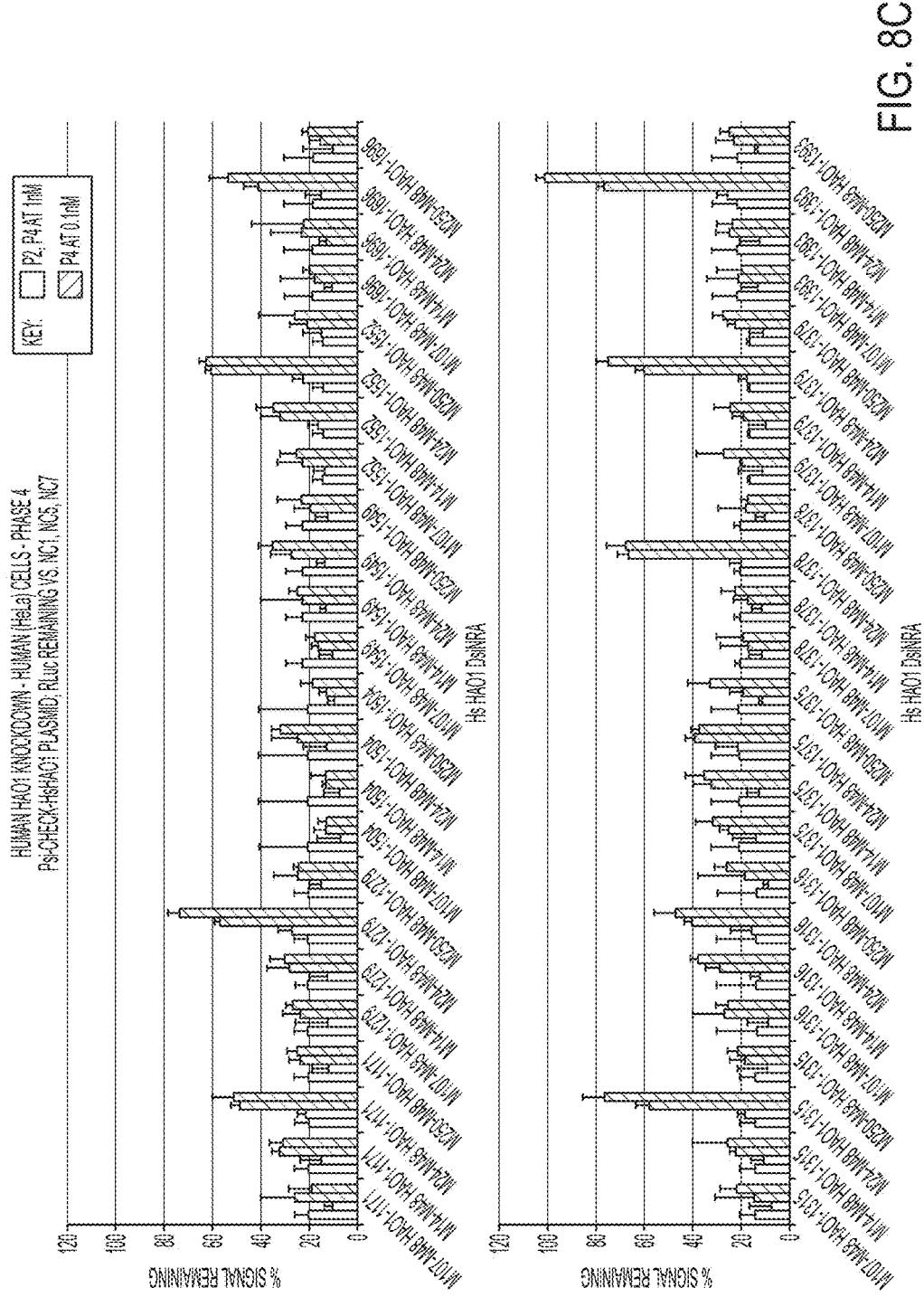

Assessment of Additionally Modified Forms of Glycolate Oxidase-Targeting DsiRNAs In Vitro The same set of 24 HAO1-targeting duplex sequences as set forth above in Example 5 were prepared to possess a range of four 2'-O-methyl passenger strand modification patterns ("M107", "M14", "M24" and "M250") coupled with a fixed "M48" guide strand modification pattern. These DsiRNAs were assayed for HAO1 inhibition at 1.0 nM and 0.1 nM (in duplicate) concentrations in the environment of the HeLa cells. FIG. 8A shows specific modification patterns for such duplexes (with shaded residues indicating those possessing 2'-O-Methyl modifications), while FIGS. 8B and 8C show human HAO1 knockdown efficacy data for each of the four modified duplexes associated with the 24 duplex sequences examined (HAO1-65, 75, 77, 80, 83, 96, 1198, 1480, 1490, 1491, 1499, 1501, 1171, 1279, 1504, 1549, 1552, 1696, 1315, 1316, 1375, 1378, 1379 and 1393). As demonstrated in FIGS. 8B and 8C, many of the additional tested duplexes were demonstrated to possess robust HAO1 knockdown efficacy at even 0.1 nM concentrations across the full range of highly modified passenger strand (with fixed guide strand modification pattern) forms tested.

Figure 8D:
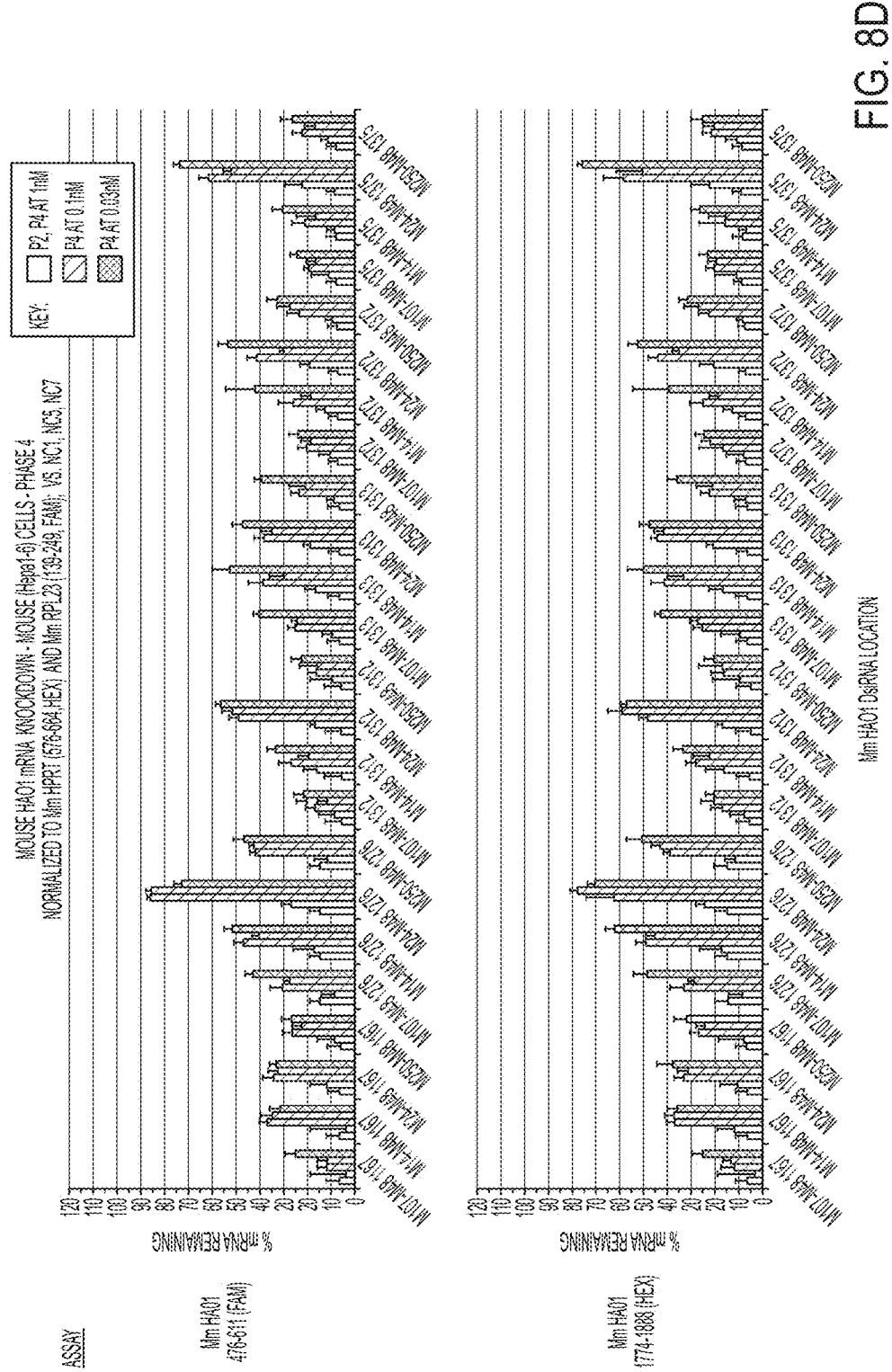
Figure 8E:
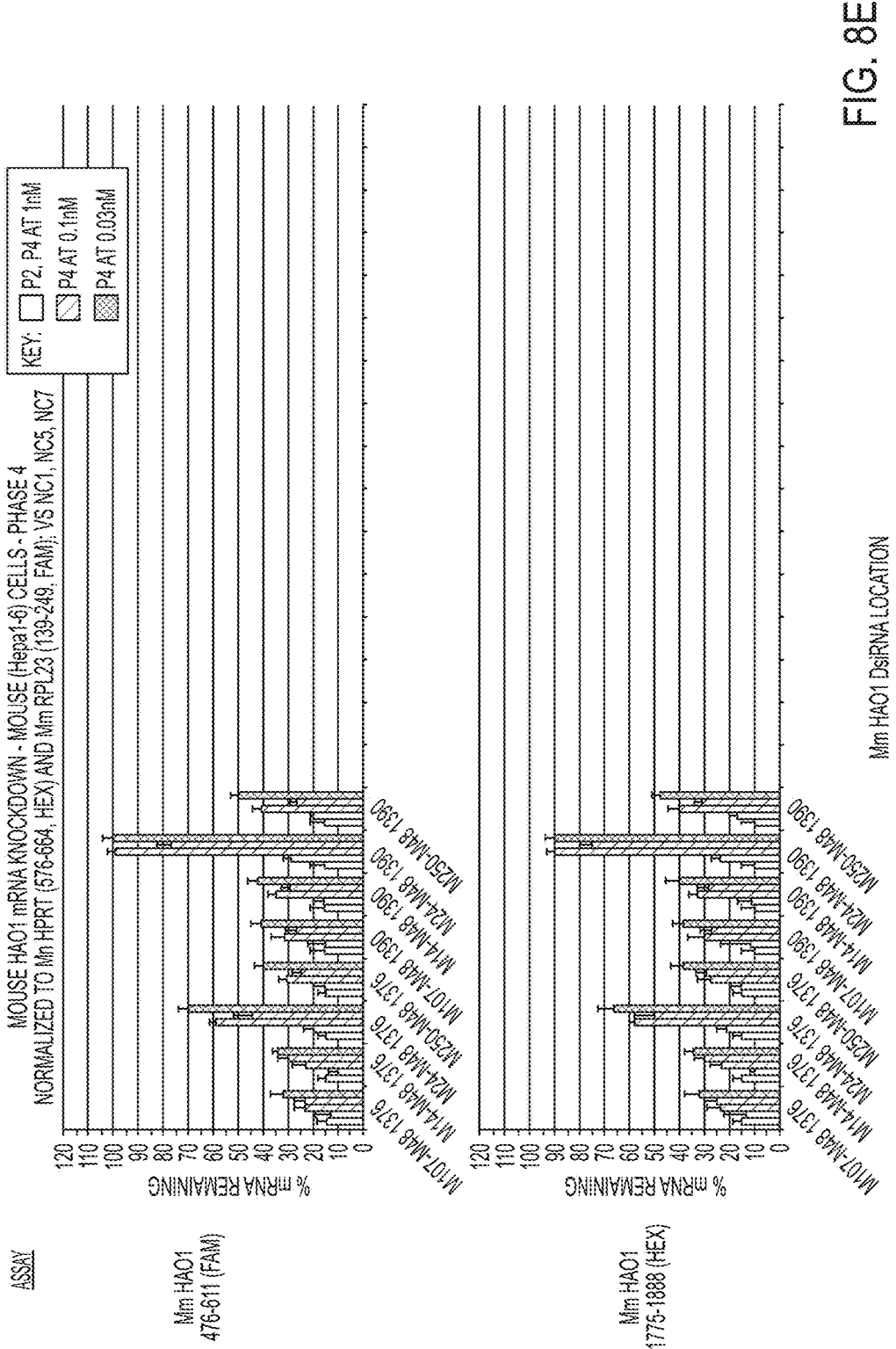
Figure 9A:
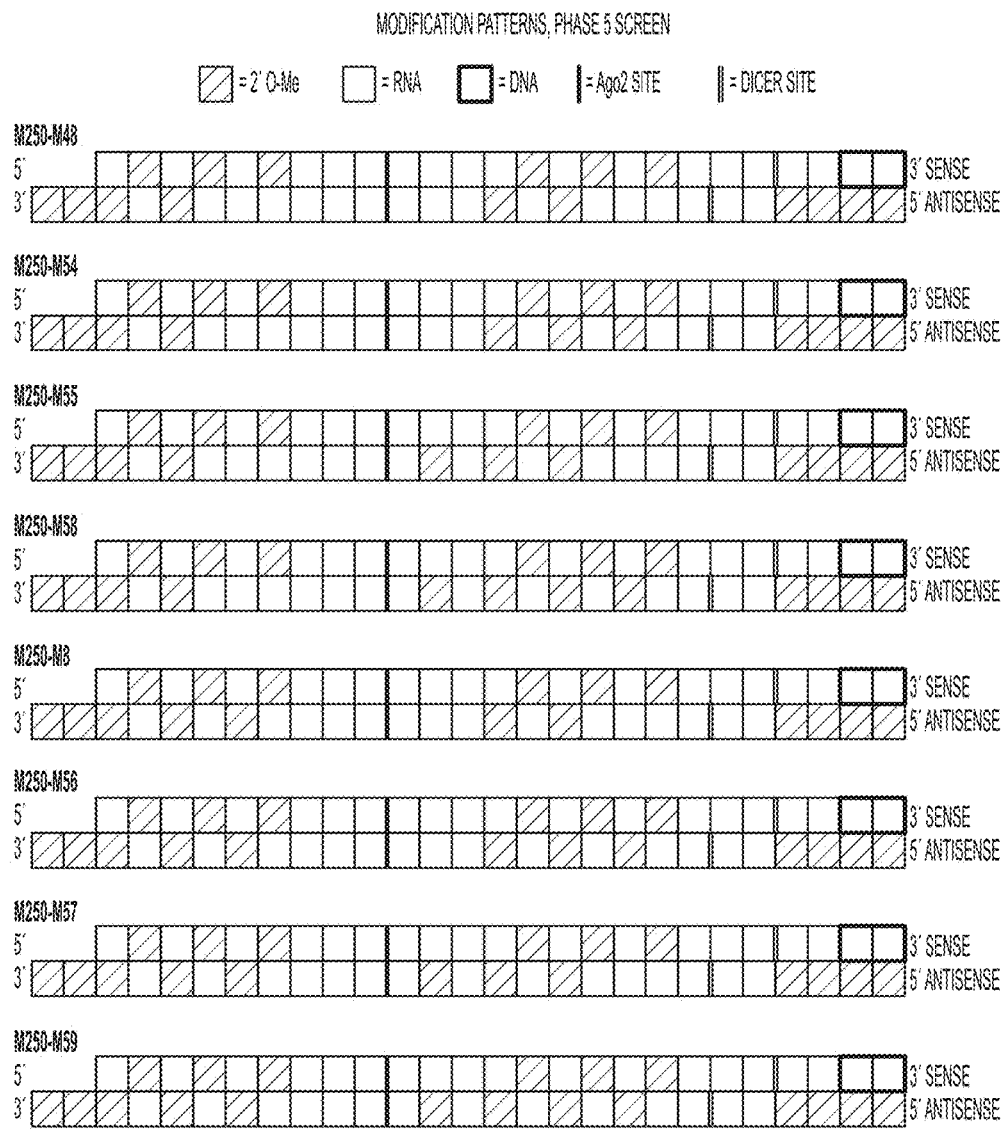
Figure 9B:
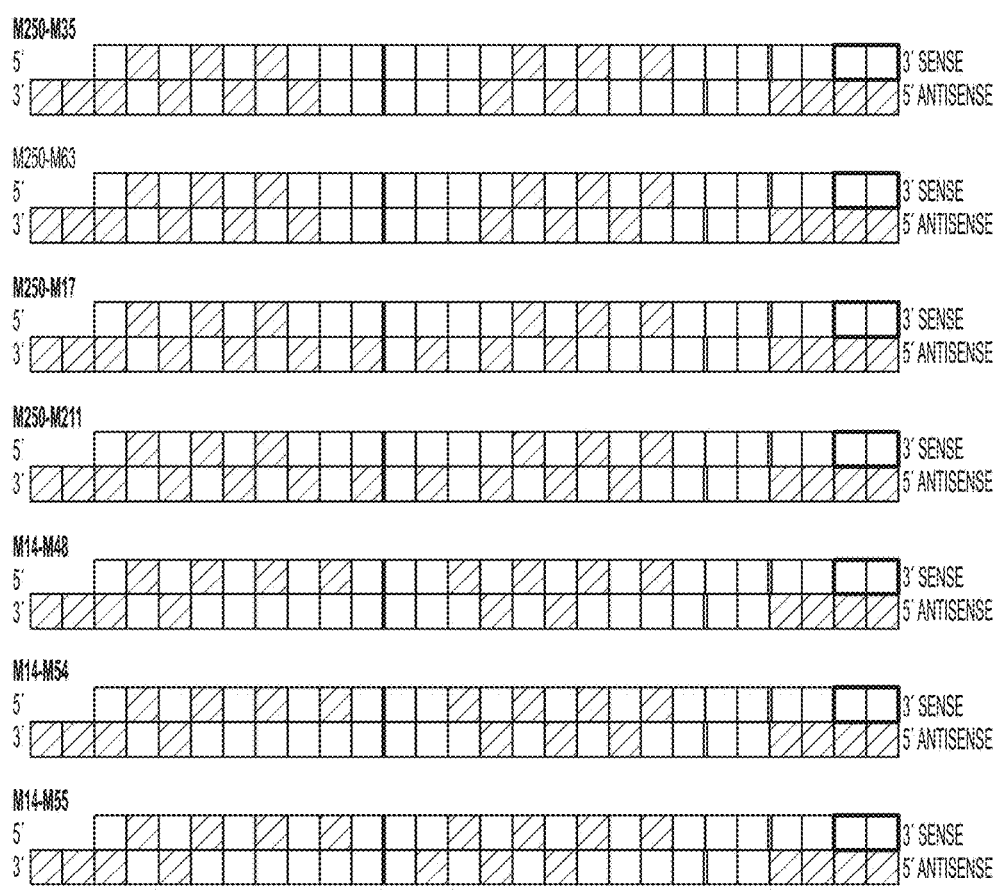
Figure 9C:
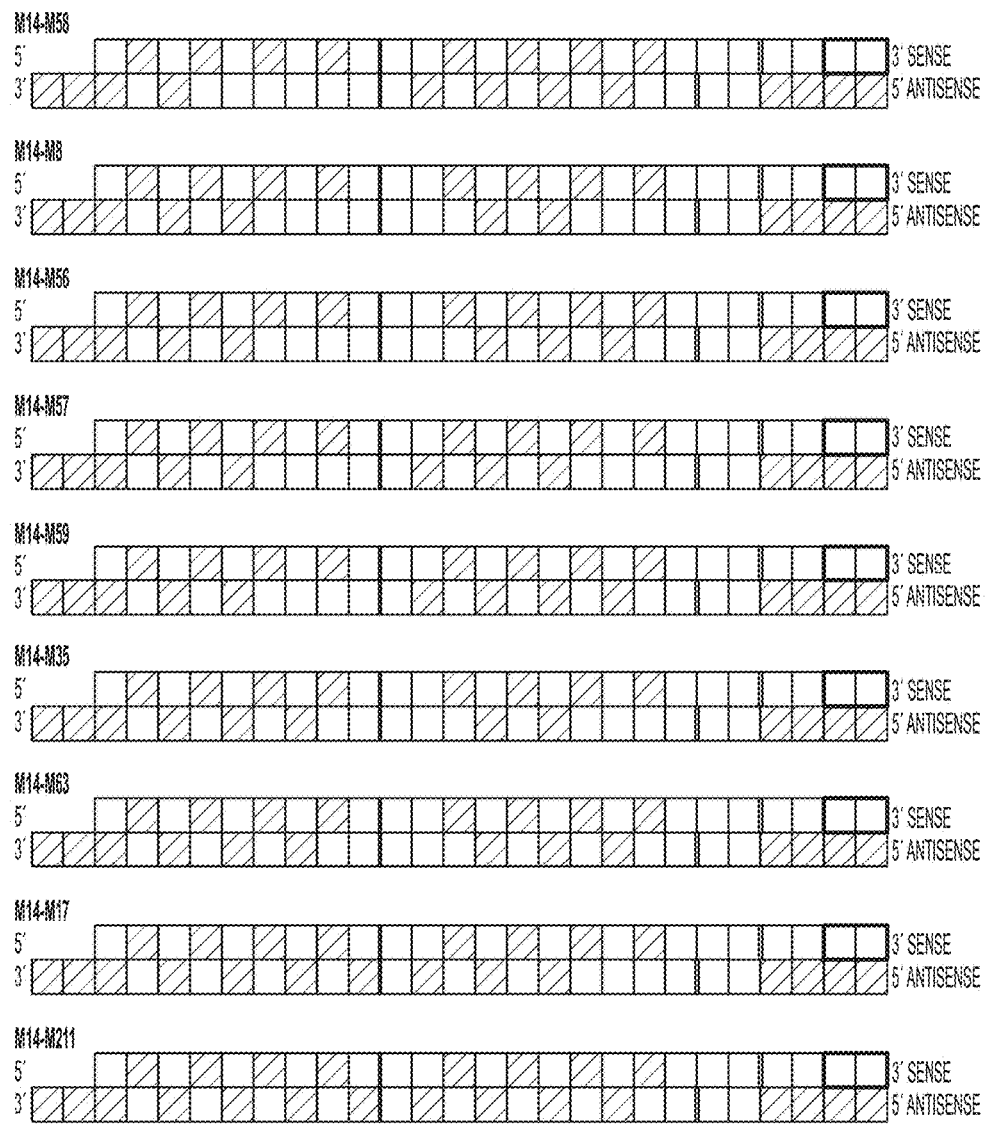
Figure 9D:
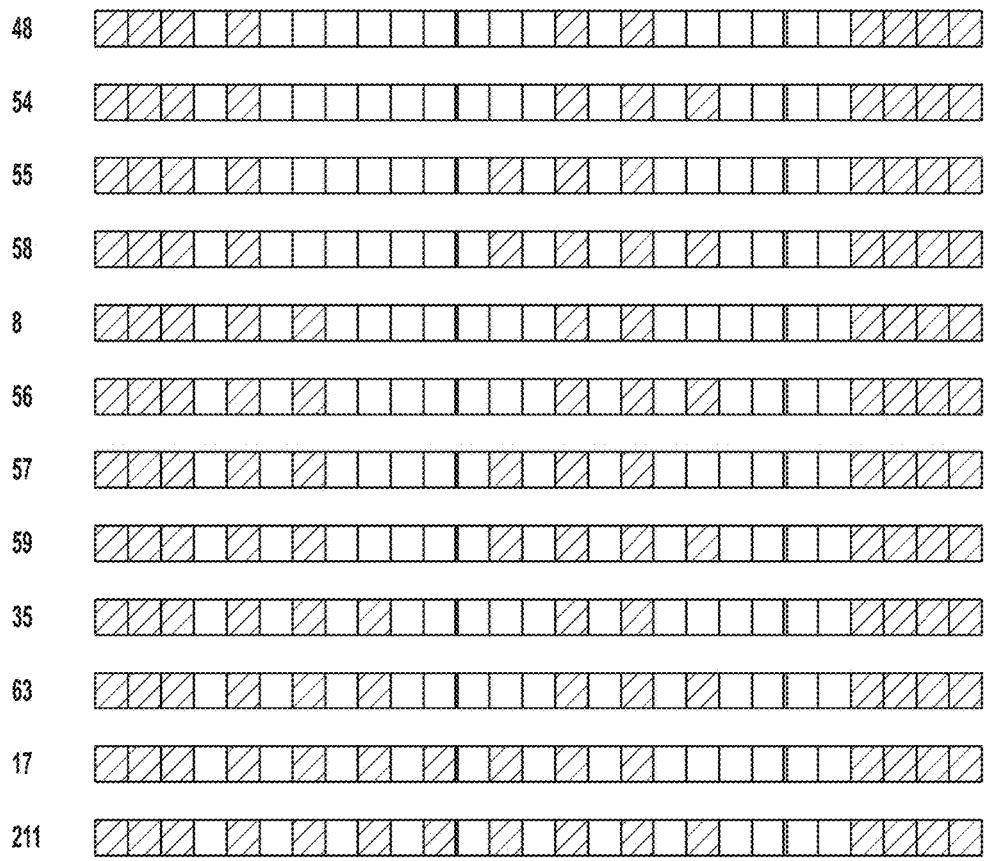
Figure 9E:
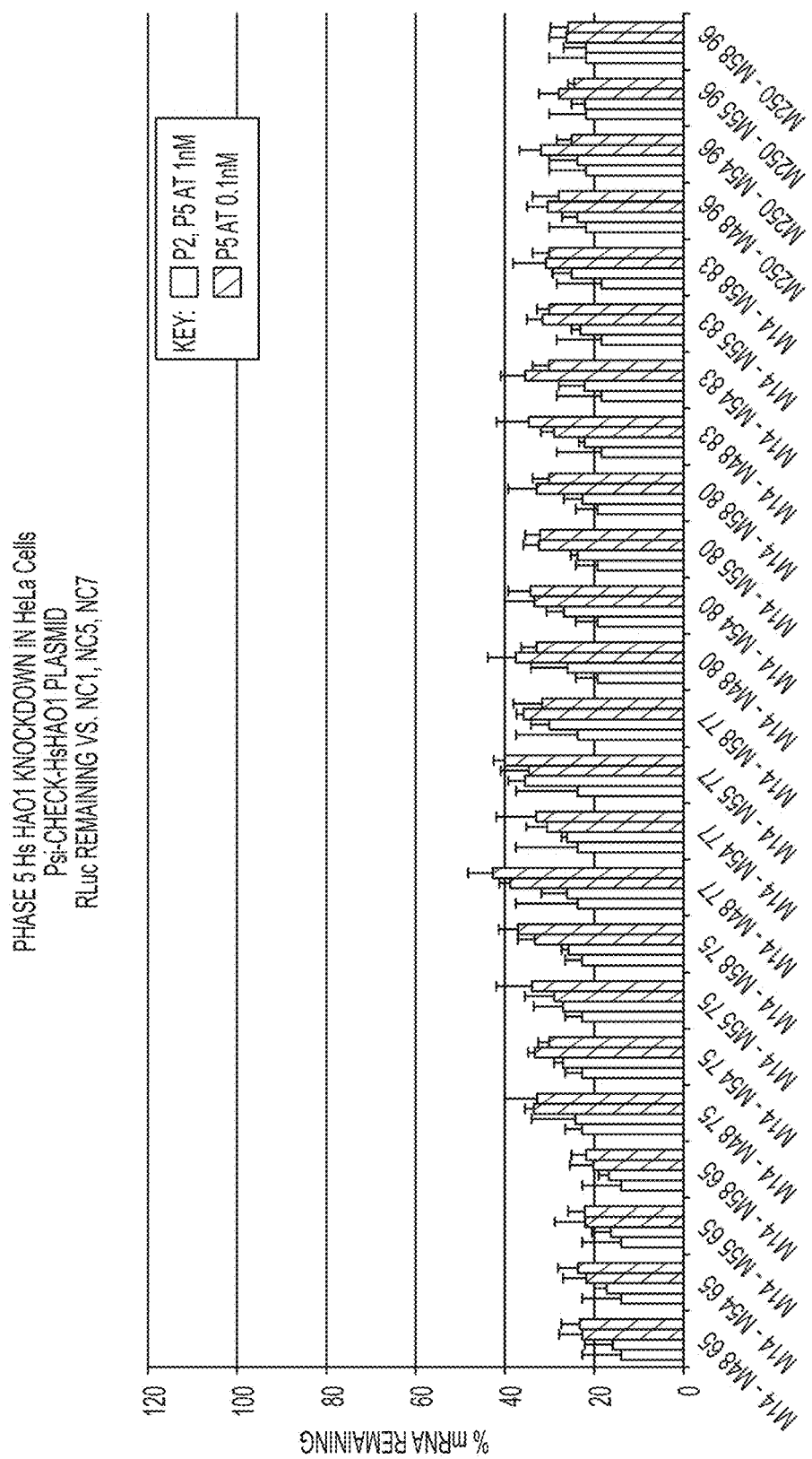
Figure 9H:
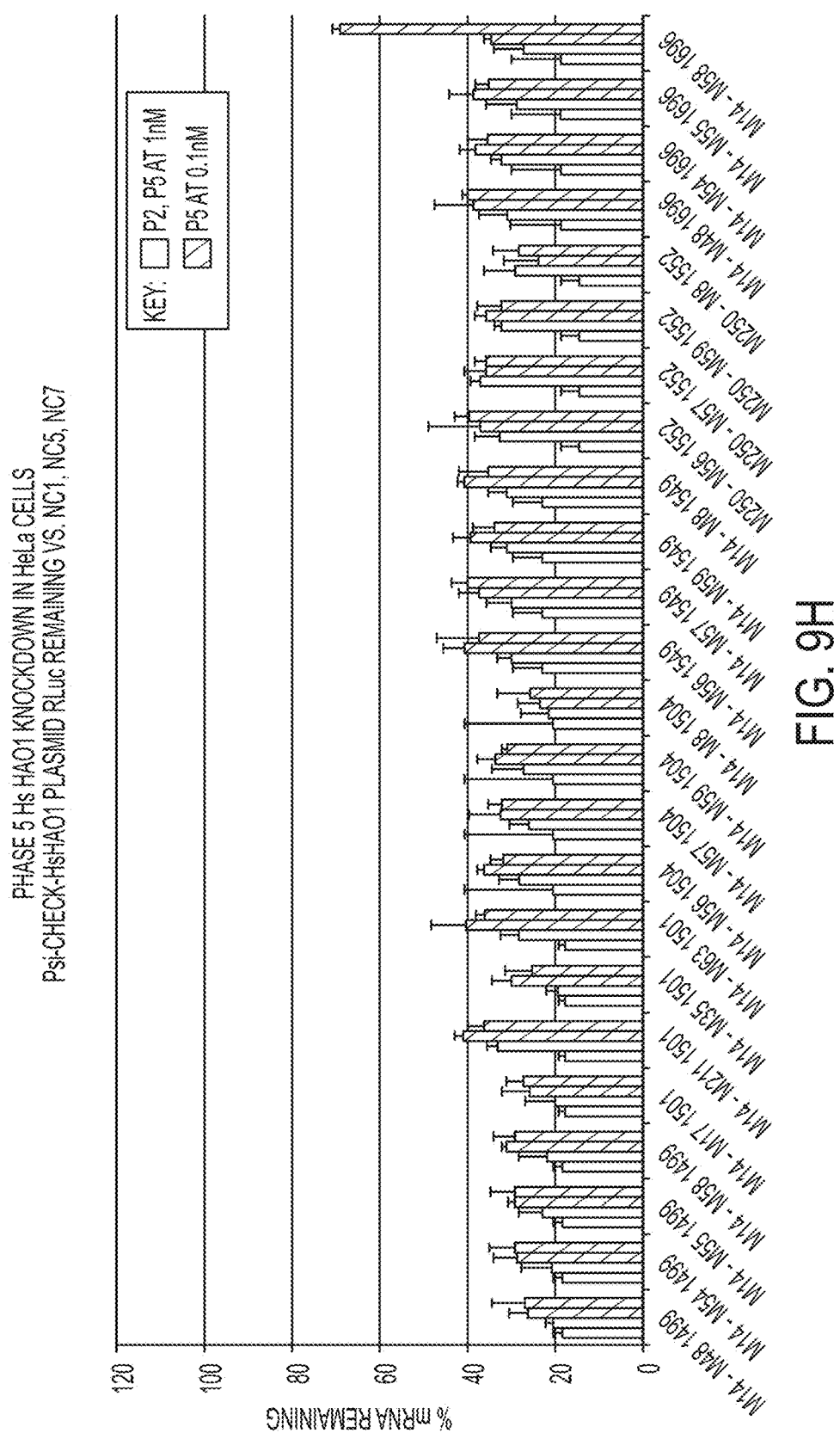
Figure 9I:
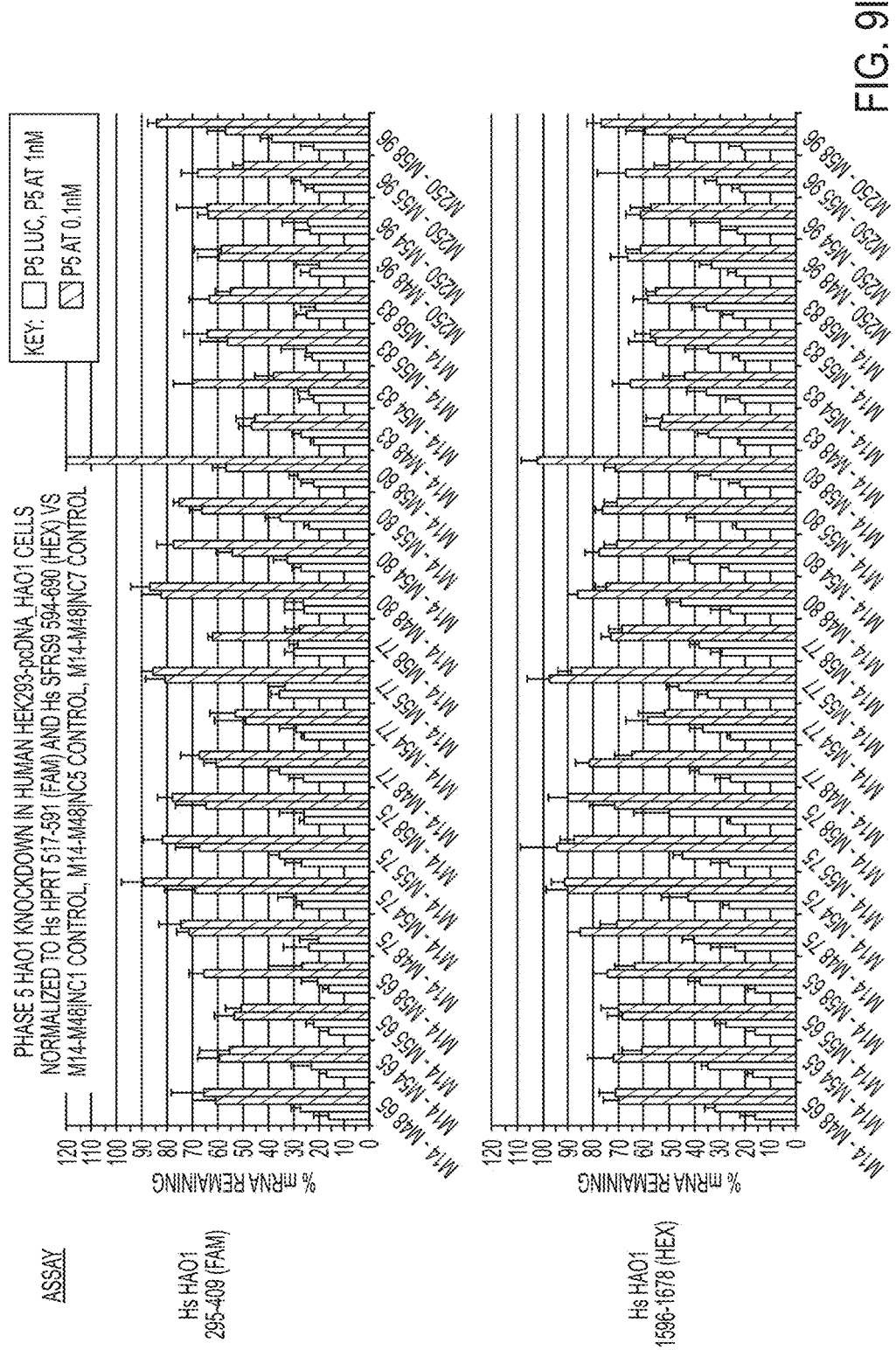
Figure 9J:
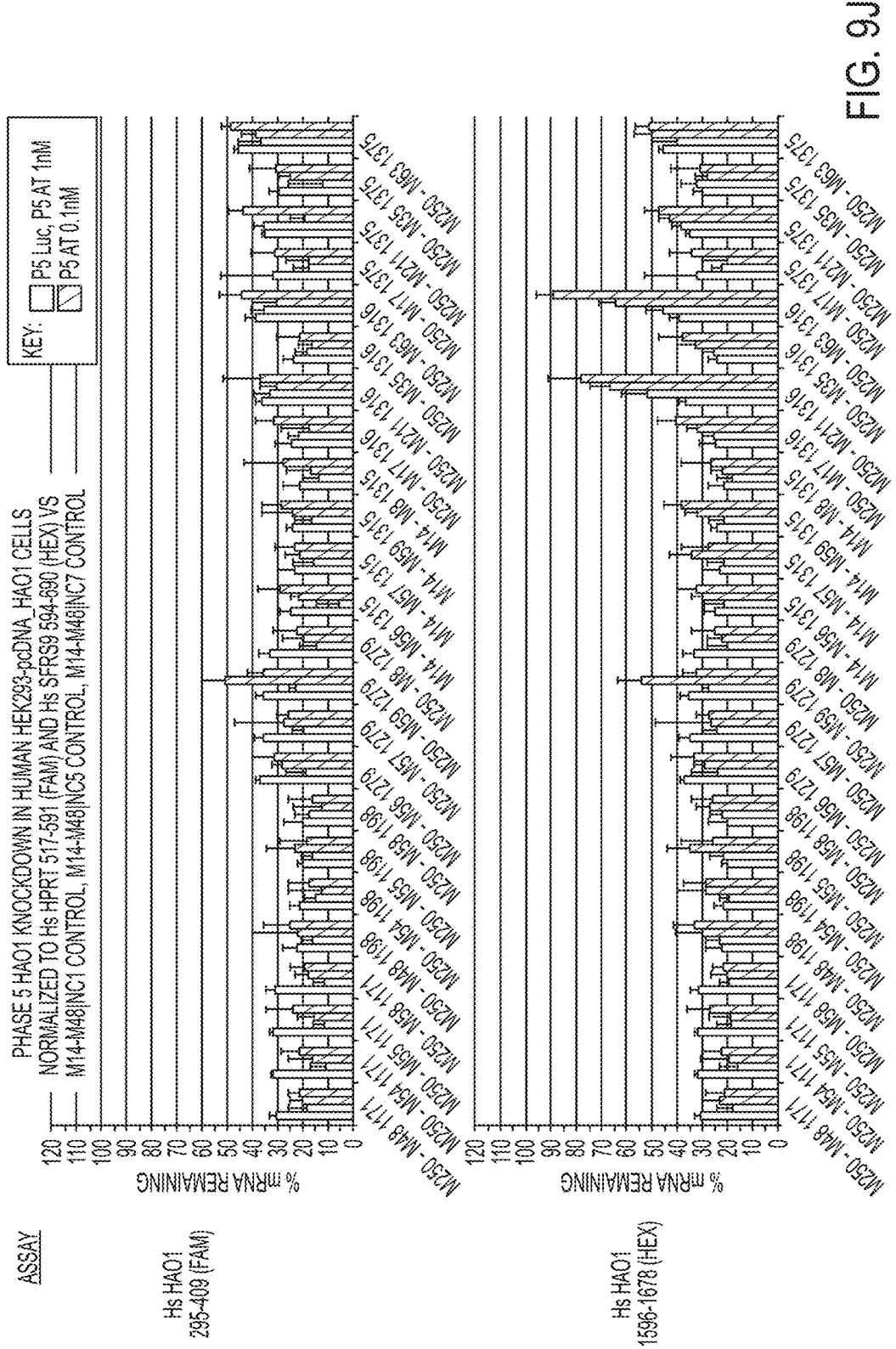
Figure 9K:
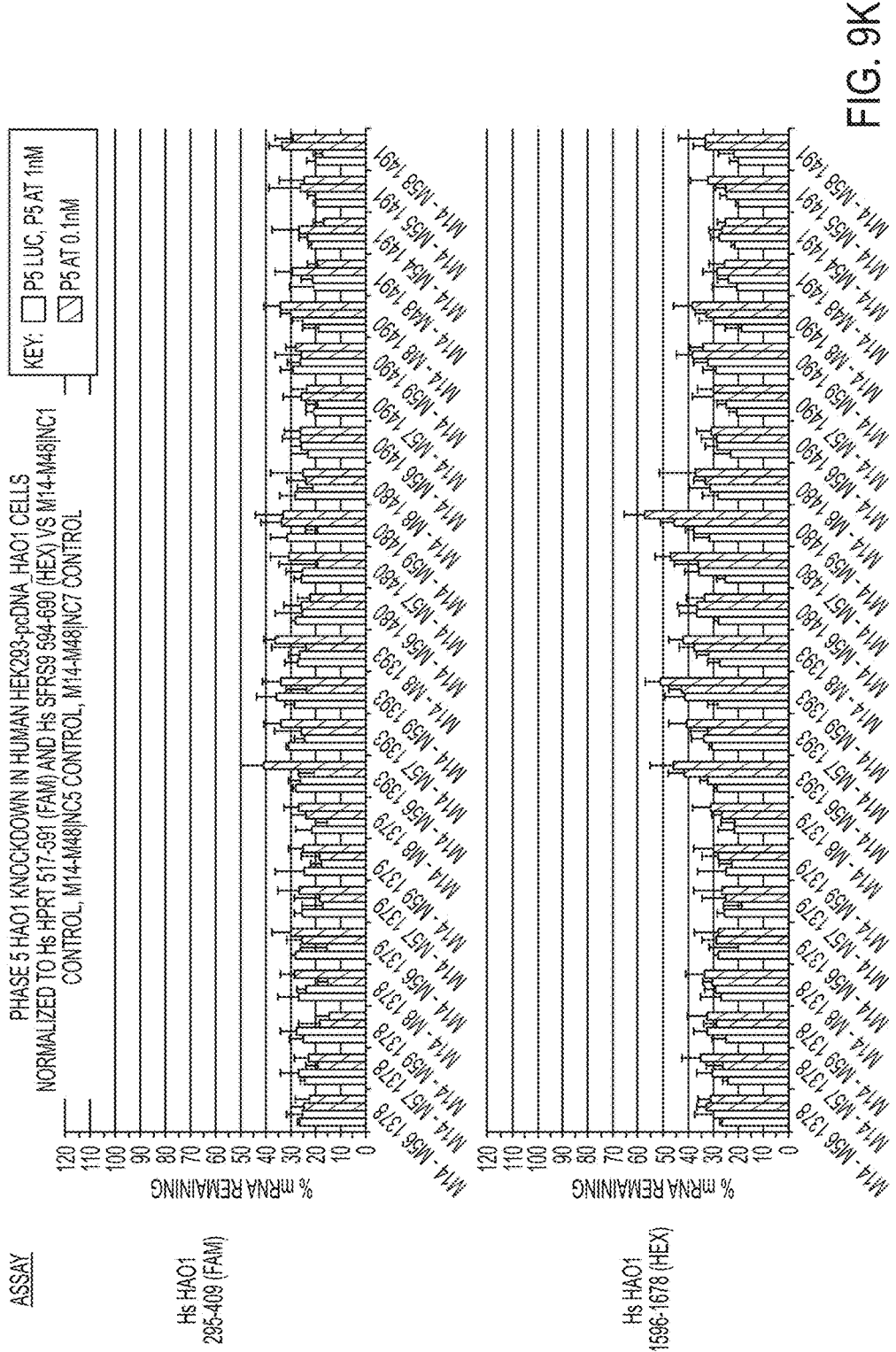
Figure 9L:
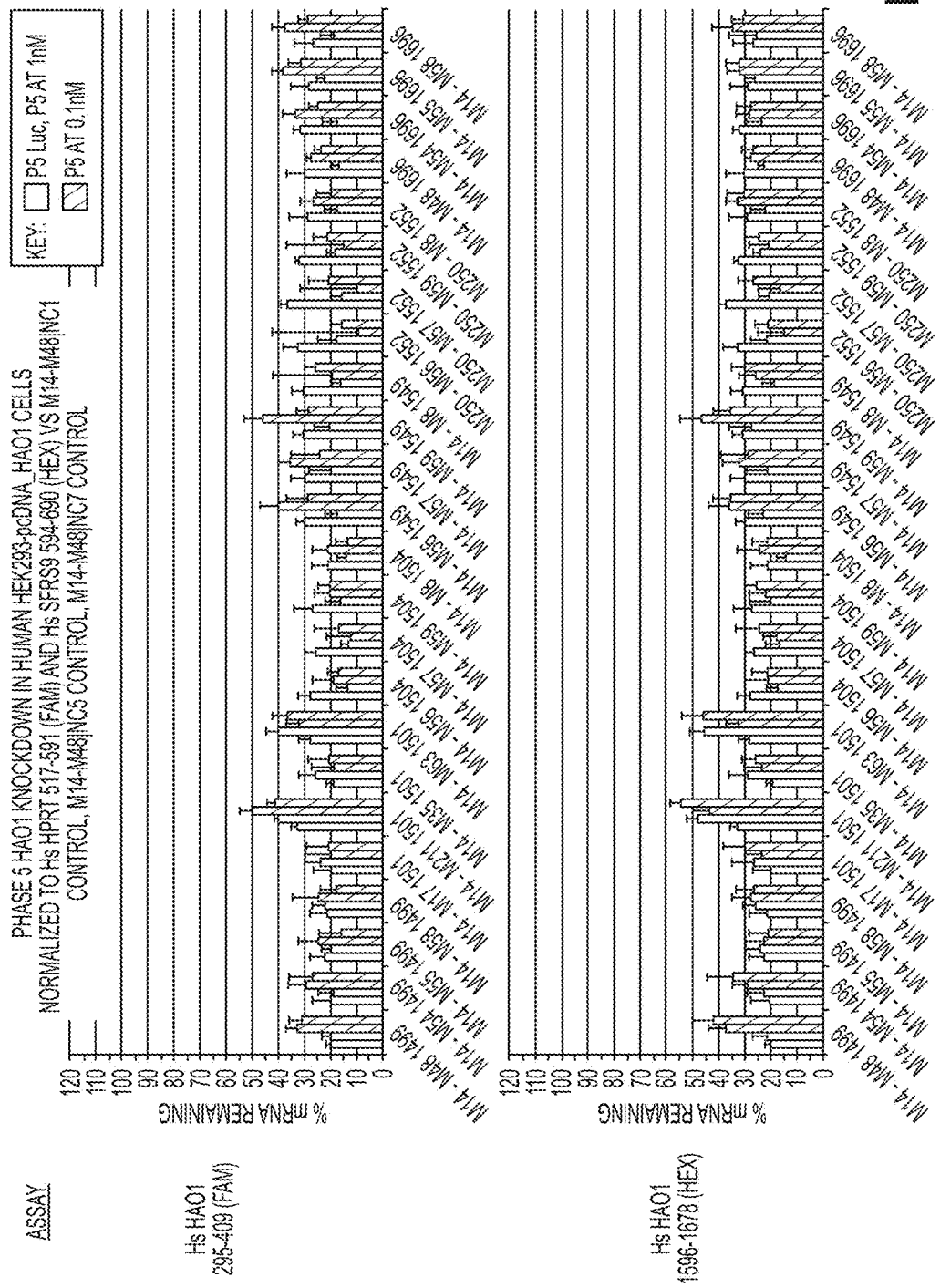
Figure 10A:
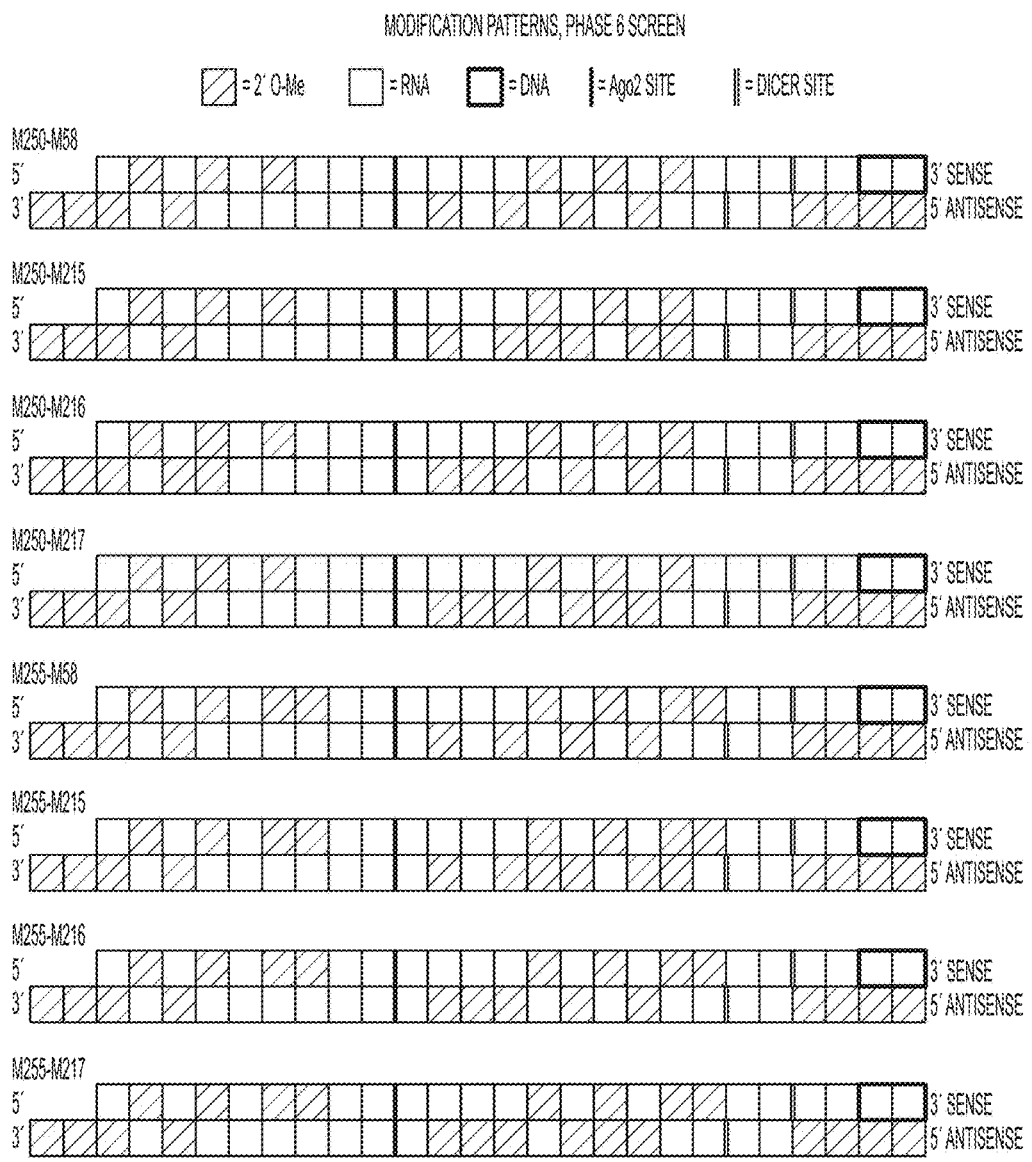
FIGS. 10A to 10O present modification pattern diagrams and histograms showing efficacy data for four independent HAO1-targeting DsiRNA sequences across indicated passenger (sense) and guide (antisense) strand 2'-O-methyl modification patterns (noting, as above, that modification patterns are recited as: passenger strand modification pattern-guide strand modification pattern) in HEK293 cells stably transfected with HAO1 (HEK293-pcDNA HAO1 Cells), assayed at 0.1 nM (duplicate assays) and 1 nM.
Figure 10B:
Figure 10C:
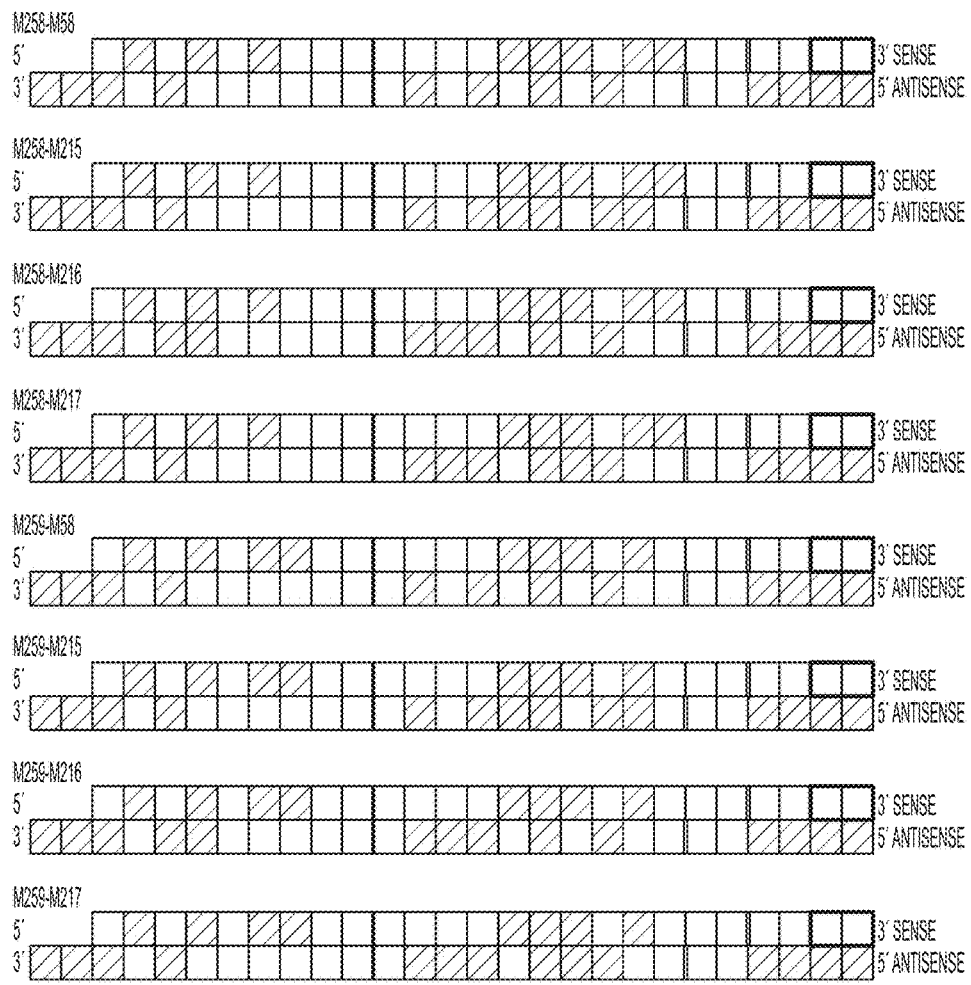
Figure 10D:
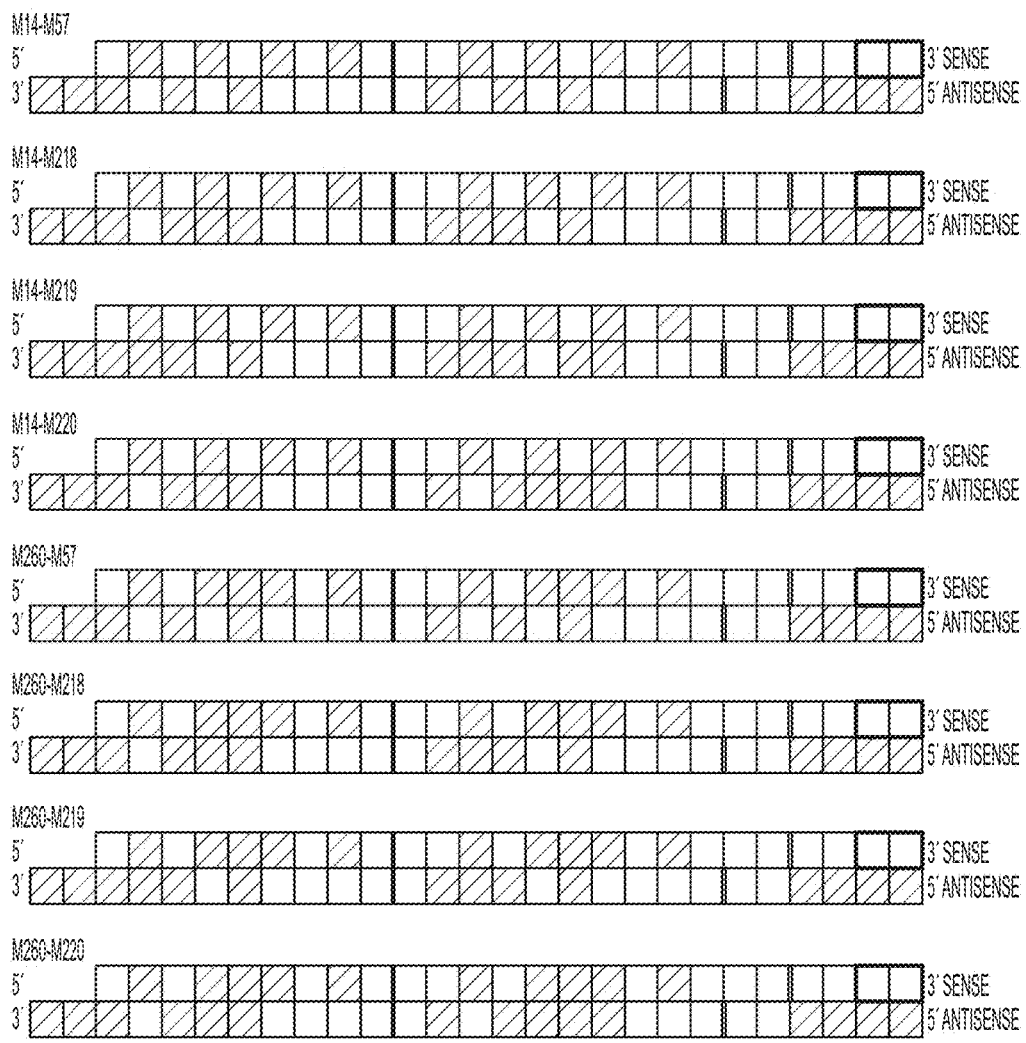
Figure 10E:
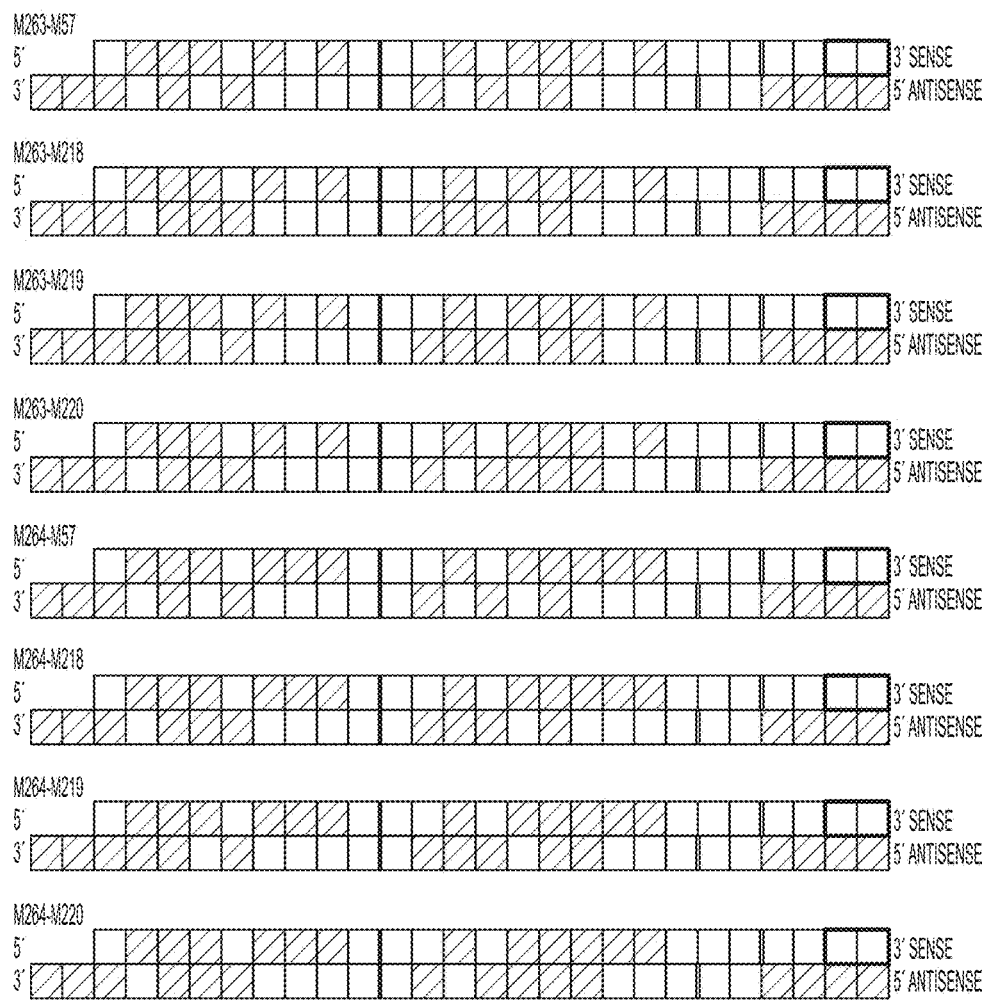
Figure 10F:
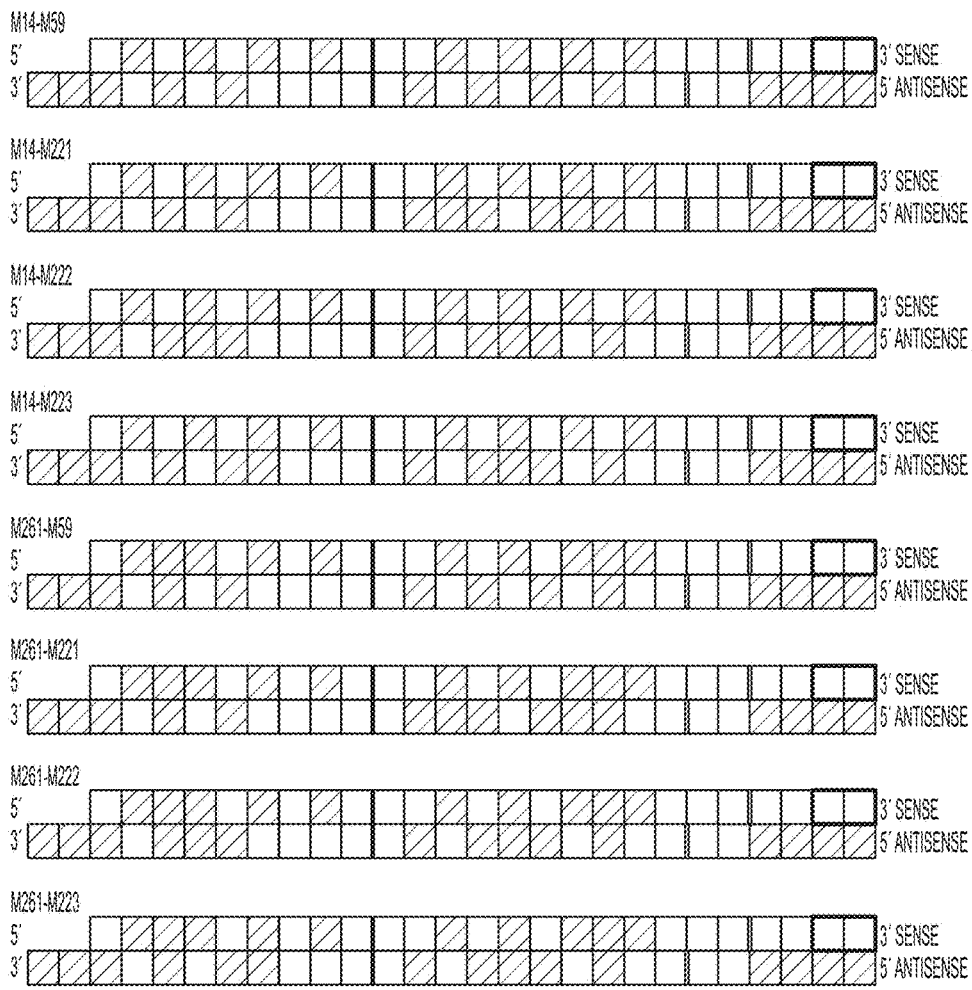
Figure 10G:
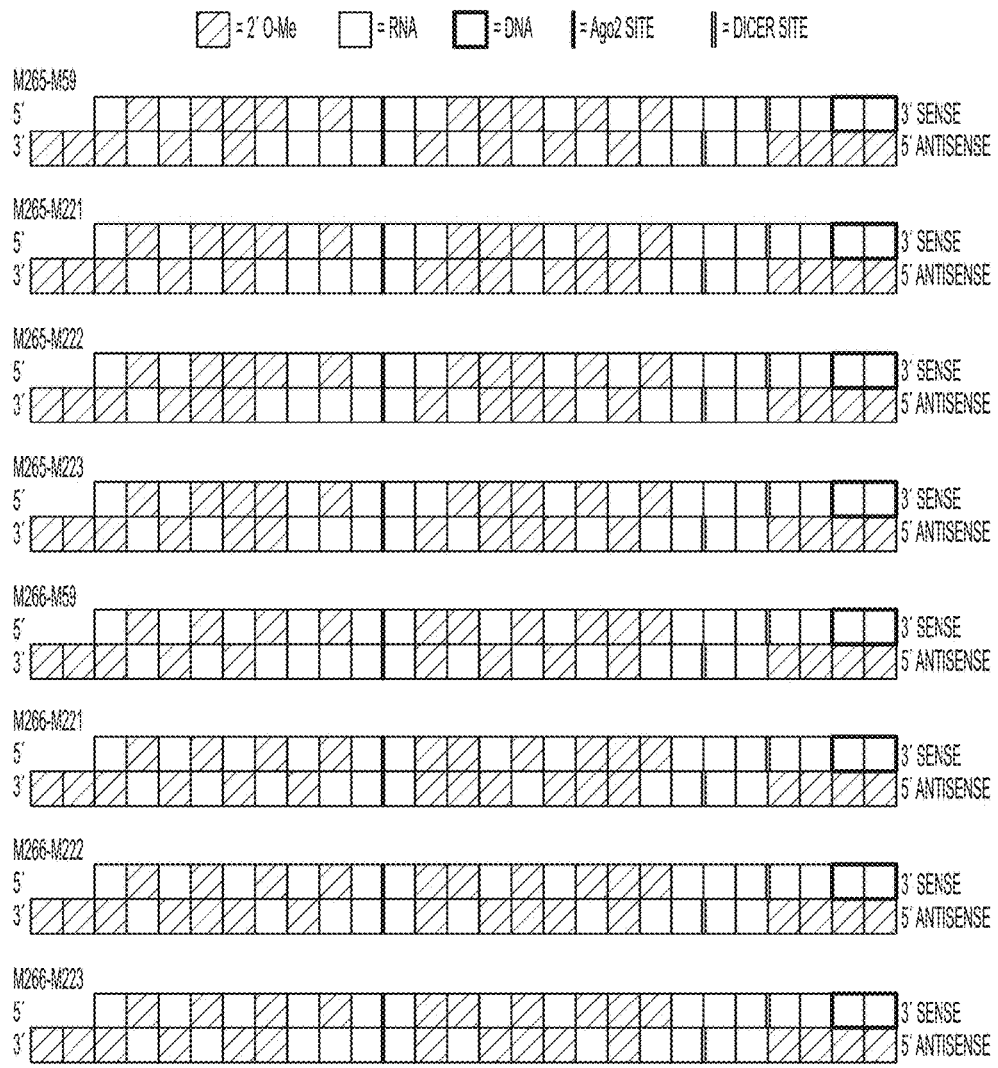
Figure 10H:
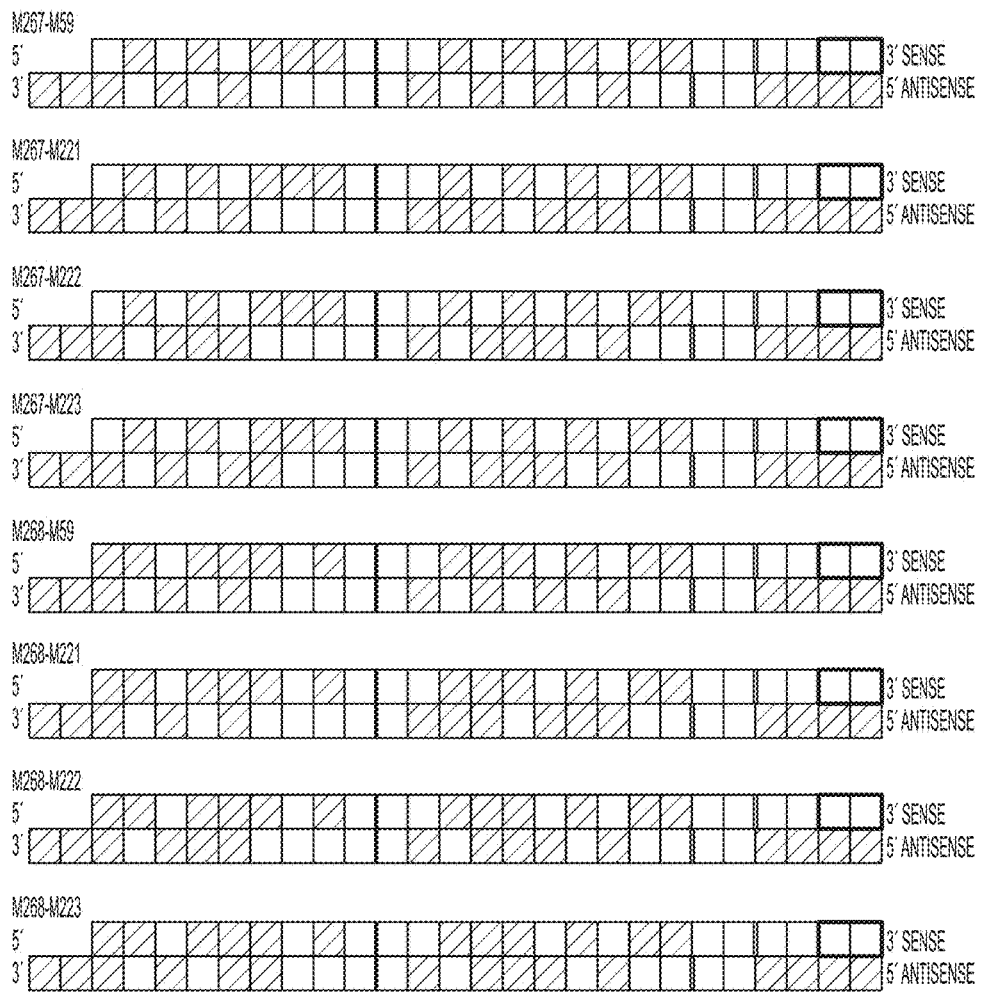
Figure 10I:
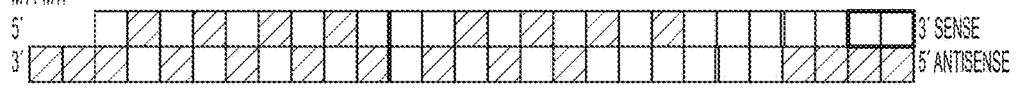
Figure 10M:
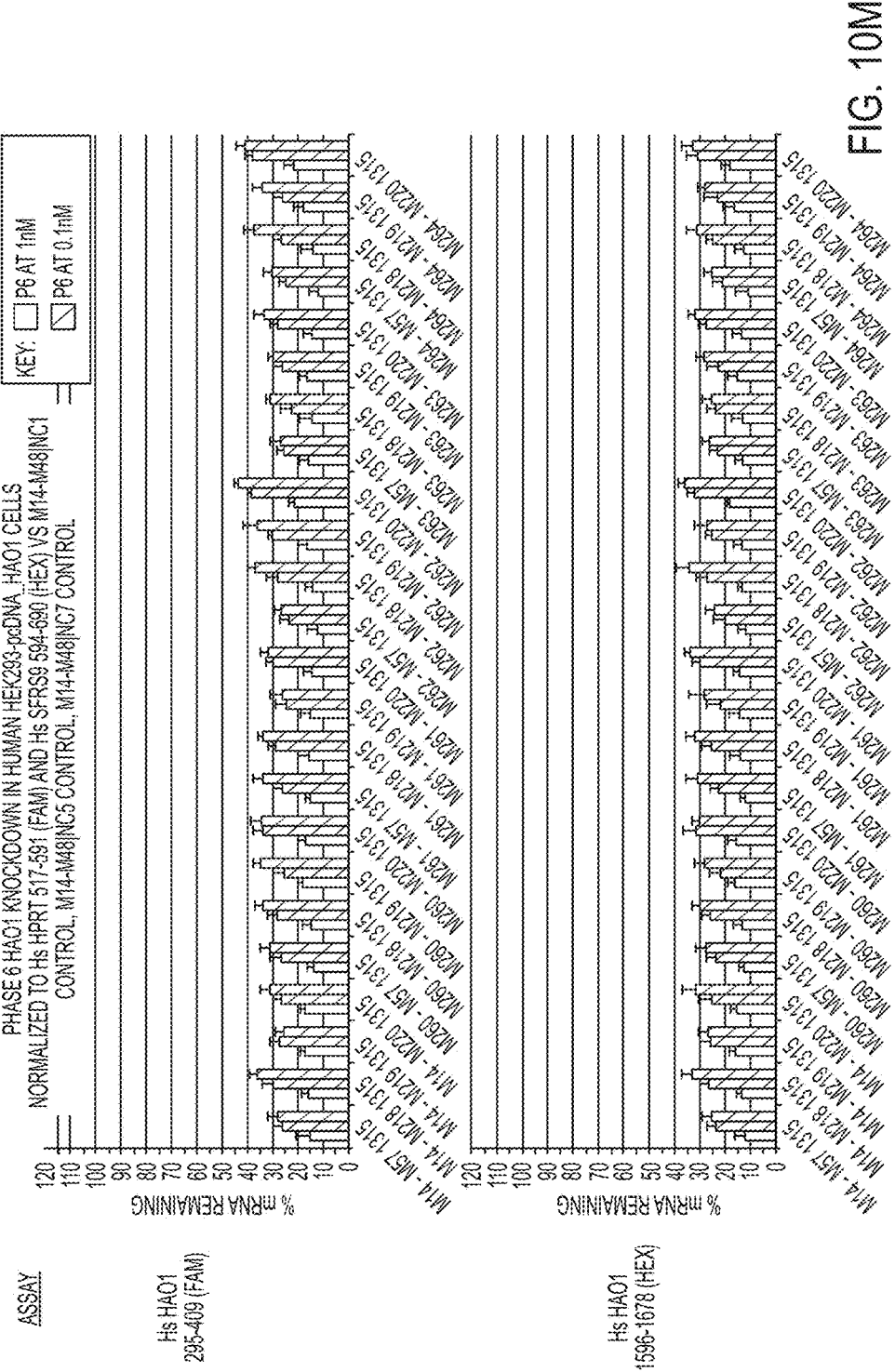
Figure 10N:
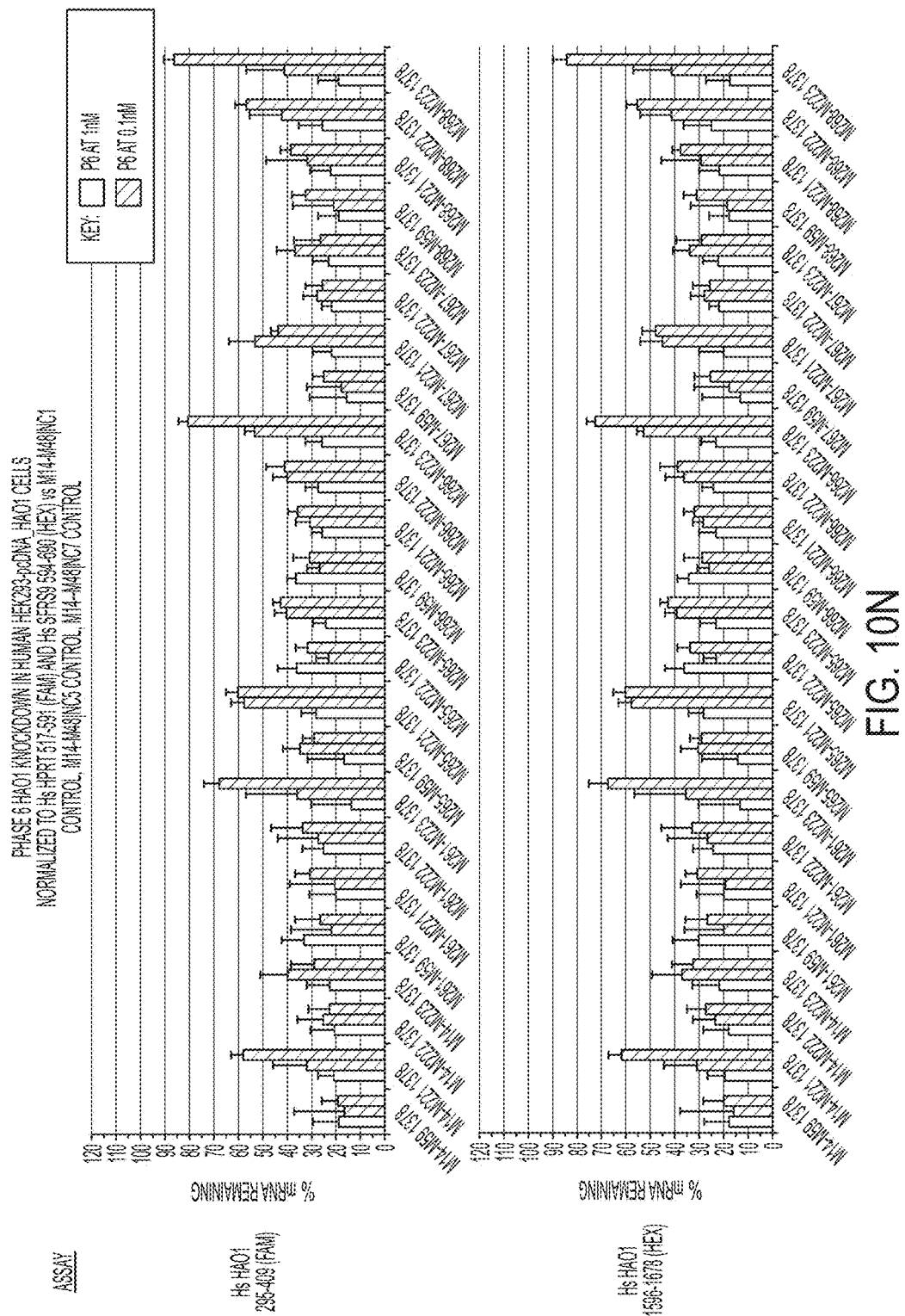
Figure 100:
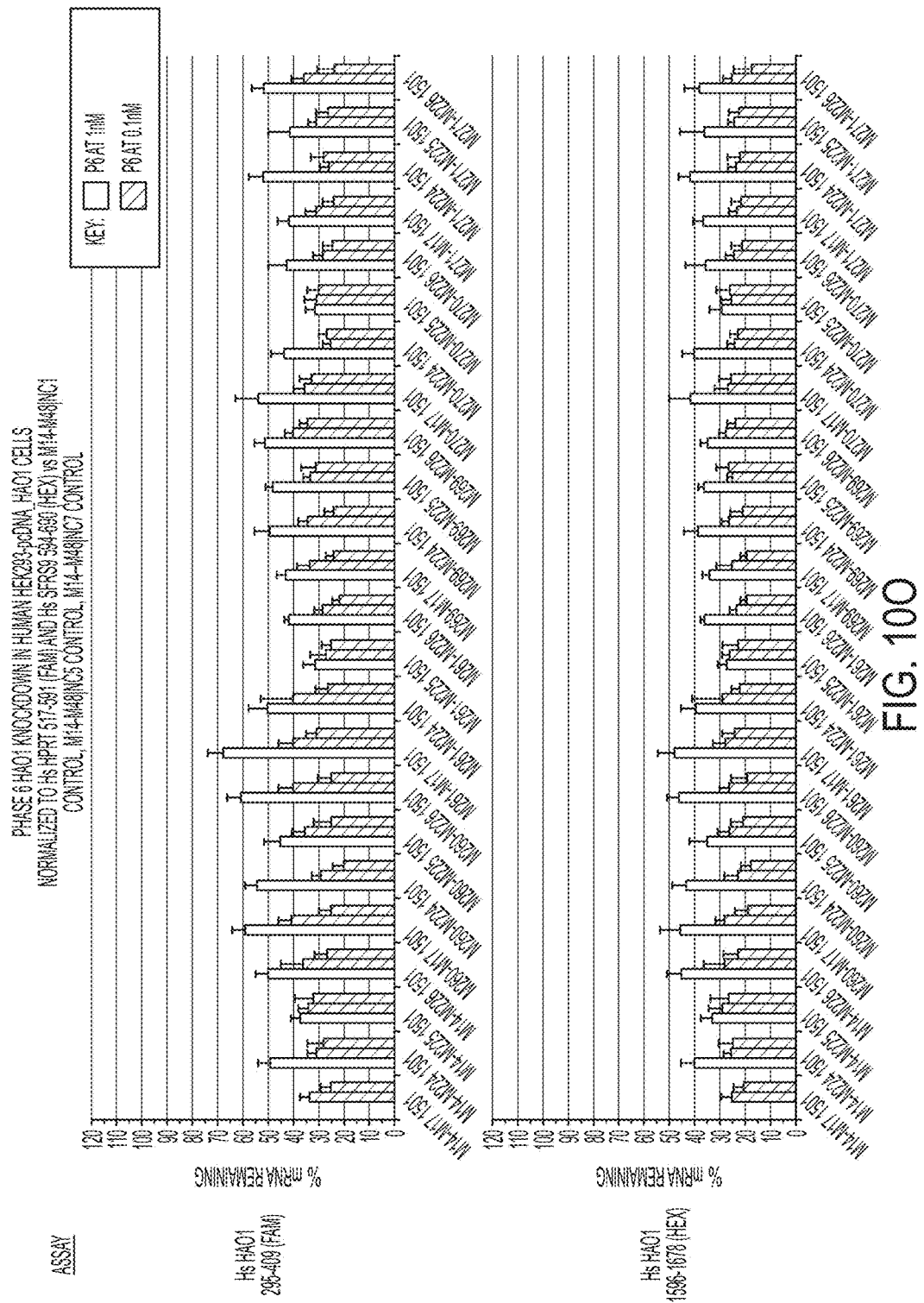

Eight duplex sequences (HAO1-m1167, m1276, m1312, m1313, m1372, m1375, m1376 and m1390, which correspond to human duplexes HAO1-1171, 1279, 1315, 1316, 1375, 1378, 1379 and 1393, respectively) were also examined for knockdown efficacy in mouse Hepa1-6 cells across the same range of four duplex modification patterns (with passenger strand modification patterns varied and guide strand modification pattern fixed, in contrast to the duplexes of Example 5 above). As shown in FIGS. 8D and 8E, a majority of these duplexes showed robust HAO1 knockdown efficacy in mouse cells across a range of duplex modification patterns, at concentrations as low as 0.03 nM.

Example 7

Further Assessment of Modified Forms of Glycolate Oxidase-Targeting DsiRNAs In Vitro Further modification patterns of both passenger (sense) and guide (antisense) strands of the above 24 HAO1-targeting duplex sequences (HAO1-65, 75, 77, 80, 83, 96, 1171, 1198, 1279, 1315, 1316, 1375, 1378, 1379, 1393, 1480, 1490, 1491, 1499, 1501, 1504, 1549, 1552 and 1696) were prepared to possess 2'-O-methyl modification patterns as shown in FIGS. 9A to 9D. These heavily modified DsiRNAs were assayed for HAO1 inhibition at 1.0 nM and 0.1 nM (in duplicate) concentrations in the environment of either HeLa cells (using the luciferase reporter system, Psi-Check-HsHAO1 plasmid; FIGS. 9E to 9H) or human HEK293 cells stably transfected with HAO1 (HEK293-pcDNA_HAO1 cells; FIGS. 9I to 9L). As demonstrated in FIGS. 9D to 9L, many of the additional tested duplexes were identified to possess robust HAO1 knockdown efficacy at even 0.1 nM concentrations across the full range of extensively modified forms tested. Indeed, for all target sequences, one or more duplexes possessing extensive 2'-O-methyl modifications upon both strands was identified as a robust inhibitor of HAO1 expression. Additionally, these results confirmed the concordance between the luciferase system employed in many of the above examples (Psi-Check-HsHAO1 plasmid) and the HEK293-pcDNA_HAO1 cell stable transfectant system.

Example 8

Additional Extensively-Modified Forms of Glycolate Oxidase-Targeting DsiRNAs were Active In Vitro Four of the above 24 HAO1-targeting duplex sequences, HAO1-1171, HAO1-1315, HAO1-1378 and HAO1-1501, were prepared to possess extensive variation in 2'-O-methyl modification patterns, as shown in FIGS. 10A to 10K. These heavily modified DsiRNAs were assayed for HAO1 inhibition at 1.0 nM and 0.1 nM (in duplicate) concentrations in the environment of stably-transfected HEK293 cells (HEK293-pcDNA_HAO1 cells; FIGS. 10L to 10O). As demonstrated in FIGS. 10L to 10O, the modified forms of HAO1-1171, HAO1-1315, and HAO1-1501 duplexes were identified to possess robust HAO1 knockdown efficacy at even 0.1 nM concentrations across the full range of extensively modified forms tested. Meanwhile, for the HAO1-1378 duplex sequence, certain of the highly modified forms showed reduced inhibitory activities at 0.1 nM when compared with other heavily modified forms (though a number of robustly active heavily 2'-O-methyl modified forms of HAO1-1378 duplexes were identified).

Figure 11A:
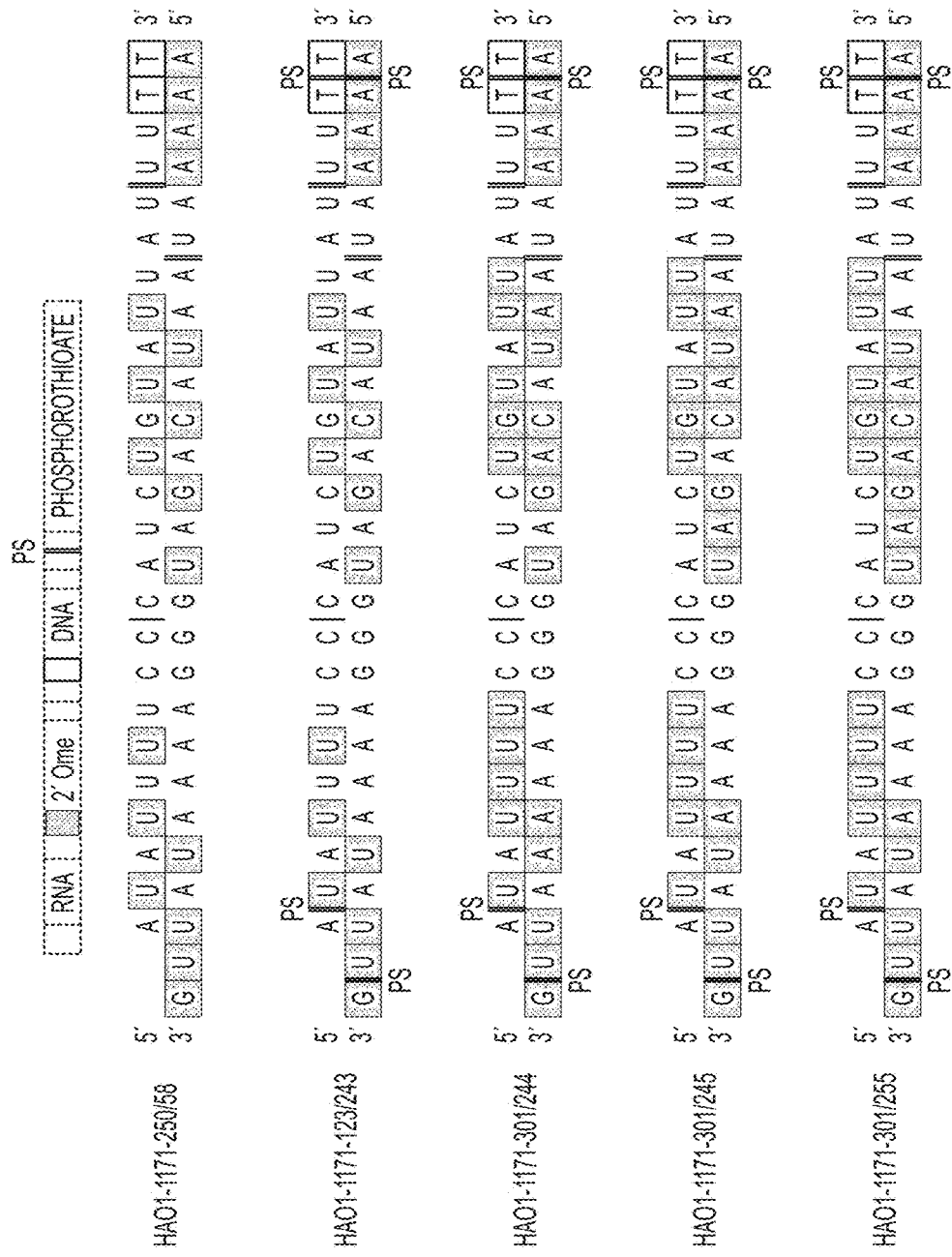
Figure 11B:
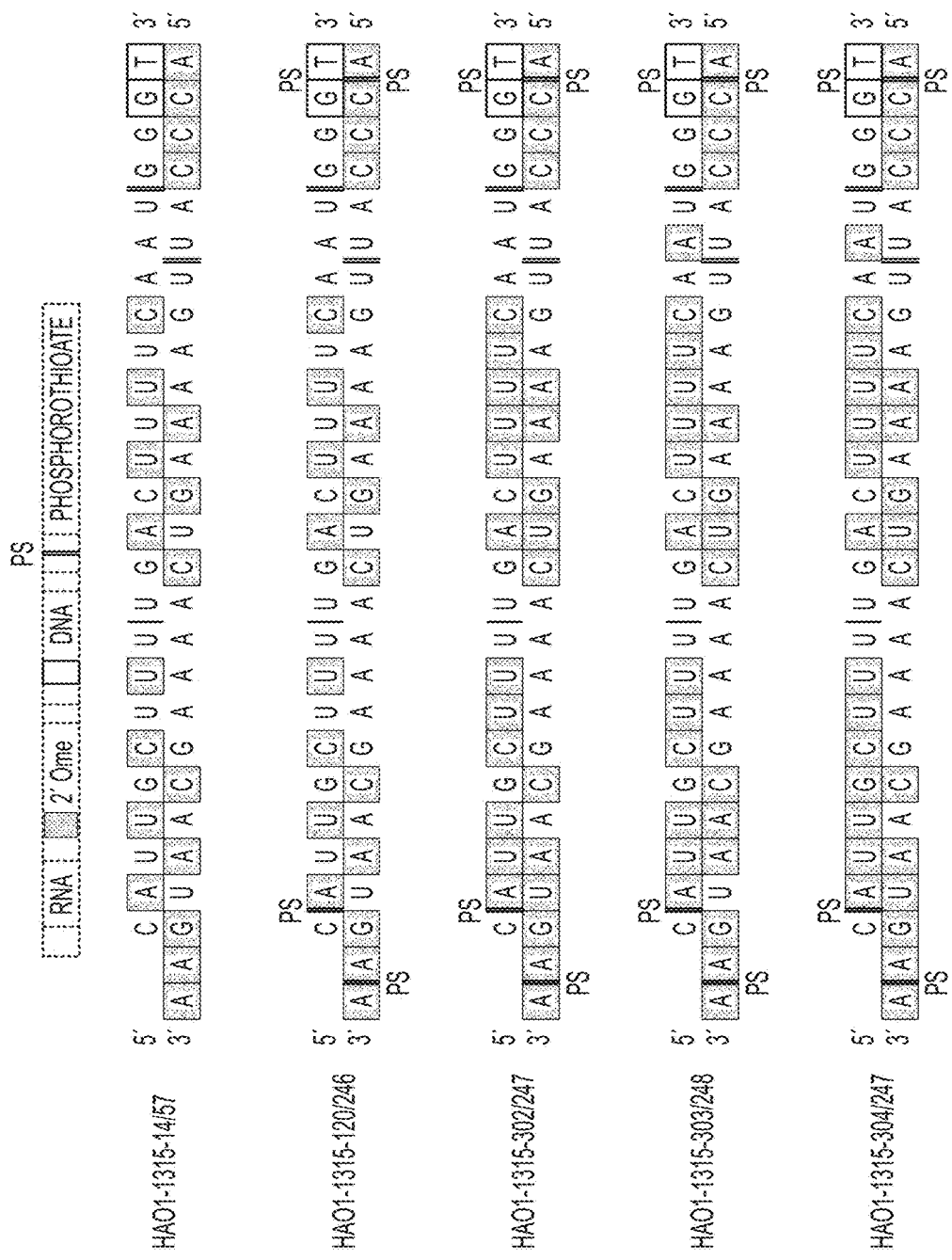
Figure 11C:
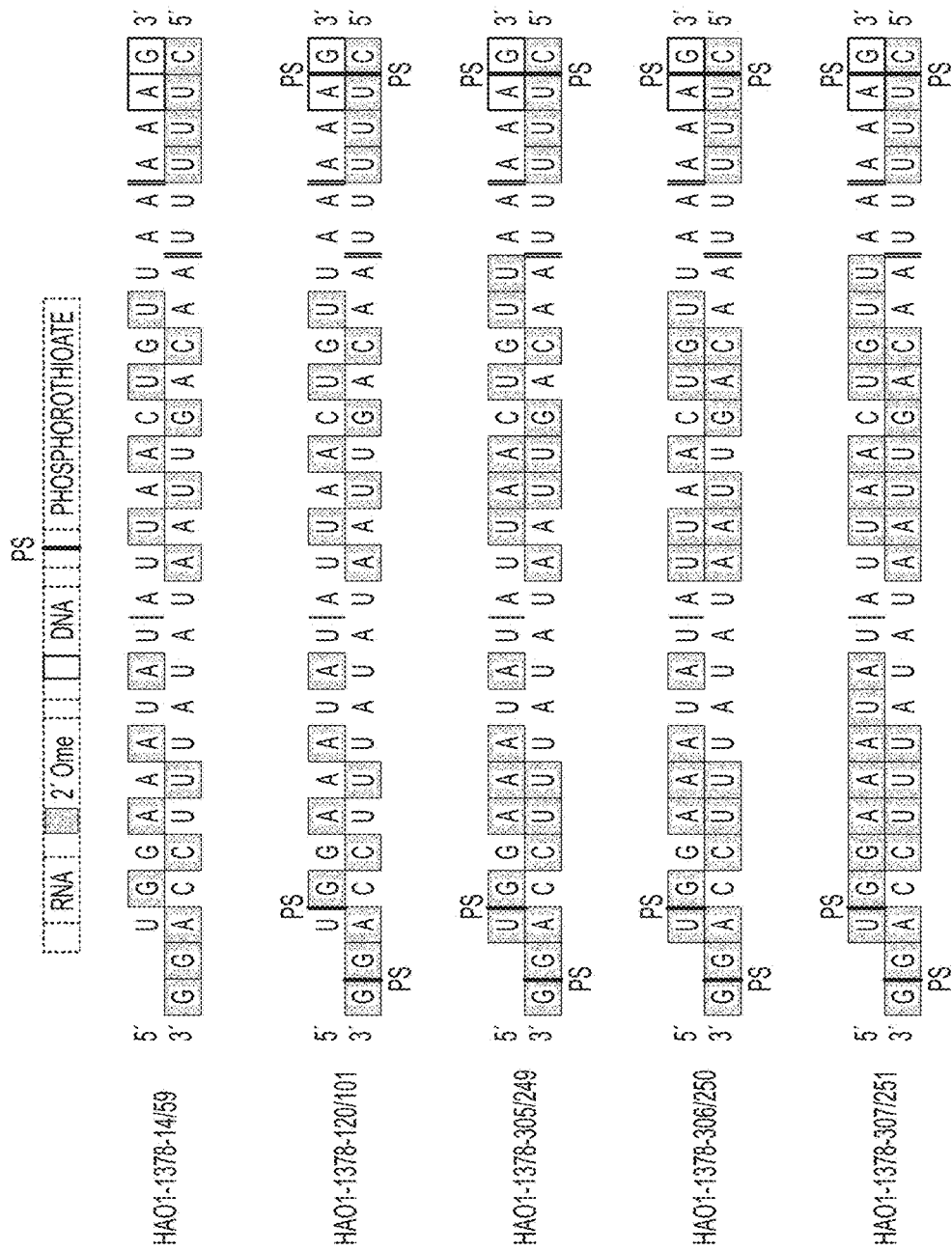
Figure 11D:
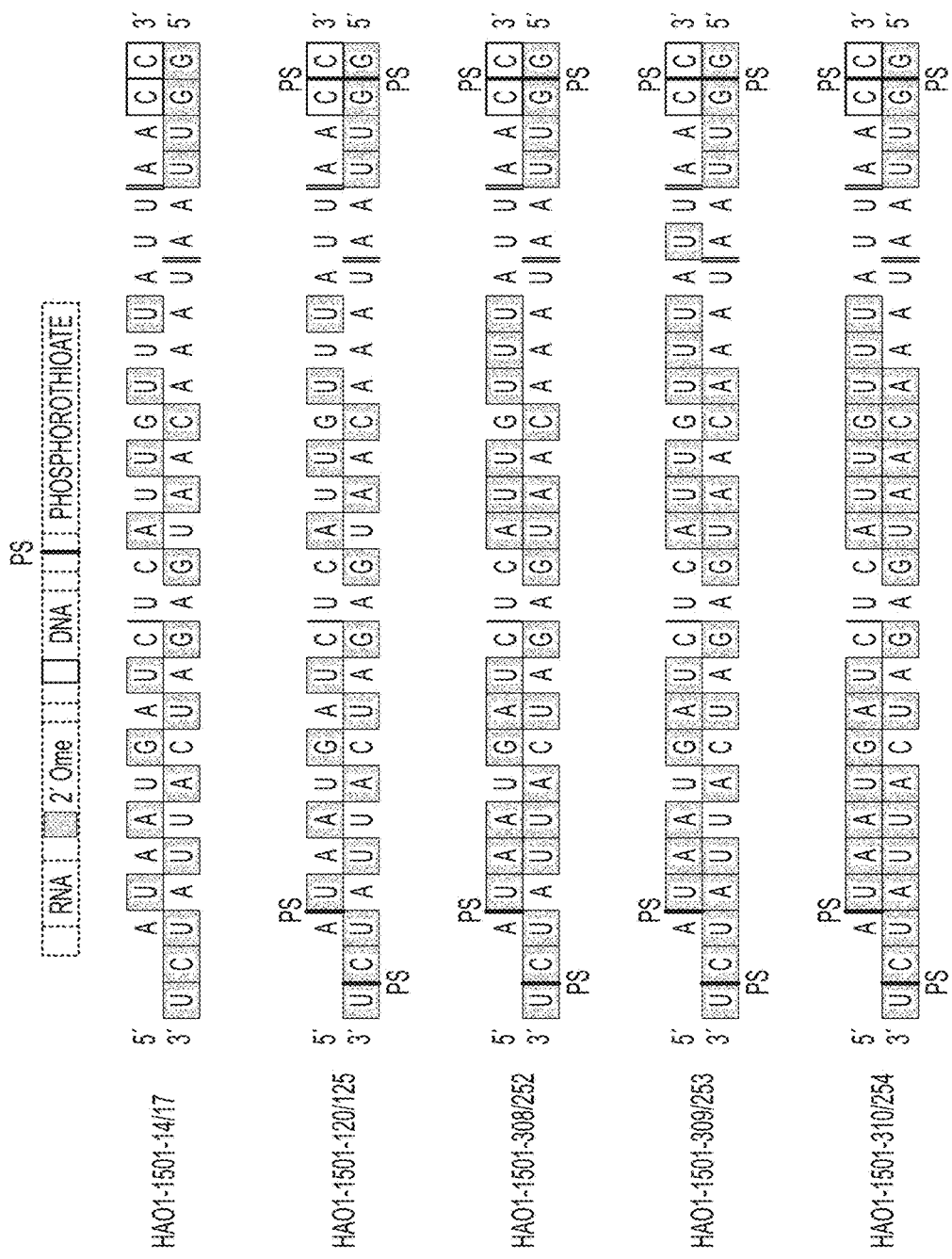
Figure 11F:
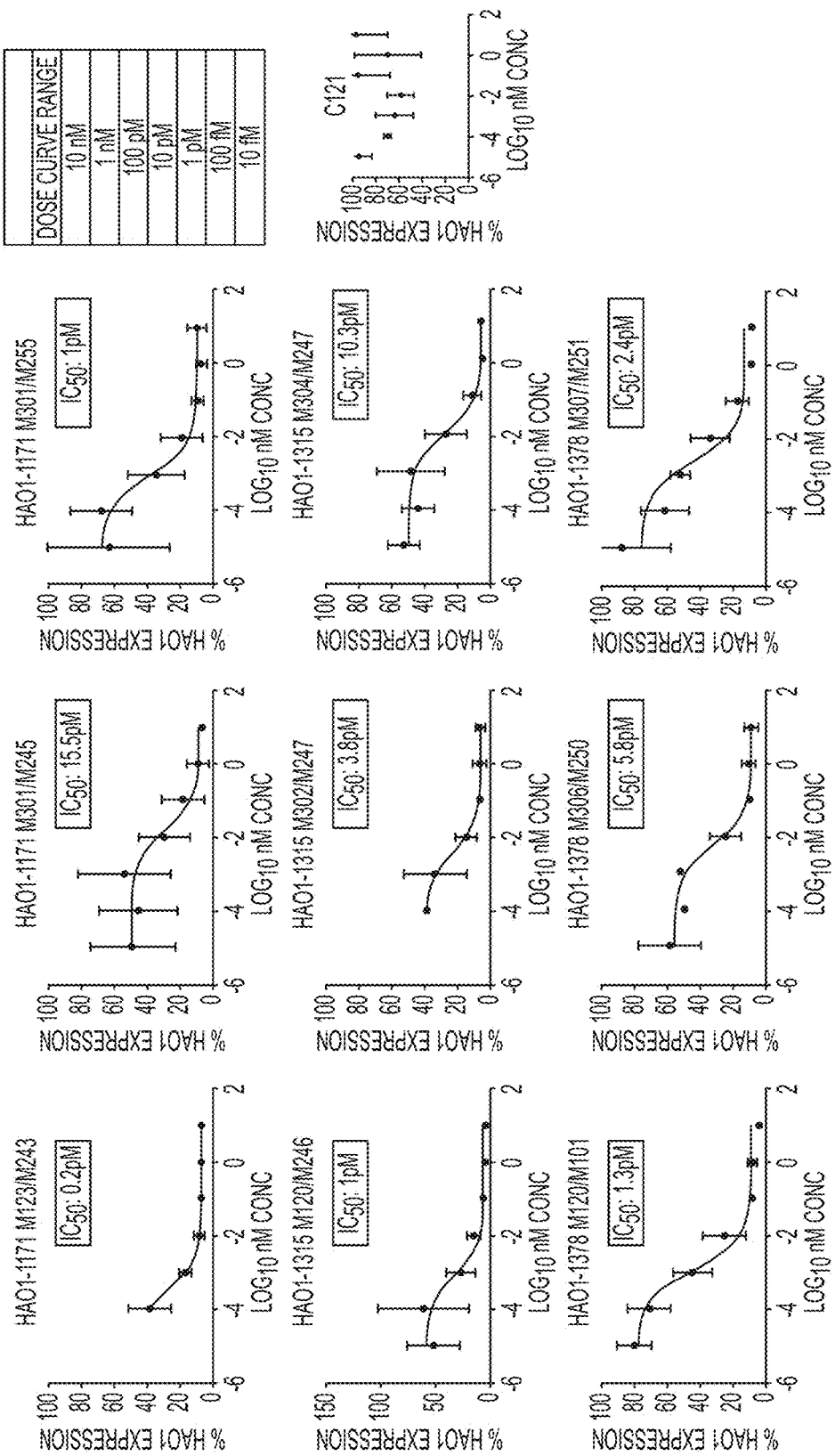

Modification of HAO1-1171, HAO1-1315, HAO1-1378 and HAO1-1501 duplexes was expanded to include phosphorothioate linkages at the final internucleotide linkages of both the 5' and 3' ends of both guide and passenger strands of variously 2'-O-methyl modified duplexes, as shown in FIGS. 11A to 11D. Five forms of each of the four duplexes were synthesized on a small scale and were tested in a stable cell line (HAO1-6-9), at doses of 100 pM, 10 pM and 1 pM, with controls. As shown in FIG. 11E, significant knockdown was observed for all duplexes tested at 100 pM and even at 10 pM for the majority of duplexes. Of the 20 forms examined, nine were selected for IC50 dose curve assessment, at concentrations ranging from 10 nM to 10 fM, decreasing in ten-fold increments, with results shown in FIG. 11F.

Figure 12A:
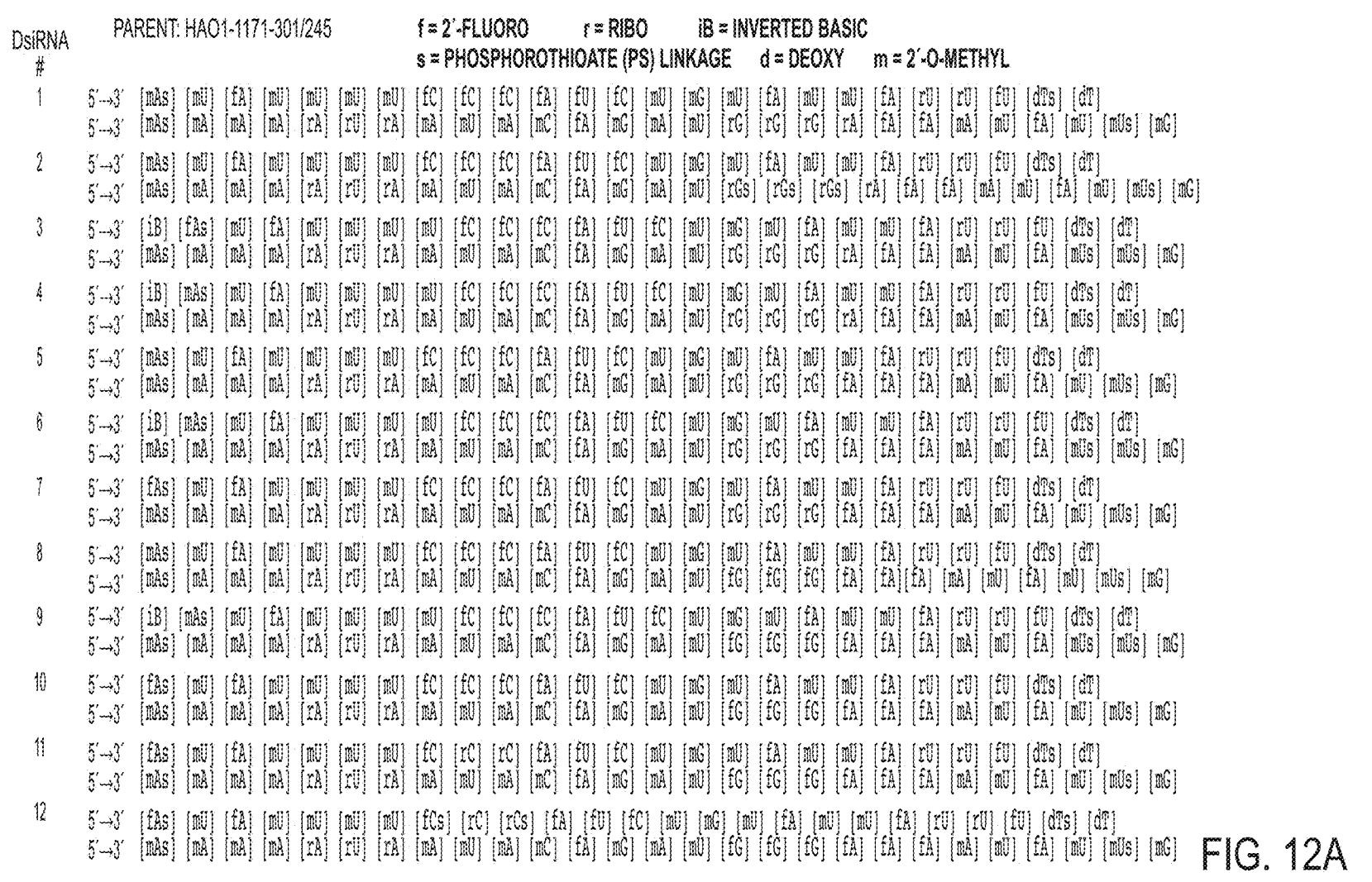
Figure 12B:
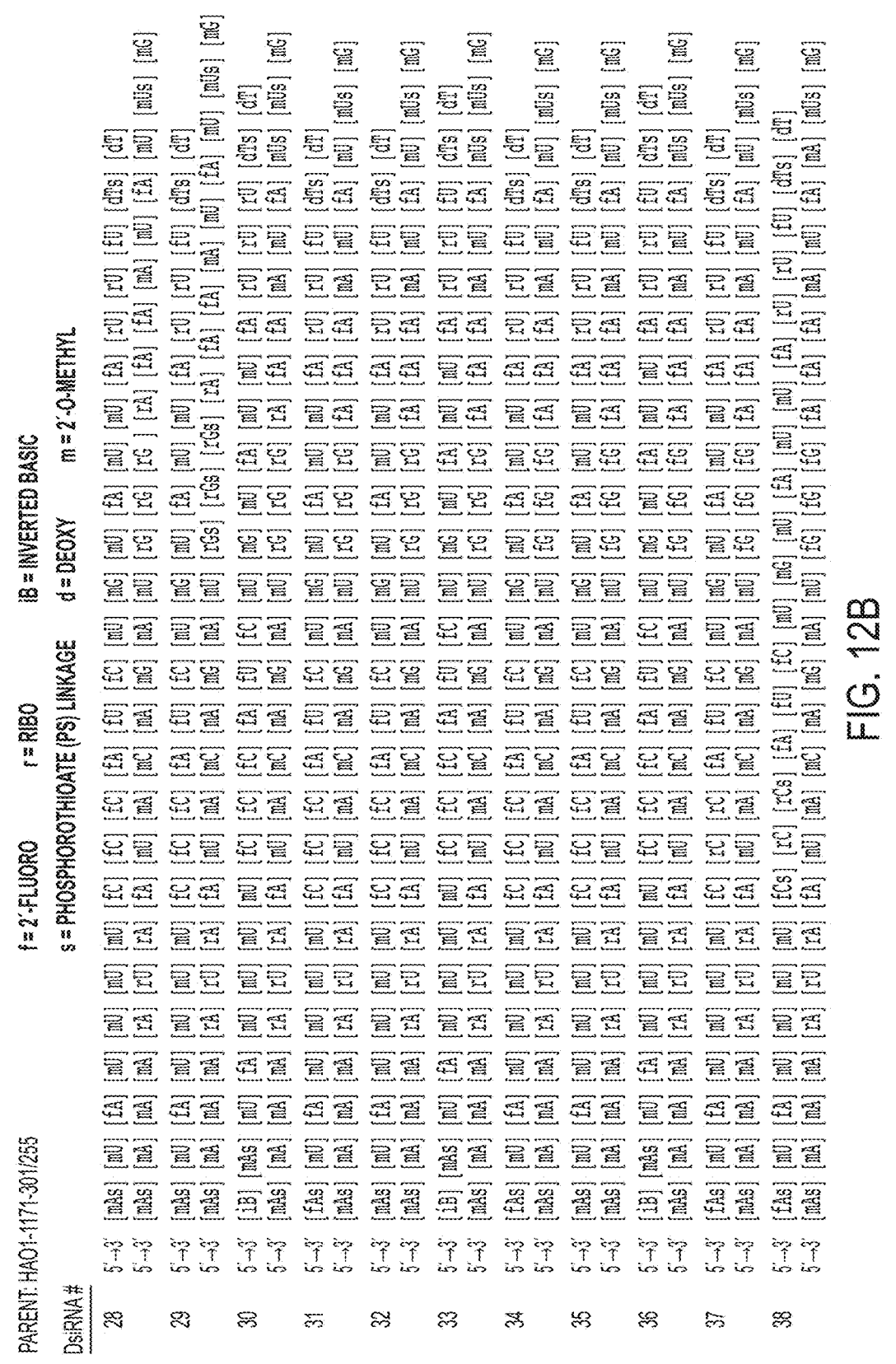
Figure 12C:
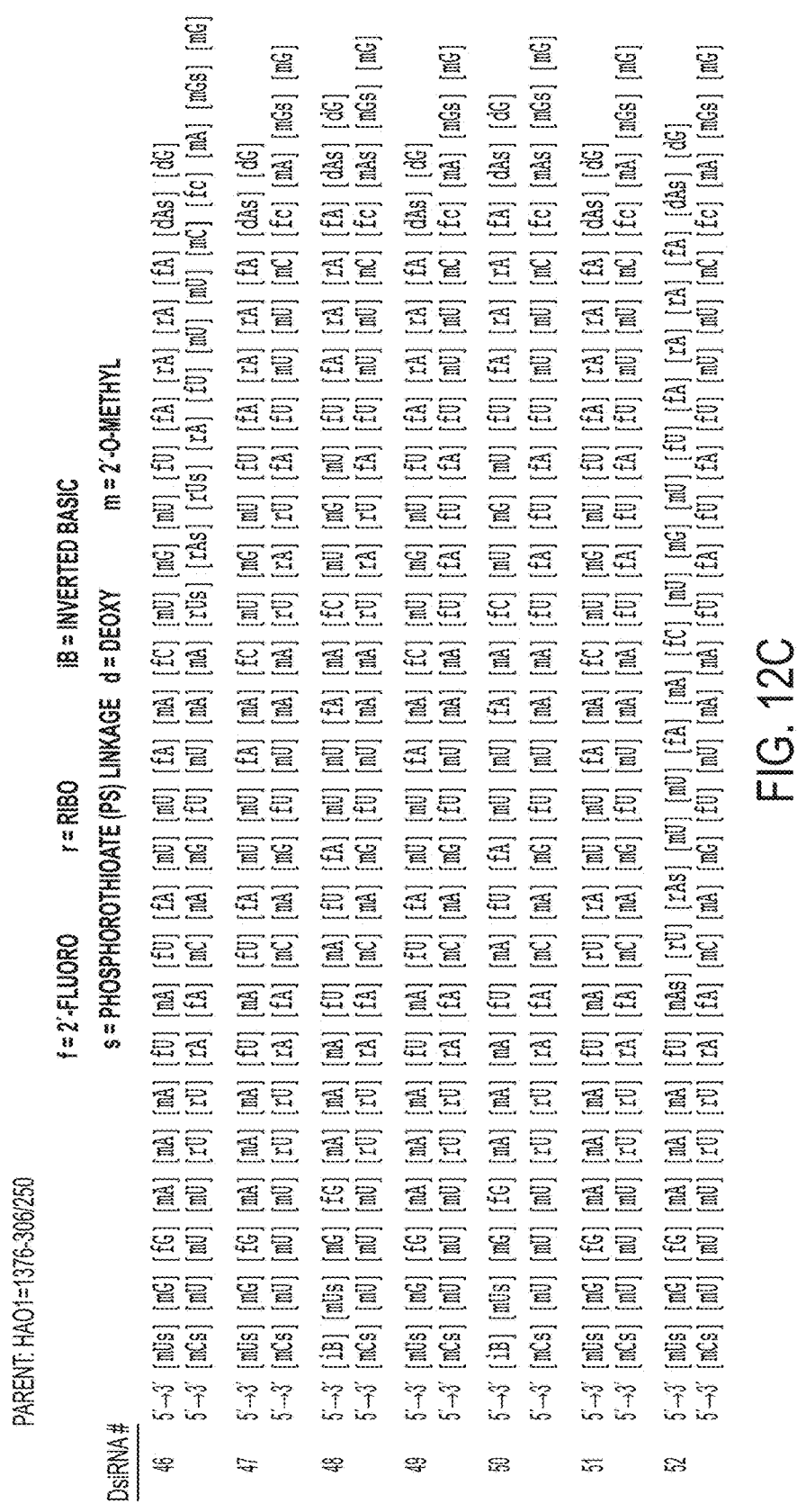
Figure 12D:
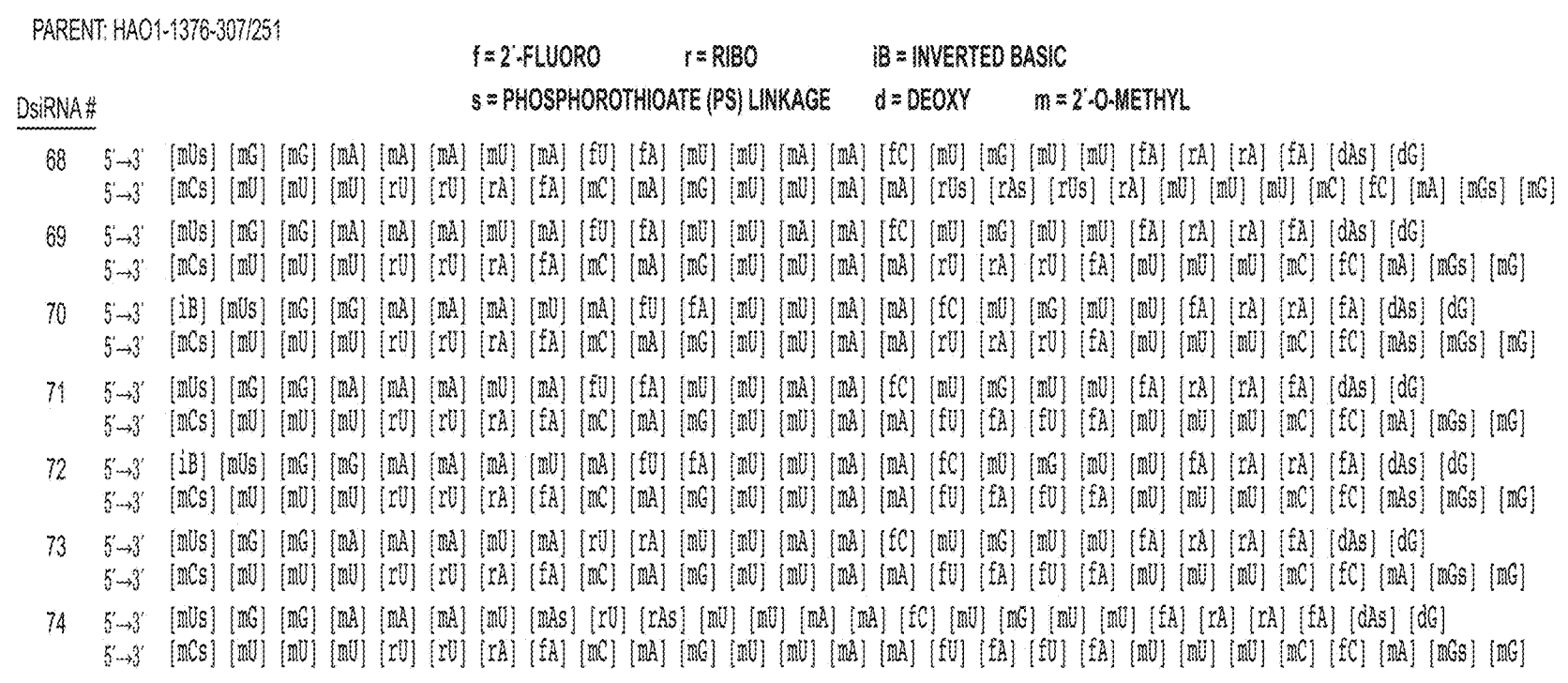
Figure 12E:
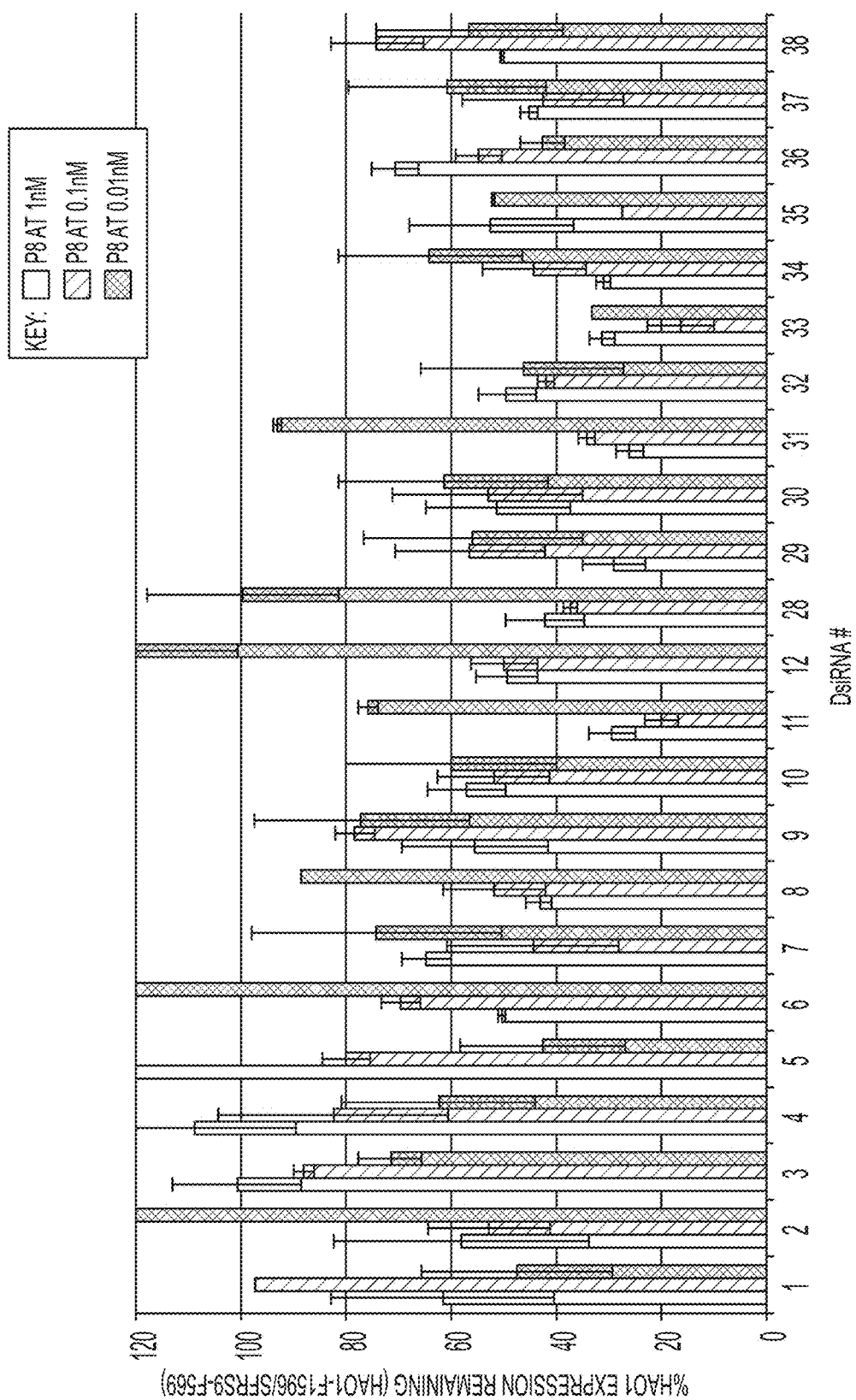
Figure 12F:
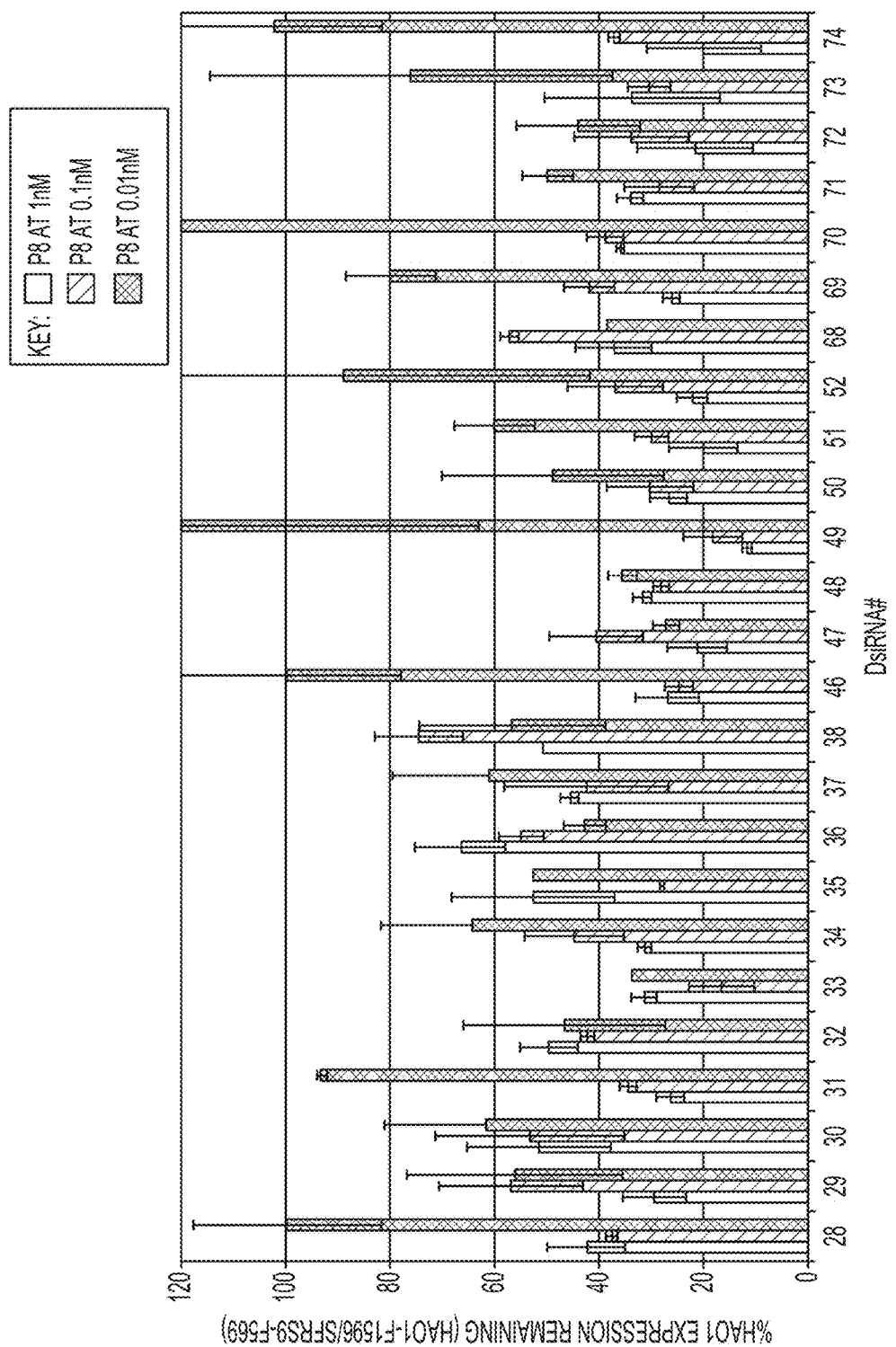

Modified forms of HAO1-1171 and HAO-1376 were further modified with 2'-fluoro and inverted basic and additional and/or alternatively positioned phosphorothioate (PS) modifications, layered upon a "parent" modification pattern, as shown in FIGS. 12A to 12D. As shown in FIGS. 12E and 12F, highly active further modified ("derivative modification pattern") forms of each "parent" modification pattern presenting duplex were identified, with significant efficacies observed at even 10 pM concentrations.

Example 9

Glycolate Oxidase-Targeting DsiRNAs were Highly Active In Vivo

Figure 13A:
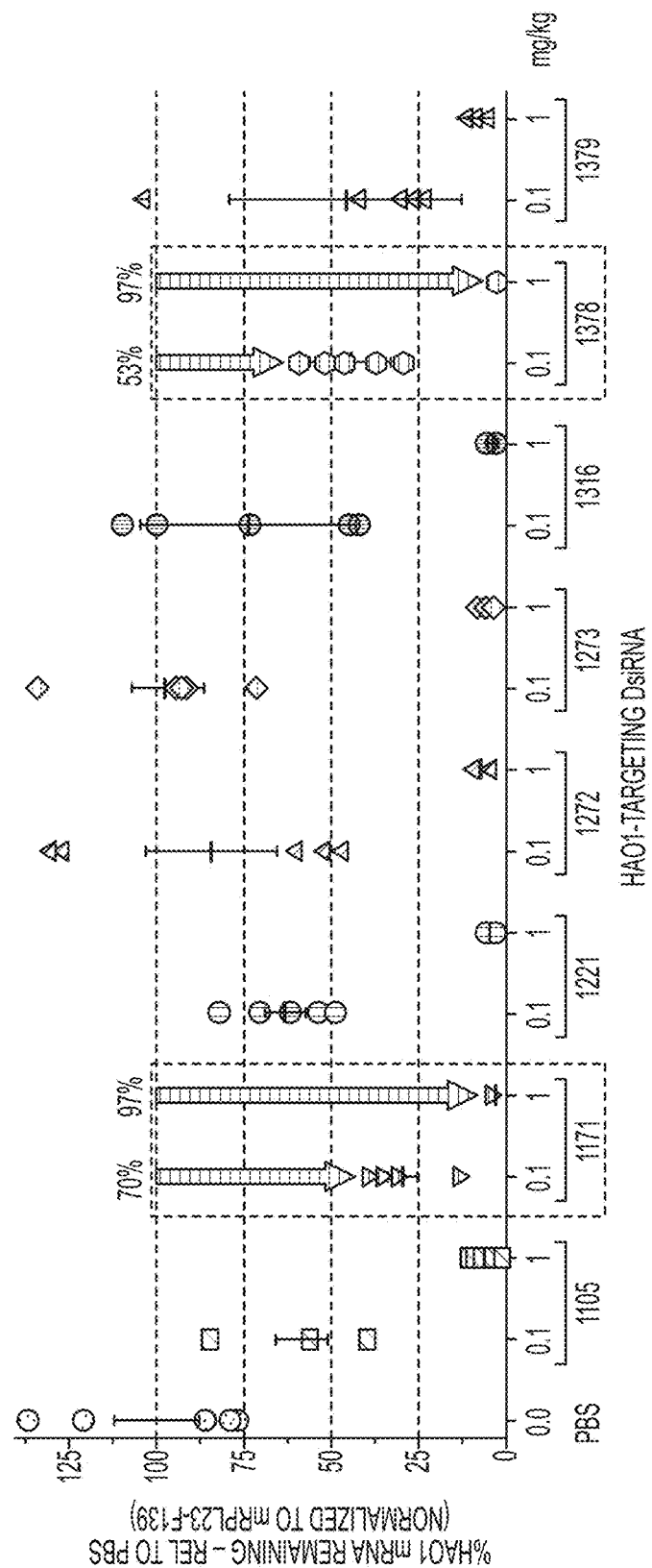

Eight HAO1-targeting duplex sequences, HAO1-1105, HAO1-1171, HAO1-1221, HAO1-1272, HAO1-1273, HAO1-1316, HAO1-1378 and HAO1-1379, possessing an M107/M48 2'-O-methyl modification pattern, were formulated for in vivo delivery in a lipid nanoparticle (LNP) formulation (EnCore 2345). A single intravenous dose at 0.1 or 1.0 mg/kg was administered to mice (n=5 per group), and livers of treated animals were harvested at 24 hours post-administration. The extent of HAO1 mRNA knockdown in treated mouse liver was assessed by qPCR. As shown in FIG. 13A, all eight HAO1-targeting DsiRNAs tested for in vivo knockdown efficacy were active at 1.0 mg/kg doses. Notably, HAO1-1171-M107/M48 and HAO1-1378-M107/M48 duplexes exhibited robust knockdown of HAO1 in livers of treated mice even at the 0.1 mg/kg dose (showing respective levels of knockdown of approximately 70% and approximately 53%).

Figure 13B:
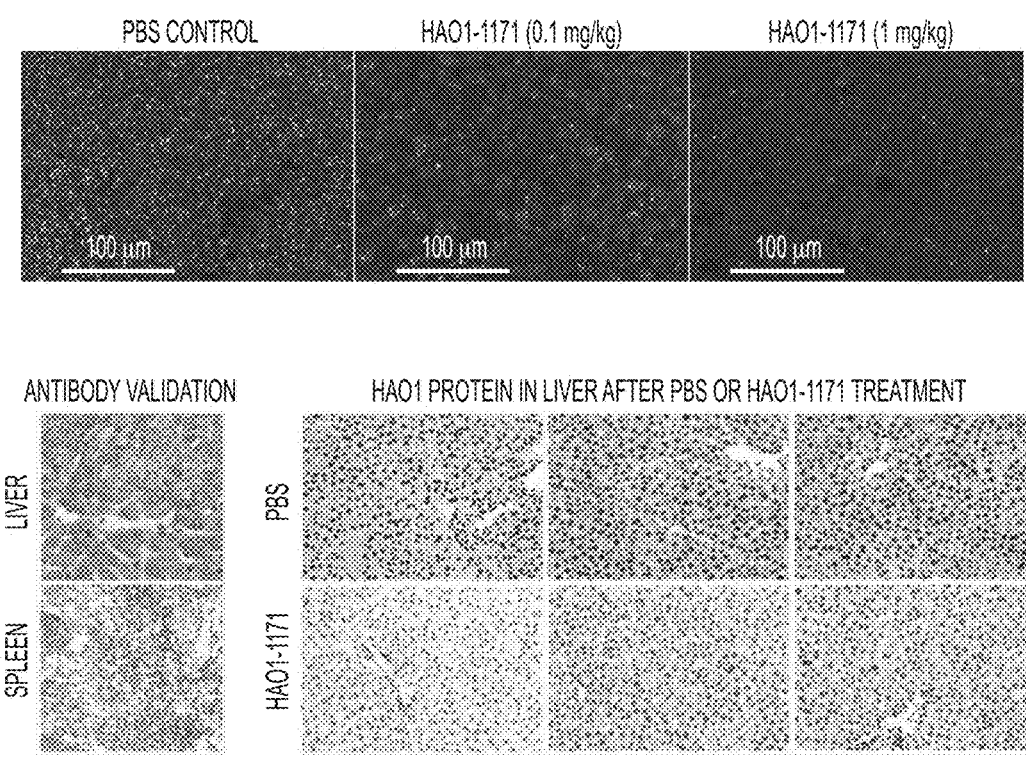

To confirm the above qPCR results, and also to verify glycolate oxidase protein knockdown, ViewRNA assays and immunohistochemistry were performed upon liver samples of treated mice. As shown in FIG. 13B, HAO1-1171-treated mice showed significant HAO1 knockdown by both ViewRNA (top panels) and immunohistochemistry.

Figure 13C:
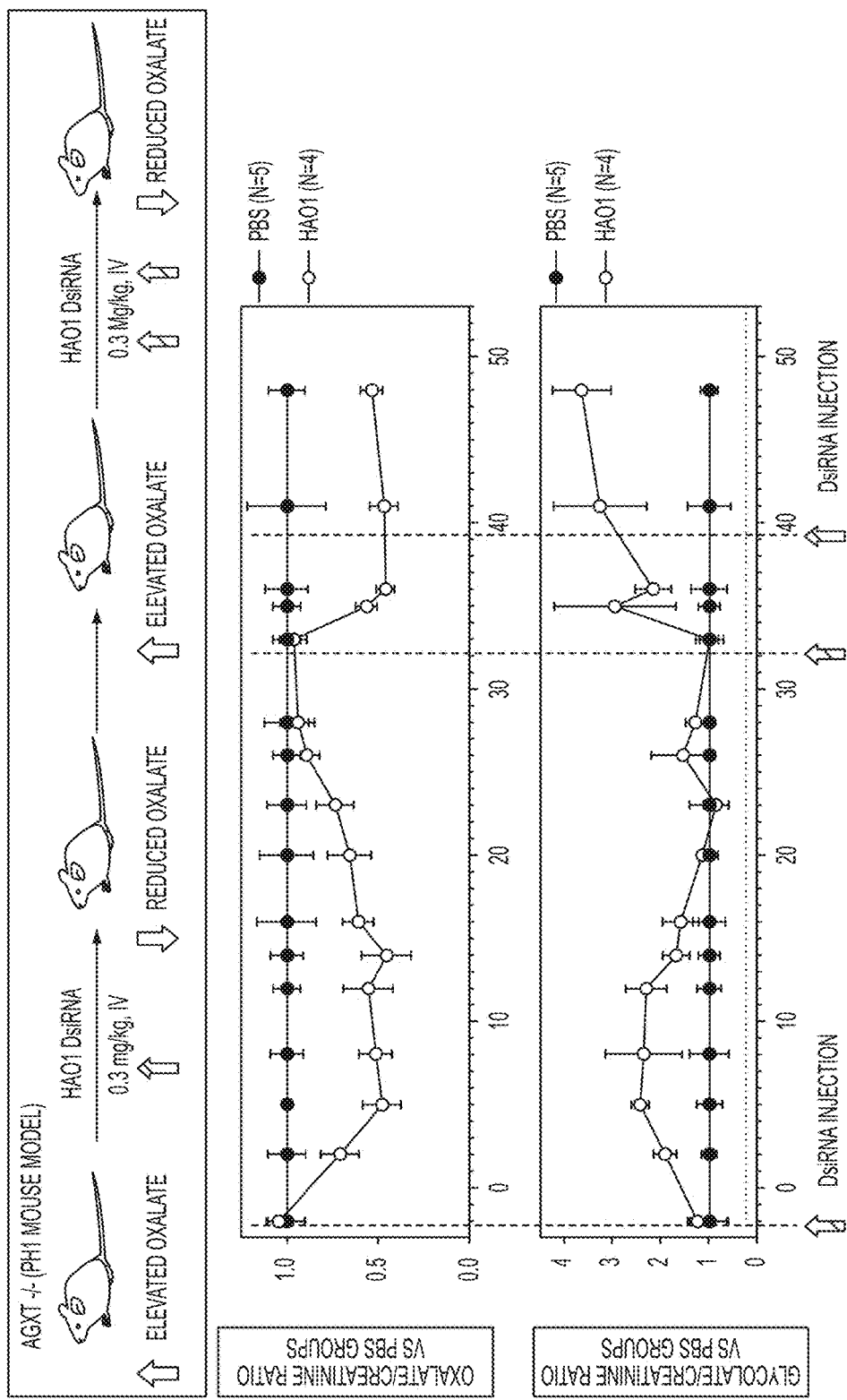

HAO1-targeting DsiRNAs were next examined for in vivo therapeutic efficacy in PH1 genetically engineered model mice. In AGXT$^{-/-}$ PH1 model mice, HAO1-targeting DsiRNA was initially intravenously administered to mice at 0.3 mg/kg. At days 32 and 39, successive additional intravenous injections of HAO1-targeting DsiRNA were administered at 0.3 mg/kg, and the effect of this dosing regimen was examined for effect upon both the oxalate/creatinine ratio and the glycolate/creatinine ratio. As shown in FIG. 13C, each administration of HAO1-targeting DsiRNA resulted in a marked decline in the oxalate/creatinine ratio of treated mice, while the glycolate/creatinine ratio of the same mice was elevated following each DsiRNA administration. Thus, formulated HAO1-targeting DsiRNA was effective at reducing the elevated oxalate levels that cause primary hyperoxaluria type 1.

Figure 13D:
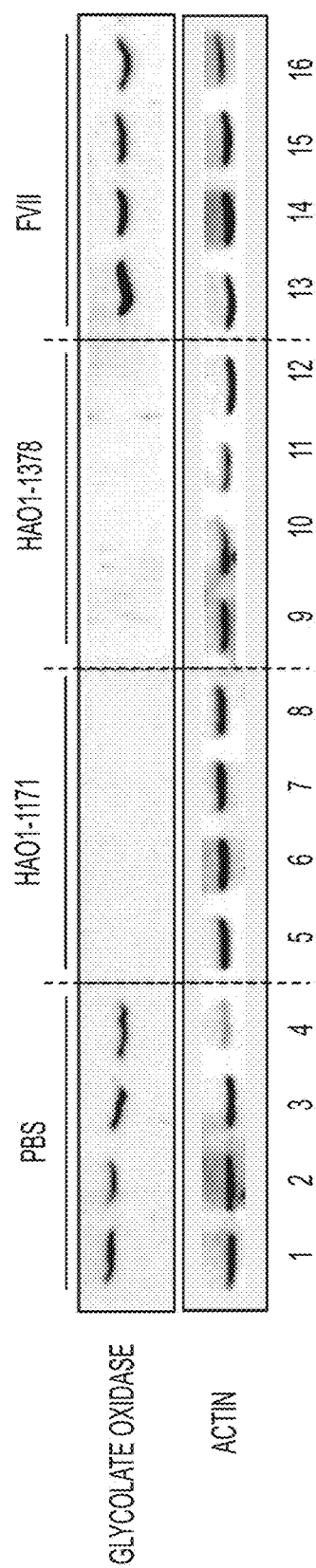

Having established the effect of HAO1-targeting DsiRNAs on the oxalate/creatinine ratio and the glycolate/creatinine ratio of treated mice, it was then examined if HAO1-targeting DsiRNAs could also reduce urine glycolate oxidase levels in treated PH1 model mice. As shown in FIG. 13D, when formulated DsiRNAs were injected on days 1, 4, 6, 10 and 14 for a total of 5 doses, into AGXT$^{-/-}$ PH1 model mice, significant reductions of glycolate oxidase protein levels in liver harvested at day 16 were observed.

Figure 13E:
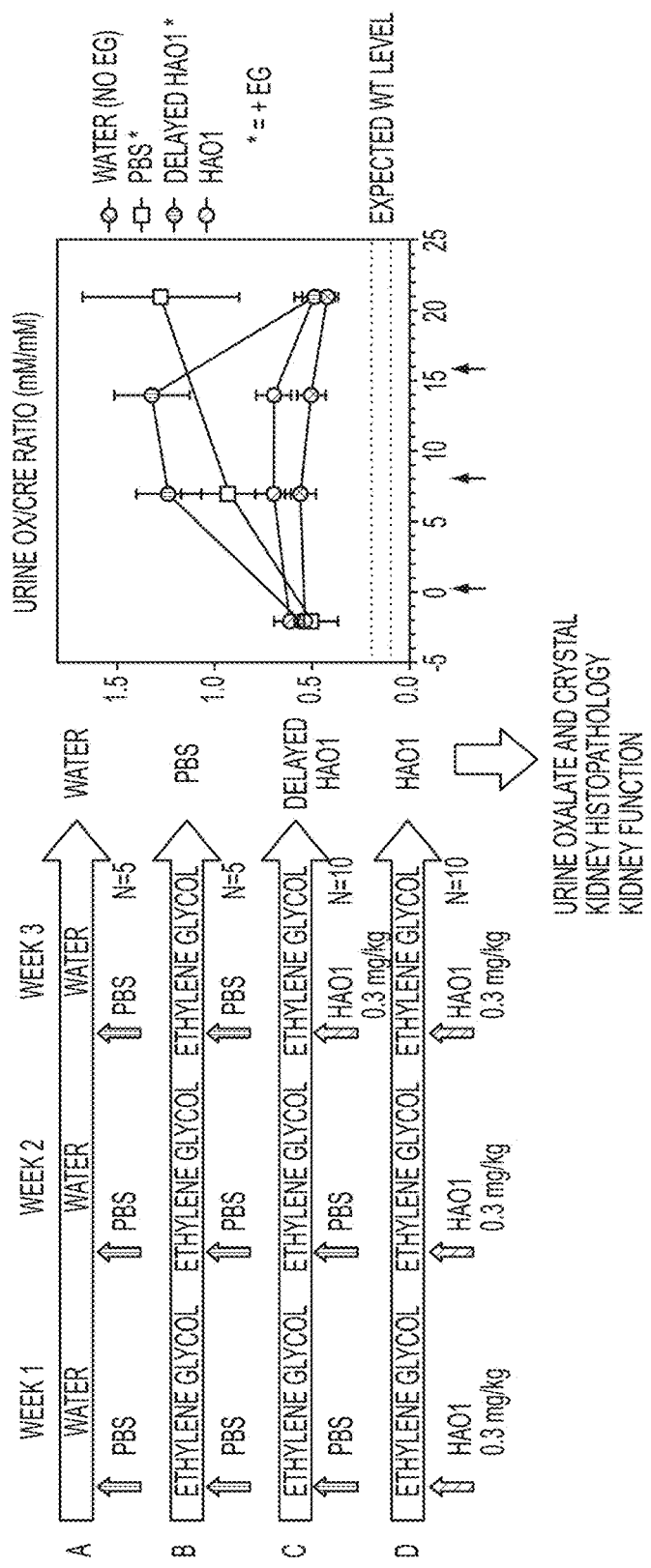

Consistent with the above-observed effects of HAO1-targeting DsiRNA administration, treatment of AGXT$^{-/-}$ PH1 model mice with HAO1-targeting DsiRNA was observed to prevent kidney damage in such mice when treated with ethylene glycol. As shown in FIG. 13E, mice administered HAO1-targeting DsiRNA at three timepoints during ethylene glycol administration were effectively protected from elevated oxalate/creatinine ratios, which were observed in control mice administered only PBS throughout ethylene glycol administration. Even a single dose of a HAO1-targeting DsiRNA at the final administration timepoint succeeded in dramatically lowering the oxalate/creatinine ratio to at or near wild type levels. Thus, kidney damage could be effectively prevented or aggressively treated with an HAO1-targeting DsiRNA of the invention.

Figure 13F:
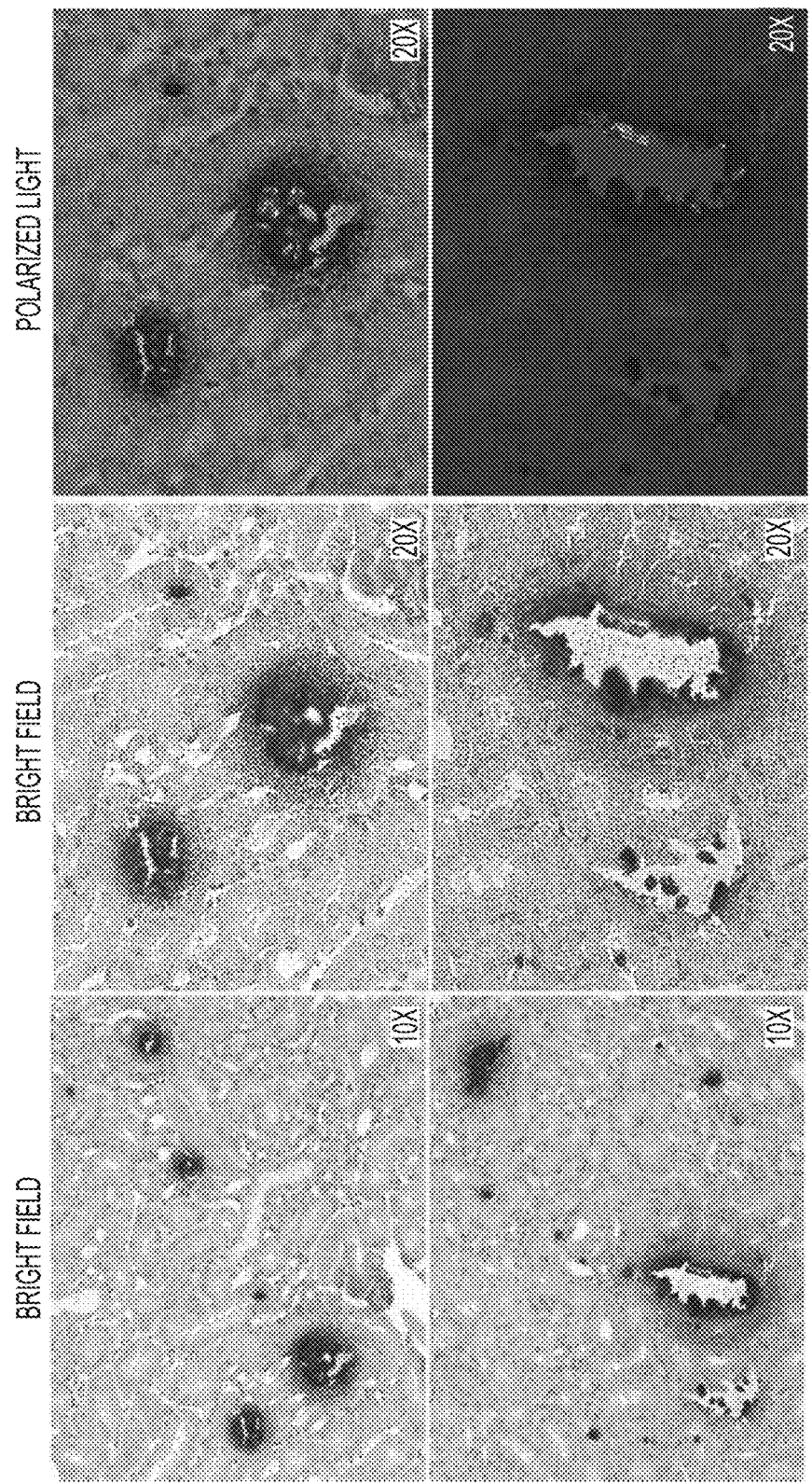
Figure 13H:
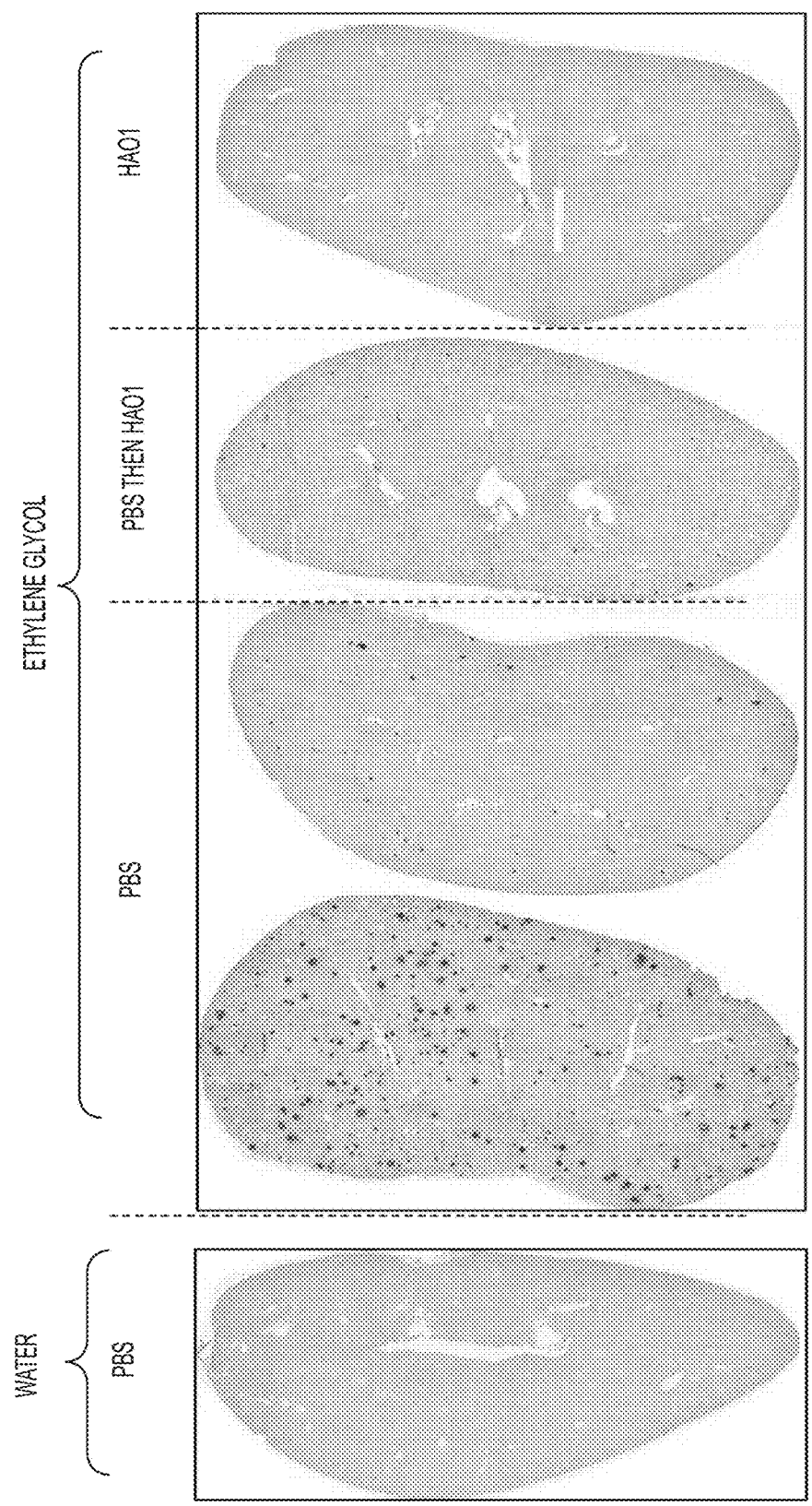

Histology confirmed the protective effect of HAO1-targeting DsiRNAs in the AGXT$^{-/-}$ PH1 mouse model. FIG. 13F shows the kidney damage that was elicted by feeding AGXT$^{-/-}$ PH1 model mice with a 0.7% ethylene glycol diet. As shown in FIGS. 13G and 13H, HAO1-targeting DsiRNA treatment effectively maintained the kidneys of a treated animal throughout ethylene glycol administration, while injection of HAO1 as only the final dose of the regimen also caused a dramatic reduction in kidney damage (as compared to mice that received no HAO1 DsiRNA treatment throughout ethylene glycol administration). Such effects were observed both in magnified sections (FIG. 13G) and at the level of the whole kidney (FIG. 13H).

Figure 13I:
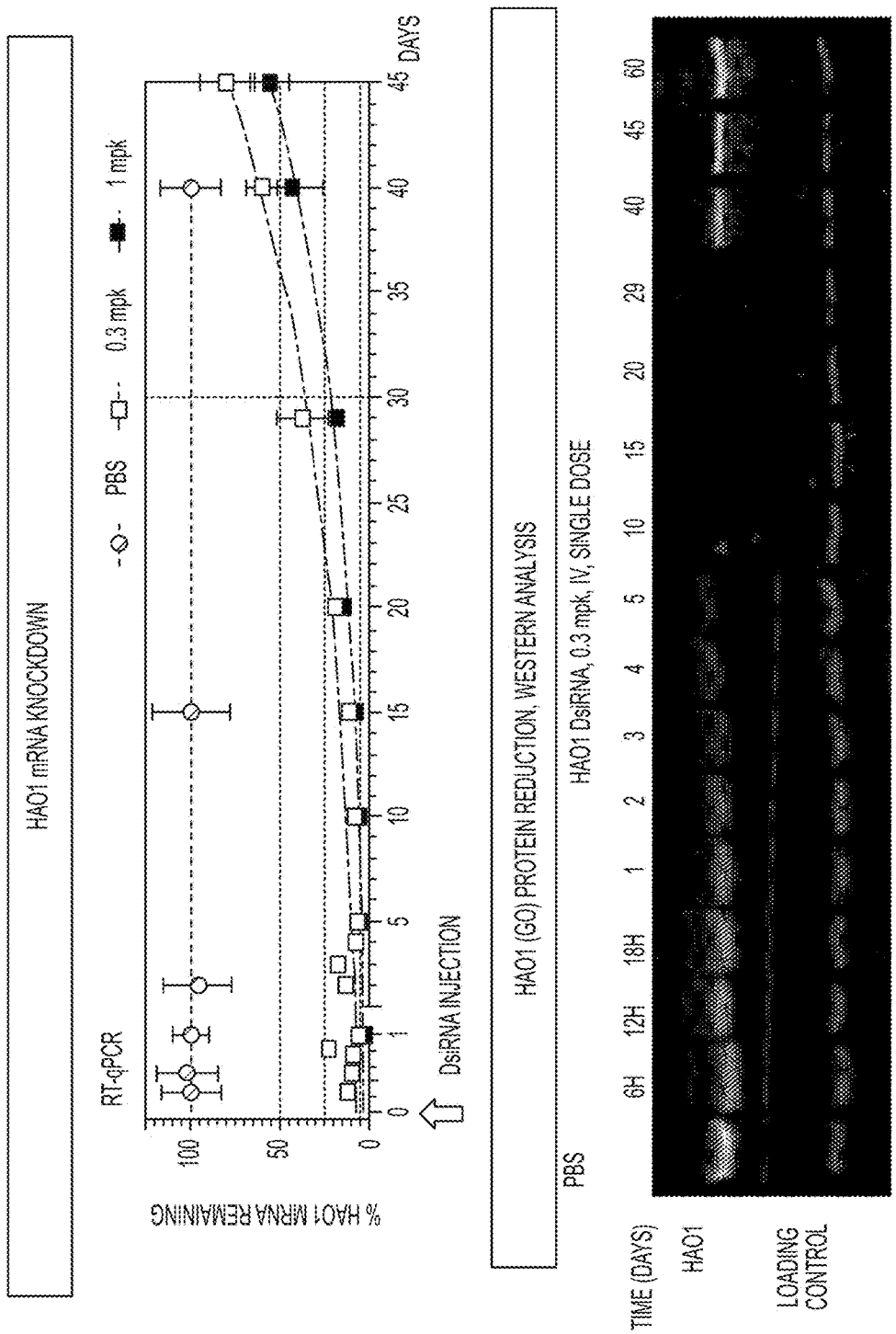
Figure 13J:
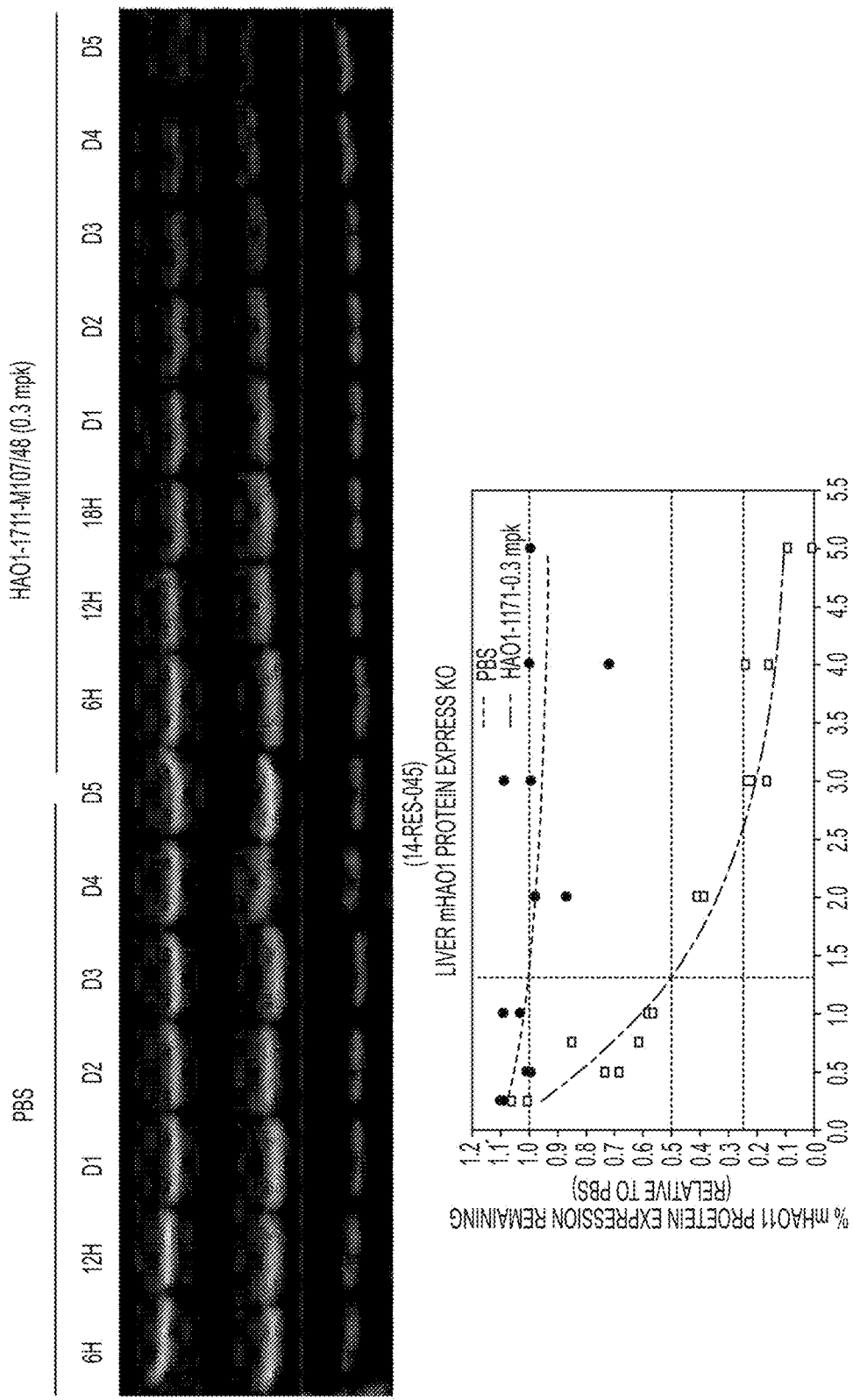

The kinetics and duration of in vivo HAO1 mRNA and protein (glycolate oxidase) inhibition were also examined. As shown in FIG. 13I, when LNP-formulated HAO-targeting DsiRNA was injected at day 0 into C57BU6 mice at either 0.3 mg/kg or 1.0 mg/kg dosage, a dramatic reduction in levels of HAO1 mRNA was immediately observed (FIG. 13I, top panel). Consistent with the glycolate oxidase protein having a short half-life (rapid turnover rate) in vivo, the dramatic inhibition of HAO1 mRNA observed following administration of an HAO1-targeting DsiRNA produced dramatic reductions in glycolate oxidase protein levels over the 1-to-5 day timeframe post-administration (FIG. 13I, lower panel, and FIG. 13J). Indeed, the half-life of the HAO1 protein in vivo was estimated to be less than 31 hours (based upon data from two sets of animals, assessed in FIG. 13J). The effect of HAO1-targeting DsiRNA on both HAO1 mRNA and glycolate oxidase protein levels in vivo was also highly durable—even at twenty-nine days after a single administration, mRNA levels were significantly reduced and no glycolate oxidase protein was detected by western analysis. Thus, HAO1 DsiRNA achieved a rapid and highly durable in vivo silencing effect on both HAO1 mRNA and protein production.

Figure 13K:
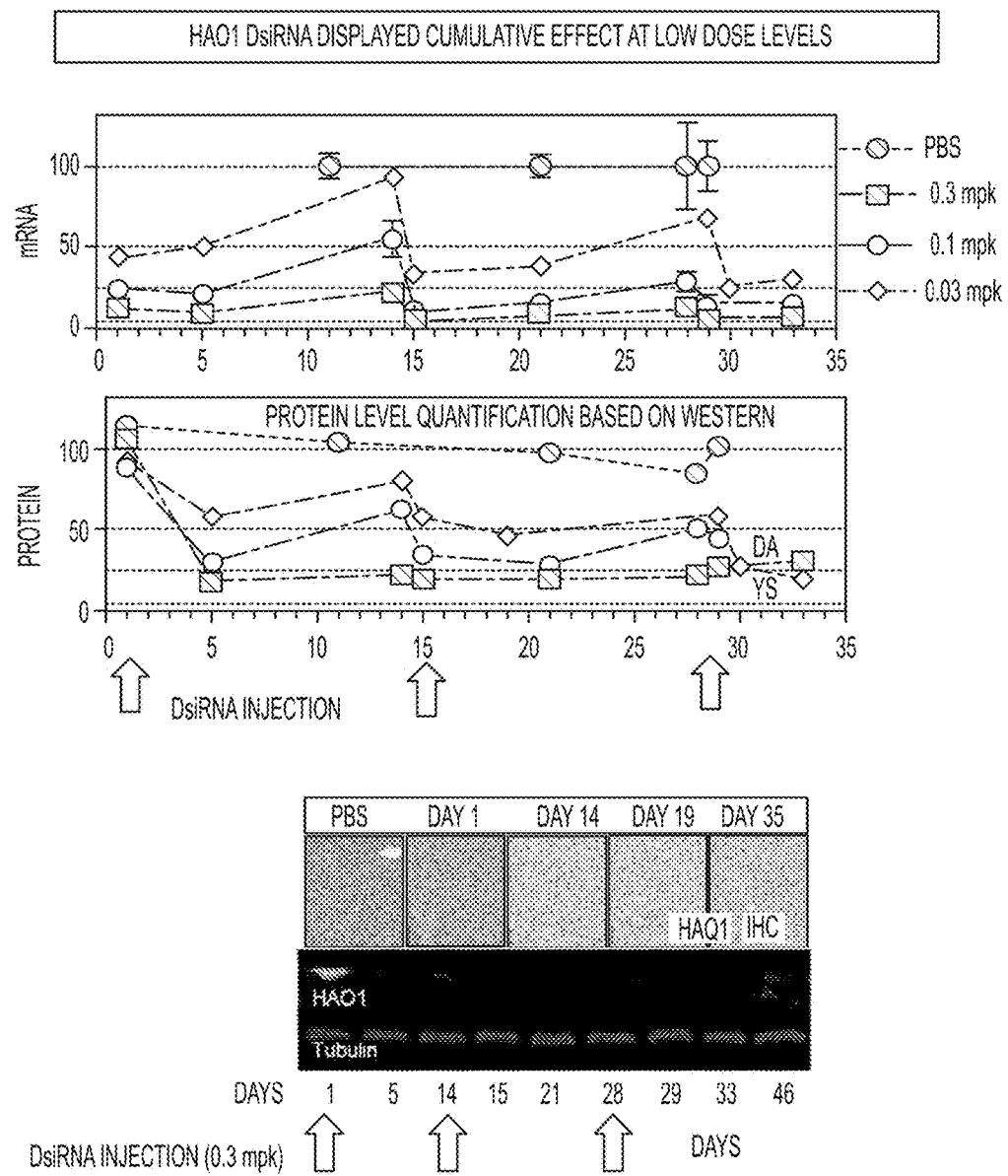

The silencing effect observed upon administration of a formulated HAO1-targeting DsiRNA was also observed to be cumulative at low dose levels. As shown in FIG. 13K, HAO1 mRNA inhibition was documented to be highly responsive to HAO1-targeting DsiRNA in vivo, While responsiveness of treated mice to HAO1-targeting DsiRNA at the HAO1 protein level was expectedly dampened as compared to that observed at the mRNA level, responsiveness at the protein level was still observed at low dose levels, further confirming the robust in vivo impact of administering LNP-formulated HAO1-targeting DsiRNAs to mice.

Figure 13L:
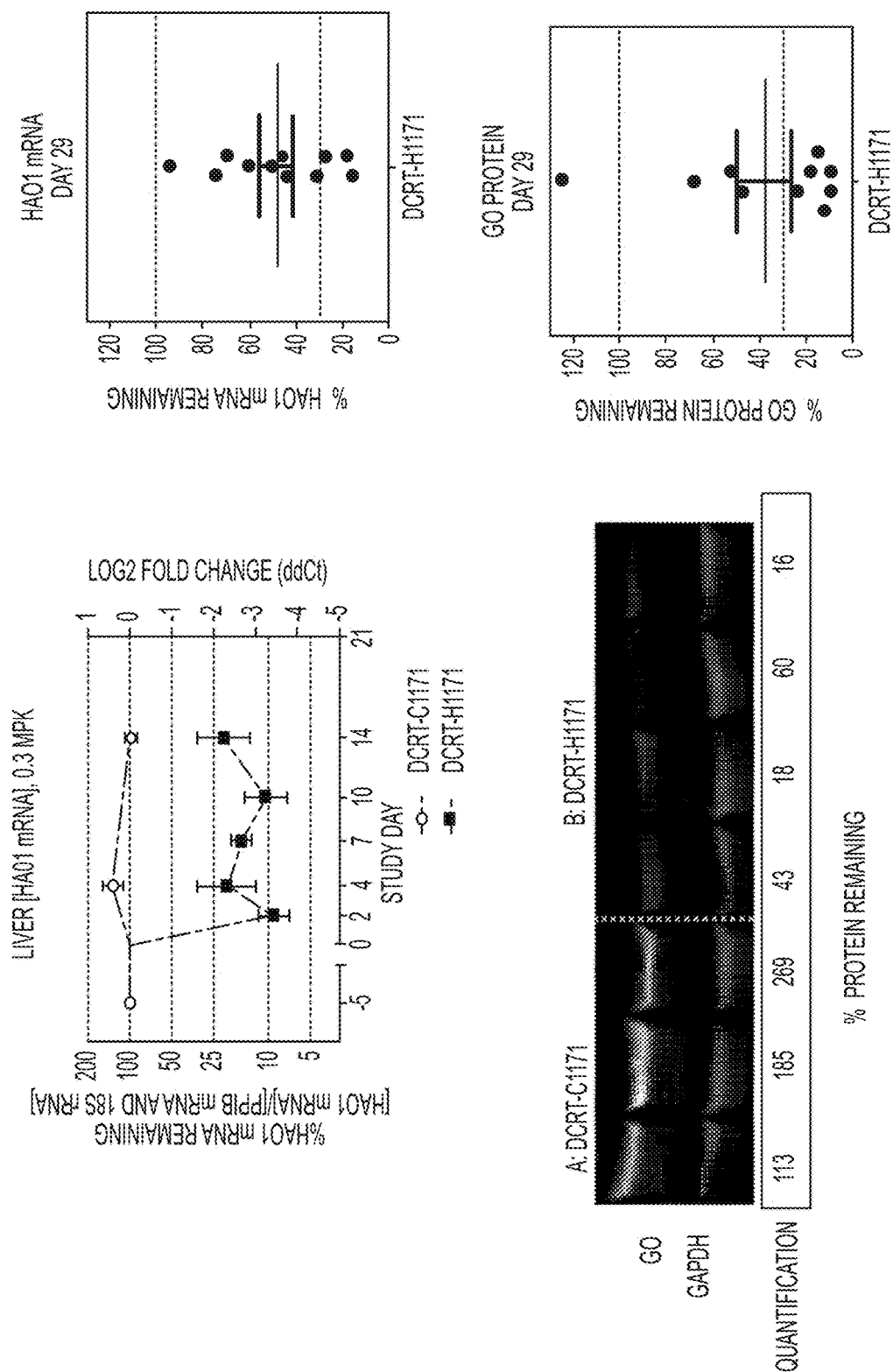

The in vivo efficacy of LNP-formulated HAO1-targeting DsiRNAs in non-human primates (NHPs) was also assessed. As shown in FIG. 13L, dramatic knockdown of both HAO1 mRNA and protein in the liver was observed in non-human primates administered an LNP-formulated HAO1-targeting DsiRNA (HAO1-1171) at 0.3 mg/kg. Consistent with the above-described mouse experiments, the inhibitory efficacy of LNP-formulated HAO1-targeting DsiRNAs was observed to be rapid, robust and of extended duration in treated non-human primates. Indeed, at 29 days post-administration, significant inhibitory efficacy persisted at both the mRNA and protein levels in non-human primates.

Thus, HAO1 DsiRNA achieved a rapid and highly durable in vivo silencing effect on both HAO1 mRNA and protein production in both mice and non-human primates.

Example 10

Indications

The present body of knowledge in HAO1 research indicates the need for methods to assay HAO1 activity and for compounds that can regulate HAO1 expression for research, diagnostic, and therapeutic use. As described herein, the nucleic acid molecules of the present invention can be used in assays to diagnose disease state related to HAO1 levels. In addition, the nucleic acid molecules can be used to treat disease state related to HAO1 functionality, misregulation, levels, etc.

Particular disorders and disease states that can be associated with HAO1 expression modulation include, but are not limited to primary hyperoxaluria 1 (PH1), including phenotypes of such disease in organs such as kidney, eye, skin, liver, etc.

Other therapeutic agents can be combined with or used in conjunction with the nucleic acid molecules (e.g. DsiRNA molecules) of the instant invention. Those skilled in the art will recognize that other compounds and therapies used to treat the diseases and conditions described herein can be combined with the nucleic acid molecules of the instant invention (e.g. siNA molecules, e.g., such as those directed to other enzymes possessing 2-hydroxyacid oxidase activity) and are hence within the scope of the instant invention. For example, for combination therapy, the nucleic acids of the invention can be prepared in one of at least two ways. First, the agents are physically combined in a preparation of nucleic acid and other agent, such as a mixture of a nucleic acid of the invention encapsulated in liposomes and other agent in a solution for intravenous administration, wherein both agents are present in a therapeutically effective concentration (e.g., the other agent in solution to deliver 1000-1250 mg/m2/day and liposome-associated nucleic acid of the invention in the same solution to deliver 0.1-100 mg/kg/ day). Alternatively, the agents are administered separately but simultaneously or successively in their respective effective doses (e.g., 1000-1250 mg/m2/d other agent and 0.1 to 100 mg/kg/day nucleic acid of the invention).

Example 11

Serum Stability for DsiRNAs

Serum stability of DsiRNA agents is assessed via incubation of DsiRNA agents in 50% fetal bovine serum for various periods of time (up to 24 h) at 37° C. Serum is extracted and the nucleic acids are separated on a 20% non-denaturing PAGE and can be visualized with Gelstar stain. Relative levels of protection from nuclease degradation are assessed for DsiRNAs (optionally with and without modifications).

Example 12

Diagnostic Uses

The DsiRNA molecules of the invention can be used in a variety of diagnostic applications, such as in the identification of molecular targets (e.g., RNA) in a variety of applications, for example, in clinical, industrial, environmental, agricultural and/or research settings. Such diagnostic use of DsiRNA molecules involves utilizing reconstituted RNAi systems, for example, using cellular lysates or partially purified cellular lysates. DsiRNA molecules of this invention can be used as diagnostic tools to examine genetic drift and mutations within diseased cells. The close relationship between DsiRNA activity and the structure of the target HAO1 RNA allows the detection of mutations in a region of the HAO1 molecule, which alters the base-pairing and three-dimensional structure of the target HAO1 RNA. By using multiple DsiRNA molecules described in this invention, one can map nucleotide changes, which are important to RNA structure and function in vitro, as well as in cells and tissues. Cleavage of target HAO1 RNAs with DsiRNA molecules can be used to inhibit gene expression and define the role of specified gene products in the progression of a HAO1-associated disease or disorder. In this manner, other genetic targets can be defined as important mediators of the disease. These experiments will lead to better treatment of the disease progression by affording the possibility of combination therapies (e.g., multiple DsiRNA molecules targeted to different genes, DsiRNA molecules coupled with known small molecule inhibitors, or intermittent treatment with combinations of DsiRNA molecules and/or other chemical or biological molecules). Other in vitro uses of DsiRNA molecules of this invention are well known in the art, and include detection of the presence of RNAs associated with a disease or related condition. Such RNA is detected by determining the presence of a cleavage product after treatment with a DsiRNA using standard methodologies, for example, fluorescence resonance emission transfer (FRET).

In a specific example, DsiRNA molecules that cleave only wild-type or mutant or polymorphic forms of the target HAO1 RNA are used for the assay. The first DsiRNA molecules (i.e., those that cleave only wild-type forms of target HAO1 RNA) are used to identify wild-type HAO1 RNA present in the sample and the second DsiRNA molecules (i.e., those that cleave only mutant or polymorphic forms of target RNA) are used to identify mutant or polymorphic HAO1 RNA in the sample. As reaction controls, synthetic substrates of both wild-type and mutant or polymorphic HAO1 RNA are cleaved by both DsiRNA molecules to demonstrate the relative DsiRNA efficiencies in the reactions and the absence of cleavage of the "non-targeted" HAO1 RNA species. The cleavage products from the synthetic substrates also serve to generate size markers for the analysis of wild-type and mutant HAO1 RNAs in the sample population. Thus, each analysis requires two DsiRNA molecules, two substrates and one unknown sample, which is combined into six reactions. The presence of cleavage products is determined using an RNase protection assay so that full-length and cleavage fragments of each HAO1 RNA can be analyzed in one lane of a polyacrylamide gel. It is not absolutely required to quantify the results to gain insight into the expression of mutant or polymorphic HAO1 RNAs and putative risk of HAO1-associated phenotypic changes in target cells. The expression of HAO1 mRNA whose protein product is implicated in the development of the phenotype (i.e., disease related/associated) is adequate to establish risk. If probes of comparable specific activity are used for both transcripts, then a qualitative comparison of HAO1 RNA levels is adequate and decreases the cost of the initial diagnosis. Higher mutant or polymorphic form to wild-type ratios are correlated with higher risk whether HAO1 RNA levels are compared qualitatively or quantitatively.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying DsiRNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

LENGTHY TABLES

The patent contains a lengthy table section. A copy of the table is available in electronic form from the USPTO web site (http://seqdata.uspto.gov/?pageRequest=docDetail&DocID=US10435692B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10435692B2). An electronic copy of the "Sequence Listing" will also be available from the USPTO upon request and payment of the fee set forth in 37 CFR 1.19(b)(3).

We claim:

1. A method of treating a subject having primary hyperoxaluria 1 (PH1), the method comprising administering to the subject a single dose of an effective amount of a double stranded nucleic acid that comprises a first oligonucleotide strand and a second oligonucleotide strand that form a duplex region, wherein the second oligonucleotide strand is sufficiently complementary to a target HAO1 mRNA along at least 15 nucleotides of the oligonucleotide strand length to reduce expression of the HAO1 target mRNA, wherein the single dose results in reduction of HAO1 mRNA in the subject that remains detectable at day 29 post administration.

2. The method of claim 1, wherein administration of the double stranded nucleic acid to the subject inhibits oxalate accumulation in the subject.

3. The method of claim 1, wherein administration of the nucleic acid to the subject results in an increase in a glycolate/creatinine ratio in urine of the subject and a decrease in a oxalate/creatinine ratio in urine of the subject.

4. The method of claim 1, wherein administration of the nucleic acid to the subject inhibits accumulation of calcium precipitates in a kidney of the subject.

5. The method of claim 1, wherein administration of the nucleic acid to the subject is performed subcutaneously.

6. The method of claim 1, wherein administration of the double stranded nucleic acid to the subject results in at least a 50% reduction of HAO1 mRNA levels in the subject.

7. The method of claim 1, wherein administration of the double stranded nucleic acid to the subject results in at least an 80-90% reduction of HAO1 mRNA levels in the subject.

8. The method of claim 1, wherein the subject is a human subject.

9. The method of claim 8, wherein the subject is a pediatric human subject.

10. The method of claim 1, wherein the subject has an AGT1 mutation that results in accumulation of oxylate.

11. The method of claim 1, wherein one or more GalNac moieties are conjugated to one or more nucleotides of the first oligonucleotide strand and/or the second oligonucleotide strand.

12. The method of claim 1, wherein one or more GalNac moieties are conjugated to the 3' terminal nucleotide of the first oligonucleotide strand.

13. The method of claim 1, wherein the first oligonucleotide strand is 15-66 nucleotides in length and the second oligonucleotide strand is 19-66 nucleotides in length.

14. The method of claim 1, wherein the first oligonucleotide strand is 21 nucleotides in length and the second oligonucleotide strand is 23 nucleotides in length.

15. The method of claim 14, wherein the second oligonucleotide strand forms a 3'-overhang of 2 nucleotides in length.

16. The method of claim 1, wherein the first oligonucleotide strand and/or the second oligonucleotide strand comprises one or more modified nucleotides.

17. The method of claim 16, wherein each of the one or more modified nucleotides is independently a 2'-O-methyl modified nucleotide or a 2'-fluoro modified nucleotide.

18. The method of claim 17, wherein the first oligonucleotide strand comprises a 3' region that extends beyond the duplex region formed with the second oligonucleotide strand and wherein the first oligonucleotide strand comprises a tetraloop structure.

19. A method of reducing or preventing kidney damage in a subject having primary hyperoxaluria 1 (PH1), the method comprising administering to the subject a single dose of an effective amount of a double stranded nucleic acid that comprises a first oligonucleotide strand and a second oligonucleotide strand that form a duplex region, wherein the second oligonucleotide strand is sufficiently complementary to a target HAO1 mRNA along at least 15 nucleotides of the oligonucleotide strand length to reduce expression of the HAO1 target mRNA by RNA interference, wherein the first oligonucleotide strand and/or the second oligonucleotide strand comprise one or more modified nucleotides independently selected from 2'-O-methyl modified nucleotides and 2'-fluoro modified nucleotides, and wherein one or more GalNac moieties are conjugated to one or more nucleotides of the first oligonucleotide strand and/or the second oligonucleotide strand, wherein the single dose results in reduction of HAO1 mRNA in the subject that remains detectable at day 29 post administration.

20. The method of claim 19, wherein the first oligonucleotide strand is 21 nucleotides in length and the second oligonucleotide strand is 23 nucleotides in length, and wherein the second oligonucleotide strand forms a 3'-overhang of 2 nucleotides in length.

* * * * *